(12) United States Patent
Shoshan-Barmatz et al.

(10) Patent No.: US 11,555,192 B2
(45) Date of Patent: Jan. 17, 2023

(54) SMAC/DIABLO INHIBITORS USEFUL FOR TREATING CANCER

(71) Applicant: THE NATIONAL INSTITUTE FOR BIOTECHNOLOGY IN THE NEGEV LTD., Beer Sheva (IL)

(72) Inventors: Varda Shoshan-Barmatz, Omer (IL); Yakov Krelin, Kiriat Arbah (IL); Avijit Paul, Kolkata (IN)

(73) Assignee: THE NATIONAL INSTITUTE FOR BIOTECHNOLOGY IN THE NEGEV LTD., Beer Sheva (IL)

( * ) Notice: Subject to any disclaimer, the term of this patent is extended or adjusted under 35 U.S.C. 154(b) by 29 days.

(21) Appl. No.: 16/633,276

(22) PCT Filed: Jul. 26, 2018

(86) PCT No.: PCT/IL2018/050835
§ 371 (c)(1),
(2) Date: Jan. 23, 2020

(87) PCT Pub. No.: WO2019/021289
PCT Pub. Date: Jan. 31, 2019

(65) Prior Publication Data
US 2021/0261965 A1    Aug. 26, 2021

Related U.S. Application Data

(60) Provisional application No. 62/537,475, filed on Jul. 27, 2017, provisional application No. 62/618,646, filed on Jan. 18, 2018.

(51) Int. Cl.
| | | |
|---|---|---|
| *C07K 14/00* | (2006.01) | |
| *C12N 15/113* | (2010.01) | |
| *A61K 47/64* | (2017.01) | |
| *A61P 35/00* | (2006.01) | |
| *C07K 14/47* | (2006.01) | |

(52) U.S. Cl.
CPC .......... *C12N 15/1135* (2013.01); *A61K 47/64* (2017.08); *A61K 47/6455* (2017.08); *A61P 35/00* (2018.01); *C07K 14/4747* (2013.01); *C12N 2310/14* (2013.01); *C12N 2310/321* (2013.01)

(58) Field of Classification Search
CPC . C12N 15/1135; A61K 47/1455; A61P 35/00; C07K 14/4747
See application file for complete search history.

(56) References Cited

U.S. PATENT DOCUMENTS

| | | | |
|---|---|---|---|
| 5,464,764 A | 11/1995 | Capecchi | |
| 5,487,992 A | 1/1996 | Capecchi | |
| 5,721,138 A | 2/1998 | Lawn | |
| 6,326,174 B1 | 12/2001 | Joyce | |
| 7,816,538 B2 | 10/2010 | Harran | |
| 7,884,211 B2 | 2/2011 | Harran | |
| 9,861,679 B2 | 1/2018 | Lalaoui | |
| 2002/0123476 A1 | 9/2002 | Emanuele | |
| 2002/0128218 A1 | 9/2002 | Emanuele | |
| 2003/0096980 A1 | 5/2003 | Froehler | |
| 2003/0170680 A1 | 9/2003 | Froehler | |
| 2008/0253966 A1 | 10/2008 | Bonavida | |
| 2013/0196927 A1 | 8/2013 | Benetatos | |
| 2016/0161495 A1 | 6/2016 | Begley | |
| 2016/0184383 A1 | 6/2016 | Lalaoui | |

FOREIGN PATENT DOCUMENTS

| | | |
|---|---|---|
| EP | 0375408 A1 | 6/1990 |
| WO | 2004005248 A1 | 1/2004 |
| WO | 2013016675 A1 | 1/2013 |
| WO | 2017109774 A1 | 6/2017 |

OTHER PUBLICATIONS

Puckett and Barton. Bioorg Med Chem. May 15, 2010; 18(10): 3564-3569. doi:10.1016/j.bmc.2010.03.081.*
Wilkinson et al. Journal of Biological Chemistry, vol. 279, No. 49, Dec. 3, pp. 51082-51090, 2004.*
Shintani et al., (2014) Smac/DIABLO expression in human gastro-intestinal carcinoma: Association with clinicopathological parameters and survivin expression. Oncol Lett 8(6): 2581-2586.
Shiozaki and Shi (2004) Caspases, IAPs and Smac/DIABLO: mechanisms from structural biology. Trends Biochem Sci 29(9): 486-494.
Shoshan-Barmatz et al., (2017) A molecular signature of lung cancer: potential biomarkers for adenocarcinoma and squamous cell carcinoma. Oncotarget 8(62): 105492-105509.
Shteinfer-Kuzmine et al., (2017) Mitochondrial VDAC1-based peptides: Attacking oncogenic properties in glioblastoma. Oncotarget 8(19): 31329-31346.
Stewart (1980) Colorimetric determination of phospholipids with ammonium ferrothiocyanate. Anal Biochem 104(1): 10-14.
Teh et al., (2006) Neuronal PAS domain protein 1 is a transcriptional repressor and requires arylhydrocarbon nuclear translocator for its nuclear localization. J Biol Chem 281(45): 34617-34629.
Tonkinson and Stein (1996) Antisense oligodeoxynucleotides as clinical therapeutic agents. Cancer Invest 14(1): 54-65.
Verhagen and Vaux (2002) Cell death regulation by the mammalian IAP antagonist Diablo/Smac. Apoptosis 7(2): 163-166.

(Continued)

*Primary Examiner* — Jeanette M Lieb
(74) *Attorney, Agent, or Firm* — Browdy and Neimark, PLLC

(57) ABSTRACT

The present invention relates to compositions and methods for treating cancer, particularly to agents that inhibit the expression and/or activity of the protein second mitochondria-derived activator of caspase/direct inhibitor of apoptosis-binding protein with low pI (SMAC/Diablo). The inhibiting agents include RNA interference molecules silencing the expression of SMAC/Diablo and peptides modulating its interactions within the cell nucleus and mitochondria. The methods and agents of the present invention are useful in treating cancers associated with overexpression of SMAC/Diablo.

8 Claims, 28 Drawing Sheets

Specification includes a Sequence Listing.

(56) References Cited

OTHER PUBLICATIONS

Verhagen et al., (2000) Identification of DIABLO, a mammalian protein that promotes apoptosis by binding to and antagonizing IAP proteins. Cell 102(1): 43-53.
Vuyisich and Beal (2000) Regulation of the RNA-dependent protein kinase by triple helix formation. Nucleic Acids Res 28(12): 2369-2374.
Wang et al., (2011) Toward an understanding of the protein interaction network of the human liver. Mol Syst Biol 7: 536; 11 pages with Corrigendum.
Welch et al., (1998) Expression of ribozymes in gene transfer systems to modulate target RNA levels. Curr Opin Biotechnol 9(5): 486-496.
Yamaguchi et al., (2003) Bax plays a pivotal role in thapsigargin-induced apoptosis of human colon cancer HCT116 cells by controlling Smac/Diablo and Omi/HtrA2 release from mitochondria. Cancer Res 63(7): 1483-1489.
Yoo et al., (2003) Immunohistochemical analysis of Smac/DIABLO expression in human carcinomas and sarcomas. APMIS 111(3): 382-388.
Yoshida et al., (1979) A simple method for measuring phosphatidylcholine as its hydrophobic complex with tetrathiocyanatocobaltate. J Biochem 86(3): 825-828.
Zhang et al., (2003) Activation of ERK1/2 protects melanoma cells from TRAIL-induced apoptosis by inhibiting Smac/DIABLO release from mitochondria. Oncogene 22(19): 2869-2881.
Zhao et al., (2012) A role for two-pore $K^+$ channels in modulating $Na^+$ absorption and $Cl^-$ secretion in normal humar bronchial epithelial cells. Am J Physiol Lung Cell Mol Physiol 302(1): L4-L12.
Kohli et al., SMAC/Diablo-dependent apoptosis induced by nonsteroidal antiinflammatory drugs (NSAIDs) in colon cancer cells. Proc Natl Acad Sci USA, Nov. 30, 2004, 101(48): 16897-16902.
Liu et al., Smac/DIABLO regulates the apoptosis of hypertrophic scar fibroblasts. International Journal of Molecular Medicine, 2013, 32(3): 615-622.
Abu-Hamad et al., (2009) The VDAC1 N-terminus is essential both for apoptosis and the protective effect of anti-apoptotic proteins. J Cell Sci 122(Pt 11): 1906-1916.
Admoni-Elisha et al., (2016) Novel Biomarker Proteins in Chronic Lymphocytic Leukemia: Impact on Diagnosis, Prognosis and Treatment. PLoS One 11(4): e0148500; 28 pages.
Adrain et al., (2001) Apoptosis-associated release of Smac/DIABLO from mitochondria requires active caspases and is blocked by Bcl-2. EMBO J 20(23): 6627-6636.
Alessenko and Burlakova (2002) Functional role of phospholipids in the nuclear events. Bioelectrochemistry 58(1): 13-21.
Anversa et al., (2011) Tissue-specific adult stem cells in the human lung. Nat Med 17(9): 1038-1039.
Arellano-Llamas et al., (2006) High Smac/DIABLO expression is associated with early local recurrence of cervical cancer. BMC Cancer 6: 256; 10 pages.
Bao et al., (2006) Relationship between expression of Smac and Survivin and apoptosis of primary hepatocellular carcinoma. Hepatobiliary Pancreat Dis Int 5(4): 580-583.
Barkauskas et al., (2013) Type 2 alveolar cells are stem cells in adult lung. J Clin Invest 123(7): 3025-3036.
Bruno and Darzynkiewicz (1992) Cell cycle dependent expression and stability of the nuclear protein detected by Ki-67 antibody in HL-60 cells. Cell Prolif 25(1): 31-40.
Cerrato et al., (2015) Novel cell-penetrating peptide targeting mitochondria. FASEB J 29(11): 4589-4599.
Chauhan et al., (2003) JNK-dependent release of mitochondrial protein, Smac, during apoptosis in multiple myeloma (MM) cells. J Biol Chem 278(20): 17593-17596.
Cheng et al., (2016) Targeting Phospholipid Metabolism in Cancer. Front Oncol 6: 266; 17 pages.
Choi et al., (2018) A novel fluorescence assay for measuring phosphatidylserine decarboxylase catalysis. J Biol Chem 293(5): 1493-1503.

Cooper et al., (2016) Long Term Culture of the A549 Cancer Cell Line Promotes Multilamellar Body Formation and Differentiation towards an Alveolar Type II Pneumocyte Phenotype. PLoS One 11(10): e0164438; 20 pages.
Deng et al., (2002) TRAIL-induced apoptosis requires Bax-dependent mitochondrial release of Smac/DIABLO. Genes Dev 16(1): 33-45.
Du et al., (2000) Smac, a mitochondrial protein that promotes cytochrome c-dependent caspase activation by eliminating IAP inhibition. Cell 102(1): 33-42.
El-Galaly et al., (2017) The number of extranodal sites assessed by PET/CT scan is a powerful predictor of CNS relapse for patients with diffuse large B-cell lymphoma: An international multicenter study of 1532 patients treated with chemoimmunotherapy. Eur J Cancer 75: 195-203.
Folch et al., (1957) A simple method for the isolation and purification of total lipides from animal tissues. J Biol Chem 226(1): 497-509.
Foster et al., (1998) Characterization of the A549 cell line as a type II pulmonary epithelial cell model for drug metabolism. Exp Cell Res 243(2): 359-366.
Fujita et al., (2016) Extracellular vesicle transfer of cancer pathogenic components. Cancer Sci 107(4): 385-390.
Gilboa et al., (1986) Transfer and expression of cloned genes using retroviral vectors. BioTechniques 4(6): 504-512.
Glunde and Serkova (2006) Therapeutic targets and biomarkers identified in cancer choline phospholipid metabolism. Pharmacogenomics 7(7): 1109-1123.
Glunde et al., (2006) Choline metabolism in cancer: implications for diagnosis and therapy. Expert Rev Mol Diagn 6(6): 821-829.
Glunde et al., (2011) Choline metabolism in malignant transformation. Nat Rev Cancer. Author manuscript; available in PMC Feb. 23, 2015. 33 pages.
Grimshaw et al., (2008) Mammosphere culture of metastatic breast cancer cells enriches for tumorigenic breast cancer cells. Breast Cancer Res 10(3): R52; 10 pages.
Hietanen et al., (1986) Fatty acid composition of phospholipids and neutral lipids and lipid peroxidation in human breast cancer and lipoma tissue. Carcinogenesis 7(12): 1965-1969.
Hu et al., (2012) Clinical significance of Smac and Ki-67 expression in pancreatic cancer. Hepatogastroenterology 59(120): 2640-2643. Abstract.
Inazu (2014) Choline transporter-like proteins CTLs/SLC44 family as a novel molecular target for cancer therapy. Biopharm Drug Dispos 35(8): 431-449.
Jacobs et al., (2010) Impaired de novo choline synthesis explains why phosphatidylethanolamine N-methyltransferase-deficient mice are protected from diet-induced obesity. J Biol Chem 285(29): 22403-22413 with supplementary information.
Kashkar et al., (2006) XIAP targeting sensitizes Hodgkin lymphoma cells for cytolytic T-cell attack. Blood 108(10): 3434-3440.
Keckesova et al., (2017) LACTB is a tumour suppressor that modulates lipid metabolism and cell state. Nature. Author manuscript; available in PMC Nov. 21, 2018. 43 pages.
Kempkensteffen et al., (2008) Expression levels of the mitochondrial IAP antagonists Smac/DIABLO and Omi/HtrA2 in clear-cell renal cell carcinomas and their prognostic value. J Cancer Res Clin Oncol 134(5): 543-550.
Khachigian (2002) DNAzymes: cutting a path to a new class of therapeutics. Curr Opin Mol Ther 4(2): 119-121.
Kotton and Fine (2008) Lung stem cells. Cell Tissue Res 331(1): 145-156.
Maraldi et al., (1993) Decrease in nuclear phospholipids associated with DNA replication. J Cell Sci 104 (Pt 3): 853-859.
Martinez-Ruiz et al., (2008) Role of Smac/DIABLO in cancer progression. J Exp Clin Cancer Res 27: 48; 7 pages.
Martinez-Ruiz et al., (2014) Ectopic expression of new alternative splice variant of Smac/DIABLO increases mammospheres formation. Int J Clin Exp Pathol 7(9): 5515-5526.
McElhinny et al., (2008) Mastermind-like transcriptional co-activators: emerging roles in regulating cross talk among multiple signaling pathways. Oncogene 27(38): 5138-5147.

(56) References Cited

OTHER PUBLICATIONS

Medes et al., (1953) Metabolism of neoplastic tissue. IV. A study of lipid synthesis in neoplastic tissue slices in vitro. Cancer Res 13(1): 27-29.

Minciacchi et al., (2015) Extracellular vesicles in cancer: exosomes, microvesicles and the emerging role of large oncosomes. Semin Cell Dev Biol. Author manuscript; available in PMC Apr. 1, 2016. 25 pages.

Mustafa et al., (2014) Mechanical stretch induces lung α-epithelial Na(+) channel expression. Exp Lung Res 40(8): 380-391.

Okada et al., (2002) Generation and characterization of Smac/DIABLO-deficient mice. Mol Cell Biol 22(10): 3509-3517.

Parra and Pérez-Gil (2015) Composition, structure and mechanical properties define performance of pulmonary surfactant membranes and films. Chem Phys Lipids 185: 153-175.

Paul et al., (2018) A New Role for the Mitochondrial Pro-apoptotic Protein SMAC/Diablo in Phospholipid Synthesis Associated with Tumorigenesis. Mol Ther 26(3): 680-694 with supplementary data.

Puckett and Barton (2010) Targeting a ruthenium complex to the nucleus with short peptides. Bioorg Med Chem. Author manuscript; available in PMC May 15, 2011. 16 pages.

Rock and Hogan (2011) Epithelial progenitor cells in lung development, maintenance, repair, and disease. Annu Rev Cell Dev Biol 27: 493-512.

Rock et al., (2009) Transmembrane protein 16A (TMEM16A) is a Ca2+-regulated Cl- secretory channel in mouse airways. J Biol Chem 284(22): 14875-14880.

Seidman and Glazer (2003) The potential for gene repair via triple helix formation. J Clin Invest 112(4): 487-494.

Shabtay-Orbach et al., (2015) Paracrine regulation of glioma cells invasion by astrocytes is mediated by glial-derived neurotrophic factor. Int J Cancer 137(5): 1012-1020.

Shibata et al., (2007) Disturbed expression of the apoptosis regulators XIAP, XAF1, and Smac/DIABLO in gastric adenocarcinomas. Diagn Mol Pathol 16(1): 1-8.

* cited by examiner

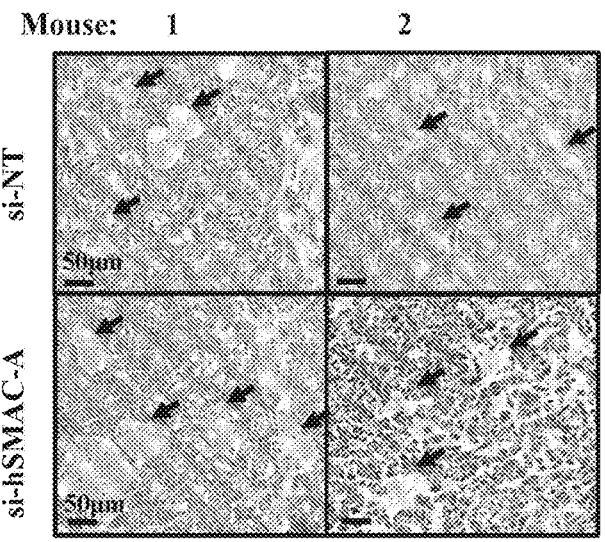
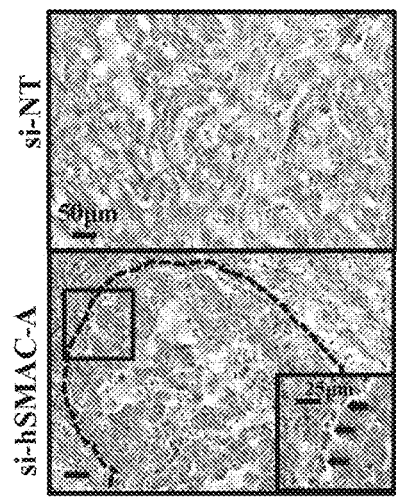
Figure 7A
Figure 7B
Figure 7C
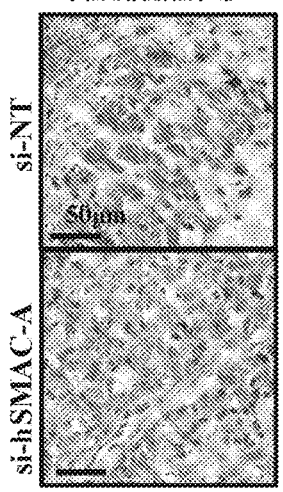
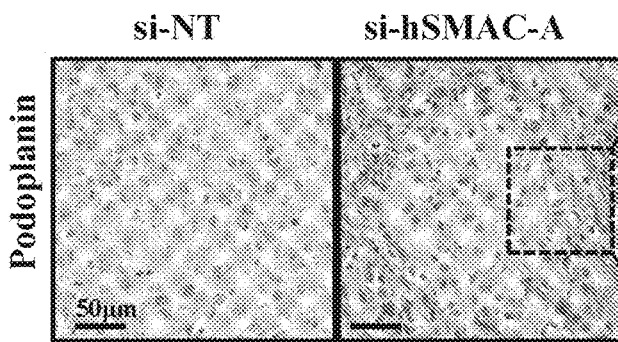
Figure 7D
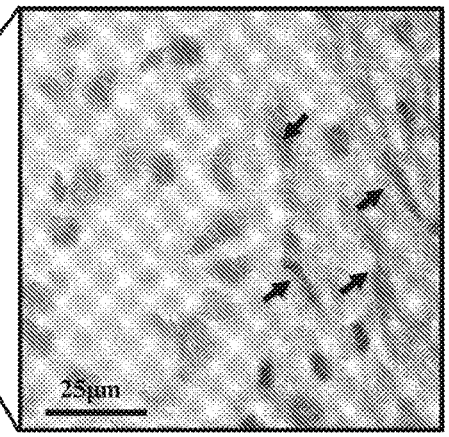
Figure 7E

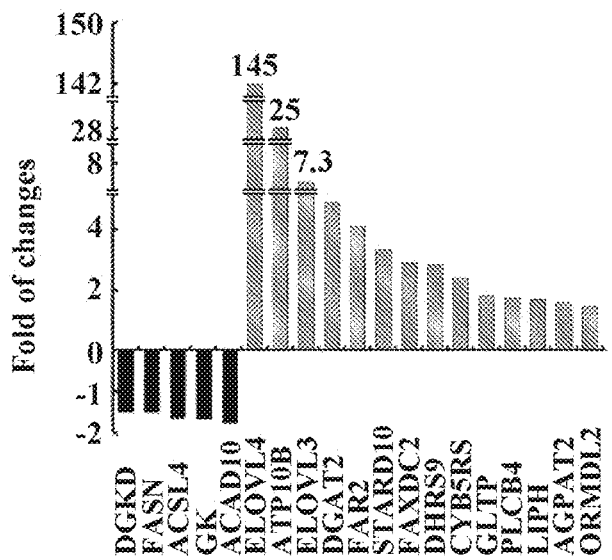
Figure 10C
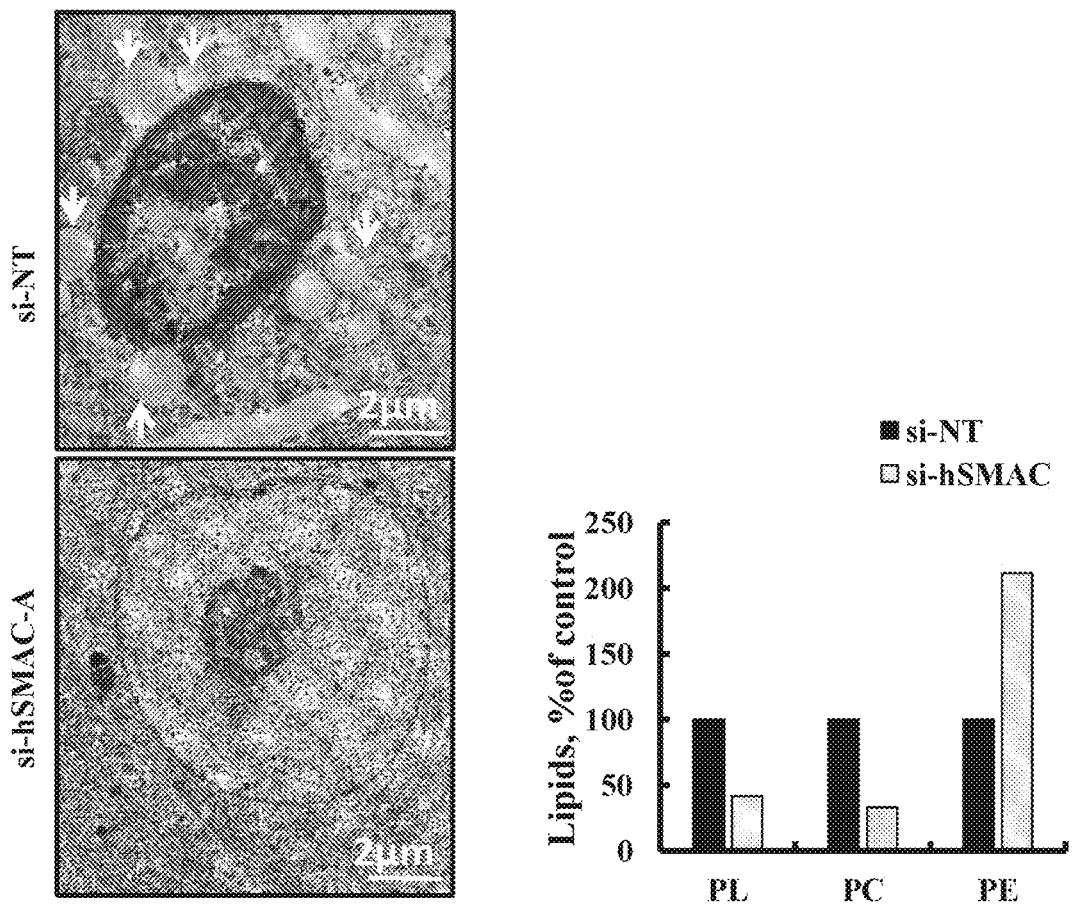
Figure 10D
Figure 10E

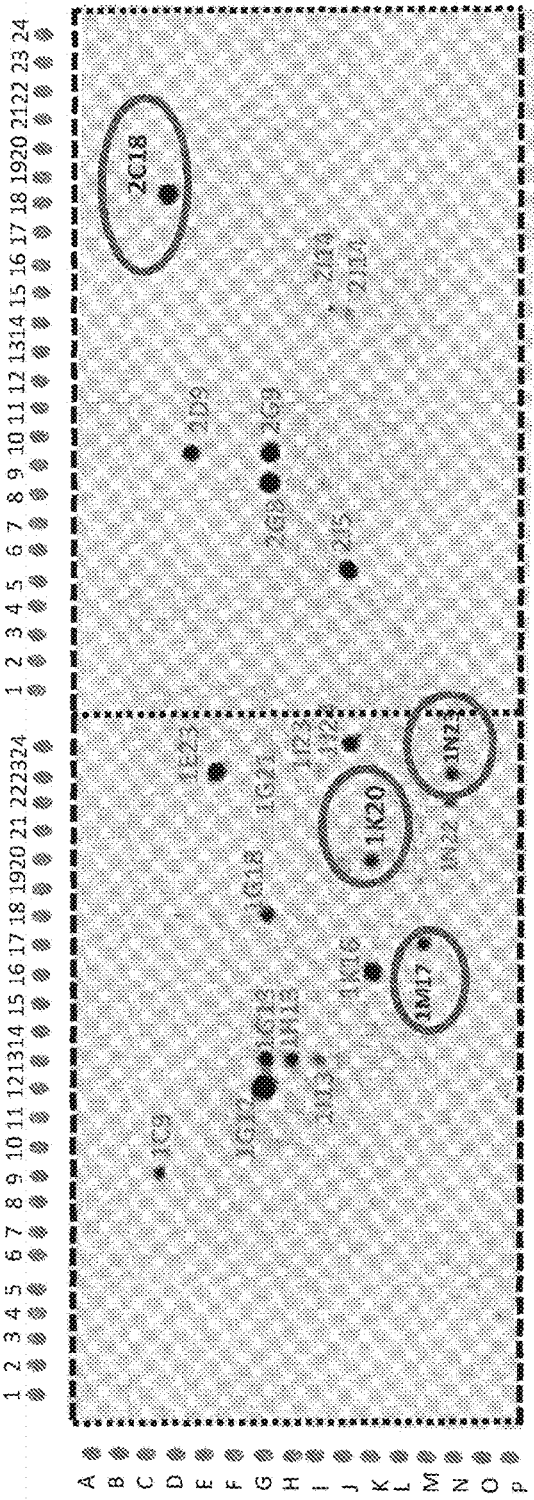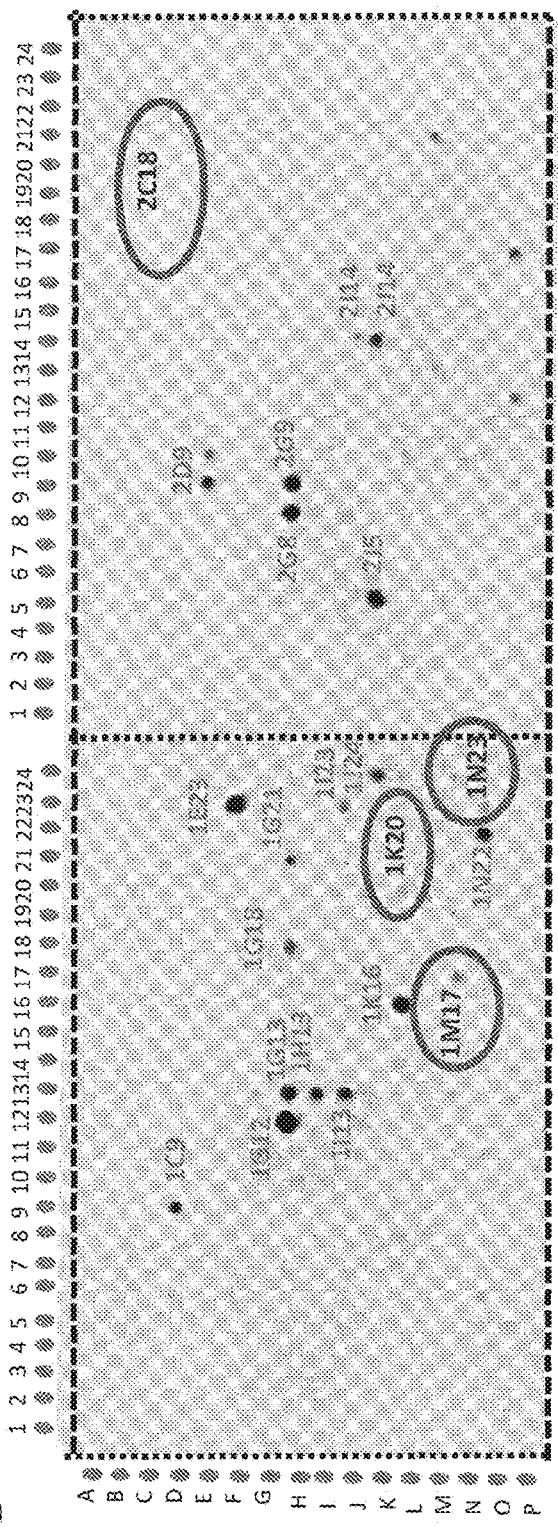
Figure 16A
Figure 16B

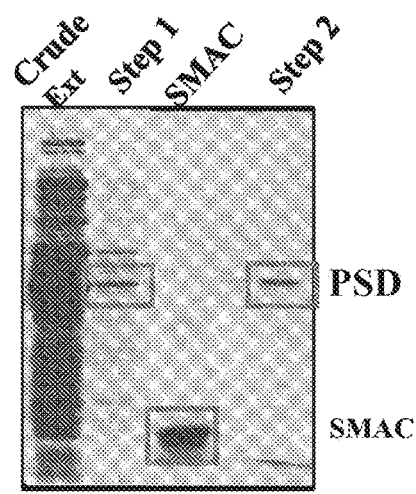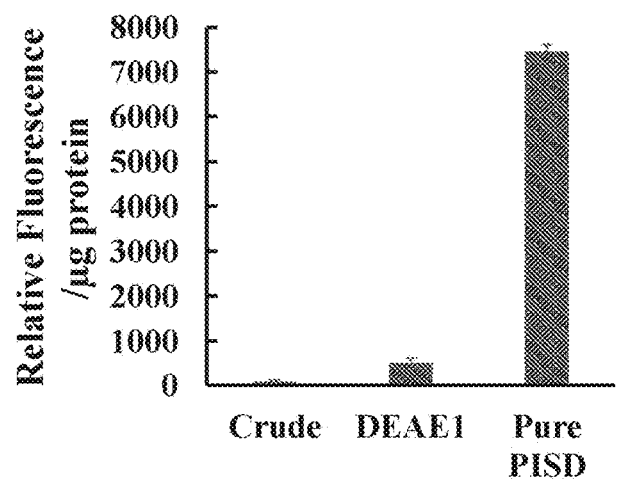
Figure 18A
Figure 18B
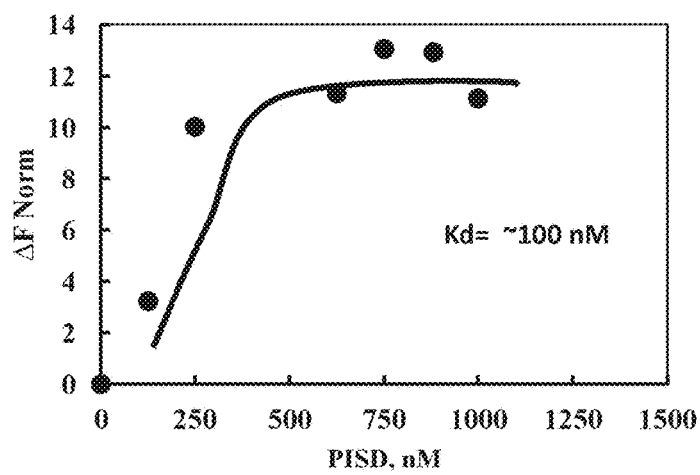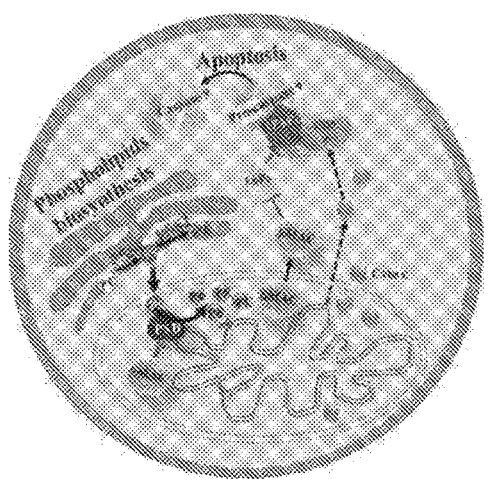
Figure 18C
Figure 18D

SEQUENCE LISTING

```
<160> NUMBER OF SEQ ID NOS: 118

<210> SEQ ID NO 1
<211> LENGTH: 19873
<212> TYPE: DNA
<213> ORGANISM: Homo sapiens

<400> SEQUENCE: 1
gagctcgggg accacgcgga ggttgtaatt ggtctctaga ccacacctag ttgttgagtg      60
ccgctgcttg aaaatctcag ttctgccgag atcgcagaat acacacaagc taccttlggg     120 caccagagca gacagaaccg cggagcttca gggtggaaga ttcgtggaaa ctttgccaag     180
taagtgaggt ggggagagaa ggaagccagt gcctgacact gtggggagtg gctgggcaaa     240
gcagcattgg aggtgttgta gggttcctac tgtctgatga gctggtgtgg ggttcttact     300
gtctgatgtc gtctctggtg gaagttagca gggctggggc agatgcacag agcacggtgg     360
cgggggtgag cccaggatcg gattgatgcc cacccaccac ctggcaccct gcagtcccag     420
ctggccagaa ggcaagcatg ctggaccaca aagcaaagat cctccagctc tgctgctggc     480
aagccttggg gccaggggac tcacagaaga gcaggtttgg gcctgtgcct tcctcctgcc     540
caaatgggtc tctctcccct tccccttcca gccagggccg cagctggggc tgcagcttga     600
```

```
gtgacgggaa aagaaaggtt tactccacca gcgcattagc ggcactcaca gcattaaaaa    660
tgcaggaggt ggtgggagga gcgggccagg gaggaaaact catgcagctg cggggcgcgg    720
ggaagagccg ggcttctgcc tcctcagccc ggatcagagc cgaagaacga gggcagtttg    780
ggttgagaag gattctccag tgtaaccgag aagcgagcgt ccaggaggct gttggggagg    840
tcggcactgt gggcttcctg gccttcgttt gctgtttcga gggccaggac ctcgtgtgtt    900
cccgtccgcc cctctgggac ggcgccagcc cggcaggccg ccgaccgtcc tggggctccc    960
gcgcagcgcg atgccggcct cgtccaccgt ccacgtgctg cagctgctgc gggagctgct   1020
cgccttcgtg ctcctcagct acacggtgct catcggggcg ctgctgctgg ccggctggac   1080
cacttacttc ctggtgctga agtgacagcg ccgtcgccgc gcccggcccc gcctcccgcc   1140
cggccccgcc tccgcccggg ccccgcctcc ctaactcacc aggaaattcc cttcaagccc   1200
tggcccgaac tgagtccccg cccacccgcc agcgtcacgg cgcccgactc agctccgcgc   1260
cggacccacc tccgcgccct caggccctgc atatgccccg ccccgcgcgg aagttccggc   1320
ggttggttgc cttgcgcggc cgttacagcc tttgccctaa gcctcgcccc ctttccccct   1380
gcctgcccaa tcccgactgc ttccttgggt ggggcgtgg ctatggggcg aggcgctctc   1440
aggtggaggc cgtgccccgc tccgcgctca cgaagctgcg tcacttccgg cgtgtgcgtc   1500
tggcgtccgc gcgctgcaca atggcggctc tgaagagttg gctgtcgcgc agcgtaactt   1560
cattcttcag gtaccgctgc ggccgcgtag aggggacagg accagaggga gggaccgacg   1620
cggacagcgc tgtggcccgg cccacggcgc ccgccttcct tacgcgctca tctctcgtcc   1680
gcccagctgg gtcgcggcgt ctcgctccgg tcgggaggac tgaggacagc cccgcctccg   1740 cccctgggt caagcccggc ttccttttca gttcgtccat cttctagaaa cgagtccccg    1800
agaccccggg ctgccttctt ggggctgctc cgcctcctga ccagccctcg tcagccactc   1860
gaagtccctg aggagacgtg gagaggagga gggacacggc atgggggag tccgggaagg    1920 gagacgagcg tctgaagacg tcctcccgag ggcagaaggg gccgggggag ctggcgcagg   1980
gctctctacc tagcgctgca ggctcctggg cgattgtagc gggaccgtca cacacaactg   2040
gcacccaggc caggggtcca gagctaaatt ctgcctgcag gagcggttat tgtggcatcc   2100
gtttctaaaa agtttaaagg caacatttta ttttattta atttttttga gacaagatct    2160
gcctctgtcg cccaggctgg agtgcagtgg cgagatctca gctcactgca acctgtgcct   2220
cccggcttca agcgattctc agcctcagcc tcccgagtag ctgggattgc aggcgcccgc   2280
caccacgccc ggctaatttt ttttttcctt tttgttttgt ttgagactca gtctcgctct   2340
gttgcccagg ctgaagtgca gtggggcgct ctcggctcac tgcaacctct gcctcccagg   2400
ttcaagcgat tctcctgcct cagcctcccg agtagctggg attacaggag cgtgccacca   2460
ctccgggcta ttttttgtgt tttaagtaga gatggggttt caccatgttg gtcaggcaga   2520
tttcgaattc ctgacctcaa gtgatccacc cgcctcggcc tttatttact tatttttttt   2580
taatagacac ggggtcatgt tgccagccat gttgcccagg ctggtcgtga actcctgggc   2640
tcaagtgatc ctcccgcctt gcccttggcc ttccaagtgc taggattaca ggcgtgagcc   2700
accaacaccc tgcctgaggc aacattttaa acttggtgta tgttgaaaat ttcaaaaccc   2760
ctcagctgtc ctgcatcctc atttaggttc ctgcttggct cgagtttgag tttacagccc   2820
ctgcaagtaa atccaagagc ctgttacaga ttggcggtcg tgccttatga aatctgactt   2880
ctacttccag gtacagacag tgtttgtgtg ttcctgttgt ggctaacttt aagaagcggt   2940
```

-continued

```
gtttctcaga attgataaga ccatggcaca aaactgtgac gattggcttt ggagtaaccc   3000
tgtgtgcggt tcctattgca caggtactgt cgtgtgcagt gattcttatc tagtgtaccg   3060
tgtcctcttg aagtctcaag tgggcggtga agcattagac aagctaccat agttttctcc   3120
agtgctccca tcccttcccc cacagtaccg gcatcttttc acagttgagc agatatatta   3180
atattctcat tttgattatc tcatttggta ggaacagcac atcaaattgt ataaagcgag   3240
tagagagaaa taagaggata ttacagtcta tcaacaaagt agtctttgat tcaacagaaa   3300
tttattgagc aacttttatg tgcaagacac tgagaatgta agaatgaaca acaaaaaatt   3360
cttgttctca caaaagcttt gtggagatga aagaggataa aatataaaat atcagctggt   3420
gataaatggt gggaagaaaa cagggccggg cacagtggct gatgcccagg ctttgggag    3480 gctgaggtgg gaggatggct tgagctcagg agtttgagac cagcctagtc aacatagga    3540 gactctgtct ctacaaaaca gaaaaattta gccgggtgtg gtggctcaca cttctagtgg   3600
caactactca ggaggctgag gcaggaagat cacttgagcc caggagtttg aggctgcagt   3660
gagctatgat ctcaccactg ctctccagcc tgggtgacag ggcaagacct tttctcaaaa   3720
acaaaacaaa acaaatgagg taagtgaata ggcaattctg ggagggagtt ttgttttaga   3780
taaaggtggt caagctactc tgataaggcg aagtagagat ctgaatgttc tgaaagagcc   3840
attatactat ctggtgcggg gaggagcttg ccaggcagaa ggaactcaga aggacaaaga   3900
cctagaagca gaagtatgcc tggtatgtct gaggagcatg gagctaatgt gtctggaggc   3960
gaatggggga gaccgtaata gatgaagcca gagagttaac tgataatcag attgtgtcct   4020
ttgtattttg tgggccattg ttgtaaggct ttgggttttc tgaaaaagaa gccgcagaag   4080 atatttttt ttttttttt taaagacaga gtctcactct gttgccaggc tgcagtgcaa   4140
tggcacaatc ttggctcact gcaacctccg cctcccaggt tcaagcaatt ctcatgcctt   4200
agcctccggg tagctgggat tacaggggtg tgccaccgca cccagctagt ttttgtattt   4260
ttagtagaga tgggggtttct ccatgcttgt gaggctggtc acgaacccct gacctcaggc   4320
gatccacacg cctcggcatc ccaaggtgct gggattacag gcctgagcca ccgtgcccgg   4380
ctgtcacaga ggattttaa cacagaacta ttatgatctg acataaattt taaaagttaa   4440
aaggttgctg tgtggaacta ggaagactag ttgctatatc taggcatgaa atgatactgg   4500 cttgaccag gcaagcagaa gaggtgggga gaatttagct caacgtagtt agcaggagtt   4560
gctgatggat tggttgtcgg gtgtattctc tagattaggg gtccccaacc cctgggctgg   4620
tactggtctg tggcctgtta ggaagcaagc tgcacagcag gaggtgagtg gtgggcaggt   4680
gagcattact gcctgagctc tgcctctggg cagatcagca gtggcatggg attctcatag   4740
gagcacgaaa cctattgtga actacacgtg cgagggatct aggttgtgtg cttcttgtaa   4800
gaatctaatg cctcatgatc tgaggtggaa cagtttcatc ctgaaaccat cctcacccca   4860
cccagtccat gaaaaaattg tcttcaacag agccggtccc tggtgccaca aacgttgggg   4920
accactgctc tagattccaa aaatttttt ttttttttt ttttggagac ggagtctcgc   4980
tctgttgccc aggaagctct gcctcctggg ttcacaccat tctcctgcct cagcctcccg   5040
agtagctggg actacaggcg cccgccacca caccctgcta atttttttgt atttgtagta   5100
gggacagggt ttcaccgtgt tagccaggat ggtctcgatc tcctgacctc gtgatccacc   5160
tgcctcggcc tcccaaagtg ctgggattac aggcgtcagc cactgcacct ggccagattc   5220 caagatttt taaaggcctt agcaactgaa tgaatggcga tgccatttag taggatggag   5280
aggagtgggt tttgaaagga aaaaaatttt ttggaaatgt catttctaag atgtctagga   5340
```

```
aacatctagg tggagctgtc aattaagtag ttgatataaa agtggcactt catttaaaaa   5400
aatcatagct tatatgcttt atggggaaga gctagagagg aaaccagcaa gctccatttc   5460
agcaaaatat tcctgccact taacgtgtgt gttcatcaca aaaggaagat taattccatg   5520
tattacaagt attttcagca tcttctgagg ctcattcatg agccctcacc ttactgtgcc   5580
tcacttcagt tgtcatctct gcatgctgat gaatccatag ccctaaaacc cctcacttga   5640
ataccaggct attttcgacc acaattggga caacctttgt ttttttcatt caaaagattt   5700
tttttaggt tgtcctttc tcagttatta tattactttc taagcccagt taacctcagt    5760
tctgggccac atgactgggg tctctagtca tttagtacag caatgccact tccattcttc   5820
aaaaccctc agtggtcagc taggcacgat ggctctctct tgtaatccca gtacttttgg   5880
aggctgaggg gggaggatca ctgtaggcca agagttcgag accagcctga gaaacatagc   5940
gagaccaccc ctctacaaaa aataattagc taggtgtggt ggcgtgtgtc ggtagtccta   6000
gctacctggg aggcaggagg atgatttgat ttcaggagtt caaggctgca gtgagctggg   6060
atcacaacac tatactccat cctgggcaac agaatgagaa atgaaaaacc tacagtggct   6120
ttccatgagg cgttcagaac taaaattaaa ctaagtctcc ctgcactcca gggccctagt   6180
gagtctcatt tctcttagct ccaaccaggc tagatccctg gacatcccct gcaacaaaag   6240
tattattttc ctcattgtta cctattctcc aggatgcgtg gccattctga ttctaggtat   6300
ctttagtacc aagtctcacc tctatttaaa gcctttcctt attcctgtcc aacaactatc   6360
tcctcctttt tggccactta atattgtata ttttgatatt tgatgataat cctttggcac   6420
cctcctgagt catcagagca taatgggaag ggtacagact ttgaagtgag atttggtttg   6480
aggtctagat gtgactttt ggaaaagtta cataactatt ctgagcttcc atgtcattgc    6540
ttgtaaataa gaaaggataa taactggact gttgtgagga acaagtgaaa acacattata   6600
aaatgtagca cattatgaag acttatcaga atattgagac aaaattagct tcttgtgagc   6660
agaggtgtct ttcttccttt tgtagtcctg tataagatgc ctaatgaata cttaattatt   6720
tgaaatataa agttcttgat tgttcatat caaaaatatt tcttgactgc ctctttcaac    6780
atgcagtgat tctgagtgtt tgtactctga atagcaaaaa caagacaaca tagagtgatt   6840
gatttttgt ttttgttttt gttttgtttt gttttgtttt gagacgagtt tcactcttac    6900
cacccaggct ggagtgcaat ggcaagatct cggctcactg caacctccac ctcctgggtt   6960
caggcaattc tcctgcctca gcctcccgag tagctgggat tacaggtacc cgccaccacg   7020
cccagctaat ttgtgtcttt ttagtagaga cggggtttca ccatgttggc caggcttgtc   7080
tcaaactcct gatctcaggt gatctgcccg cctcagcctc ccaaagtgct gggattacag   7140
gtgtaagagt gctttgctga ggaggaaaaa ggcagagagt cagggaggat gtgtcattac   7200
agttgccagt atttagtcca ggtggccaca gtcccttaac tcttaaggta attatattag   7260
tctttccttt tttaaaatag ctgaggtcag ggtgggcatg gtggctcaca cctgtaatcc   7320
cagcactttg ggaggccaaa gcatgtgtat cacttgaggt caggagttca aaccagcct   7380
gggcaacatg atgaaacccc atctctacta aatataccaa aaaaatagca aagcgtggtg   7440
gcaggtgcct gaaatcccag ccactgggga agctgaggca ggagaatcgc ttgaacccag   7500
gaggcggagg ttgcaatgag ccaagattga accactgcac tccagcctgg gtgatagagt   7560
gagactctgt ctcaaaaaaa aaaaataaaa taaccgaggt ccccccatca acactgtact   7620
gcttcattct gctcagaatt gccctccccc atccactttt tttttttttg gcgaaagagt   7680
```

```
cttgctctgt cgcccaggct ggagtgaagt ggcacgatct tggctctcac tgcaacctcc    7740
acctcctggg ttcaagcgat tctcctgcct cagcctctca agtagctggg actacaggtg    7800
cccaccacca tgcccagcta attttttttt ttttgtattt ttagtagagt tggggtttcg    7860
ccatgttggc caggctggtc tcgatctctt gaccttgtga tccacccgcc tcggcctccc    7920
aaactattgg gattacaggc gttagccacc atgcctggcc cactttatta gactcagctt    7980
aatcctcatc aaacttgtga agccttttct aagctattag cactcaacat agaactgatt    8040
gctcccttct gcatgccccc agtgtagctc atacatactc ctcccacagc ttccatgata    8100
catgattgtg ttcattttc tagttctgtt agcccatcat cctgctctct ctaccccta     8160 acctgtgttt gagggcagag aatgtcttgt tgagacttgc gtctcaagta tctaacactg    8220
ttaatgaatg aattgtaatc ttatcaattt gttggttata atcaatagtt ttggggggttt    8280 ttttggtttt ttgttttttt tttgagatgt agtctcgctc tgtcaccagg ctggagcgca    8340
gtggtgcaat ctcggctcac tgcaacctct gcctcctggg ttcaagtgat tcttctgcct    8400
cagcctccca agtagctggg actacaggcg tgtgccacca cgcccagcta attttgtat    8460 ttttagtaga cgggggttt caccatgttg gccaggatcg tctcaatctc ctgacctcgt    8520
gatctgcctg cctcagcctc ccaaagtgct gggattacag gcgtgagcca ccgtgccgg    8580 cactttttt tttttttttt tagtcttgct ctgtcaccca ggctggagtg cagtggcagt    8640
ctcggctcac tgtaacctct gcctcctggg ttcagtcgat tctcctgcct cagcctcccg    8700
agtagctggg attaaagacg cacaccacta cggcccagct aattttttgta tttttttagt    8760 agagacgggg tttcaccatg ttggccagga tcgtctcaat ctcctgacct cgtgatctgc    8820
ctgcctcagc ctcccaaagt gctggtatta caggtgtgag ccaccgtacc cgccacaat    8880 ttatttata tgtaaagaaa taatttgctt tttggagcag agaatgaaag ttggtagaaa    8940
gcatactccg gaattatttc tctatattgt cttaaattgc caaataagg ccttaaaaaa    9000 tataacccaa agaaatatag tgcagtttca gcctaaaaca ctaagcagca tgacaattac    9060
gttttttgct tgcctattgg tgaaaaagtt ctcagtttga gctttagagg ttgagtgaca    9120
atgtttgtgt ctttcagaaa tcagagcctc attcccttag tagtgaagca ttgatgagga    9180
gagcagtgtc tttggtaaca gatagcacct ctaccttct ctctcagacc acatatgcgt    9240
tgattgaagc tattactgaa atactaagg tatgtctcct cttaactctt gatcttctaa    9300
accatggttt agcaaataat ggctcacaac caaattgtgt ctgatacca tgttggtatt    9360 tgattgaaac atagccaggc ctatttgttt atgtgttgtc aataacggtt tttgaggatt    9420
tgagtagttt caacagaggc tgtaaggccc acaaagccca aaatatttac tgtcaggccc    9480
ttcaaaaagt ttgctgagcc ctgatctaaa tcactcgttt ttagactttt cccaggaacc    9540
tttttttttt ttttttacaga aaaatcttaa atgtggcagc ctagtatata aaacaggagt    9600
gaagctgata tggttcagtt aagggcacag gggcctgtgg tccatcaaca gaggttgctc    9660
tgtgaggatt atttaaaagc cactgatcta acctaataga aaagagagta tatgggccag    9720
gcgtggtggc tcacatctgt aatcccagca gtttgggagg ccaaggcggg aggatcactt    9780
ggggccagga gttcaagacc aacccagtca atgtagcaag ccccatctct agcagaaaaa    9840
aaattttaaa cttagccagg catggtgtgt tgtgtgcctg tagtcccagt tactccaggg    9900
gctgaggtgg gaggatcact tgagtctagg agtttgagat tacagtgagc tatgaacatg    9960
ccagtgcact tccgtctggg tgacatagca tcctgttgt aaaaaataat aaattttttt    10020
ttttgagatg gagtcttgct tacgcaggct ggagtgcagt ggagtgatgt cagctcgctg    10080
```

```
caatctccgc ctcctgggtt caagcgattt tccttcctca gcctcctgag tagctgggat   10140
tacaggtgtg tgccaccatg cccggctaat ttttttgtat ttttagtaga cgggggttt    10200 tgccatgttg gccaagctgg tctcgaactc ctgacttcag gtgatccacg tgtcttagcc   10260
tcccaaagtg ctaggattac aggcatgagc cactgcaccc ggccaataaa aatttttag    10320 cgtatatgga taatcaaaag tattgaagtc tcatttgtgc atttgtttta catatatttt   10380
ccagcagctt ttttcccctc aacctttaaa gttttccctt gcattgtttt ctctttctgt   10440
gtctgaattg ctgacaagct tttaaaaaca cagaagttta cagatggaga tactaatgtc   10500
ctgatacctt tacttcatag gataatagtg caatttcatt gaggcagcag gatggaagag   10560
ccagtttgct gtaatgggac ttaatttcct tgaggtggaa atctctctat tccttctgat   10620
atgtctcact tactttactc agacttgttc attctctatt tgtaggctgt ttataccttA   10680
acttctcttt accgacaata tacaagttta cttgggaaaa tgaattcaga ggaggaagat   10740
gaagtgtggc aggtgatcat aggagccaga gctgaggtaa gcagaaagtt ctaggcattt   10800
ctgtgttagt gcacctacct catgtggtat ctaaattatt gaattaagtc taatcaatat   10860
aatcagtgtt ctctaaatct actactttaa gtccatttaa atgggctaga cctcttatgc   10920
tgtctgaagc actttgcttg atttatatag atgacttcaa aacaccaaga gtacttgaag   10980
ctggaaacca cttggatgac tgcagttggt ctttcagaga tggcagcaga agctgcatat   11040
caaactggta ggttcaagtt ttgtgttggg tttttttttt aatttttaa ctaggaaggt    11100 accatttgag ttttcatctg gttttctaaa atgagggctt tatagtaaat ggtctaagtg   11160
gctctcactt tgagaaattt tccccatttc ctacatatta acctacattt tatttgcaca   11220
atagaaacaa tgagcatacc cttgcagacc agaccagtag aagctaggtt atgtcttcaa   11280
aatgaaaaat gataaaacta ttaccattgg aaaattggat tgcttccaaa tagttttagc   11340
ttcttttggt aatacaattt attaacaatc atagaattac accgttggct gagacttgag   11400
atgagtaatc tatgtgaacc ttttttgtaca gatggagaaa atgagacctg gaatcatagt   11460
cagtggcaaa accaggacaa attatttgtc tatgtcaggc tttgtggtag gcatttcgta   11520
ggcacttttt atatgtgaag aaactagagg gcagatgggc cagatcattc ggctaagatg   11580
acacggtatg gtgagtaagc agccaagctg agattcagct gagtaggtct ttttttttt    11640 ttttttttt tccttcataa aatagagatg gggttttaca atgttgcaca ggctaatctc    11700
gaaatcctag gctcaagcag tctacccacc ttggcctccc aaagtgctgg gattataggc   11760
atgagccacg gagccaagta ggtcgaattc caaagcctct gcttctccta ttctcccagc   11820
agccagtgct ttgtcctttg caccgtggtg ccccaaggtg cccatcatag aacatcctac   11880
ctgagtggtc ccaacctagg taggtaggct cacagaaaaa aaaattttt ttaatggagt    11940 tttgttcctg tcacccaggc tggagtgcac tggcgccatc taggctcact gcaacctcca   12000
cctcctgggt tcaagtgatt ctcctgcctc agcctcccaa gtagctggga ttacaggcac   12060
ccgccaccac gcccagctag ttttttgtatt tttaatagag aatagttttt gtattttaa    12120 tagagaaggg gttttgccat gttggccagg ctggtcttga actcctgacc tcaggtgatc   12180
cacccgcctt ggcctcccaa agtgctggga ttacaggcat gagccactgt gtccggccaa   12240 atttttttt tttgagaca gagtttcact cttggtgccc aggctgcagt ggtagcactt     12300
tctcagctca ctgcaacctc tgcctctcca gttcaagcaa ttttcctgcc tcagcctccc   12360
gattacaagc atgcaccacc acgcctggct aatttttgta tttttagtag aggcaggttt   12420
```

```
cgtcatgttg ttcctcactt cagcctctca aagtgctggg attacaggtg cgagccaccg   12480
cacccagccg gctcaccaaa gttatagctt agtactagtt cttattaaga aactggttgc   12540
agtggctcat gcctataatc ccagcacttt gggggggccaa ggagggcgga tcacttgagg   12600
tgggtcactt gaggtcaaga gtttgacact accctggcca ccgtggtgaa accctgtctc   12660
tactaaaaat acaaaaatta gccaggtgta gtggcacacg cctgtgcagg agaatggctt   12720
gaacccaggg ggtggaggct gcagtgagcc tagatggctc cactgcacct caagccttgg   12780
tgacagagca agactctgtc tcaagaaaaa aaaagaaac tgggatgagt caggcacagg   12840
gactcaacgc gtgtctttgg gaagccaagg caggcagatt gctggagccc aggagttcaa   12900
gggcaacaca gtgaaacccc atctctacca aaaatacaaa aattagctgg gcgtattggc   12960
gctcgcctgt agtcccagct actcgggagg cagaggtggg aggattgctt gaacccagga   13020
gctcaaggct gcagtgagct atgatcatgc ctgtgcactc catcctaggc aaaagagcta   13080
gaccctgtct caaaaagaa attgttatat aaaacatac tcttgttttc tgatgtcaag   13140
attagcaggc tagggttctc aatcatcaaa tcttaaaaat gatacaaagg ctgggtgtg   13200 gtggctcaca cctgcaatcc cagctacttg ggagggtaag ataggaggat cacttgagcc   13260
tgggaggcag aggttgcagt gaggtgagat cattgcactc cagcctgtgc aacagagtga   13320
gaccccatct caaagaaaag atataaaaca tttttttaagg taagtgttgt gtcatcatac   13380 tgaaaacaa aaaataattc tttttagaagg ttttttttgt tgttgttagt ttttttgttt   13440 gtttgtttt ttgagacagt ctcattccat cccccaggct ggagtgcagt ggtgtgaact   13500
cagctcactg caacctccac ctccctgctt caagcaattc tcttgcctct gcctcctgag   13560
tagttgggct tggaagcgcc tgccaccatg cctggctaat ttttttattt ttagtagaga   13620
cggagtttca ccatgttggc cagaccggtc ttgaattcct gatctcaggt gatctgcctg   13680
cctcggcctc ccaaagtgct gggattacag acatgagcca ctgcgcttgg cccagaaaaa   13740
gtagtgatcc tgagaaaaag tagtgatcct gagggatcag agatttggaa caagaatgaa   13800
acaacggaag tgtggaagca gcattatagt tgtgccacac aaacatggca gaggatttct   13860
aggtgcagtg aacaggagga tatgcttata tctagaagga gaaaggaga atatctagaa   13920 ggagaaaagg agggggatgta taagcattat ttgagaaaag tagacatttt cctagaactc   13980
atagaaaggg ctaacaaagt tgtaaacgga atttttttt tttttttccc tgagacaagg   14040
tcttactctg ttaccaggct ggagtacagt ggcacaatca tggctcactg cttactacag   14100
ccttagcctc tgggctcaag cgatcctacc atgtcagtct cccaggtagc tgggattata   14160
tgtttccggt agagacagga ttttgccatg ttgtccaggc tggtcttgaa ctcctgagct   14220
caagtgatcc acccgccttg gcctctcaaa ctgctgggat tacagacatg agacactgtg   14280
cacggcctta tgatttcact tttttaacca aaaatctggt ccaggtgcag tggctcatac   14340
ctgttgtaat cccagcactt cgggatgcct aagcaggtgg atcacttgag ctcaggagtt   14400
cgagaccaga cttgacaaca cgatgaaacc ctgtctctac aaaaaaatta gccaggcatg   14460
gtgatgggcg cctgtagtcc cagcttcttg ggaggctgag gtgagaggat cacttgggcc   14520
ctggaggtcg aggctgcagt gagccatgat caggccagtg tacccagcc tggttgacaa   14580 agcaagaccc tgtcttaaaa acaaaaaaat ggccgggcgc agtggctcac gcctgtaatc   14640
ccagcacttt aggaggctga ggtgggcgga tcatgtggtc aggagataaa gaccatcctg   14700
gttaacatgg taaaaccccg tctctactaa aaatacaaaa aaattagcta tgtgtggtgg   14760
cgggtgcctg tagtcccagc tactcgggag gctgaggcag gagaatggcg tgaacctggg   14820
```

```
aggcagagct tgcagtgagc agagatcaca ccactgcact ccaccctggg caacagagca   14880
agactccatc tcaaaaaaaa aaacaaaaat aaataaataa gcgaacaata aagtaacagc   14940
ataacaaaaa gattcagagc aaaatcccaa aagctactaa gaaaaaatag attacctaca   15000
aaggaagtag aatcaaacat caggcatctt ctccgcaaca ctagaggtga cgataaatcc   15060
ataacctagg attttatgta tagccaacta ccatcaaaaa gtgagaataa aagatatcct   15120
cagacataga ctcaaagtac cacctgtata cactttctgg aagaactatg aagaaggaaa   15180
aatcagtttt gagagaagct actaagattt tttttcaaaa gttctgagtg taaaacaagt   15240
ttttaaattt gggaaagtga aaacatgcta agcacattga cattagacat tgttaaacac   15300
tgcaaagaga attagtagga gtgggaggaa acttggtagc tccagttgag gcaggaaagg   15360
tttaaaaaga aaacccgtca attagaaaat acaaaattgg gccacgtgca gtagttcaca   15420
cctatgatcc cagcactttg gaaggccaag tcagatggat cagctgaggt caagagttcg   15480
agaccagcct ggccaacatg gcaaaactcc atctgtaatt taaaaaaaaa aaaaaaaaat   15540
tataggaata atttcaaaca tcagtgattg cagtaaaaat aaacttatta aatgacacgt   15600
ttagattgtg ttccaaaatt tagctaaaac tagctaaatc aaagaattca agataaaaag   15660
taatcagtag gacagaacaa ttcattaaga cattatcaat catgaaatgt acttaatgag   15720
gcaaaaactg atagaattac aaggagatct gagatgtgtg taatactcaa ttttctgagc   15780
acgcttgcag gtcaagacaa ccaaaaaaat taaagctatt aaagctatta aggattagaa   15840
cagaatttgt tttggagaca gggtcttgct ctgttgccca ggctggagtg taatggcatg   15900
atcacagctt actgcagcct tgacctgggc tcaagccatc ttcccatttc agcgtcccaa   15960
gcagcccaac taattttctt ttttttttttt aagagttggt gtcttgttat gttcccagg   16020 ctgattttga actcatgggc tcaagtgatc ctcccgtctt ggcctgccag agtgctagga   16080
tcacaggcgt gagctgagcc actgcaccca gctcagtgtg attgtttttt attttggaga   16140
cagggtctca ctctgtcacc cgggttggag tgcagttcct tgatcttggc tcaccgttac   16200
ttctgcctcc cagggtcaag caatcctgtc tcagcctcct gagtagctgg gaccacaggc   16260
agtcaccacc acgcccgatt aatctttttt attttttggt agagatgggg tttcaccatg   16320
ttgcccaggc tagtctcgaa ctcctgagct aaggcagtcc acctgcctca gcctcccaaa   16380
gtgctgggat tacaggcgtg agccactgtg cccgtctgtg atttttttt ttttttttt   16440 tttttttttt ttttttact tttaactaaa caaggaaaa tcagatttgt gtgtgtgaga   16500
gagacagggt ccatgcggga atgctgtggt gggatcatag atcatagctt gctgtagtct   16560
caacctcctg gactcaagtg atcctcccca ctttagcctc cccagtagct gggattacag   16620
gtgcacacca ccatgcccca gctaattttt ttatttttag tagaaacaga gttttgctaa   16680
gtttcccagg ctggttttgc agagtggttt ttaaacacct aacaaatgta tatatactaa   16740
atataaaact ttgcccctc cctctaaatt tacatactct tctaagacac acagtaaatt   16800
ttgtaccagg tgacaaaagg aagagacaac aaaatcattt aaaaagttga tatatcacct   16860
gggcgcggtg gctcacgcct gtaatcccag cactttggga ggccaaggcg ggtggatcac   16920
gaggtcagga tcaagacc atcctggcta acgtggtgaa accccgtctc tactaaaata   16980
aaaaaaataa ataaataaat taggcatggt ggtgggcacc tgtagtccca gctactcagg   17040
aggctgaggc aggagaatgg cgtgaacccg ggaggtggag cttacagtga gccgagatcg   17100
cgccactgca ctccagcctg ggtgataagt gagactccat ctcaaaaaaa aaaaaaaaaa   17160
```

```
aaaggtagaa atggtattcg aagattttga tgtccccaaa atggacacca gggcctagga    17220
tgtttcgtgg gagagtttta tcaaatcttc caaaactata ataccatgt tactgtaagt     17280 gtaccagcgc aaagaaagta atgacaagcc tcctcttact actgtatgaa gccagcatag    17340
ccccgatccc aaactggact agggcagcac caaaacgaaa agctcagtat cacttcaaaa    17400
tgtagccgta aatcaaacgt agccatttac cctcaaaata gaatgatagt tcaacactgt    17460
aaaaaactat agagtgagac tccttctcaa acaaatataa ttcactgttt gagatgatat    17520
atccatagat taaaggagaa aaaccactta acatatgccc aaaacatctt cagtgtagta    17580
gccatttatg attcgaatct aagtacaatt atgaagagat aattttctta atgtaataaa    17640
ggttaagtaa tcctacttaa ttgtgtggac tttcagaagt gttttcatcg aagttagaag    17700
aggaggatgc ctgccattct ccactacctg tcaacattgt cctgaaggtt cttgttaatg    17760
cagtaagatc aaaatgttct acagacgaat tgataaaatg tatataccca gatggtgaaa    17820
tacactaact agcagcaggt aaaatgagag agctcatttt tttttttggg ggggagacga    17880
gtttcactct cacctaggct ggagtgaagt ggcgcgatct cagctcactg caacctccgc    17940
ctcccaggtt caagcaattc tcctgcttca ggctcccaag tagctgagac tgcaggtgca    18000
ctctgccaca cccagctact tttttgtat tttagtagaa acggggtttc accgtgttac     18060
ccaggctggt cttgaactcc tgagctcagg cagtccaccc acctcggcat cccaaagtgc    18120
taggattaca ggcacgagcc actgcaccca gccttttttc tttttttctt ttttttttga    18180
gacggagtct gtcgcccagg ctggagtgca gtggcacgat cttggctcac ttcagccttc    18240
gcctcccggg tccaagctat tctcctgcct cagcctccca agtagctggg attacaggca    18300
tgcgccacca tgcctggcta atttttttt gtattttgg tagagacggg ttcaccatgt      18360
tagccaggct ggtctcgaac ttctgaccct caggtgatct gcctgccttg gcttcccaaa    18420
gttctgagat tagaggcgtg agccactgcg cccggccttc aaaacatgtt taagtgaaaa    18480
aattataaaa catatttaat accttttatg ctgttacata aatttatagt aaaaaaatat    18540
ttttctatgc attcctttac ctttaaagat tagtcaaggt gatgaaaggg atctttgaca    18600
attttattca tgatctcttt gtcaaaaaga aatggaagat gtgtagttaa aaaaattaat    18660
caaaggtctg tactaaaagc tctgtagcta taaagatgat tgtgagagtt gcatttaata    18720
attgtgatgt tggccgctga cagctgaaga aaaatgctgt ttttgacaga gtgtcagtta    18780
aatccagacc tgaacataga ggtggaagtt tctttgcaga gagagaagac agggaggtca    18840
aggaaagtga ccccaagagg ggttcagatg acagccacag cacccccagg ccaacgtcca    18900
catgagcctt ccgcgccctg cacggctgct caacccgatt gtcccatctt ttggcaggcg    18960
cagatcaggc ctctataacc gccaggaatc acattcagct ggtgaaactg caggtggaag    19020
aggtgcacca gctctcccgg aaagcagaaa ccaagctggc agaagcacag atagaagagc    19080
tccgtcagaa aacacaggag gaaggggagg agcgggctga gtcggagcag gaggcctacc    19140
tgcgtgagga ttgagggcct gagcacactg ccctgtctcc ccactcagtg gggaaagcag    19200
gggcagatgc caccctgccc agggttggca tgactgtctg tgcaccgaga agaggcggca    19260
gatcctgccc tggccaatca ggcgagacgc ctttgtgagc tgtgagtgcc tcctgtggtc    19320
tcaggcttgc gctggacctg gttcttagcc cttgggcact gcaccctgtt taacatttca    19380
ccccactctg tacagctgct cttacccatt ttttttacct cacacccaaa gcattttgcc    19440
tacctgggtc agagagagga gtccttttg tcatgccctt aagttcagca actgtttaac     19500
ctgttttcag tcttatttac gtcgtcaaaa atgatttagt acttgttccc tctgttggga    19560
```

-continued

```
tgccagttgt ggcagggggga ggggaacctg tccagtttgt acgatttctt tgtatgtatt      19620
tctgatgtgt tctctgatct gcccccactg tcctgtgagg acagctgagg ccaaggagtg      19680
aaaaacctat tactactaag agaaggggtg cagagtgttt acctggtgct ctcaacagga      19740
cttaacatca acaggactta acacaggcct cttgttcctt cctttctttc cgtttctcta      19800
ttgtatccaa aggagaagag tgtaagattt tgtttgcatc tgaaagagaa aatgcgtctc      19860
tcctggggtc cta                                                         19873
```

<210> SEQ ID NO 2
<211> LENGTH: 239
<212> TYPE: PRT
<213> ORGANISM: Homo sapiens

<400> SEQUENCE: 2

```
Met Ala Ala Leu Lys Ser Trp Leu Ser Arg Ser Val Thr Ser Phe Phe
1               5                  10                  15

Arg Tyr Arg Gln Cys Leu Cys Val Pro Val Val Ala Asn Phe Lys Lys
            20                  25                  30

Arg Cys Phe Ser Glu Leu Ile Arg Pro Trp His Lys Thr Val Thr Ile
        35                  40                  45

Gly Phe Gly Val Thr Leu Cys Ala Val Pro Ile Ala Gln Lys Ser Glu
    50                  55                  60

Pro His Ser Leu Ser Ser Glu Ala Leu Met Arg Arg Ala Val Ser Leu
65                  70                  75                  80

Val Thr Asp Ser Thr Ser Thr Phe Leu Ser Gln Thr Thr Tyr Ala Leu
                85                  90                  95

Ile Glu Ala Ile Thr Glu Tyr Thr Lys Ala Val Tyr Thr Leu Thr Ser
            100                 105                 110

Leu Tyr Arg Gln Tyr Thr Ser Leu Leu Gly Lys Met Asn Ser Glu Glu
        115                 120                 125

Glu Asp Glu Val Trp Gln Val Ile Ile Gly Ala Arg Ala Glu Met Thr
    130                 135                 140

Ser Lys His Gln Glu Tyr Leu Lys Leu Glu Thr Thr Trp Met Thr Ala
145                 150                 155                 160

Val Gly Leu Ser Glu Met Ala Ala Glu Ala Ala Tyr Gln Thr Gly Ala
                165                 170                 175

Asp Gln Ala Ser Ile Thr Ala Arg Asn His Ile Gln Leu Val Lys Leu
            180                 185                 190

Gln Val Glu Glu Val His Gln Leu Ser Arg Lys Ala Glu Thr Lys Leu
        195                 200                 205

Ala Glu Ala Gln Ile Glu Glu Leu Arg Gln Lys Thr Gln Glu Glu Gly
    210                 215                 220

Glu Glu Arg Ala Glu Ser Glu Gln Glu Ala Tyr Leu Arg Glu Asp
225                 230                 235
```

<210> SEQ ID NO 3
<211> LENGTH: 2278
<212> TYPE: DNA
<213> ORGANISM: Homo sapiens

<400> SEQUENCE: 3

```
gagctcgggg accacgcgga ggttgtaatt ggtctctaga ccacacctag ttgttgagtg        60
ccgctgcttg aaaatctcag ttctgccgag atcgcagaat acacacaagc tacctttggg       120
caccagagca gacagaaccg cggagcttca gggtggaaga ttcgtggaaa ctttgccaag       180
```

-continued

```
gccaggacct cgtgtgttcc cgtccgcccc tctgggacgg cgccagcccg gcaggccgcc    240
gaccgtcctg gggctcccgc gcagcgcgat gccggcctcg tccaccgtcc acgtgctgca    300
gctgctgcgg gagctgctcg ccttcgtgct cctcagctac acggtgctca tcggggcgct    360
gctgctggcc ggctggacca cttacttcct ggtgctgaag tgacagcgcc gtcgccgcgc    420
ccggccccgc ctcccgcccg gcccgcctc ccgcccggcc cgcctccct aactcaccag     480 gaaattccct tcaagccctg gcccgaactg agtccccgcc cacccgccag cgtcacggcg    540
cccgactcag ctccgcgccg gacccacctc cgcgccctca ggccctgcat atgccccgcc    600
ccgcgcggaa gttccggcgg ttggttgcct tgcgcggccg ttacagcctt tgccctaagc    660
ctcgccccct ttcccctgc ctgcccaatc ccgactgctt ccttgggtgg gggcgtggct     720
atggggcgag cgctctcag gtggaggccg tgccccgctc cgcgctcacg aagctgcgtc     780
acttccggcg tgtgcgtctg gcgtccgcgc gctgcacaat ggcggctctg aagagttggc    840
tgtcgcgcag cgtaacttca ttcttcaggt acagacagtg tttgtgtgtt cctgttgtgg    900
ctaactttaa gaagcggtgt ttctcagaat tgataagacc atggcacaaa actgtgacga    960
ttggctttgg agtaaccctg tgtgcggttc ctattgcaca gaaatcagag cctcattccc   1020
ttagtagtga agcattgatg aggagagcag tgtctttggt aacagatagc acctctacct   1080
ttctctctca gaccacatat gcgttgattg aagctattac tgaatatact aaggctgttt   1140
ataccttaac ttctctttac cgacaatata caagtttact tgggaaaatg aattcagagg   1200
aggaagatga agtgtggcag gtgatcatag gagccagagc tgagatgact tcaaaacacc   1260
aagagtactt gaagctggaa accacttgga tgactgcagt tggtctttca gagatggcag   1320
cagaagctgc atatcaaact ggcgcagatc aggcctctat aaccgccagg aatcacattc   1380
agctggtgaa actgcaggtg gaagaggtgc accagctctc ccggaaagca gaaaccaagc   1440
tggcagaagc acagatagaa gagctccgtc agaaaacaca ggaggaaggg gaggagcggg   1500
ctgagtcgga gcaggaggcc tacctgcgtg aggattgagg gcctgagcac actgccctgt   1560
ctccccactc agtggggaaa gcaggggcag atgccaccct gcccagggtt ggcatgactg   1620
tctgtgcacc gagaagaggc ggcagatcct gccctggcca atcaggcgag acgcctttgt   1680
gagctgtgag tgcctcctgt ggtctcaggc ttgcgctgga cctggttctt agcccttggg   1740
cactgcaccc tgtttaacat ttcacccac tctgtacagc tgctcttacc catttttttt    1800
acctcacacc caaagcattt tgcctacctg ggtcagagag aggagtcctt tttgtcatgc   1860
ccttaagttc agcaactgtt taacctgttt tcagtcttat ttacgtcgtc aaaaatgatt   1920
tagtacttgt tccctctgtt gggatgccag ttgtggcagg gggagggaa cctgtccagt    1980 ttgtacgatt tctttgtatg tatttctgat gtgttctctg atctgccccc actgtcctgt   2040
gaggacagct gaggccaagg agtgaaaaac ctattactac taagagaagg ggtgcagagt   2100
gtttacctgg tgctctcaac aggacttaac atcaacagga cttaacacag gcctcttgtt   2160
ccttcctttc tttccgtttc tctattgtat ccaaaggaga agagtgtaag attttgtttg   2220
catctgaaag agaaaatgcg tctctcctgg ggtcctaaaa aaaaaaaaaa aaaaaaaa    2278
```

<210> SEQ ID NO 4
<211> LENGTH: 195
<212> TYPE: PRT
<213> ORGANISM: Homo sapiens
<400> SEQUENCE: 4

```
Met Ala Ala Leu Lys Ser Trp Leu Ser Arg Ser Val Thr Ser Phe
1               5                   10                  15

Arg Tyr Arg Gln Cys Leu Cys Val Pro Val Val Ala Asn Phe Lys Lys
            20                  25                  30

Arg Cys Phe Ser Glu Leu Ile Arg Pro Trp His Lys Thr Val Thr Ile
                35                  40                  45

Gly Phe Gly Val Thr Leu Cys Ala Val Pro Ile Ala Gln Ala Val Tyr
        50                  55                  60

Thr Leu Thr Ser Leu Tyr Arg Gln Tyr Thr Ser Leu Leu Gly Lys Met
65                  70                  75                  80

Asn Ser Glu Glu Glu Asp Glu Val Trp Gln Val Ile Ile Gly Ala Arg
                85                  90                  95

Ala Glu Met Thr Ser Lys His Gln Glu Tyr Leu Lys Leu Glu Thr Thr
                100                 105                 110

Trp Met Thr Ala Val Gly Leu Ser Glu Met Ala Ala Glu Ala Ala Tyr
            115                 120                 125

Gln Thr Gly Ala Asp Gln Ala Ser Ile Thr Ala Arg Asn His Ile Gln
            130                 135                 140

Leu Val Lys Leu Gln Val Glu Val His Gln Leu Ser Arg Lys Ala
145                 150                 155                 160

Glu Thr Lys Leu Ala Glu Ala Gln Ile Glu Glu Leu Arg Gln Lys Thr
                165                 170                 175

Gln Glu Glu Gly Glu Glu Arg Ala Glu Ser Glu Gln Ala Tyr Leu
            180                 185                 190

Arg Glu Asp
        195

<210> SEQ ID NO 5
<211> LENGTH: 1882
<212> TYPE: DNA
<213> ORGANISM: Homo sapiens

<400> SEQUENCE: 5
cgcgatgccg gcctcgtcca ccgtccacgt gctgcagctg ctgcgggagc tgctcgcctt     60
cgtgctcctc agctacacgg tgctcatcgg ggcgctgctg ctggccggct ggaccactta    120
cttcctggtg ctgaagtgac agcgccgtcg ccgcgcccgg ccccgcctcc cgcccggccc    180
cgcctcccgc ccggccccgc ctccctaact caccaggaaa ttcccttcaa gccctggccc    240
gaactgagtc ccgcccaccc gccagcgtca acggcgcccg actcagctcc gcgccggacc    300
cacctccgcg ccctcaggcc ctgcatatgc cccgcccgc gcggaagttc cggcggttgg     360
ttgccttgcg cggccgttac agcctttgcc ctaagcctcg ccccctttcc ccctgcctgc    420
ccaatcccga ctgcttcctt gggtgggggc gtggctatgg ggcgaggcgc tctcaggtgg    480
aggccgtgcc ccgctccgcg ctcacgaagc tgcgtcactt ccggcgtgtg cgtctggcgt    540
ccgcgcgctg cacaatggcg gctctgaaga gttggctgtc gcgcagcgta acttcattct    600
tcaggtacag acagtgtttg tgtgttcctg ttgtggctaa ctttaagaag cggtgtttct    660
cagaattgat aagaccatgg cacaaaactg tgacgattgg cttttggagta accctgtgtg    720 cggttcctat tgcacaggct gtttatacct taacttctct ttaccgacaa tatacaagtt    780
tacttgggaa aatgaattca gaggaggaag atgaagtgtg gcaggtgatc ataggagcca    840
gagctgagat gacttcaaaa caccaagagt acttgaagct ggaaaccact tggatgactg    900
cagttggtct ttcagagatg gcagcagaag ctgcatatca aactggcgca gatcaggcct    960
```

```
ctataaccgc caggaatcac attcagctgg tgaaactgca ggtggaagag gtgcaccagc    1020
tctcccggaa agcagaaacc aagctggcag aagcacagat agaagagctc cgtcagaaaa    1080
cacaggagga aggggaggag cgggctgagt cggagcagga ggcctacctg cgtgaggatt    1140
gagggcctga gcacactgcc ctgtctcccc actcagtggg gaaagcaggg gcagatgcca    1200
ccctgcccag ggttggcatg actgtctgtg caccgagaag aggcggcaga tcctgccctg    1260
gccaatcagg cgagacgcct ttgtgagctg tgagtgcctc ctgtggtctc aggcttgcgc    1320
tggacctggt tcttagccct tgggcactgc accctgttta acatttcacc ccactctgta    1380
cagctgctct tacccatttt ttttacctca cacccaaagc attttgccta cctgggtcag    1440
agagaggagt cctttttgtc atgcccttaa gttcagcaac tgtttaacct gttttcagtc    1500
ttatttacgt cgtcaaaaat gatttagtac ttgttccctc tgttgggatg ccagttgtgg    1560 caggggagg ggaacctgtc cagtttgtac gatttctttg tatgtatttc tgatgtgttc    1620
tctgatctgc ccccactgtc ctgtgaggac agctgaggcc aaggagtgaa aaacctatta    1680
ctactaagag aaggggtgca gagtgtttac ctggtgctct caacaggact taacatcaac    1740
aggacttaac acaggcctct tgttccttcc tttctttccg tttctctatt gtatccaaag    1800
gagaagagtg taagattttg tttgcatctg aaagagaaaa tgcgtctctc ctggggtcct    1860
aaaaaaaaaa aaaaaaaaaa aa                                             1882
```

<210> SEQ ID NO 6
<211> LENGTH: 186
<212> TYPE: PRT
<213> ORGANISM: Homo sapiens

<400> SEQUENCE: 6

Met Lys Ser Asp Phe Tyr Phe Gln Lys Ser Glu Pro His Ser Leu Ser
1               5                   10                  15

Ser Glu Ala Leu Met Arg Arg Ala Val Ser Leu Val Thr Asp Ser Thr
            20                  25                  30

Ser Thr Phe Leu Ser Gln Thr Thr Tyr Ala Leu Ile Glu Ala Ile Thr
        35                  40                  45

Glu Tyr Thr Lys Ala Val Tyr Thr Leu Thr Ser Leu Tyr Arg Gln Tyr
    50                  55                  60

Thr Ser Leu Leu Gly Lys Met Asn Ser Glu Glu Asp Glu Val Trp
65                  70                  75                  80

Gln Val Ile Ile Gly Ala Arg Ala Glu Met Thr Ser Lys His Gln Glu
                85                  90                  95

Tyr Leu Lys Leu Glu Thr Thr Trp Met Thr Ala Val Gly Leu Ser Glu
            100                 105                 110

Met Ala Ala Glu Ala Ala Tyr Gln Thr Gly Ala Asp Gln Ala Ser Ile
        115                 120                 125

Thr Ala Arg Asn His Ile Gln Leu Val Lys Leu Gln Val Glu Glu Val
    130                 135                 140

His Gln Leu Ser Arg Lys Ala Glu Thr Lys Leu Ala Glu Ala Gln Ile
145                 150                 155                 160

Glu Glu Leu Arg Gln Lys Thr Gln Glu Glu Gly Glu Glu Arg Ala Glu
                165                 170                 175

Ser Glu Gln Glu Ala Tyr Leu Arg Glu Asp
            180                 185

<210> SEQ ID NO 7
<211> LENGTH: 2483

<212> TYPE: DNA
<213> ORGANISM: Homo sapiens

<400> SEQUENCE: 7

```
agctgggtcg cggcgtctcg ctccggtcgg gaggactgag gacagccccg cctccgcccc      60
ctgggtcaag cccggcttcc tttttcagttc gtccatcttc tagaaacgag tccccgagac    120
cccgggctgc cttcttgggg ctgctccgcc tcctgaccag ccctcgtcag ccactcgaag     180
tccctgagga gacgtggaga ggaggaggga cacggcatgg gggagtccg ggaagggaga      240
cgagcgtctg aagacgtcct cccgagggca gaaggggccg ggggagctgg cgcagggctc    300
tctacctagc gctgcaggct cctgggcgat tgtagcggga ccgtcacaca caactggcac    360
ccaggccagg ggtccagagc taaattctgc ctgcaggagc ggttattgtg gcatccgttt    420
ctaaaaagtt taaaggcaac attttatttt attttaattt ttttgagaca agatctgcct    480
ctgtcgccca ggctggagtg cagtggcgag atctcagctc actgcaacct gtgcctcccg    540
gcttcaagcg attctcagcc tcagcctccc gagtagctgg gattgcaggc gcccgccacc    600
acgcccggct aattttttttt tttcttttttg ttttgtttga gactcagtct cgctctgttg   660
cccaggctga agtgcagtgg ggcgctctcg gctcactgca acctctgcct cccaggttca    720
agcgattctc ctgcctcagc ctcccgagta gctgggatta caggagcgtg ccaccactcc    780
gggctaattt ttgtgtttta agtagagatg gggtttcacc atgttggtca ggcagatttc    840
gaattcctga cctcaagtga tccacccgcc tcggccttta tttacttatt ttttttaat    900
agacacgggg tcatgttgcc agccatgttg cccaggctgg tcgtgaactc ctgggctcaa    960
gtgatcctcc cgccttgccc ttggccttcc aagtgctagg attacaggcg tgagccacca  1020
acacctgcc tgaggcaaca ttttaaactt ggtgtatgtt gaaaatttca aaacccctca   1080
gctgtcctgc atcctcattt aggttcctgc ttggctcgag tttgagttta cagcccctgc  1140
aagtaaatcc aagagcctgt tacagattgg cggtcgtgcc ttatgaaatc tgacttctac  1200
ttccagaaat cagagcctca ttcccttagt agtgaagcat tgatgaggag agcagtgtct  1260
ttggtaacag atagcacctc tacctttctc tctcagacca catatgcgtt gattgaagct  1320
attactgaat atactaaggc tgtttatacc ttaacttctc tttaccgaca atatacaagt  1380
ttacttggga aaatgaattc agaggaggaa gatgaagtgt ggcaggtgat cataggagcc  1440
agagctgaga tgacttcaaa acaccaagag tacttgaagc tggaaccac ttggatgact    1500
gcagttggtc tttcagagat ggcagcagaa gctgcatatc aaactggcgc agatcaggcc  1560
tctataaccg ccaggaatca cattcagctg gtgaaactgc aggtggaaga ggtgcaccag  1620
ctctcccgga agcagaaac caagctggca gaagcacaga tagaagagct ccgtcagaaa   1680
acacaggagg aaggggagga gcgggctgag tcggagcagg aggcctacct gcgtgaggat  1740
tgagggcctg agcacactgc cctgtctccc cactcagtgg ggaaagcagg ggcagatgcc  1800
accctgccca gggttggcat gactgtctgt gcaccgagaa gaggcggcag atcctgccct  1860
ggccaatcag gcgagacgcc tttgtgagct gtgagtgcct cctgtggtct caggcttgcg  1920
ctggacctgg ttcttagccc ttgggcactg caccctgttt aacatttcac cccactctgt  1980
acagctgctc ttacccattt ttttttacctc acacccaaag cattttgcct acctgggtca  2040
gagagaggag tccttttttgt catgcccttta agttcagcaa ctgtttaacc tgttttcagt  2100
cttatttacg tcgtcaaaaa tgatttagta cttgttccct ctgttgggat gccagttgtg  2160
gcaggggggag gggaacctgt ccagtttgta cgatttcttt gtatgtattt ctgatgtgtt  2220
```

| | | |
|---|---|---|
| ctctgatctg cccccactgt cctgtgagga cagctgaggc caaggagtga aaaacctatt | 2280 | |
| actactaaga aagggggtgc agagtgttta cctggtgctc tcaacaggac ttaacatcaa | 2340 | |
| caggacttaa cacaggcctc ttgttccttc ctttctttcc gtttctctat tgtatccaaa | 2400 | |
| ggagaagagt gtaagatttt gtttgcatct gaaagagaaa atgcgtctct cctggggtcc | 2460 | |
| taaaaaaaaa aaaaaaaaaa aaa | 2483 | |

<210> SEQ ID NO 8
<211> LENGTH: 142
<212> TYPE: PRT
<213> ORGANISM: Homo sapiens

<400> SEQUENCE: 8

Met Lys Ser Asp Phe Tyr Phe Gln Ala Val Tyr Thr Leu Thr Ser Leu
1               5                   10                  15

Tyr Arg Gln Tyr Thr Ser Leu Leu Gly Lys Met Asn Ser Glu Glu Glu
                20                  25                  30

Asp Glu Val Trp Gln Val Ile Ile Gly Ala Arg Ala Glu Met Thr Ser
            35                  40                  45

Lys His Gln Glu Tyr Leu Lys Leu Glu Thr Thr Trp Met Thr Ala Val
        50                  55                  60

Gly Leu Ser Glu Met Ala Ala Glu Ala Ala Tyr Gln Thr Gly Ala Asp
65                  70                  75                  80

Gln Ala Ser Ile Thr Ala Arg Asn His Ile Gln Leu Val Lys Leu Gln
                85                  90                  95

Val Glu Glu Val His Gln Leu Ser Arg Lys Ala Glu Thr Lys Leu Ala
                100                 105                 110

Glu Ala Gln Ile Glu Glu Leu Arg Gln Lys Thr Gln Glu Glu Gly Glu
            115                 120                 125

Glu Arg Ala Glu Ser Glu Gln Glu Ala Tyr Leu Arg Glu Asp
        130                 135                 140

<210> SEQ ID NO 9
<211> LENGTH: 1853
<212> TYPE: DNA
<213> ORGANISM: Homo sapiens

<400> SEQUENCE: 9

| | | |
|---|---|---|
| cgcgatgccg gcctcgtcca ccgtccacgt gctgcagctg ctgcgggagc tgctcgcctt | 60 | |
| cgtgctcctc agctacacgg tgctcatcgg ggcgctgctg ctggccggct ggaccactta | 120 | |
| cttcctggtg ctgaagtgac agcgccgtcg ccgcgcccgg ccccgcctcc cgcccggccc | 180 | |
| cgcctcccgc ccggccccgc ctccctaact caccaggaaa ttcccttcaa gccctggccc | 240 | |
| gaactgagtc cccgcccacc cgccagcgtc acggcgcccg actcagctcc cgccggacc | 300 | |
| cacctccgcg ccctcaggcc ctgcatatgc cccgccccgc gcggaagttc cggcggttgg | 360 | |
| ttgccttgcg cggccgttac agcctttgcc ctaagcctcg ccccctttcc ccctgcctgc | 420 | |
| ccaatcccga ctgcttcctt gggtgggggc gtggctatgg ggcgaggcgc tctcaggtgg | 480 | |
| aggccgtgcc ccgctccgcg ctcacgaagc tgcgtcactt ccggcgtgtg cgtctggcgt | 540 | |
| ccgcgcgctg cacaatggcg gctctgaaga gttggctgtc gcgcagcgta acttcattct | 600 | |
| tcaggttcct gcttggctcg agtttgagtt tacagcccct gcaagtaaat ccaagagcct | 660 | |
| gttacagatt ggcggtcgtg ccttatgaaa tctgacttct acttccaggc tgtttatacc | 720 | |
| ttaacttctc tttaccgaca atatacaagt ttacttggga aaatgaattc agaggaggaa | 780 | |

-continued

```
gatgaagtgt ggcaggtgat cataggagcc agagctgaga tgacttcaaa acaccaagag      840
tacttgaagc tggaaaccac ttggatgact gcagttggtc tttcagagat ggcagcagaa      900
gctgcatatc aaactggcgc agatcaggcc tctataaccg ccaggaatca cattcagctg      960
gtgaaactgc aggtggaaga ggtgcaccag ctctcccgga aagcagaaac caagctggca     1020
gaagcacaga tagaagagct ccgtcagaaa acacaggagg aaggggagga gcgggctgag     1080
tcggagcagg aggcctacct gcgtgaggat tgagggcctg agcacactgc cctgtctccc     1140
cactcagtgg ggaaagcagg ggcagatgcc accctgccca gggttggcat gactgtctgt     1200
gcaccgagaa gaggcggcag atcctgccct ggccaatcag gcgagacgcc tttgtgagct     1260
gtgagtgcct cctgtggtct caggcttgcg ctggacctgg ttcttagccc ttgggcactg     1320
caccctgttt aacatttcac cccactctgt acagctgctc ttacccattt tttttacctc     1380
acacccaaag cattttgcct acctgggtca gagagaggag tccttttgt catgcccta      1440 agttcagcaa ctgtttaacc tgttttcagt cttatttacg tcgtcaaaaa tgatttagta     1500
cttgttccct ctgttgggat gccagttgtg caggggag gggaacctgt ccagtttgta     1560
cgatttcttt gtatgtattt ctgatgtgtt ctctgatctg ccccactgt cctgtgagga     1620 cagctgaggc caaggagtga aaaacctatt actactaaga gaaggggtgc agagtgttta     1680
cctggtgctc tcaacaggac ttaacatcaa caggacttaa cacaggcctc ttgttccttc     1740 cttctttcc gttctctat tgtatccaaa ggagaagagt gtaagatttt gtttgcatct     1800
gaaagagaaa atgcgtctct cctggggtcc taaaaaaaa aaaaaaaaaa aaa            1853
```

<210> SEQ ID NO 10
<211> LENGTH: 166
<212> TYPE: PRT
<213> ORGANISM: Homo sapiens

<400> SEQUENCE: 10

```
Met Arg Arg Ala Val Ser Leu Val Thr Asp Ser Thr Ser Thr Phe Leu
1               5                   10                  15

Ser Gln Thr Thr Tyr Ala Leu Ile Glu Ala Ile Thr Glu Tyr Thr Lys
            20                  25                  30

Ala Val Tyr Thr Leu Thr Ser Leu Tyr Arg Gln Tyr Thr Ser Leu Leu
        35                  40                  45

Gly Lys Met Asn Ser Glu Glu Glu Asp Glu Val Trp Gln Val Ile Ile
    50                  55                  60

Gly Ala Arg Ala Glu Met Thr Ser Lys His Gln Glu Tyr Leu Lys Leu
65                  70                  75                  80

Glu Thr Thr Trp Met Thr Ala Val Gly Leu Ser Glu Met Ala Ala Glu
                85                  90                  95

Ala Ala Tyr Gln Thr Gly Ala Asp Gln Ala Ser Ile Thr Ala Arg Asn
            100                 105                 110

His Ile Gln Leu Val Lys Leu Gln Val Glu Glu Val His Gln Leu Ser
        115                 120                 125

Arg Lys Ala Glu Thr Lys Leu Ala Glu Ala Gln Ile Glu Glu Leu Arg
    130                 135                 140

Gln Lys Thr Gln Glu Glu Gly Glu Glu Arg Ala Glu Ser Glu Gln Glu
145                 150                 155                 160

Ala Tyr Leu Arg Glu Asp
                165
```

<210> SEQ ID NO 11

<211> LENGTH: 1881
<212> TYPE: DNA
<213> ORGANISM: Homo sapiens

<400> SEQUENCE: 11

| | | | | | |
|---|---|---|---|---|---|
| cgcgatgccg | gcctcgtcca | ccgtccacgt | gctgcagctg | ctgcgggagc | tgctcgcctt | 60 |
| cgtgctcctc | agctacacgg | tgctcatcgg | ggcgctgctg | ctggccggct | ggaccactta | 120 |
| cttcctggtg | ctgaagtgac | agcgccgtcg | ccgcgcccgg | cccgcctcc | cgcccggccc | 180 |
| cgcctcccgc | ccggccccgc | ctccctaact | caccaggaaa | ttcccttcaa | gccctggccc | 240 |
| gaactgagtc | cccgcccacc | cgccagcgtc | acggcgcccg | actcagctcc | gcgcggacc | 300 |
| cacctccgcg | ccctcaggcc | ctgcatatgc | cccgccccgc | gcggaagttc | cggcggttgg | 360 |
| ttgccttgcg | cggccgttac | agcctttgcc | ctaagcctcg | cccccttcc | ccctgcctgc | 420 |
| ccaatcccga | ctgcttcctt | gggtggggc | gtggctatgg | ggcgaggcgc | tctcaggtgg | 480 |
| aggccgtgcc | ccgctccgcg | ctcacgaagc | tgcgtcactt | ccggcgtgtg | cgtctggcgt | 540 |
| ccgcgcgctg | cacaatggcg | gctctgaaga | gttggctgtc | gcgcagcgta | acttcattct | 600 |
| tcagaaatca | gagcctcatt | cccttagtag | tgaagcattg | atgaggagag | cagtgtcttt | 660 |
| ggtaacagat | agcacctcta | cctttctctc | tcagaccaca | tatgcgttga | ttgaagctat | 720 |
| tactgaatat | actaaggctg | tttataccct | aacttctctt | taccgacaat | atacaagttt | 780 |
| acttgggaaa | atgaattcag | aggaggaaga | tgaagtgtgg | caggtgatca | taggagccag | 840 |
| agctgagatg | acttcaaaac | accaagagta | cttgaagctg | gaaaccactt | ggatgactgc | 900 |
| agttggtctt | tcagagatgg | cagcagaagc | tgcatatcaa | actggcgcag | atcaggcctc | 960 |
| tataaccgcc | aggaatcaca | ttcagctggt | gaaactgcag | gtggaagagg | tgcaccagct | 1020 |
| ctcccggaaa | gcagaaacca | agctggcaga | agcacagata | gaagagctcc | gtcagaaaac | 1080 |
| acaggaggaa | ggggaggagc | gggctgagtc | ggagcaggag | gcctacctgc | gtgaggattg | 1140 |
| agggcctgag | cacactgccc | tgtctcccca | ctcagtgggg | aaagcagggg | cagatgccac | 1200 |
| cctgcccagg | gttggcatga | ctgtctgtgc | accgagaaga | ggcggcagat | cctgccctgg | 1260 |
| ccaatcaggc | gagacgcctt | tgtgagctgt | gagtgcctcc | tgtggtctca | ggcttgcgct | 1320 |
| ggacctggtt | cttagcccttt | gggcactgca | ccctgtttaa | catttcaccc | cactctgtac | 1380 |
| agctgctctt | acccattttt | tttacctcac | acccaaagca | ttttgcctac | ctgggtcaga | 1440 |
| gagaggagtc | cttttttgtca | tgcccttaag | ttcagcaact | gtttaacctg | ttttcagtct | 1500 |
| tatttacgtc | gtcaaaaatg | atttagtact | tgttccctct | gttgggatgc | cagttgtggc | 1560 |
| aggggagg | gaacctgtcc | agtttgtacg | atttcttttgt | atgtatttct | gatgtgttct | 1620 |
| ctgatctgcc | cccactgtcc | tgtgaggaca | gctgaggcca | aggagtgaaa | aacctattac | 1680 |
| tactaagaga | aggggtgcag | agtgtttacc | tggtgctctc | aacaggactt | aacatcaaca | 1740 |
| ggacttaaca | caggcctctt | gttccttcct | ttctttccgt | ttctctattg | tatccaaagg | 1800 |
| agaagagtgt | aagattttgt | ttgcatctga | aagagaaaat | gcgtctctcc | tggggtccta | 1860 |
| aaaaaaaaa | aaaaaaaaa | a | | | | 1881 |

<210> SEQ ID NO 12
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 12
aagcgguguu ucucagaauu g                                              21

<210> SEQ ID NO 13
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 13
aacaauucug agaaacccgc                                                20

<210> SEQ ID NO 14
<211> LENGTH: 19
<212> TYPE: RNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 14
gcagaucagg ccucuauaa                                                 19

<210> SEQ ID NO 15
<211> LENGTH: 19
<212> TYPE: RNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 15
uuauagaggc cugaucugc                                                 19

<210> SEQ ID NO 16
<211> LENGTH: 19
<212> TYPE: RNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 16
cccggaaagc agaaaccaa                                                 19

<210> SEQ ID NO 17
<211> LENGTH: 19
<212> TYPE: RNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 17
uugguuucug cuuuccggg 19

<210> SEQ ID NO 18
<211> LENGTH: 19
<212> TYPE: RNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 18
gcuggcagaa gcacagaua 19

<210> SEQ ID NO 19
<211> LENGTH: 19
<212> TYPE: RNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 19
uaucugugcu ucugccagc 19

<210> SEQ ID NO 20
<211> LENGTH: 23
<212> TYPE: DNA
<213> ORGANISM: Artificial sequence
<220> FEATURE:
<223> OTHER INFORMATION: siRNA

<400> SEQUENCE: 20
aagcgguguu ucucagaauu gtt 23

<210> SEQ ID NO 21
<211> LENGTH: 22
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 21
aacaauucug agaaacccgc tt 22

<210> SEQ ID NO 22
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 22
gcagaucagg ccucuauaat t 21

<210> SEQ ID NO 23
<211> LENGTH: 21
<212> TYPE: DNA
<213> ORGANISM: Artificial sequence

```
<220> FEATURE:
<223> OTHER INFORMATION: siRNA
<220> FEATURE:
<221> NAME/KEY: misc_feature
<223> OTHER INFORMATION: Synthetic

<400> SEQUENCE: 23
uuauagaggc cugaucugct t                                              21

<210> SEQ ID NO 24
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 24
cccggaaagc agaaaccaat t                                              21

<210> SEQ ID NO 25
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 25
uugguuucug cuuccgggt t                                               21

<210> SEQ ID NO 26
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 26
gcuggcagaa gcacagauat t                                              21

<210> SEQ ID NO 27
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 27
uaucugugcu ucugccagct t                                              21

<210> SEQ ID NO 28
<211> LENGTH: 23
<212> TYPE: DNA
<213> ORGANISM: Artificial sequence
<220> FEATURE:
<223> OTHER INFORMATION: siRNA
<220> FEATURE:
<221> NAME/KEY: misc_feature
```

-continued

<223> OTHER INFORMATION: Synthetic
<220> FEATURE:
<221> NAME/KEY: modified_base
<222> LOCATION: (5)..(5)
<223> OTHER INFORMATION: 2'-O-methyl-modified guanine
<220> FEATURE:
<221> NAME/KEY: modified_base
<222> LOCATION: (10)..(10)
<223> OTHER INFORMATION: 2'-O-methyl-modified uridine
<220> FEATURE:
<221> NAME/KEY: modified_base
<222> LOCATION: (16)..(16)
<223> OTHER INFORMATION: 2'-O-methyl-modified guanine
<220> FEATURE:
<221> NAME/KEY: modified_base
<222> LOCATION: (21)..(21)
<223> OTHER INFORMATION: 2'-O-methyl-modified guanine

<400> SEQUENCE: 28
aagcgguguu ucucagaauu gtt                                              23

<210> SEQ ID NO 29
<211> LENGTH: 22
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (6)..(6)
<223> OTHER INFORMATION: 2'-O-methyl-modified uridine
<220> FEATURE:
<221> NAME/KEY: modified_base
<222> LOCATION: (12)..(12)
<223> OTHER INFORMATION: 2'-O-methyl-modified guanine
<220> FEATURE:
<221> NAME/KEY: modified_base
<222> LOCATION: (19)..(19)
<223> OTHER INFORMATION: 2'-O-methyl-modified guanine

<400> SEQUENCE: 29
aacaauucug agaaacccgc tt                                               22

<210> SEQ ID NO 30
<211> LENGTH: 23
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (6)..(6)
<223> OTHER INFORMATION: 2'-O-methyl-modified guanine
<220> FEATURE:
<221> NAME/KEY: modified_base
<222> LOCATION: (9)..(9)
<223> OTHER INFORMATION: 2'-O-methyl-modified uridine
<220> FEATURE:
<221> NAME/KEY: modified_base
<222> LOCATION: (21)..(21)
<223> OTHER INFORMATION: 2'-O-methyl-modified guanine

<400> SEQUENCE: 30
aagcgguguu ucucagaauu gtt                                              23

<210> SEQ ID NO 31
<211> LENGTH: 22

```
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (7)..(7)
<223> OTHER INFORMATION: 2'-O-methyl-modified uridine
<220> FEATURE:
<221> NAME/KEY: modified_base
<222> LOCATION: (12)..(12)
<223> OTHER INFORMATION: 2'-O-methyl-modified guanine

<400> SEQUENCE: 31
aacaauucug agaaacccgc tt                                              22

<210> SEQ ID NO 32
<211> LENGTH: 23
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (3)..(3)
<223> OTHER INFORMATION: 2'-O-methyl-modified guanine
<220> FEATURE:
<221> NAME/KEY: modified_base
<222> LOCATION: (7)..(7)
<223> OTHER INFORMATION: 2'-O-methyl-modified uridine
<220> FEATURE:
<221> NAME/KEY: modified_base
<222> LOCATION: (11)..(11)
<223> OTHER INFORMATION: 2'-O-methyl-modified uridine
<220> FEATURE:
<221> NAME/KEY: modified_base
<222> LOCATION: (16)..(16)
<223> OTHER INFORMATION: 2'-O-methyl-modified guanine

<400> SEQUENCE: 32
aagcgguguu ucucagaatt gtt                                             23

<210> SEQ ID NO 33
<211> LENGTH: 22
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (6)..(6)
<223> OTHER INFORMATION: 2'-O-methyl-modified uridine
<220> FEATURE:
<221> NAME/KEY: modified_base
<222> LOCATION: (10)..(10)
<223> OTHER INFORMATION: 2'-O-methyl-modified guanine
<220> FEATURE:
<221> NAME/KEY: modified_base
<222> LOCATION: (19)..(19)
<223> OTHER INFORMATION: 2'-O-methyl-modified guanine

<400> SEQUENCE: 33
aacaauucug agaaacccgc tt                                              22
```

```
<210> SEQ ID NO 34
<211> LENGTH: 23
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (3)..(3)
<223> OTHER INFORMATION: 2'-O-methyl-modified guanine
<220> FEATURE:
<221> NAME/KEY: modified_base
<222> LOCATION: (6)..(6)
<223> OTHER INFORMATION: 2'-O-methyl-modified guanine
<220> FEATURE:
<221> NAME/KEY: modified_base
<222> LOCATION: (11)..(11)
<223> OTHER INFORMATION: 2'-O-methyl-modified uridine
<220> FEATURE:
<221> NAME/KEY: modified_base
<222> LOCATION: (21)..(21)
<223> OTHER INFORMATION: 2'-O-methyl-modified guanine

<400> SEQUENCE: 34
aagcgguguu ucucagaatt gtt                                          23

<210> SEQ ID NO 35
<211> LENGTH: 22
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (6)..(6)
<223> OTHER INFORMATION: 2'-O-methyl-modified uridine
<220> FEATURE:
<221> NAME/KEY: modified_base
<222> LOCATION: (19)..(19)
<223> OTHER INFORMATION: 2'-O-methyl-modified guanine

<400> SEQUENCE: 35
aacaauucug agaaacccgc tt                                           22

<210> SEQ ID NO 36
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (4)..(4)
<223> OTHER INFORMATION: 2'-O-methyl-modified guanine
<220> FEATURE:
<221> NAME/KEY: modified_base
<222> LOCATION: (9)..(9)
<223> OTHER INFORMATION: 2'-O-methyl-modified guanine
<220> FEATURE:
<221> NAME/KEY: modified_base
<222> LOCATION: (15)..(15)
<223> OTHER INFORMATION: 2'-O-methyl-modified uridine

<400> SEQUENCE: 36
gcagaucagg ccucuauaat t                                            21
```

<210> SEQ ID NO 37
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (4)..(4)
<223> OTHER INFORMATION: 2'-O-methyl-modified uridine
<220> FEATURE:
<221> NAME/KEY: modified_base
<222> LOCATION: (9)..(9)
<223> OTHER INFORMATION: 2'-O-methyl-modified guanine
<220> FEATURE:
<221> NAME/KEY: modified_base
<222> LOCATION: (15)..(15)
<223> OTHER INFORMATION: 2'-O-methyl-modified uridine
<220> FEATURE:
<221> NAME/KEY: modified_base
<222> LOCATION: (18)..(18)
<223> OTHER INFORMATION: 2'-O-methyl-modified guanine

<400> SEQUENCE: 37
uuauagaggc cugaucugct t                                              21

<210> SEQ ID NO 38
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (4)..(4)
<223> OTHER INFORMATION: 2'-O-methyl-modified guanine
<220> FEATURE:
<221> NAME/KEY: modified_base
<222> LOCATION: (9)..(9)
<223> OTHER INFORMATION: 2'-O-methyl-modified guanine
<220> FEATURE:
<221> NAME/KEY: modified_base
<222> LOCATION: (13)..(13)
<223> OTHER INFORMATION: 2'-O-methyl-modified uridine
<220> FEATURE:
<221> NAME/KEY: modified_base
<222> LOCATION: (17)..(17)
<223> OTHER INFORMATION: 2'-O-methyl-modified uridine

<400> SEQUENCE: 38
gcagaucagg ccucuauaat t                                              21

<210> SEQ ID NO 39
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (6)..(6)
<223> OTHER INFORMATION: 2'-O-methyl-modified guanine
<220> FEATURE:
<221> NAME/KEY: modified_base -continued
<222> LOCATION: (12)..(12)
<223> OTHER INFORMATION: 2'-O-methyl-modified uridine
<220> FEATURE:
<221> NAME/KEY: modified_base
<222> LOCATION: (18)..(18)
<223> OTHER INFORMATION: 2'-O-methyl-modified guanine

<400> SEQUENCE: 39
uuauagaggc cugaucugct t                                         21

<210> SEQ ID NO 40
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (6)..(6)
<223> OTHER INFORMATION: 2'-O-methyl-modified uridine
<220> FEATURE:
<221> NAME/KEY: modified_base
<222> LOCATION: (10)..(10)
<223> OTHER INFORMATION: 2'-O-methyl-modified guanine
<220> FEATURE:
<221> NAME/KEY: modified_base
<222> LOCATION: (15)..(15)
<223> OTHER INFORMATION: 2'-O-methyl-modified uridine

<400> SEQUENCE: 40
gcagaucagg ccucuauaat t                                         21

<210> SEQ ID NO 41
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (2)..(2)
<223> OTHER INFORMATION: 2'-O-methyl-modified uridine
<220> FEATURE:
<221> NAME/KEY: modified_base
<222> LOCATION: (9)..(9)
<223> OTHER INFORMATION: 2'-O-methyl-modified guanine
<220> FEATURE:
<221> NAME/KEY: modified_base
<222> LOCATION: (17)..(17)
<223> OTHER INFORMATION: 2'-O-methyl-modified uridine

<400> SEQUENCE: 41
uuauagaggc cugaucugct t                                         21

<210> SEQ ID NO 42
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: modified_base
<222> LOCATION: (4)..(4)
<223> OTHER INFORMATION: 2'-O-methyl-modified guanine

```
<220> FEATURE:
<221> NAME/KEY: modified_base
<222> LOCATION: (13)..(13)
<223> OTHER INFORMATION: 2'-O-methyl-modified uridine
<220> FEATURE:
<221> NAME/KEY: modified_base
<222> LOCATION: (17)..(17)
<223> OTHER INFORMATION: 2'-O-methyl-modified uridine

<400> SEQUENCE: 42
gcagaucagg ccucuauaat t                                              21

<210> SEQ ID NO 43
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic
<220> FEATURE:
<221> NAME/KEY: misc_feature
<223> OTHER INFORMATION: Synthetic
<220> FEATURE:
<221> NAME/KEY: modified_base
<222> LOCATION: (8)..(8)
<223> OTHER INFORMATION: 2'-O-methyl-modified guanine
<220> FEATURE:
<221> NAME/KEY: modified_base
<222> LOCATION: (13)..(13)
<223> OTHER INFORMATION: 2'-O-methyl-modified guanine
<220> FEATURE:
<221> NAME/KEY: modified_base
<222> LOCATION: (18)..(18)
<223> OTHER INFORMATION: 2'-O-methyl-modified guanine

<400> SEQUENCE: 43
uuauagaggc cugaucugct t                                              21

<210> SEQ ID NO 44
<211> LENGTH: 19
<212> TYPE: RNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 44
gcaaacaucc cagagguau                                                 19

<210> SEQ ID NO 45
<211> LENGTH: 19
<212> TYPE: RNA
<213> ORGANISM: Artificial sequence
<220> FEATURE:
<223> OTHER INFORMATION: siRNA
<220> FEATURE:
<221> NAME/KEY: misc_feature
<223> OTHER INFORMATION: Synthetic

<400> SEQUENCE: 45
auaccucugg gauguuugc                                                 19

<210> SEQ ID NO 46
<211> LENGTH: 24
<212> TYPE: PRT
<213> ORGANISM: Artificial Sequence
<220> FEATURE:
```

<223> OTHER INFORMATION: Synthetic

<400> SEQUENCE: 46

Ser Gly Cys Ala Phe Leu Ser Val Lys Lys Gln Phe Glu Glu Leu Thr
1               5                   10                  15

Leu Gly Glu Phe Leu Lys Leu Asp
            20

<210> SEQ ID NO 47
<211> LENGTH: 25
<212> TYPE: PRT
<213> ORGANISM: Artificial Sequence
<220> FEATURE:
<223> OTHER INFORMATION: Synthetic

<400> SEQUENCE: 47

Val Arg Phe Ile Thr Lys Ile Trp His Pro Asn Ile Ser Ser Val Thr
1               5                   10                  15

Gly Ala Ile Cys Leu Asp Ile Leu Lys
            20                  25

<210> SEQ ID NO 48
<211> LENGTH: 25
<212> TYPE: PRT
<213> ORGANISM: Artificial Sequence
<220> FEATURE:
<223> OTHER INFORMATION: Synthetic

<400> SEQUENCE: 48

Leu Ile Arg Lys Asn Arg Met Ala Leu Phe Gln Gln Leu Thr Cys Val
1               5                   10                  15

Leu Pro Ile Leu Asp Asn Leu Leu Lys
            20                  25

<210> SEQ ID NO 49
<211> LENGTH: 25
<212> TYPE: PRT
<213> ORGANISM: Artificial Sequence
<220> FEATURE:
<223> OTHER INFORMATION: Synthetic

<400> SEQUENCE: 49

Phe Gln Gln Leu Thr Cys Val Leu Pro Ile Leu Asp Asn Leu Leu Lys
1               5                   10                  15

Ala Asn Val Ile Asn Lys Gln Glu His
            20                  25

<210> SEQ ID NO 50
<211> LENGTH: 25
<212> TYPE: PRT
<213> ORGANISM: Artificial Sequence
<220> FEATURE:
<223> OTHER INFORMATION: Synthetic

<400> SEQUENCE: 50

Ser Ala Ser Leu Gly Ser Thr Ser Lys Asn Thr Ser Pro Met Arg Asn
1               5                   10                  15

Ser Phe Ala His Ser Leu Ser Pro Thr
            20                  25

<210> SEQ ID NO 51
<211> LENGTH: 25
<212> TYPE: PRT
<213> ORGANISM: Artificial Sequence
<220> FEATURE:
<223> OTHER INFORMATION: Synthetic

<400> SEQUENCE: 51

Leu Val Lys Gly Asn Ala Ala Asn Ile Phe Lys Asn Cys Leu Lys
1               5                   10                  15

Glu Ile Asp Ser Thr Leu Tyr Lys Asn
            20                  25

<210> SEQ ID NO 52
<211> LENGTH: 26
<212> TYPE: PRT
<213> ORGANISM: Artificial Sequence
<220> FEATURE:
<223> OTHER INFORMATION: Synthetic

<400> SEQUENCE: 52

Phe Val Asp Lys Asn Met Lys Tyr Ile Pro Thr Glu Asp Val Ser Gly
1               5                   10                  15

Leu Ser Leu Glu Glu Gln Leu Arg Arg Leu
            20                  25

<210> SEQ ID NO 53
<211> LENGTH: 27
<212> TYPE: PRT
<213> ORGANISM: Artificial Sequence
<220> FEATURE:
<223> OTHER INFORMATION: Synthetic

<400> SEQUENCE: 53

Met Ala Ala Ala Ser Val Thr Pro Pro Gly Ser Leu Glu Leu Leu Gln
1               5                   10                  15

Pro Gly Phe Ser Lys Thr Leu Leu Gly Thr Lys
            20                  25

<210> SEQ ID NO 54
<211> LENGTH: 25
<212> TYPE: PRT
<213> ORGANISM: Artificial Sequence
<220> FEATURE:
<223> OTHER INFORMATION: Synthetic

<400> SEQUENCE: 54

Asp Gly Cys Gly Lys Lys Lys Ile Pro Arg Glu Lys Phe Gln Asp His
1               5                   10                  15

Val Lys Thr Cys Gly Lys Cys Arg Val
            20                  25

<210> SEQ ID NO 55
<211> LENGTH: 25
<212> TYPE: PRT
<213> ORGANISM: Artificial Sequence
<220> FEATURE:
<223> OTHER INFORMATION: Synthetic

<400> SEQUENCE: 55

Ala Gly Arg Ile Pro Ala Ile Phe Ser Pro Ala Phe Tyr Thr Ser Arg
1               5                   10                  15

Tyr Gly Tyr Lys Met Cys Leu Arg Ile
            20                  25

<210> SEQ ID NO 56
<211> LENGTH: 25
<212> TYPE: PRT

```
<213> ORGANISM: Artificial Sequence
<220> FEATURE:
<223> OTHER INFORMATION: Synthetic

<400> SEQUENCE: 56

His Leu Ser Leu Phe Phe Val Val Met Lys Gly Pro Asn Asp Ala Leu
1               5                   10                  15

Leu Arg Trp Pro Phe Asn Gln Lys Val
            20                  25

<210> SEQ ID NO 57
<211> LENGTH: 25
<212> TYPE: PRT
<213> ORGANISM: Artificial Sequence
<220> FEATURE:
<223> OTHER INFORMATION: Synthetic

<400> SEQUENCE: 57

Gly Ala Gly Leu Leu Gly Gly Ser Val Thr Pro Arg Val His Ser
1               5                   10                  15

Ala Ile Val Glu Arg Leu Arg Ala Arg
            20                  25

<210> SEQ ID NO 58
<211> LENGTH: 24
<212> TYPE: PRT
<213> ORGANISM: Artificial Sequence
<220> FEATURE:
<223> OTHER INFORMATION: Synthetic

<400> SEQUENCE: 58

Gln Gln Gln Gln Gln Gln Gln Pro Ser Ser Gln Pro Ala Gln Ser Leu
1               5                   10                  15

Pro Ser Gln Pro Leu Leu Arg Ser
            20

<210> SEQ ID NO 59
<211> LENGTH: 26
<212> TYPE: PRT
<213> ORGANISM: Artificial Sequence
<220> FEATURE:
<223> OTHER INFORMATION: Synthetic

<400> SEQUENCE: 59

Ser Ser Gln Pro Ala Gln Ser Leu Pro Ser Gln Pro Leu Leu Arg Ser
1               5                   10                  15

Pro Leu Pro Leu Gln Gln Lys Leu Leu Leu
            20                  25

<210> SEQ ID NO 60
<211> LENGTH: 25
<212> TYPE: PRT
<213> ORGANISM: Artificial Sequence
<220> FEATURE:
<223> OTHER INFORMATION: Synthetic

<400> SEQUENCE: 60

Met Ala Ala Thr Thr Ala Asn Pro Glu Met Thr Ser Asp Val Pro Ser
1               5                   10                  15

Leu Gly Pro Ala Ile Ala Ser Gly Asn
            20                  25

<210> SEQ ID NO 61
<211> LENGTH: 25
```

```
<212> TYPE: PRT
<213> ORGANISM: Artificial Sequence
<220> FEATURE:
<223> OTHER INFORMATION: Synthetic

<400> SEQUENCE: 61

Val Ser His Met Lys Ser Leu Arg Gly Thr Gly Asn Thr Ser Thr Asp
1               5                   10                  15

Gly Ser Tyr Lys Pro Ser Phe Leu Thr
            20                  25

<210> SEQ ID NO 62
<211> LENGTH: 25
<212> TYPE: PRT
<213> ORGANISM: Artificial Sequence
<220> FEATURE:
<223> OTHER INFORMATION: Synthetic

<400> SEQUENCE: 62

Asp Val Asp Lys Leu Arg Glu Gln Leu Ser Thr Ser Glu Asn Ala Leu
1               5                   10                  15

Thr Gly Arg Ile Leu Asp Leu Lys Thr
            20                  25

<210> SEQ ID NO 63
<211> LENGTH: 25
<212> TYPE: PRT
<213> ORGANISM: Artificial Sequence
<220> FEATURE:
<223> OTHER INFORMATION: Synthetic

<400> SEQUENCE: 63

Gly Asp Asn Ala Ser Cys Gln His Tyr Gly Val Arg Thr Cys Glu Gly
1               5                   10                  15

Cys Lys Gly Phe Phe Lys Arg Thr Val
            20                  25

<210> SEQ ID NO 64
<211> LENGTH: 25
<212> TYPE: PRT
<213> ORGANISM: Artificial Sequence
<220> FEATURE:
<223> OTHER INFORMATION: Synthetic

<400> SEQUENCE: 64

Ala Ser Cys Leu Lys Glu His Val Ala Ala Val Ala Gly Glu Pro Gln
1               5                   10                  15

Pro Ala Ser Cys Leu Ser Arg Leu Leu
            20                  25

<210> SEQ ID NO 65
<211> LENGTH: 25
<212> TYPE: PRT
<213> ORGANISM: Artificial Sequence
<220> FEATURE:
<223> OTHER INFORMATION: Synthetic

<400> SEQUENCE: 65

Ala Val Ala Gly Glu Pro Gln Pro Ala Ser Cys Leu Ser Arg Leu Leu
1               5                   10                  15

Gly Lys Leu Pro Glu Leu Arg Thr Leu
            20                  25

<210> SEQ ID NO 66
```

```
<211> LENGTH: 25
<212> TYPE: PRT
<213> ORGANISM: Artificial Sequence
<220> FEATURE:
<223> OTHER INFORMATION: Synthetic

<400> SEQUENCE: 66

Leu Val Val Gln Gln Ala Gly Thr Asn Lys Thr Asp Val Val Cys Gly
1               5                   10                  15

Pro Gln Asp Arg Leu Arg Ala Leu Val
            20                  25

<210> SEQ ID NO 67
<211> LENGTH: 25
<212> TYPE: PRT
<213> ORGANISM: Artificial Sequence
<220> FEATURE:
<223> OTHER INFORMATION: Synthetic

<400> SEQUENCE: 67

Ala Leu Gly Gly Ile Arg Trp Gly Arg Arg Pro Arg Leu Thr Pro Asp
1               5                   10                  15

Leu Arg Ala Leu Leu Thr Ser Gly Thr
            20                  25

<210> SEQ ID NO 68
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-Arg

<400> SEQUENCE: 68

Arg Xaa Arg Lys
1

<210> SEQ ID NO 69
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (26)..(26)
<223> OTHER INFORMATION: D-Arg

<400> SEQUENCE: 69

Ser Gly Cys Ala Phe Leu Ser Val Lys Lys Gln Phe Glu Glu Leu Thr
1               5                   10                  15

Leu Gly Glu Phe Leu Lys Leu Asp Arg Xaa Arg Lys
            20                  25

<210> SEQ ID NO 70
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)
<223> OTHER INFORMATION: D-Arg
```

<400> SEQUENCE: 70

Leu Ile Arg Lys Asn Arg Met Ala Leu Phe Gln Gln Leu Thr Cys Val
1               5                   10                  15

Leu Pro Ile Leu Asp Asn Leu Leu Lys Arg Xaa Arg Lys
            20                  25

<210> SEQ ID NO 71
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-Arg

<400> SEQUENCE: 71

Arg Xaa Arg Lys Leu Ile Arg Lys Asn Arg Met Ala Leu Phe Gln Gln
1               5                   10                  15

Leu Thr Cys Val Leu Pro Ile Leu Asp Asn Leu Leu Lys
            20                  25

<210> SEQ ID NO 72
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: 2,6-dimethyl-L-tyrosine
<220> FEATURE:
<221> NAME/KEY: MISC_FEATURE
<222> LOCATION: (3)..(3)
<223> OTHER INFORMATION: Ornithine

<400> SEQUENCE: 72

Xaa Xaa Xaa Phe
1

<210> SEQ ID NO 73
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (25)..(25)
<223> OTHER INFORMATION: D-Arg
<220> FEATURE:
<221> NAME/KEY: MISC_FEATURE
<222> LOCATION: (26)..(26)
<223> OTHER INFORMATION: 2,6-dimethyl-L-tyrosine
<220> FEATURE:
<221> NAME/KEY: MISC_FEATURE
<222> LOCATION: (27)..(27)
<223> OTHER INFORMATION: Ornithine
<220> FEATURE:
<221> NAME/KEY: MISC_FEATURE
<222> LOCATION: (28)..(28)
<223> OTHER INFORMATION: Phenyl alanine with C-terminal amide group

<400> SEQUENCE: 73

```
Ser Gly Cys Ala Phe Leu Ser Val Lys Lys Gln Phe Glu Glu Leu Thr
1               5                   10                  15

Leu Gly Glu Phe Leu Lys Leu Asp Xaa Xaa Xaa Phe
            20                  25
```

<210> SEQ ID NO 74
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(2)
<223> OTHER INFORMATION: 2,6-dimethyl-L-tyrosine
<220> FEATURE:
<221> NAME/KEY: MISC_FEATURE
<222> LOCATION: (3)..(3)
<223> OTHER INFORMATION: Ornithine

<400> SEQUENCE: 74

```
Xaa Xaa Xaa Phe Val Arg Phe Ile Thr Lys Ile Trp His Pro Asn Ile
1               5                   10                  15

Ser Ser Val Thr Gly Ala Ile Cys Leu Asp Ile Leu Lys
            20                  25
```

<210> SEQ ID NO 75
<211> LENGTH: 41
<212> TYPE: PRT
<213> ORGANISM: Artificial Sequence
<220> FEATURE:
<223> OTHER INFORMATION: Synthetic

<400> SEQUENCE: 75

```
Met Arg Gln Ile Lys Ile Trp Phe Gln Asn Arg Arg Met Lys Trp Lys
1               5                   10                  15

Val Arg Phe Ile Thr Lys Ile Trp His Pro Asn Ile Ser Ser Val Thr
            20                  25                  30

Gly Ala Ile Cys Leu Asp Ile Leu Lys
        35                  40
```

<210> SEQ ID NO 76
<211> LENGTH: 31
<212> TYPE: PRT
<213> ORGANISM: Artificial Sequence
<220> FEATURE:
<223> OTHER INFORMATION: Synthetic

<400> SEQUENCE: 76

```
His Ala Ile Tyr Pro Arg Leu Ile Arg Lys Asn Arg Met Ala Leu Phe
1               5                   10                  15

Gln Gln Leu Thr Cys Val Leu Pro Ile Leu Asp Asn Leu Leu Lys
            20                  25                  30
```

<210> SEQ ID NO 77
<211> LENGTH: 6
<212> TYPE: PRT
<213> ORGANISM: Artificial Sequence
<220> FEATURE:
<223> OTHER INFORMATION: Synthetic

<400> SEQUENCE: 77

His Ala Ile Tyr Pro Arg
1               5

<210> SEQ ID NO 78
<211> LENGTH: 16
<212> TYPE: PRT
<213> ORGANISM: Artificial Sequence
<220> FEATURE:
<223> OTHER INFORMATION: Synthetic

<400> SEQUENCE: 78

Met Arg Gln Ile Lys Ile Trp Phe Gln Asn Arg Arg Met Lys Trp Lys
1               5                   10                  15

<210> SEQ ID NO 79
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 79
actcttccag ccttccttcc                                           20

<210> SEQ ID NO 80
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 80
tgttggcgta caggtctttg                                           20

<210> SEQ ID NO 81
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 81
ctgacttcta cttccaggct gtt                                       23

<210> SEQ ID NO 82
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 82
gctcctatga tcacctgcca                                           20

<210> SEQ ID NO 83
<211> LENGTH: 21

```
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 83
gcacggatct ttactttttgg g                                              21

<210> SEQ ID NO 84
<211> LENGTH: 18
<212> TYPE: DNA
<213> ORGANISM: Artificial seqence
<220> FEATURE:
<223> OTHER INFORMATION: Primer
<220> FEATURE:
<221> NAME/KEY: misc_feature
<223> OTHER INFORMATION: Synthetic

<400> SEQUENCE: 84
gggtcttcac tgggcttc                                                   18

<210> SEQ ID NO 85
<211> LENGTH: 21
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 85
atctagtgtt ccagttcagc c                                               21

<210> SEQ ID NO 86
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 86
accacttggc atgttctacc                                                 20

<210> SEQ ID NO 87
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 87
catgccaagt ggtttccaag                                                 20

<210> SEQ ID NO 88
<211> LENGTH: 21
<212> TYPE: DNA
<213> ORGANISM: Artificial sequence
<220> FEATURE:
<223> OTHER INFORMATION: Primer
```

```
<220> FEATURE:
<221> NAME/KEY: misc_feature
<223> OTHER INFORMATION: Synthetic

<400> SEQUENCE: 88
tctgcatttt catctcctgg g                                          21

<210> SEQ ID NO 89
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 89
aagcacgctc taacatctgg                                            20

<210> SEQ ID NO 90
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 90
ttctccagcc aatcttccac                                            20

<210> SEQ ID NO 91
<211> LENGTH: 25
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 91
tttggatcca atgggtgatg ttgag                                      25

<210> SEQ ID NO 92
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 92
ttgaattcct cattagtagc tttttttgag                                 29

<210> SEQ ID NO 93
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic
```

<400> SEQUENCE: 93
ggagctgctc ttccgaatta                                              20

<210> SEQ ID NO 94
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 94
gcaggttcat gtcatcatcc                                              20

<210> SEQ ID NO 95
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 95
ctagtttgcc cacacccagt                                              20

<210> SEQ ID NO 96
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 96
tgctcaaaga tgtcgtccag                                              20

<210> SEQ ID NO 97
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 97
aggactctag acggcatcca                                              20

<210> SEQ ID NO 98
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 98
tgacagccag tgagacttgg                                              20

```
<210> SEQ ID NO 99
<211> LENGTH: 19
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 99
ctttgggtgc gacttgacg                                                    19

<210> SEQ ID NO 100
<211> LENGTH: 18
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 100
gtcgaccccg ctccttt                                                      18

<210> SEQ ID NO 101
<211> LENGTH: 25
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 101
ctcaatatta gagtctcaac cccca                                             25

<210> SEQ ID NO 102
<211> LENGTH: 19
<212> TYPE: DNA
<213> ORGANISM: artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 102
aaggcgcttg tggagaagg                                                    19

<210> SEQ ID NO 103
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 103
gcttttgtca gcgatggagt                                                   20

<210> SEQ ID NO 104
<211> LENGTH: 23
<212> TYPE: DNA
```

```
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 104
tctgctaatg acgttatcca gtt                                           23

<210> SEQ ID NO 105
<211> LENGTH: 25
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 105
cagtgatgat aggataaagg aggga                                         25

<210> SEQ ID NO 106
<211> LENGTH: 18
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 106
catcatgagc ccgtccgc                                                 18

<210> SEQ ID NO 107
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 107
taaacgtagt gtccacggca                                               20

<210> SEQ ID NO 108
<211> LENGTH: 21
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 108
tttccacacg cttatctgcg a                                             21

<210> SEQ ID NO 109
<211> LENGTH: 20
<212> TYPE: DNA
<213> ORGANISM: Artificial sequence
<220> FEATURE:
<223> OTHER INFORMATION: Primer
<220> FEATURE:
```

```
<221> NAME/KEY: misc_feature
<223> OTHER INFORMATION: Synthetic

<400> SEQUENCE: 109
tcaacctccc aagtagctgg                                                    20

<210> SEQ ID NO 110
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 110
ttaggaggcc aagacaggtg                                                    20

<210> SEQ ID NO 111
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 111
ctcctgtgcc tgatgattgc                                                    20

<210> SEQ ID NO 112
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 112
aactgatgcg tgaagtgctg                                                    20

<210> SEQ ID NO 113
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 113
tggcacagtc taccggaaat                                                    20

<210> SEQ ID NO 114
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 114
```

-continued

```
cctgagagtg gaatggtggt                                               20

<210> SEQ ID NO 115
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 115
ggcttcttct ctcccacagt                                               20

<210> SEQ ID NO 116
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 116
ttcttggttt gatgccggtg                                               20

<210> SEQ ID NO 117
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 117
ggagaagaca ccaccatcca                                               20

<210> SEQ ID NO 118
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<223> OTHER INFORMATION: Synthetic

<400> SEQUENCE: 118
tcccaggttg attcagtccc                                               20
```

SMAC/DIABLO INHIBITORS USEFUL FOR TREATING CANCER

The Sequence Listing in ASCII text file format of 81,175 bytes in size, created on May 10, 2021, with the file name "2021-05-10SequenceListing_SHOSHAN11," filed in the U.S. Patent and Trademark Office on even date herewith, is hereby incorporated herein by reference.

FIELD OF THE INVENTION

The present invention relates to compositions and methods for treating cancer, particularly to agents that inhibit the expression and/or activity of the protein second mitochondria-derived activator of caspase/direct inhibitor of apoptosis-binding protein with low pI (SMAC/Diablo), including RNA interference molecules silencing the expression of SMAC/Diablo and peptides modulating its activity, useful for treating cancers associated with overexpression of SMAC/Diablo.

BACKGROUND OF THE INVENTION

The canonical SMAC/Diablo (second mitochondria-derived activator of caspase/direct inhibitor of apoptosis-binding protein with low pI) isoform, SMAC-α, is a mitochondrial intermembrane space (IMS) pro-apoptotic protein (Verhagen, A. M., et al. 2000. Cell 102, 43-53; Du, Cet al. 2000. Cell 102, 33-42). The N-terminus of SMAC/Diablo serves as a mitochondrial targeting signal (MTS), and is cleaved to form the mature 26 kDa protein. Following the induction of apoptosis, SMAC/Diablo is released into the cytosol (Du, Cet al. 2000, ibid; Deng, Y., et al. 2002. Genes Dev. 16, 33-45), where it interacts with members of the protein family designated "inhibitor of apoptosis proteins" (IAPs), including cIAP1, cIAP2, and XIAP to neutralize the inhibitory effects of IAPB on caspases and, thus, initiates apoptosis (Shiozaki, E. N., and Shi, Y. 200). Trends Biochem. Sci. 29, 486-494; Verhagen, A. M., and Vaux, D. L. 2002. Apoptosis 7, 163-166). This interaction neutralizes the inhibitory effects of IAPB on caspases, and thus initiates apoptosis. In interacting with IAPB, SMAC/Diablo acts as a homodimer, mediated via an N-terminal motif (Ala-Val-Pro-Ile). In addition, SMAC/Diablo was shown to be controlled by several other proteins including the Bcl-2 family of proteins, mitogen-activated protein kinase family members, (e.g. Erk1/2) and c-Jun N-terminal kinase.

Although there are number of SMAC/Diablo variants generated by alternative splicing, SMAC/Diablo-α is the main IAP inhibitor (Adrain, C., et al. 2001. EMBO J 20, 6627-6636). Another isoform, SMAC/Diablo-β (Also known as SMAC-S), which lacks both the IAP-binding motif (IBM) and the MTS, can sensitize cells to apoptosis when over-expressed, suggesting that SMAC/Diablo may also serve functions that are IBM- and mitochondria-independent. A cytosolic form, SMAC/Diablo-ε, which also lacks both IBM and MTS elements, is ubiquitously expressed in normal human tissues and cancer cell lines (Martinez-Ruiz, G. U., et al., 2014. Int J Clin Exp Pathol 7, 5515-5526), is not involved in apoptosis and has been shown to be associated with tumorigenicity (Grimshaw, M. J., et al., 2008 Breast Cancer Res 10, R52). Additional isoforms of SMAC/Diablo are SMAC/Diablo-δ (also known as SMAC/Diablo-3), SMAC/Diablo-4 and SMAC/Diablo-γ (also known as SMAC/Diablo-5).

Mice lacking SMAC/Diablo are viable, grow and mature normally, present embryonic fibroblasts, lymphocytes, and hepatocytes without any histological abnormalities, and exhibit wild-type responses to all types of apoptotic stimuli (Okada, H., et al., 2002 Mol Cell Biol 22, 3509-3517).

SMAC/Diablo was found to be down-regulated in certain types of cancers. For instance, the expression levels of both SMAC/Diablo mRNA and protein were reduced in hepatocellular carcinoma cells, as compared to normal hepatic tissue (Bao, S. T., et al., 2006. Hepatobiliary Pancreat Dis Int 5, 580-583). Over-expression of recombinant SMAC/Diablo was found to sensitize neoplastic cells to apoptotic death (Kashkar, H., et al., 2006. Blood 108, 3434-3440). SMAC/Diablo or mimetic molecules thereof have been proposed as anti-cancer agents capable of inhibiting IAPB and thus promoting cancer cell death (for example, U.S. Application Publication Nos. 2013/0196927; U.S. Pat. Nos. 7,816,538, 7,884,211, and 9,861,679).

U.S. Patent Application Publication No. 2008/0253966 discloses methods for diagnosing and providing prognosis of cancer diseases that underexpress SMAC/Diablo, and methods for treating or inhibiting such diseases.

Unexpectedly, despite its role in promoting cell death, SMAC/Diablo was found to be over-expressed in some cancers and higher levels of both SMAC/Diablo protein and its encoding mRNA were reported in cervical cancer (Arellano-Llamas, A., et al., 2006. BMC Cancer 6, 256), lung, ovarian and prostate carcinomas, different types of sarcoma (Yoo, N. J., et al., 2003. APMIS 111, 382-388), gastric carcinomas (Shintani, M., et al., 2014. Oncol Lett 8, 2581-2586), pancreatic cancer (Hu H. Y. et al., 2012. Hepatogastroenterology 59(120):2640-3), testis cancer (Yoo N. J. et al., 2003. APMIS 111(3):382-388) and renal cell carcinoma (Kempkensteffen, C., et al., 2008. J Cancer Res Clin Oncol 134, 543-550).

There is a growing awareness of the understanding that cancer is not a single disease. Thus, there is a need for and it would be highly advantageous to have compositions and methods for treating cancer diseases that share common characteristics.

SUMMARY OF THE INVENTION

The present invention provides compositions and methods for treating cancers that overexpress SMAC/Diablo. The present invention provides agents that inhibit the expression and/or activity of SMAC/Diablo. In particular embodiments the present invention provides RNA inhibitory agents that silence or otherwise down regulate the expression of SMAC/Diablo and peptides that interact with SMAC/Diablo protein within the mitochondria and/or nucleus.

The present invention is based in part on the unexpected discovery that silencing the expression of SMAC/Diablo encoding mRNA, using small interfering RNA (siRNA) molecules, in cancer cell lines overexpressing the mRNA and encoded protein, markedly reduced the cell proliferation. Silencing SMAC/Diablo in mice subcutaneous xenografts of lung cancer cells or of breast triple negative cancer cells significantly reduced tumor growth. Furthermore, following SMAC/Diablo silencing treatment, residual lung tumors demonstrated morphological changes, including the development of alveoli-like anatomical structures and elimination of intracellular organelles, such as lamellar bodies, which are typical to alveolar type 2 (AT2) cells in lung tissue and non-small cells lung carcinoma cells. Next-generation sequencing of mRNA material obtained from tumors treated with SMAC-silencing siRNA molecules revealed altered expression of genes associated with intercellular membranal and exosomal networks, cells differentiation, lipid metabolism and transport activities. SMAC/Diablo silencing in lung cancer tumors decreased the level of phospholipids, including phosphatidylcholine, and the expression of enzymes associated with their synthesis. The present invention further discloses peptides derived from proteins interacting with SMAC/Diablo and modulate its activity. The peptides specifically bind to SMAC/Diablo and, when targeted into the mitochondria and/or nucleus of cancerous cells overexpressing SMAC/Diablo, inhibit the cell proliferation.

According to one aspect, the present invention provides a method for treating cancer associated with over-expression of second mitochondria-derived activator of caspase/direct inhibitor of apoptosis-binding protein with low pI (SMAC/Diablo) in a subject in need thereof, comprising administering to the subject a therapeutically effective amount of at least one agent that inhibits the expression and/or activity of the SMAC/Diablo.

According to certain exemplary embodiments, inhibiting the expression and/or activity of SMAC/Diablo results in reduced proliferation of cancerous cells.

According to certain embodiments, the agent that inhibits the expression and/or activity of SMAC/Diablo is selected from the group consisting of an inhibitory nucleic acid, an inhibitory peptide, an inhibitory small molecule, an inhibitory aptamer, and combinations thereof.

According to certain embodiments, the agent is SMAC/Diablo silencing oligonucleotide or a recombinant construct encoding same, targeted to the gene or mRNA sequence encoding SMAC/Diablo protein.

According to certain embodiments, the SMAC/Diablo encoding gene comprises a nucleic acid sequence at least 80%, at least 85%, at least 90%, at least 95% or more homologous to the nucleic acid sequence set forth in SEQ ID NO:1 (NG_029459.1).

According to certain embodiments, the SMAC/Diablo protein is selected from the group consisting of SMAC/Diablo-α, having an amino acids sequence at least 80%, at least 85%, at least 90% or more homologous to the amino acid sequence set forth in SEQ ID NO:2; SMAC/Diablo-δ, having an amino acids sequence at least 80%, at least 85%, at least 90% or more homologous to the amino acid sequence set forth in SEQ ID NO:4; SMAC/Diablo-β, having an amino acids sequence at least 80%, at least 85%, at least 90% or more homologous to the amino acid sequence set forth in SEQ ID NO:6; SMAC/Diablo-4, having an amino acids sequence at least 80%, at least 85%, at least 90% or more homologous to the amino acid sequence set forth in SEQ ID NO:8; and SMAC/Diablo-γ, having an amino acids sequence at least 80%, at least 85%, at least 90% or more homologous to the amino acid sequence set forth in SEQ ID NO:10. Each possibility represents a separate embodiment of the present invention.

According to certain embodiments, the SMAC/Diablo-α is encoded by a nucleic acid sequence at least 80%, at least 85%, at least 90% or more homologous to the nucleic acid sequence set forth in SEQ ID NO:3 (NM_019887.5); the SMAC/Diablo-δ is encoded by a nucleic acid sequence at least 80%, at least 85%, at least 90% or more homologous to the nucleic acid sequence set forth in SEQ ID NO:5 (NM_001278342.1); the SMAC/Diablo-β is encoded by a nucleic acid sequence at least 80%, at least 85%, at least 90% or more homologous to the nucleic acid sequence set forth in SEQ ID NO:7 (NM_001278304.1; NM_138930.3); the SMAC/Diablo-4 is encoded by a nucleic acid sequence at least 80%, at least 85%, at least 90% or more homologous to the nucleic acid sequence set forth in SEQ ID NO:9 (NM_001278302.1); and the SMAC/Diablo-γ is encoded by a nucleic acid sequence at least 80%, at least 85%, at least 90% or more homologous to the nucleic acid sequence set forth in SEQ ID NO:11 (NM_001278303.1). Each possibility represents a separate embodiment of the present invention.

According to certain embodiments, the SMAC/Diablo protein is human protein (hSMAC/Diablo) selected from the group consisting of hSMAC/Diablo-α, having the amino acid sequence set forth in SEQ ID NO:2; hSMAC/Diablo-δ, having the amino acid sequence set forth in SEQ ID NO:4; hSMAC/Diablo-δ, having the amino acid sequence set forth in SEQ ID NO:6; hSMAC/Diablo-4, having the amino acid sequence set forth in SEQ ID NO:8; and hSMAC/Diablo-γ, having the amino acid sequence set forth in SEQ ID NO:10. Each possibility represents a separate embodiment of the present invention.

According to certain embodiments, the hSMAC/Diablo-α is encoded by the nucleic acid sequence having SEQ ID NO:3; hSMAC/Diablo-δ is encoded by the nucleic acid sequence having SEQ ID NO:5; hSMAC/Diablo-β is encoded by the nucleic acid sequence having SEQ ID NO:7; hSMAC/Diablo-4 is encoded by the nucleic acid sequence having SEQ ID NO:9; and hSMAC/Diablo-γ is encoded by the nucleic acid sequence having SEQ ID NO:11. Each possibility represents a separate embodiment of the present invention.

According to some embodiments, the SMAC/Diablo protein is selected from the group consisting of SMAC/Diablo-α and SMAC/Diablo-δ.

According to certain embodiments, the SMAC/Diablo silencing molecule comprises at least 15 consecutive nucleic acid bases targeted to (hybridizable with) a nucleic acid sequence encoding SMAC/Diablo protein or to a complementary polynucleotide thereof.

According to certain embodiments, the SMAC/Diablo silencing molecule comprises at least 15 consecutive nucleic acid bases substantially identical to a nucleic acid sequence at least 80%, at least 85%, at least 90% or more homologous to the nucleic acid sequence set forth in SEQ ID NO:3 or to a nucleic acid sequence complementary to SEQ ID NO:3.

According to certain exemplary embodiments, the SMAC/Diablo protein is hSMAC/Diablo-α having the amino acid sequence set forth in SEQ ID NO:2, encoded by the nucleic acid sequence set forth in SEQ ID NO:3.

According to certain embodiments, the SMAC/Diablo silencing molecule comprises at least 15 consecutive nucleic acid bases substantially homologous to nucleic acid bases at positions 900-1,500 of SEQ ID NO:3 or to a complementary polynucleotide thereof.

According to certain embodiments, the inhibitory nucleic acid comprises a nucleic acid sequence selected from the group consisting of SEQ ID NOs:12-17, 20-25, and 28-43, a DNA or RNA sequence corresponding thereto, analogs, derivatives and combinations thereof. Each possibility represents separate embodiment of the present invention.

According to certain embodiments, the inhibitory nucleic acid is selected from the group consisting of an interfering RNA (RNAi), an antisense polynucleotide, a catalytic RNA, and an RNA-DNA chimera.

According to certain embodiments, the nucleic acid agent inhibiting the expression of SMAC/Diablo (SMAC/Diablo silencing oligonucleotide) is selected from the group consisting of RNA interference (RNAi) molecule and antisense molecule. According to some embodiments, the RNAi molecule is an unmodified and/or modified double stranded (ds) RNA molecules including, but not limited to, short-temporal RNA (stRNA), small interfering RNA (siRNA), short-hairpin RNA (shRNA), and microRNA (miRNA). In some embodiments, the SMAC/Diablo inhibitor is a biosynthetic precursor of a SMAC/Diablo-targeted dsRNA.

According to certain exemplary embodiments, the SMAC/Diablo silencing oligonucleotide is siRNA. siRNAs are typically short double-stranded RNA species with phosphorylated 5' ends and hydroxylated 3' ends. The siRNA molecules of the invention comprise a first oligonucleotide and a second oligonucleotide essentially complementary thereto (sense and antisense RNA strands) that can form an RNA duplex. Typically, each strand of the siRNA molecule is no more than 30 nucleotides in length, and is preferably about 19-25 nucleotides in length.

The siRNA molecules may further comprise 3' nucleotide overhangs on either or both strands, i.e. terminal portions of the nucleotide sequence that are not base paired between the two strands of the double stranded siRNA molecule. Preferably, the overhang is about 1-5 nucleotides in length, more preferably 2 nucleotides in length.

According to certain embodiments, the SMAC/Diablo silencing oligonucleotide is siRNA molecule comprising a first oligonucleotide comprising a nucleic acid sequence substantially homologous to at least 15 consecutive nucleic acid bases of SEQ ID NO:3 and a second polynucleotide sequence substantially complementary to the first oligonucleotide; wherein said first and second oligonucleotides are able to anneal to each other to form the siRNA molecule.

According to certain exemplary embodiments, the SMAC/Diablo silencing oligonucleotide is an siRNA molecule comprising a first oligonucleotide having the nucleic acid sequence set forth in SEQ ID NO:12 (AAGCGGUGUUUCUCAGAAUUG) and a second oligonucleotide substantially complementary thereto. According to some embodiments, the second oligonucleotide comprises the nucleic acid sequence set forth in SEQ ID NO:13 (AACAAUUCUGAGAAACCCGC). According to certain further exemplary embodiments, the targeted SMAC/Diablo polynucleotide comprises the nucleic acid sequence set forth in any one of SEQ ID NO:3 and SEQ ID NO:5.

According to certain exemplary embodiments, the SMAC/Diablo silencing oligonucleotide is an siRNA molecule comprising a first oligonucleotide having the nucleic acid sequence set forth in SEQ ID NO:14 (GCAGAUCAGGCCUCUAUAA) and a second oligonucleotide substantially complementary thereto. According to some embodiments, the second oligonucleotide comprises the nucleic acid sequence set forth in SEQ ID NO:15 (UUAUAGAGGCCUGAUCUGC). According to certain further exemplary embodiments, the targeted SMAC/Diablo polynucleotide comprises the nucleic acid sequence set forth in any one of SEQ ID NO:3, SEQ ID NO:5, SEQ ID NO:7, SEQ ID NO:9, and SEQ ID NO:11.

According to certain exemplary embodiments, the SMAC/Diablo silencing oligonucleotide is an siRNA molecule comprising a first oligonucleotide having the nucleic acid sequence set forth in SEQ ID NO:16 (CCCGGAAAGCAGAAACCAA) and a second oligonucleotide substantially complementary thereto. According to some embodiments, the second oligonucleotide comprises the nucleic acid sequence set forth in SEQ ID NO:17 (UUGGUUUCUGCUUUCCGGG). According to certain further exemplary embodiments, the targeted SMAC/Diablo polynucleotide comprises the nucleic acid sequence set forth in any one of SEQ ID NO:3, SEQ ID NO:5, SEQ ID NO:7, SEQ ID NO:9, and SEQ ID NO:11.

According to certain embodiments, the first and/or second oligonucleotide of the siRNA molecules of the present invention further comprises 3' overhang of two thymine nucleotides. According to these embodiments, the SMAC/Diablo siRNA molecule is selected from the group consisting of an siRNA molecule comprising a first nucleotide having the nucleic acid sequence set forth in SEQ ID NO:20 and a second oligonucleotide having the nucleic acid sequence set forth in SEQ ID NO:21; an siRNA molecule comprising a first nucleotide having the nucleic acid sequence set forth in SEQ ID NO:22 and a second oligonucleotide having the nucleic acid sequence set forth in SEQ ID NO:23; and an siRNA molecule comprising a first nucleotide having the nucleic acid sequence set forth in SEQ ID NO:24 and a second oligonucleotide having the nucleic acid sequence set forth in SEQ ID NO:25. Each possibility represents a separate embodiment of the present invention.

According to certain embodiments, the SMAC/Diablo silencing oligonucleotide is chemically modified. According to some embodiments, the SMAC/Diablo silencing oligonucleotide comprises at least one 2'-sugar modification. In a particular embodiment, the 2'-sugar modification is a 2'-O-methyl (2'-O-Me) modification.

According to certain embodiments, the SMAC/Diablo silencing oligonucleotide is modified (typically by a 2'-O-Me) at least at one position selected from the group consisting of position 3, 5, 6, 7, 9, 10, 11, 16 and 21 of SEQ ID NO:12 or SEQ ID NO:20.

According to certain embodiments, the hSMAC/Diablo silencing oligonucleotide is modified (typically by a 2'-O-Me) at least at one position selected from the group consisting of position 6, 7, 10, 12, and 19 of SEQ ID NO:13 or SEQ ID NO:21.

According to some exemplary embodiments, the SMAC/Diablo silencing oligonucleotide is an siRNA molecule comprising a first oligonucleotide having the nucleic acid sequence set forth in SEQ ID NO:20 derivatized by 2-O'-Me at positions 5, 10, 16 and 21 (SEQ ID NO:28) and a second oligonucleotide having the nucleic acid sequence set forth in SEQ ID NO:21 derivatized by 2-O'-Me at positions at positions 6, 12 and 19 (SEQ ID NO:29).

According to some exemplary embodiments, the SMAC/Diablo silencing oligonucleotide is an siRNA molecule comprising a first oligonucleotide having the nucleic acid sequence set forth in SEQ ID NO:20 derivatized by 2-O'-Me at positions 3, 6, 11, and 21 (SEQ ID NO:34) and a second oligonucleotide having the nucleic acid sequence set forth in SEQ ID NO:21 derivatized by 2-O'-Me at positions at positions 6, and 19 (SEQ ID NO:35).

According to certain embodiments, the SMAC/Diablo silencing oligonucleotide is modified (typically by a 2'-O-Me) at least at one position selected from the group consisting of position 4, 6, 9, 10, 13, 15 and 17 of SEQ ID NO:14 or SEQ ID NO:22.

According to certain embodiments, the hSMAC/Diablo silencing oligonucleotide is modified (typically by a 2'-O-Me) at least at one position selected from the group consisting of position 2, 4, 6, 8, 9, 12, 13, 15, 17 and 18 of SEQ ID NO:15 or SEQ ID NO:23.

According to some exemplary embodiments, the SMAC/Diablo silencing oligonucleotide is an siRNA molecule comprising a first oligonucleotide having the nucleic acid sequence set forth in SEQ ID NO:22 derivatized by 2-O'-Me at positions 4, 9, 13, and 17 (SEQ ID NO:38) and a second oligonucleotide having the nucleic acid sequence set forth in SEQ ID NO:7 derivatized by 2-O'-Me at positions at positions 6, 12, and 18 (SEQ ID NO:39).

According to some exemplary embodiments, the SMAC/Diablo silencing oligonucleotide is an siRNA molecule comprising a first oligonucleotide having the nucleic acid sequence set forth in SEQ ID NO:22 derivatized by 2-O'-Me at positions 6, 10, and 15 (SEQ ID NO:40) and a second oligonucleotide having the nucleic acid sequence set forth in SEQ ID NO:23 derivatized by 2-O'-Me at positions at positions 2, 9, and 17 (SEQ ID NO:41).

According to some embodiments, the siRNA is a single-stranded short hairpin RNA (shRNA) wherein the first oligonucleotide sequence is separated from the second oligonucleotide sequence by a linker which forms a loop structure upon annealing of the first and second oligonucleotide sequences. In some embodiments the linker length is about 3 to about 60 nucleotides.

According to certain embodiments, the method of the present invention comprises administering to the subject a nucleic acid construct capable of expressing at least one inhibitory nucleic acid.

According to some embodiments, the expressed inhibitory nucleic acid comprises a sequence selected from the group consisting of SEQ ID NOs:12-17, 20-25, 28-29, 34-35 and 38-41. According to certain embodiments, the nucleic acid construct is capable of expressing at least one siRNA molecule. According to certain exemplary embodiments, the method comprises administrating to the subject a construct capable of expressing siRNA molecule comprising a first oligonucleotide having the nucleic acid sequence set forth in SEQ ID NO:12 or SEQ ID NO:20 and a second oligonucleotide having the nucleic acid sequence set forth in SEQ ID NO:13 or SEQ ID NO:21.

The present invention discloses novel peptides derived from hSMAC/Diablo-associated proteins that can bind to hSMAC/Diablo. When the peptide derived from hSMAC/Diablo-interacting protein is targeted into the cell and further into the nucleus and/or the mitochondria, such that the interaction with hSMAC/Diablo occurs within the organelle(s), the interaction results in inhibition or intervention in phospholipid biosynthesis, cell growth and/or cell proliferation.

According to further embodiments of the invention, the agent that inhibits the activity of SMAC/Diablo is an inhibitory peptide targeted to the nucleus and/or to the mitochondria of a cell. According to certain embodiments, the cell is overexpressing SMAC/Diablo.

According to certain embodiments, the inhibiting peptide is a conjugate comprising a peptide derived from hSMAC/Diablo-interacting protein having an amino acid sequence at least 80% homologous to an amino acid sequence selected from the group consisting of SEQ ID NOs:46-67, analogs, derivatives and/or fragments thereof, and a mitochondria and/or nucleus targeting moiety. The mitochondria and/or nucleus targeting moiety can be peptidic or non-peptidic, and is covalently linked to the peptide derived from SMAC/Diablo-interacting protein directly or via linker. The targeting moiety may be linked to the peptide derived from hSMAC/Diablo-interacting protein at any position. According to some embodiments, the targeting moiety is linked to the N- or the C-terminus of the peptide derived from hSMAC/Diablo-interacting protein. When the conjugate comprises a combination of mitochondria and nucleus targeting moieties each moiety may be independently linked to the N- or C-terminus of the peptide or the mitochondria and nucleus targeting moieties can be linked in tandem to the N- or C-terminus of the peptide. According to some embodiments, the conjugate further comprises a cell penetration moiety enhancing the permeability of the conjugate through the cell plasma membrane. Any cell penetrating moiety as is known in the art can be used according to the teachings of the present invention.

According to some embodiments, the inhibiting peptide is a conjugate of a peptide derived from hSMAC/Diablo-interacting protein having an amino acid sequence at least 80% homologous to an amino acid sequence selected from the group consisting of SEQ ID NOs:46-67, analogs, derivatives and/or fragments thereof, and a nucleus targeting moiety. Any nucleus targeting (localization) moiety as is known in the art can be used according to the teachings of the present invention. According to certain exemplary embodiments, the nucleus targeting moiety is the tetrapeptide RrRK, wherein r is D-arginine (SEQ ID NO:68). The nucleus targeting tetrapeptide can be independently located at the C- or N-terminus of the peptide derived from hSMAC/Diablo-interacting protein.

According to some embodiments, the inhibiting peptide is a conjugate of a peptide derived from hSMAC/Diablo-interacting protein having an amino acid sequence at least 80% homologous to an amino acid sequence selected from the group consisting of SEQ ID NOs:46-67, analogs, derivatives and/or fragments thereof, and a mitochondria targeting moiety. Any mitochondria targeting (localization) moiety as is known in the art can be used according to the teachings of the present invention. According to certain exemplary embodiments, the mitochondria targeting moiety comprises the amino acid sequence set forth in SEQ ID NO:72. The mitochondria targeting peptide can be independently located at the C- or N-terminus of the peptide derived from hSMAC/Diablo-interacting protein. When the mitochondria targeting peptide having SEQ ID NO:72 is located at the C-terminus of the peptide derived from hSMAC/Diablo-interacting protein, its C-terminus may be amidated.

According to certain embodiments, the peptide derived from hSMAC/Diablo-interacting protein comprises an amino acid sequence selected from the group consisting of SEQ ID NOs:46-67. According to some embodiments, the peptide derived from hSMAC/Diablo-interacting protein comprises an amino acid sequence selected from the group consisting of SEQ ID NO:46, SEQ ID NO:47, SEQ ID NO:48 and SEQ ID NO:49. Each possibility represents a separate embodiment of the present invention.

According to certain exemplary embodiments, the inhibiting peptide conjugate targeted to the nucleus comprises an amino acid sequence selected from the group consisting of SEQ ID NO:69, SEQ ID NO: 70 and SEQ ID NO:71.

According to certain exemplary embodiments, the inhibiting peptide conjugate targeted to the mitochondria comprises an amino acid sequence selected from the group consisting of SEQ ID NO:73 and SEQ ID NO:74.

According to certain embodiments, the cancer is selected from the group consisting of lung cancer, breast cancer, colon cancer, lymphoma, sarcomas, stomach cancer, skin cancer, renal cancer, prostate cancer, testicular cancer, cervical cancer, leukemia and pancreatic cancer. Each possibility represents a separate embodiment of the present invention.

According to certain currently exemplary embodiments, the cancer is lung cancer.

According to certain additional currently exemplary embodiments, the cancer is breast cancer.

According to certain embodiments treating the cancer comprises re-programming the cancerous cells to at least one of attenuated lipid synthesis, decreased proliferation, and differentiation.

According to certain exemplary embodiments, the cancer is lung cancer and treating the lung cancer comprises at least one of inducing differentiation of AT2-like cells to differentiated non-proliferating AT1 cells; reducing proliferation of AT2-like undifferentiated cells and a combination thereof. These activities lead to the appearance of alveolar healthy-like morphology.

Any method as is known in the art for administering the agent that inhibits the expression and/or activity of the SMAC/Diablo can be used according to the teachings of the present invention. According to some embodiment, the inhibitory agent is administered within a pharmaceutical composition. According to certain exemplary embodiments, the pharmaceutical composition further comprises pharmaceutically acceptable excipients, diluents or carriers.

According to certain embodiments, the inhibitory agent is an RNA inhibitory molecule or a peptide. According to certain currently exemplary embodiments, the inhibitory agent is siRNA molecule. According to additional certain currently exemplary embodiments, the inhibitory agent is a peptide conjugate comprising a peptide derived from hSMAC/Diablo-interacting protein and a nucleus and/or mitochondria targeting moiety. According to these embodiments, the RNAi molecule, the construct comprising same or the peptide conjugate is administered within a pharmaceutical composition, said pharmaceutical composition optionally further comprises pharmaceutically acceptable excipients, diluents or carriers.

According to additional exemplary embodiments, the RNAi molecule is encapsulated within a nanoparticle or a liposome. According to some embodiments, the RNAi molecule is encapsulated within Polyethylenimine (PEI)-Poly (D,L-lactide-co-glycolide) (PLGA) nanoparticle or any other siRNA-delivery system as is known in the art.

The mode of administering the inhibitory agent according to the teachings of the present invention will depend upon the type of the agent, the type and severity of the cancer and parameters related to the subject (age, gender, weight etc.).

According to certain embodiments, the inhibitory agent or a pharmaceutical composition comprising same is administered via intravenous, intradermal, intramuscular, intra-arterial, intralesional, percutaneous, subcutaneous, intranasal or oral administration or by inhalation or by aerosol administration, or by combinations thereof. In some embodiments, administration is prophylactic administration, and in alternative embodiments, administration is therapeutic administration. Each possibility represents a separate embodiment of the present invention.

According to certain embodiments, the method of the present invention further comprises administering to the subject at least one additional anti-cancer agent or anti-cancer therapy.

Any agent and/or therapy as is known in the art for treating the cancerous disease of the subject can be employed as long as its activity does not interfere with the inhibition of SMAC/Diablo expression and/or activity according to the teachings of the present invention.

According to another aspect, the present invention provides at least one agent that inhibits the expression and/or activity of SMAC/Diablo for use in treating cancer associated with over-expression of SMAC/Diablo.

According to additional aspect, the present invention provides the use of at least one agent that inhibits the expression and/or activity of SMAC/Diablo for the preparation of a medicament for treating cancer associated with over-expression of SMAC/Diablo.

The at least one agent and the cancer types are as described hereinabove.

According to further aspect, the present invention provides an isolated SMAC/Diablo silencing molecule comprising a first oligonucleotide comprising the nucleic acid sequence set forth in SEQ ID NO:12 and optionally a 3' overhang of 1-5 nucleotides, derivatized by 2'-O-methyl (2'-O-Me) at positions 5, 10, 16, and 21 and a second oligonucleotide comprising the nucleic acid sequence set forth in SEQ ID NO:13 and optionally a 3' overhang of 1-5 nucleotides, derivatized by 2'-O-Me at positions 6, 12 and 19.

According to certain embodiments, the SMAC/Diablo silencing oligonucleotide comprising a first oligonucleotide comprising the nucleic acid sequence set forth in SEQ ID NO:20 derivatized by 2'-O-Me at positions 5, 10, 16, and 21 and a second oligonucleotide comprising the nucleic acid sequence set forth in SEQ ID NO:21 derivatized by 2'-O-Me at positions 6, 12 and 19.

According to yet further aspect, the present invention provides an isolated SMAC/Diablo silencing molecule comprising a first oligonucleotide comprising the nucleic acid sequence set forth in SEQ ID NO:12 and optionally a 3' overhang of 1-5 nucleotides, derivatized by 2'-O-methyl (2'-O-Me) at positions 3, 6, 11 and 21, and a second oligonucleotide comprising the nucleic acid sequence set forth in SEQ ID NO:13 and optionally a 3' overhang of 1-5 nucleotides, derivatized by 2'-O-Me at positions 6 and 19.

According to certain embodiments, the SMAC/Diablo silencing molecule comprises a first oligonucleotide comprising the nucleic acid sequence set forth in SEQ ID NO:20 derivatized by 2'-O-Me at positions 3, 6, 11, and 21 and a second oligonucleotide comprising the nucleic acid sequence set forth in SEQ ID NO:21 derivatized by 2'-O-Me at positions 6 and 19.

According to additional aspect, the present invention provides an isolated SMAC/Diablo silencing molecule comprises a first oligonucleotide having the nucleic acid sequence set forth in SEQ ID NO:14 and optionally a 3' overhang of 1-5 nucleotides and a second oligonucleotide having the nucleic acid sequence set forth in SEQ ID NO:15 and optionally a 3' overhang of 1-5 nucleotides. According to certain embodiments, the first oligonucleotide is derivatized by 2'-O-Me at positions 4, 9, 13 and 17 and the second oligonucleotide is derivatized by 2'-O-Me at positions 6, 12 and 18. According to other embodiments, the first oligonucleotide is derivatized by 2'-O-Me at positions 6, 10, and 15 and the second oligonucleotide is derivatized by 2'-O-Me at positions 2, 9 and 17.

According to some embodiments, the isolated SMAC/Diablo silencing molecule comprises a first oligonucleotide having the nucleic acid sequence set forth in SEQ ID NO:22 and a second oligonucleotide having the nucleic acid sequence set forth in SEQ ID NO:23. According to certain embodiments, the first oligonucleotide is derivatized by 2'-O-Me at positions 4, 9, 13 and 17 and the second oligonucleotide is derivatized by 2'-O-Me at positions 6, 12 and 18. According to other embodiments, the first oligonucleotide is derivatized by 2'-O-Me at positions 6, 10, and 15 and the second oligonucleotide is derivatized by 2'-O-Me at positions 2, 9 and 17.

According to additional aspect, the present invention provides an isolated SMAC/Diablo silencing molecule comprises a first oligonucleotide having the nucleic acid sequence set forth in SEQ ID NO:16 and optionally a 3' overhang of 1-5 nucleotides and a second oligonucleotide having the nucleic acid sequence set forth in SEQ ID NO:17 and optionally a 3' overhang of 1-5 nucleotides. According to certain embodiments, the first oligonucleotide comprises the nucleic acid sequence set forth in SEQ ID NO:24 and the second oligonucleotide comprises the nucleic acid sequence set forth in SEQ ID NO:25.

According to yet additional aspect, the present invention provides an isolated synthetic or recombinant peptide having an amino acid sequence at least 80% homologous to an amino acid sequence selected from the group consisting of SEQ ID NOs:46-67, an analog, derivative or a fragment thereof, wherein the peptide is capable of binding to human SMAC/Diablo. According to certain embodiments, the peptide comprises the amino acid sequence set forth in any one of SEQ ID NOs:46-67.

According to certain embodiments, the peptide further comprises a nucleus and/or mitochondria targeting moiety. The nucleus or mitochondria targeting moiety can be linked to the peptide at any position, typically at the N- or at the C-terminus, directly or via a linker. According to some embodiments, the conjugate further comprises a cell-penetrating moiety.

According to certain embodiments, the present invention provides a peptide conjugate comprising a peptide having an amino acid sequence at least 80% homologous to an amino acid sequence selected from the group consisting of SEQ ID NOs:46-67, an analog, derivative or a fragment thereof, and a nucleus targeting peptide having the amino acid sequence set forth in SEQ ID NO:68. According to some embodiments, the peptide conjugate comprises a peptide having an amino acid sequence selected from the group consisting of SEQ ID NOs:46-67, an analog, derivative or a fragment thereof, and a nucleus targeting peptide having the amino acid sequence set forth IN SEQ ID NO:68. According to certain exemplary embodiments, the peptide conjugate comprises an amino acid sequence selected from the group consisting of SEQ ID NO: 69, SEQ ID NO:70, and SEQ ID NO:71. Each possibility represents a separate embodiment of the present invention.

According to certain embodiments, the present invention provides a peptide conjugate comprising a peptide having an amino acid sequence at least 80% homologous to an amino acid sequence selected from the group consisting of SEQ ID NOs:46-67, an analog, derivative or a fragment thereof, and a mitochondria targeting peptide having the amino acid sequence set forth IN SEQ ID NO:72. According to some embodiments, the peptide conjugate comprises a peptide having an amino acid sequence selected from the group consisting of SEQ ID NOs:46-67, an analog, derivative or a fragment thereof, and a nucleus targeting peptide having the amino acid sequence set forth IN SEQ ID NO:72. According to certain exemplary embodiments, the peptide conjugate comprises an amino acid sequence selected from the group consisting of SEQ ID NO:73, and SEQ ID NO:74. Each possibility represents a separate embodiment of the present invention.

It is to be understood explicitly that the scope of the present invention encompasses homologs, analogs, variants and derivatives, including shorter and longer peptides, polypeptides, proteins and polynucleotides, as well as peptides, polypeptides, proteins and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these variants and modifications must preserve the capacity of inhibiting the expression and/or the activity of SMAC/Diablo according to the teachings of the present invention.

It is to be understood that any combination of each of the aspects and the embodiments disclosed herein is explicitly encompassed within the disclosure of the present invention.

Other objects, features and advantages of the present invention will become clear from the following description and drawings.

BRIEF DESCRIPTION OF THE FIGURES

FIG. 18 shows that SMAC/Diablo interacts with phosphatidylserine decarboxylase (PSD/PISD). (A) SMAC and PSD purification: lane 1, bacteria extract (Crude ext); lane 2 partially purified PSD (Step 1); lane, 3, purified SMAC; and lane 4, purified PSD (step 2). (B) PSD activity measured by following the formation of phosphatidylethanolamine (PE). (C) PSD binding to SMAC/Diablo using the microscale thermophoresis MST method. (D). A model of mitochondria with proposed SMAC functions in the regulation of PE synthesis at ER-mitochondria contact sites. PS is produced in the ER from PC and PE, and PS then is transferred to the mitochondria, where it is converted by PSD into PE.

DETAILED DESCRIPTION OF THE INVENTION

Figure 1A:
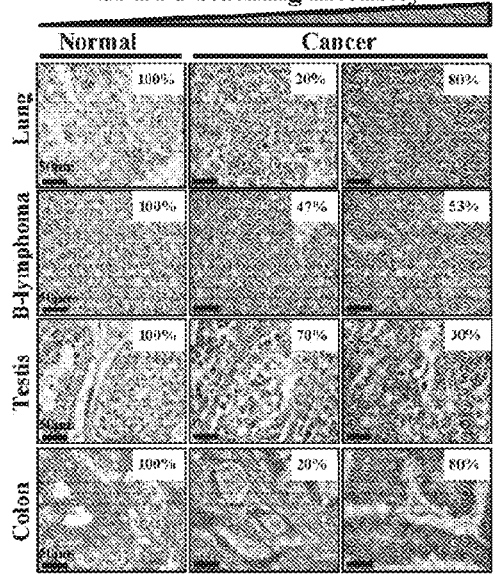
FIG. 1 demonstrates SMAC/Diablo over-expression in various types of tumors and cell lines: (A) Representative IHC staining of SMAC/Diablo in normal (n=5) and cancerous (n=20) tissue samples from tissue microarray slides (Biomax). The percentages of samples that stained at the indicated intensities are denoted; (B) Representative immunoblot staining of tissue lysates of healthy (H) and tumor (T) tissues with anti-SMAC/Diablo antibodies, with each pair of samples (H,T) being derived from the same patient lung; (C) Representative immunoblots showing SMAC/Diablo expression in PBMCs derived from CLL patients or healthy donors. As a loading control, actin levels were probed using anti-β-actin antibodies; (D) Quantitative analysis of SMAC/Diablo expression levels indicating the fold increase in the NSCLC tumor, in comparison to healthy tissue from the same patient (n=20), and in PBMCs from CLL patients, as compared to healthy donors (n=32); and (E, F) SMAC/Diablo expression levels in different cell lines, with the levels in the cancer cells being presented relative to those in the non-cancerous cells (bottom of the blot).
Figure 1A:
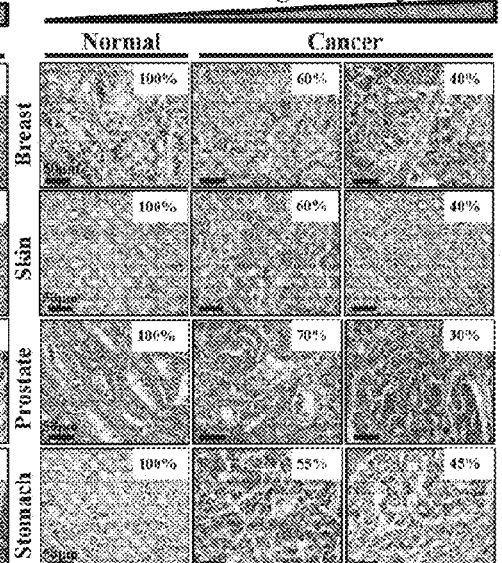

The present invention addresses the paradox of overexpression of SMAC/Diablo, a protein participating in promoting apoptosis by negatively regulating the inhibitor of apoptosis protein (IAP) family, in several types of cancer. The present invention shows for the first time that silencing SMAC/Diablo expression and/or modulating its activity within the nucleus and/or mitochondria in cancerous cells over-expressing this protein, reduced the proliferation of the cells and/or the growth of tumors comprising cells with the modulated expression and or activity of SMAC/Diablo. According to some embodiments, SMAC/Diablo expression is silenced by RNA inhibitory molecules and its activity within the nucleus and/or mitochondria is modulated using peptides derived with proteins interacting with SMAC/Diablo.

Using as example lung cancer xenografts treated with SMAC/Diablo silencing siRNA molecule, immunohistochemistry and electron-microscopy of residual lung tumor tissue demonstrated morphological changes, including the development of glandular, alveoli-like structures and elimination of lamellar bodies. Next-generation sequencing of lung tumors treated with SMAC/Diablo specific siRNA molecule revealed altered expression of genes associated with intercellular membranal and exosomal networks, cells differentiation, lipid metabolism and transporter expression and/or activity compared to lung tumors treated with non-targeted-siRNA molecule. Silencing of SMAC/Diablo expression decreased phospholipids and phosphatidylcholine levels, and the expression of enzymes associated with their synthesis. Without wishing to be bound by any specific theory or mechanism of action, the above-described phenomena suggest that SMAC/Diablo possesses an additional, non-apoptotic function associated with, inter alia, regulation of lipid synthesis essential for cancer cell growth. Agents inhibiting the expression and/or activity of SMAC/Diablo within the nucleus and/or the mitochondria in cancer types overexpressing this protein can thus be used as therapeutics.

Definitions

As used herein, the terms "SMAC/Diablo" and "SMAC" are used herein interchangeably and refer to the second mitochondria-derived activator of caspase/direct inhibitor of apoptosis-binding protein with low pI protein. Several SMAC/Diablo variants, generated by alternative splicing, are known in the art, all encompassed within the teachings of the present invention. According to certain embodiments, the terms as used herein refer to a protein having an amino acid sequence at least 80% homologous to the human SMAC/Diablo (hSMAC/Diablo) protein having an amino acids sequence set forth in any one of SEQ ID NO:2, SEQ ID NO:4, SEQ ID NO: 6, SEQ ID NO:8 and SEQ ID NO:10. According to certain exemplary embodiments, the terms refers to hSMAC/Diablo protein having an amino acids sequence selected from the group consisting of SEQ ID NO:2, SEQ ID NO:4, SEQ ID NO: 6, SEQ ID NO:8 and SEQ ID NO:10.

As used herein, the term "treatment" or "treating" refers to clinical intervention designed to alter the natural course of the individual or cell being treated during the course of clinical pathology, e.g., cancer. Desirable effects of treatment include decreasing the rate of disease progression (delaying progression of a disease), ameliorating or palliating the disease state, and remission or improved prognosis of the disease. For example, an individual is successfully "treated" if one or more symptoms associated with cancer are mitigated or eliminated, including, but are not limited to, reducing the proliferation of cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein, "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

The terms "cell growth" and "cell proliferation" are used herein interchangeably and refer to the number of viable cells of a particular type observed after a certain growth period.

The terms "inhibit" "decrease", "reduce" and 'silence" with regard to the expression or activity of SMAC/Diablo are used herein interchangeably and includes any decrease in expression or protein activity or level of the SMAC/Diablo gene or mRNA or protein encoded by the SMAC/Diablo. According to certain embodiments, inhibition of SMAC/Diablo activity refers to modulation or inhibition of SMAC/Diablo association with partner proteins within the nucleus and/or mitochondria, resulting in an inhibition/decrease/reduction of cell growth (proliferation). The decrease may be of at least 20%, 30%, 40%, 50%, 60%, 70%, 80%, 90%, 95% or 99% or more as compared to the expression of a target gene/mRNA or level of the protein encoded by a gene which has not been targeted by an inhibiting agent and/or as compared to the proliferation rate of cells in which the target gene/mRNA was not silenced or of cells in which the activity of the protein was not modulated.

The terms "polynucleotide", "nucleic acid sequence", "polynucleotide sequence" and "oligonucleotide" are used interchangeably herein and refer to an oligomer or polymer of ribonucleic acid (ribo-oligonucleotide or ribo-oligonucleoside) or deoxyribonucleic acid comprising up to about 100-1,000 nucleic acid residues. These terms encompass nucleotide sequences strands composed of naturally-occurring nucleobases, sugars and covalent inter-sugar linkages as well as polynucleotides having non-naturally-occurring portions which function similarly. Such modified or substituted polynucleotides may be preferred over native forms because of the valuable characteristics including, for example, increased stability in the presence of plasma nucleases and enhanced cellular uptake. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids. It is to be explicitly understood that the polynucleotide sequences provided herein can be of DNA or RNA molecules.

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene, thereby inhibiting expression of the target gene. In some embodiments, the RNA is double stranded RNA (dsRNA). This process has been described in plants, invertebrates, and mammalian cells. In nature, RNAi is initiated by the dsRNA-specific endonuclease Dicer, which promotes cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, inhibition by RNAi includes any decrease in expression or protein activity or level of the SMAC/Diablo gene or mRNA or protein encoded by the target gene, i.e., SMAC/Diablo. The decrease may be of at least 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

"Small interfering RNA" (siRNA), also referred to herein as "short interfering RNA" is defined as an agent which functions to inhibit expression of a target gene (silencing the gene) e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA). According to other embodiment, an siRNA is a small hairpin (also called stem loop) RNA (shRNA). In some embodiments, these shRNAs are composed of a short (e.g., 19-25 nucleotides) antisense strand, followed by a 5-9 nucleotide loop, and the analogous sense strand. Alternatively, the sense strand may precede the nucleotide loop structure and the antisense strand may follow. RNA interfering agents, e.g., siRNA molecules, may be administered to a subject having or at risk for having cancer associated with over-expression of SMAC/Diablo, to inhibit expression of SMAC/Diablo, and thereby treat, ameliorate, or inhibit the cancer in the subject.

The terms "construct", or "RNAi expression construct" are used herein interchangeably to describe an artificially assembled or isolated nucleic acid molecule which includes the polynucleotide of interest. In general, a construct may include the polynucleotide or polynucleotides of interest, a marker gene which in some cases can also be a gene of interest and appropriate regulatory sequences. According to certain embodiments of the invention, the polynucleotide of interest encode siRNA molecule. It should be appreciated that the inclusion of regulatory sequences in a construct is optional, for example, such sequences may not be required in situations where the regulatory sequences of a host cell are to be used. The regulatory elements typically include a promoter sequence for directing transcription of the polynucleotide of interest in the cell in a constitutive or inducible manner. The term construct includes vectors but should not be seen as being limited thereto. According to certain embodiments, the term "vector," is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome (such as an adenoviral vector, a lentiviral vector, etc.). Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with, the host genome.

The terms "complementary" or "complement thereof" are used herein to refer to the sequence of polynucleotide which is capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind. The terms "substantially complementary" and "sufficiently complementary" are used herein interchangeably. An oligomeric compound need not be 100% complementary to its target nucleic acid to be specifically hybridizable. Moreover, an oligomeric compound may hybridize over one or more segments such that intervening or adjacent segments are not involved in the hybridization (e.g., a bulge, a loop structure or a hairpin, structure). A "non-complementary nucleobase" means a nucleobase of an antisense oligonucleotide that is unable to undergo precise base pairing with a nucleobase at a corresponding position in a target nucleic acid. In some embodiments there are non-complementary positions, also known as "mismatches", between the oligomeric compound and the target nucleic acid, and such non-complementary positions may be tolerated between an oligomeric compound and the target nucleic acid provided that the oligomeric compound remains substantially complementary to the target nucleic acid.

As used herein, the term "peptide" indicates a sequence of amino acids linked by peptide bonds. Peptides according to some embodiments of the present invention consist of 10-50 amino acids, for example 15-35 amino acids or 20-25 amino acids.

In some embodiments, a peptide according to the present invention is up to 30 amino acids, for example up to 29 amino acids, 28 amino acids, 27 amino acids, 26 amino acids, 25 amino acids, 24 amino acids, 23 amino acids, 22 amino acids, 21 amino acids, 20 amino acids, 19 amino acids, 18 amino acids, 17 amino acids, 16 amino acids, 15 amino acids, 14 amino acids, 13 amino acids, 12 amino acids, 11 amino acids, or up to 10 amino acids. Each possibility represents a separate embodiment of the invention.

The term "amino acid" refers to compounds, which have an amino group and a carboxylic acid group, preferably in a 1,2-1,3-, or 1,4-substitution pattern on a carbon backbone. α-Amino acids are most preferred, and include the 20 natural amino acids (which are L-amino acids except for glycine) which are found in proteins, the corresponding D-amino acids, the corresponding N-methyl amino acids, side chain modified amino acids, the biosynthetically available amino acids which are not found in proteins (e.g., 4-hydroxy-proline, 5-hydroxy-lysine, citrulline, ornithine (Orn), canavanine, djenkolic acid, β-cyanoalanine), and synthetically derived α-amino acids, such as aminoisobutyric acid, norleucine (Nle), norvaline (NorVal, Nva), homocysteine and homoserine. β-Alanine and γ-amino butyric acid are examples of 1,3 and 1,4-amino acids, respectively, and many others as well known to the art.

Some of the amino acids used in this invention are those which are available commercially or are available by routine synthetic methods. Certain residues may require special methods for incorporation into the peptide, and either sequential, divergent or convergent synthetic approaches to the peptide sequence are useful in this invention. Natural coded amino acids and their derivatives are represented by one-letter codes or three-letter codes according to IUPAC conventions. When there is no indication, the L isomer was used. The D isomers are indicated by "D" or "(D)" before the residue abbreviation.

As used herein, an "amino acid residue" means the moiety which remains after the amino acid has been conjugated to additional amino acid(s) to form a peptide, or to a moiety (such as a cell penetrating moiety (CPP) and/or mitochondria and/or nucleus targeting moiety), typically through the alpha-amino and carboxyl of the amino acid.

As used herein, the terms "targeting moiety" and "localization moiety" with reference to targeting of a peptide of the invention to the nucleus and/or mitochondria are used herein interchangeably and refer to a molecule which is able to target the peptide to the specific organelle and facilitate or enhance its penetration into the nucleus or mitochondria. The targeting moiety typically enhances the permeability of the peptide, i.e. its ability to penetrate, pervade, or diffuse through a barrier or membrane, typically a phospholipid membrane. The nucleus and/or mitochondria targeting moiety may also enhance the penetration of the peptide through the plasma membrane. Additionally or alternatively, a cell penetrating moiety (CPP) specifically designed to enhance the permeability of the peptide through the plasma membrane is added to the targeting moiety.

The term "expression", as used herein, refers to the production of a functional end-product e.g., an mRNA or a protein.

According to one aspect, the present invention provides a method for treating or delaying progression of cancer associated with over-expression of second mitochondria-derived activator of caspase/direct inhibitor of apoptosis-binding protein with low pI (SMAC/Diablo) in a subject in need thereof, comprising administering to the subject an effective amount of at least one agent that decreases or inhibits the expression of SMAC/Diablo gene and/or protein and/or modulate the protein activity, and/or its interaction with associated proteins (partners).

According to certain embodiments, the agent that decreases or inhibits the expression and/or activity of SMAC/Diablo is selected from the group consisting of an inhibitory nucleic acid, an inhibitory small molecule, an inhibitory polypeptide or peptide and an inhibitory aptamer.

According to certain aspects, the present invention provides a method for treating or delaying progression of cancer associated with over-expression of second mitochondria-derived activator of caspase/direct inhibitor of apoptosis-binding protein with low pI (SMAC/Diablo) in a subject in need thereof, comprising administering to the subject an effective amount of at least one RNAi molecule, the RNAi molecule comprises a nucleic acid sequence set forth in any one of SEQ ID NOs:12-43.

According to certain embodiments, the method comprises administering an effective amount of an RNAi molecule comprises a nucleic acid sequence set forth in any one of SEQ ID NOs:12-17, 20-25, 28-29, 34-35, and 38-42. Each possibility represents a separate embodiment of the present invention.

Inhibitory Nucleic Acids

According to certain embodiments, the agent is an inhibitory nucleic acid Nucleic acid inhibitors can be used to decrease the expression of SMAC/Diablo gene. Nucleic acid inhibitors include a siRNA, a dsRNA, a ribozyme, a triple-helix former, an aptamer, or an antisense nucleic acid. siRNAs are small double stranded RNAs (dsRNAs) as described hereinabove. Antisense agents can include, for example, from about 8 to about 80 nucleobases (i.e. from about 8 to about 80 nucleotides), e.g., about 8 to about 50 nucleobases, or about 12 to about 30 nucleobases. Antisense compounds include ribozymes, external guide sequence (EGS) oligonucleotides, and other short catalytic RNAs or catalytic oligonucleotides which hybridize to the target nucleic acid and modulate its expression. Antisense compounds can include a stretch of at least eight consecutive nucleobases that are complementary to a sequence in the target gene.

According to certain embodiments, the inhibitory nucleic acid comprises at least 15 consecutive nucleic acids substantially identical to a gene or mRNA at least 80% homologous to the gene or mRNA encoding human SMAC/Diablo (hSMAC/Diablo) protein or to a complementary polynucleotide thereof.

According to certain embodiments, the inhibitory nucleic acid is targeted to a SMAC/Diablo encoding gene comprising a nucleic acid sequence at least 80%, at least 85%, at least 90%, at least 95% or more homologous to the nucleic acid sequence set forth in SEQ ID NO:1 (NG_029459.1).

According to certain embodiments, the hSMAC/Diablo protein is selected from the group consisting of SMAC/Diablo-α, having the amino acid sequence set forth in SEQ ID NO:2; SMAC/Diablo-δ, having the amino acid sequence set forth in SEQ ID NO:4; SMAC/Diablo-β, having the amino acid sequence set forth in SEQ ID NO:6; SMAC/Diablo-4, having the amino acid sequence set forth in SEQ ID NO:8; and SMAC/Diablo-γ, having the amino acid sequence set forth in SEQ ID NO:10. Each possibility represents a separate embodiment of the present invention.

According to certain embodiments, the hSMAC/Diablo-α is encoded by the nucleic acid sequence having SEQ ID NO:3; hSMAC/Diablo-δ is encoded by the nucleic acid sequence having SEQ ID NO:5; hSMAC/Diablo-β is encoded by the nucleic acid sequence having SEQ ID NO:7; hSMAC/Diablo-4 is encoded by the nucleic acid sequence having SEQ ID NO:9; and hSMAC/Diablo-γ is encoded by the nucleic acid sequence having SEQ ID NO:11. Each possibility represents a separate embodiment of the present invention.

The nucleic acid agents of the present invention are of at least 10, at least 11, at least 12, at least 13, at least 14, at least 15, at least 16, at least 17 at least 18, at least 19, at least 20, or at least 21 bases specifically hybridizable with SMAC/Diablo RNA, but excluding the full length SMAC/Diablo transcript or known variants thereof. The SMAC/Diablo-silencing oligonucleotides of the invention are preferably no more than about 1000 bases in length, more preferably no more than about 100 bases in length. In other preferable embodiments, the oligonucleotides are no more than 30 nucleotides (or base pairs) in length.

According to certain embodiments, the RNAi molecule comprises a nucleic acid sequence selected from the group consisting of SEQ ID NO:12-43.

According to certain exemplary embodiments, the SMAC/Diablo inhibitory nucleic acid is siRNA molecule selected from the group consisting of:

siRNA comprising a sense strand having the nucleic acid sequence set forth in SEQ ID NO:12 and an antisense strand having the nucleic acid sequence set forth in SEQ ID NO:13;

siRNA comprising a sense strand having the nucleic acid sequence set forth in SEQ ID NO:14 and an antisense strand having the nucleic acid sequence set forth in SEQ ID NO:15;

siRNA comprising a first sense strand having the nucleic acid sequence set forth in SEQ ID NO:16 and an antisense strand having the nucleic acid sequence set forth in SEQ ID NO:17; and siRNA comprising a sense strand having the nucleic acid sequence set forth in SEQ ID NO:18 and second polynucleotide having the nucleic acid sequence set forth in SEQ ID NO:19.

According to certain embodiments, the hSMAC/Diablo protein is hSMAC/Diablo-β having the amino acid sequence set forth in SEQ ID NO:6, encoded by the nucleic acid sequence set forth in NO:7. According to these embodiments, wherein the inhibitory nucleic acid is siRNA molecule, the siRNA molecule is selected from the group consisting of siRNA comprising a sense strand having the nucleic acid sequence set forth in SEQ ID NO:22 and second polynucleotide having the nucleic acid sequence set forth in SEQ ID NO:23; siRNA comprising a sense strand having the nucleic acid sequence set forth in SEQ ID NO:24 and an antisense strand having the nucleic acid sequence set forth in SEQ ID NO:25; and siRNA comprising a sense strand having the nucleic acid sequence set forth in SEQ ID NO:26 and an anti sense strand having the nucleic acid sequence set forth in SEQ ID NO:27.

According to certain embodiments, the hSMAC/Diablo protein is hSMAC/Diablo-δ having the amino acid sequence set forth in SEQ ID NO:4, encoded by the nucleic acid sequence set forth in SEQ ID NO:5. According to these embodiments, wherein the inhibitory nucleic acid is siRNA molecule, the siRNA molecule is selected from the group consisting of siRNA comprising a sense strand having the nucleic acid sequence set forth in SEQ ID NO:20 and an anti sense strand having the nucleic acid sequence set forth in SEQ ID NO:21; siRNA comprising a sense strand having the nucleic acid sequence set forth in SEQ ID NO:22 and an antisense strand having the nucleic acid sequence set forth in SEQ ID NO:23; and siRNA comprising a sense strand having the nucleic acid sequence set forth in SEQ ID NO:24 and an antisense strand having the nucleic acid sequence set forth in SEQ ID NO:25.

According to certain embodiments, the hSMAC/Diablo protein is hSMAC/Diablo-4 having the amino acid sequence set forth in SEQ ID NO:8, encoded by the nucleic acid sequence set forth in SEQ ID NO:9. According to these embodiments, wherein the inhibitory nucleic acid is siRNA molecule, the siRNA molecule is selected from the group consisting of siRNA comprising a sense strand having the nucleic acid sequence set forth in SEQ ID NO:22 and an antisense strand having the nucleic acid sequence set forth in SEQ ID NO:23; siRNA comprising a sense strand having the nucleic acid sequence set forth in SEQ ID NO:24 and an antisense strand having the nucleic acid sequence set forth in SEQ ID NO:25; and siRNA comprising a sense strand having the nucleic acid sequence set forth in SEQ ID NO:26 and an antisense strand having the nucleic acid sequence set forth in SEQ ID NO:27.

According to certain embodiments, the hSMAC/Diablo protein is hSMAC/Diablo-γ having the amino acid sequence set forth in SEQ ID NO:10, encoded by the nucleic acid sequence set forth in SEQ ID NO:11. According to these embodiments, wherein the inhibitory nucleic acid is siRNA molecule, the siRNA molecule is selected from the group consisting of siRNA comprising a sense strand having the nucleic acid sequence set forth in SEQ ID NO:22 and an antisense strand having the nucleic acid sequence set forth in SEQ ID NO:23; and siRNA comprising a sense strand having the nucleic acid sequence set forth in SEQ ID NO:24 and an antisense strand having the nucleic acid sequence set forth in SEQ ID NO:25.

In some embodiments, the sense and antisense strands of the present siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

Preferably, one or both strands of the siRNA of the invention can also comprise a 3' overhang. As used herein, a "3' overhang" refers to at least one unpaired nucleotide extending from the 3'-end of an RNA strand. Thus in one embodiment, the siRNA of the invention comprises at least one 3' overhang of from 1 to about 6 nucleotides (which includes ribonucleotides or deoxynucleotides) in length, from 1 to about 5 nucleotides in length, from 1 to about 4 nucleotides in length, or from about 2 to about 4 nucleotides in length. In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA of the invention can comprise 3' overhangs of dithymidylic acid ("TT") or diuridylic acid ("UU").

As illustrated in the Example section hereinbelow, exemplary siRNA oligonucleotides of the present invention are 19 to 21 base pairs in length with two 3' overhang on each strand, selected from the group consisting of:

siRNA comprising a sense strand having the nucleic acid sequence set forth in SEQ ID NO:20 and an antisense strand having the nucleic acid sequence set forth in SEQ ID NO:21;

siRNA comprising a sense strand having the nucleic acid sequence set forth in SEQ ID NO:22 and an antisense strand having the nucleic acid sequence set forth in SEQ ID NO:23;

siRNA comprising a first sense strand having the nucleic acid sequence set forth in SEQ ID NO:24 and an antisense strand having the nucleic acid sequence set forth in SEQ ID NO:25; and siRNA comprising a sense strand having the nucleic acid sequence set forth in SEQ ID NO:26 and second polynucleotide having the nucleic acid sequence set forth in SEQ ID NO:27.

While a preferable embodiment of the invention is directed to double-stranded siRNA molecules wherein the two 3' nucleotides are deoxythymidine residues (SEQ ID Nos. 20-27), it is to be understood that other modifications are within the scope of the present invention. Thus, the use of analogs, variants and derivatives of the sequences set forth in any one of SEQ ID NOS: 12-27 is contemplated, as long as the inhibitory activity of the SMAC/Diablo expression is retained. For example, in a particular embodiment, the siRNA may contain 2'-O-methyl and/or phosphorothioate substituent nucleotides. According to certain exemplary embodiments, the siRNA may contain 2'-O-methyl (2'-O-ME) modification. According to these embodiments, the siRNA is selected from the group consisting of siRNA comprising a sense strand having the nucleic acid sequence set forth in SEQ ID NO:28 and an antisense strand having the nucleic acid sequence set forth in SEQ ID N0:29; siRNA comprising a sense strand having the nucleic acid sequence set forth in SEQ ID NO:30 and an antisense strand having the nucleic acid sequence set forth in SEQ ID N0:31; siRNA comprising a first sense strand having the nucleic acid sequence set forth in SEQ ID NO:32 and an antisense strand having the nucleic acid sequence set forth in SEQ ID NO:33; siRNA comprising a sense strand having the nucleic acid sequence set forth in SEQ ID NO:34 and second polynucleotide having the nucleic acid sequence set forth in SEQ ID NO:35; siRNA comprising a sense strand having the nucleic acid sequence set forth in SEQ ID NO:36 and an antisense strand having the nucleic acid sequence set forth in SEQ ID NO:37; siRNA comprising a sense strand having the nucleic acid sequence set forth in SEQ ID NO:38 and an antisense strand having the nucleic acid sequence set forth in SEQ ID NO:39; siRNA comprising a first sense strand having the nucleic acid sequence set forth in SEQ ID NO:40 and an antisense strand having the nucleic acid sequence set forth in SEQ ID NO:41; and siRNA comprising a sense strand having the nucleic acid sequence set forth in SEQ ID NO:42 and second polynucleotide having the nucleic acid sequence set forth in SEQ ID NO:43.

In other particular embodiments, the siRNA is a variant, homolog or derivative of any one of SEQ ID NOs:12-27.

As used herein, the term "variant" refers to substantially similar sequences possessing common qualitative biological activities. An oligonucleotide variant includes a pharmaceutically acceptable salt, homolog, analog, extension or fragment of a nucleotide sequence useful for the invention. Encompassed within the term "variant" are chemically modified natural and synthetic nucleotide molecules (derivatives). Also encompassed within the term "variant" are substitutions, additions or deletions within the nucleotide sequence of the molecule, as long as the required function is sufficiently maintained. Oligonucleotide variants may share at least 50%, 55%, 60%, 65%, 70%, 75%, 80%, 85%, 90%, 95%, 96%, 97%, 98% or 99% sequence identity (homology). In different embodiments, "homolog" may refer e.g. to any degree of homology disclosed herein.

Another agent capable of silencing the expression of a SMAC/Diablo RNA is a DNAzyme molecule capable of specifically cleaving its encoding polynucleotides. DNAzymes are single-stranded nucleic acid agents which are capable of cleaving both single and double stranded target sequences. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (for a review of DNAzymes see Khachigian, L. M. 2002. Curr Opin Mol Ther 4, 119-21). Examples of construction and amplification of synthetic, engineered DNAzymes recognizing single and double-stranded target cleavage sites have been disclosed in U.S. Pat. No. 6,326,174.

Another agent capable of silencing SMAC/Diablo is a ribozyme molecule capable of specifically cleaving its encoding polynucleotides. Ribozymes are being increasingly used for the sequence-specific inhibition of gene expression by the cleavage of mRNAs encoding proteins of interest (Welch et al., 1998. Curr Opin Biotechnol. 9:486-96). The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms has demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—http://www.rpi.com/index.html).

An additional method of silencing SMAC/Diablo is via triplex forming oligonucleotides (TFOs). In the last decade, studies have shown that TFOs can be designed which can recognize and bind to polypurine/polypirimidine regions in double-stranded helical DNA in a sequence-specific manner. Thus the DNA sequence encoding the SMAC/Diablo RNA of the present invention can be targeted thereby downregulating the RNA molecule.

The recognition rules governing TFOs are outlined e.g. by EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, 2003. J Clin Invest; 112:487-94).

In general, the triplex-forming oligonucleotide has the sequence correspondence:

| oligo  | 3'--A | G | G | T |
|--------|-------|---|---|---|
| duplex | 5'--A | G | C | T |
| duplex | 3'--T | C | G | A |

However, it has been shown that the A-AT and G-GC triplets have the greatest triple helical stability. The same authors have demonstrated that TFOs designed according to the A-AT and G-GC rule do not form non-specific triplexes, indicating that the triplex formation is indeed sequence specific.

Thus for any given sequence in the regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and subsequent formation of the triple helical structure with the target DNA, induces steric and functional changes, blocking transcription initiation and elongation, allowing the introduction of desired sequence changes in the endogenous DNA and results in the specific downregulation of gene expression. In addition, Vuyisich and Beal have recently shown that sequence specific TFOs can bind to dsRNA, inhibiting activity of dsRNA-dependent enzymes such as RNA-dependent kinases (Vuyisich and Beal, 2000. Nuc. Acids Res 28:2369-74). Additionally, TFOs designed according to the abovementioned principles can induce directed mutagenesis capable of effecting DNA repair, thus providing both downregulation and upregulation of expression of endogenous genes (Seidman and Glazer, 2003, ibid). Detailed description of the design, synthesis and administration of effective TFOs can be found in U.S. Patent Application Nos. 2003/017068; 2003/0096980; 2002/0128218 and 2002/0123476 and U.S. Pat. No. 5,721,138.

It will be appreciated that nucleic acid agents capable of hybridizing SMAC/Diablo RNA may down-regulate an activity thereof by preventing SMAC/Diablo RNA binding to another downstream agent.

The inhibitory acid agents of the present invention (e.g., an siRNA molecule such as those set forth by any one of SEQ ID NOs:12-27) can be directly administered to the subject or can be expressed within the subject cell. To express such an agent (i.e., to produce an RNA molecule) in mammalian cells, a nucleic acid sequence encoding the agents of the present invention is preferably ligated into a nucleic acid construct suitable for mammalian cell expression. Such a nucleic acid construct includes a promoter sequence and additional regulatory elements for directing transcription of the polynucleotide sequence in the cell in a constitutive or inducible manner. The nucleic acid construct may preferably include additional sequences to form an expression vector suitable for replication and/or integration in eukaryotes, and preferably also in prokaryotes.

The type of vector may be selected e.g. for producing single-stranded or double-stranded RNA or DNA. Suitable vectors for producing various silencing oligonucleic acids are known in the art. For example, RNAi expression vectors (also referred to as a dsRNA-encoding plasmid) are replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

Some of these vectors have been engineered to express small hairpin RNAs (shRNAs), which get processed in vivo into siRNA-like molecules capable of carrying out gene-specific silencing. Another type of siRNA expression vector encodes the sense and antisense siRNA strands under control of separate pol III promoters. The siRNA strands from this vector, like the shRNAs of the other vectors, have 3' thymidine termination signals. Silencing efficacy by both types of expression vectors was comparable to that induced by transiently transfecting siRNA.

Expression vectors containing regulatory elements from eukaryotic viruses such as retroviruses can be also used.

Various vectors for delivering and expressing silencing RNA molecules such as siRNAs are known in the art, and include for example plasmid vectors, inducible vectors, adenoviral vectors, retroviral vectors and lentiviral vectors and CMV-based vectors. Exemplary vectors include pSilencer™ vectors (Ambion), Genescript siRNA vectors, Imagenex vectors (e.g. IMG-1000, IMG-700 and IMG-1200), among others.

Various methods can be used to introduce the expression vector of the present invention into cells. Such methods are generally described in Sambrook et al, (1989, 1992), in Ausubel et al., (1989), Chang et al., (1995), Vega et al., (1995), and Gilboa et at. (1986), and include, for example, stable or transient transfection, lipofection, electroporation and infection with recombinant viral vectors. In addition, see U.S. Pat. Nos. 5,464,764 and 5,487,992 for positive-negative selection methods.

Useful lipids for lipid-mediated transfer of the RNA inhibitory molecule of the invention or construct comprising same are, for example, DOTMA, DOPE, and DC-Chol (Tonkinson et al., 1996. Cancer Investigation, 14(1): 54-65). Other vectors can be used, such as cationic lipids, polylysine, and dendrimers.

Other than containing the necessary elements for the transcription of the inserted coding sequence, the expression construct of the present invention can also include sequences engineered to enhance stability, production, purification, yield or toxicity of the expressed RNA.

According to another aspect, the present invention provides an isolated SMAC/Diablo silencing molecule selected from the group consisting of:

siRNA comprising a sense strand having the nucleic acid sequence set forth in SEQ ID NO:14 and an antisense strand having the nucleic acid sequence set forth in SEQ ID NO:15;
siRNA comprising a sense strand having the nucleic acid sequence set forth in SEQ ID NO:16 and an antisense strand having the nucleic acid sequence set forth in SEQ ID NO:17;
siRNA comprising a sense strand having the nucleic acid sequence set forth in SEQ ID NO:18 and an antisense strand having the nucleic acid sequence set forth in SEQ ID NO:19;
siRNA comprising a sense strand having the nucleic acid sequence set forth in SEQ ID NO:22 and an antisense strand having the nucleic acid sequence set forth in SEQ ID NO:23;
siRNA comprising a sense strand having the nucleic acid sequence set forth in SEQ ID NO:24 and an antisense strand having the nucleic acid sequence set forth in SEQ ID NO:25;
siRNA comprising a sense strand having the nucleic acid sequence set forth in SEQ ID NO:26 and an antisense strand having the nucleic acid sequence set forth in SEQ ID NO:27;
siRNA comprising a sense strand having the nucleic acid sequence set forth in SEQ ID NO:28 and an antisense strand having the nucleic acid sequence set forth in SEQ ID NO:29;
siRNA comprising a sense strand having the nucleic acid sequence set forth in SEQ ID NO:30 and an antisense strand having the nucleic acid sequence set forth in SEQ ID NO:31;
siRNA comprising a sense strand having the nucleic acid sequence set forth in SEQ ID NO:32 and an antisense strand having the nucleic acid sequence set forth in SEQ ID NO:33;
siRNA comprising a sense strand having the nucleic acid sequence set forth in SEQ ID NO:34 and an antisense strand having the nucleic acid sequence set forth in SEQ ID NO:35;
siRNA comprising a sense strand having the nucleic acid sequence set forth in SEQ ID NO:36 and an antisense strand having the nucleic acid sequence set forth in SEQ ID NO:37;
siRNA comprising a sense strand having the nucleic acid sequence set forth in SEQ ID NO:38 and an antisense strand having the nucleic acid sequence set forth in SEQ ID NO:39;
siRNA comprising a sense strand having the nucleic acid sequence set forth in SEQ ID NO:40 and an antisense strand having the nucleic acid sequence set forth in SEQ ID NO:41; and
siRNA comprising a sense strand having the nucleic acid sequence set forth in SEQ ID NO:42 and an antisense strand having the nucleic acid sequence set forth in SEQ ID NO:43. Each possibility represents a separate embodiment of the present invention.

According to certain aspects, the present invention provides a method for treating or delaying progression of cancer associated with over-expression of second mitochondria-derived activator of caspase/direct inhibitor of apoptosis-binding protein with low pI (SMAC/Diablo) in a subject in need thereof, comprising administering to the subject an effective amount of at least one peptide conjugate comprising a peptide derived from SMAC/Diablo-interacting protein having an amino acid sequence at least 80% homologous to an amino acid sequence selected from the group consisting of SEQ ID NOs:46-67, analogs, derivatives and/or fragments thereof, and a mitochondria and/or nucleus targeting moiety.

According to certain embodiments, the method comprises administering an effective amount of a peptide conjugate comprising the amino acid sequence set forth in any one of SEQ ID NOs:69-71 and 73-74. Each possibility represents a separate embodiment of the present invention.

Inhibitory Peptides

The present invention discloses novel peptides derived from proteins that interact with SMAC/Diablo. When the peptide derived from SMAC/Diablo-interacting protein is targeted into the cell and further into the nucleus and/or the mitochondria, such that the interaction with hSMAC/Diablo occurs within the organelle(s), the interaction results in inhibition or intervention with at least one of phospholipid biosynthesis, cell growth, cell proliferation and any combination thereof.

According to further embodiments of the invention, the agent that inhibits the activity of SMAC/Diablo is an inhibitory peptide targeted to the nucleus and/or to the mitochondria of a cell overexpressing SMAC/Diablo.

According to certain embodiments, the inhibiting molecule is a peptide conjugate comprising a peptide derived from SMAC/Diablo-interacting protein having an amino acid sequence at least 80% homologous to an amino acid sequence selected from the group consisting of SEQ ID NOs:46-67, analogs, derivatives and/or fragments thereof, and a mitochondria and/or nucleus targeting moiety. The mitochondria and/or nucleus targeting moiety can be peptidic or non-peptidic, and is covalently linked to the peptide derived from SMAC/Diablo-interacting protein directly or via linker. The targeting moiety may be linked to the peptide derived from SMAC/Diablo-interacting protein at any position. According to some embodiments, the targeting moiety is linked to the N- or the C-terminus of the peptide derived from SMAC/Diablo-interacting protein. When the conjugate comprises a combination of mitochondria and nucleus targeting moieties each moiety may be independently linked to the N- or C-terminus of the peptide or the mitochondria and nucleus targeting moieties can be linked in tandem to the N- or C-terminus of the peptide. According to certain exemplary embodiments, each of the nucleus and mitochondria targeting moiety also enhances the permeability of the peptide conjugate through the cell membrane.

The peptides derived from SMAC/Diablo-interacting proteins and/or the peptide conjugate can be synthetic or recombinant.

According to certain embodiments, the nucleus and/or mitochondria targeting moiety enhances the permeability of the peptide derived from SMAC/Diablo-interacting protein through the nuclear or mitochondrial membrane, respectively, and typically also through the cell membrane.

According to certain embodiments, the C-terminus of the peptide conjugate is a modified carboxy terminal group selected from the group consisting of an amide, ester and alcohol group. Each possibility represents a separate embodiment of the present invention.

According to certain embodiments, the peptide conjugate comprises a peptide derived from hSMAC/Diablo-interacting protein having an amino acid sequence at least 80% homologous to an amino acid sequence selected from the group consisting of SEQ ID NOs:46-67, analogs, derivatives and/or fragments thereof, and a nucleus targeting moiety.

According to certain embodiments, the peptide conjugate comprises a peptide derived from hSMAC/Diablo-interacting protein having an amino acid sequence at least 80% homologous to an amino acid sequence selected from the group consisting of SEQ ID NOs:46-67, analogs, derivatives and/or fragments thereof, and a mitochondria targeting moiety.

According to some embodiments, the peptide conjugate comprises an amino acid sequence selected from the group consisting of SEQ ID NO:69; SEQ ID NO:70; SEQ ID NO:71; SEQ ID NO:73; and SEQ ID NO:74. Each possibility represents a separate embodiment of the present invention.

According to certain embodiments, the peptide conjugate further comprises at least one additional moiety selected from the group consisting of cell penetration moiety, a detectable label and a carrier. Each possibility represents a separate embodiment of the present invention. In some embodiments, the cell penetration moiety is a fatty acid residue. The additional moiety can be linked to the peptide conjugate directly or via a linker. Each possibility represents a separate embodiment of the present invention.

According to some embodiments, the conjugated peptides of the present invention comprise a cell penetrating moiety.

In some embodiments, the amino terminus of the peptides disclosed herein is modified. In some embodiments, the amino terminal modification is addition of a cell penetration moiety.

In some embodiments, the carboxy terminus of the conjugated peptides disclosed herein is modified. In some embodiments, the carboxy terminal modification is addition of a permeability-enhancing moiety.

Non-limitative examples of cell permeability moieties include hydrophobic moieties such as lipids, fatty acids, steroids and bulky aromatic or aliphatic compounds. According to certain embodiments, the cell penetrating moiety is a peptide (CPP).

In some embodiments, the cell permeability moiety is covalently linked to the N- or C-terminus of the peptide conjugate via a direct bond. In other embodiments, the cell permeability moiety is covalently linked to the N- or C-terminus of the peptide via a linker. In some embodiments, the cell permeability moiety is a fatty acid residue. In some embodiments, the fatty acid residue is selected from C12-C20 fatty acids. In some particular embodiments, the fatty acid residue is a myristoyl group (Myr). In additional particular embodiments, the fatty acid residue is a stearoyl group (Stear). In yet additional embodiments, the fatty acid residue is a palmitoyl group (Palm).

In some embodiments, the peptide-conjugate amino terminus is modified with an amino terminal blocking group. In some embodiments, the amino terminal blocking group is selected from the group consisting of an acetyl and alkyl. Each possibility represents a separate embodiment of the present invention.

In some embodiments, the carboxy terminus of the peptide conjugates disclosed herein is modified. In some embodiments, the carboxy terminus is modified with a carboxy terminal group. In some embodiments, the carboxy terminal group is selected from the group consisting of amide, ester and alcohol group. Each possibility represents a separate embodiment of the present invention. In some particular embodiments, the carboxy terminal group is an amide group.

The procedures utilized to construct peptide compounds of the present invention generally rely on the known principles and methods of peptide synthesis, such as solid phase peptide synthesis, partial solid phase synthesis, fragment condensation and classical solution synthesis.

Some of the peptides of the present invention, that do not comprise non-coded amino acids, can be synthesized using recombinant methods know in the art. Peptide conjugates may be synthesized chemically or alternatively may be produced recombinantly and coupled synthetically with the conjugating moiety.

The peptides of the invention can be used in the form of pharmaceutically acceptable salts. As used herein the term "salts" refers to both salts of carboxyl groups and to acid addition salts of amino or guanido groups of the peptide molecule. The term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans. Pharmaceutically acceptable salts include those salts formed with free amino groups such as salts derived from non-toxic inorganic or organic acids such as acetic acid, citric acid or oxalic acid and the like, and those salts formed with free carboxyl groups such as salts derived from non-toxic inorganic or organic bases such as sodium, calcium, potassium, ammonium, calcium, ferric or zinc, isopropylamine, triethylamine, procaine, and the like.

Analogs and derivatives of the peptides are also within the scope of the present application.

"Derivatives" of the peptides of the invention as used herein cover derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it, and do not adversely affect the immunogenic properties thereof.

These derivatives may include, for example, aliphatic esters of the carboxyl groups, amides of the carboxyl groups produced by reaction with ammonia or with primary or secondary amines, N-acyl derivatives of free amino groups of the amino acid residues, e.g., N-acetyl, formed by reaction with acyl moieties (e.g., alkanoyl or carbocyclic aroyl groups), or 0-acyl derivatives of free hydroxyl group (e.g., that of seryl or threonyl residues) formed by reaction with acyl moieties.

"Analogs" of the peptides of the invention as used herein cover compounds which have the amino acid sequence according to the invention except for one or more amino acid changes, typically, conservative amino acid substitutions.

In some embodiments, an analog has at least about 75% identity to the sequence of the peptide of the invention, for example at least about 80%, at least about 85%, at least about 90%, at least about 99% identity to the sequence of the peptide of the invention.

Conservative substitutions of amino acids as known to those skilled in the art are within the scope of the present invention. Conservative amino acid substitutions include replacement of one amino acid with another having the same type of functional group or side chain e.g. aliphatic, aromatic, positively charged, negatively charged.

Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K), Histidine (H);
5) Isoleucine (I), Leucine (L), Methionine (M), Valine (V); and
6) Phenylalanine (F), Tyrosine (Y), Tryptophan (W).

Analogs according to the present invention may comprise also peptidomimetics. "Peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with another covalent bond. A peptidomimetic according to the present invention may optionally comprise at least one bond which is an amide replacement bond such as urea bond, carbamate bond, sulfonamide bond, hydrazine bond, or any other covalent bond. The design of appropriate analogs may be computer assisted. Analogs are included in the invention as long as they remain pharmaceutically acceptable and their activity is not damaged.

The inhibitory agents of the present invention can be administered to a subject per se, or in a pharmaceutical composition where they are mixed with suitable carriers or excipients.

According to yet additional aspect, the present invention provides an isolated synthetic or recombinant peptide having an amino acid sequence at least 80% homologous to an amino acid sequence selected from the group consisting of SEQ ID NOs:46-67, an analog, derivative or a fragment thereof, wherein the peptide is capable of binding to human SMAC/Diablo. According to certain embodiments, the peptide comprises the amino acid sequence set forth in any one of SEQ ID NOs:46-67. Each possibility represents a separate embodiment of the present invention.

According to certain embodiments, the peptide further comprises a nucleus and/or mitochondria targeting moiety. The nucleus or mitochondria targeting moiety can be linked to the peptide at any position, typically at the N- or at the C-terminus, directly or via a linker. According to some embodiments, the conjugate further comprises a cell-penetrating moiety.

According to certain embodiments, the present invention provides a synthetic or recombinant peptide having the amino acid sequence set forth in SEQ ID NO:69.

According to certain embodiments, the present invention provides a synthetic or recombinant peptide having the amino acid sequence set forth in SEQ ID NO:70.

According to certain embodiments, the present invention provides a synthetic or recombinant peptide having the amino acid sequence set forth in SEQ ID NO:71.

According to certain embodiments, the present invention provides a synthetic or recombinant peptide having the amino acid sequence set forth in SEQ ID NO:73.

According to certain embodiments, the present invention provides a synthetic or recombinant peptide having the amino acid sequence set forth in SEQ ID NO:74.

Pharmaceutical Compositions

The agents of the present invention can be administered to a subject per se, or in a pharmaceutical composition where they are mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accounting for silencing the expression of SMAC/Diablo and/or modulating its activity within a nucleus or mitochondria of a cancerous cell overexpressing SMAC/Diablo. According to certain exemplary embodiments, the active ingredient of the invention inhibits the proliferation of cancerous cell and/or reduces the growth of a tumor in cancers wherein SMAC/Diablo is overexpressed.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, or intranasal injections.

Alternately, one may administer the pharmaceutical composition in a local rather than systemic manner, for example, by intra-articular injections or by microinjections, under arthroscopy, into the inflammatory synovial tissue (i.e. in situ).

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Preferably the pharmaceutical composition can also include DOTMA, DOPE, and DC-Chol (Tonkinson et al., 1996, ibid) as transfection agents or as additives to transfection agents neutralizing the negative charge of the nucleotides in the RNA inhibiting molecules. A preferred example of a transfection agent is poly(ethylamine) (PEI).

Pharmaceutical compositions suitable for use in context of the present invention include compositions wherein the active ingredients are contained in an amount effective to achieve the intended purpose. More specifically, a therapeutically effective amount means an amount of active ingredients (nucleic acid agent) effective to prevent, alleviate or ameliorate symptoms of a disorder or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975. In: "The Pharmacological Basis of Therapeutics", Ch. 1 p. 1).

Dosage amount and interval may be adjusted individually to provide plasma levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as the U.S. Food and Drug Administration (FDA) approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The present invention demonstrates over-expression of SMAC/Diablo in many types of cancer, additional to those reported in other studies (Bao, S. T., et al., 2006, ibid; Arellano-Llamas, A., et al., 2006, ibid; Yoo, N. J., et al., 2003, ibid; Shintani, M., et al., 2014 ibid; Kempkensteffen, C., et al., 2008, ibid; and Shibata, T., et al., 2007. Diagn Mol Pathol 16, 1-8). This is unexpected in view of the pro-apoptotic activity of the protein, which promotes caspase activation by binding IAPB. The present invention demonstrates that silencing SMAC/Diablo expression in various cancer cell lines over-expressing SMAC/Diablo inhibited their growth, and, furthermore, in lung cancer xenografts inhibited tumor growth and resulted in the formation of glandular alveoli-like structures, and morphological changes indicative of cell differentiation. Cell growth inhibition was not observed in non-cancerous cell lines, although SMAC/Diablo expression was inhibited. Inhibition of the cancer-cell growth as a result of SMAC/Diablo silencing, but not in non-cancerous cells, implies for an important functional role of the protein in cancer. The results presented herein implies for SMAC/Diablo as an important regulator of phospholipids transport and synthesis, The present study has taken several approaches to elucidate the molecular mechanism underlying the effects of reducing hSMAC levels in lung A549-derived tumors, including immunoblotting, immunohistochemistry, electron microscopy, q-PCR, NGS and functional analysis of the data. SMAC/Diablo-silencing resulted in reduction of Ki-67, a cellular marker of proliferation, both in culture (FIG. 2K) and in tumors (FIG. 4F, G), leading to a quiescent population of cells, as well as to a significant up-regulation of differentiation pathways (FIGS. 10A, B Tables 3-5).

Figure 2A:
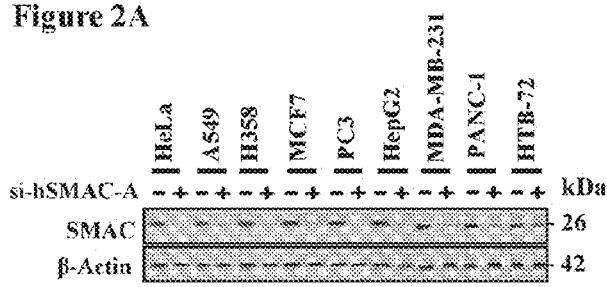
FIG. 2 demonstrates inhibition of cell growth resulted from silencing of SMAC/Diablo using si-hSMAC-A: (A) The indicated cancer cell lines were transfected with si-hSMAC-A (50 nM) and 48 h post-transfection, levels of SMAC/Diablo in the cells were evaluated by immunoblotting FIG. 2A). β-actin was used as a loading control; (B, D) A549 and H358 cells (B) and HeLa cells (D) were transfected with si-NT or si-hSMAC-A and at the indicated time, cells were harvested and analyzed for SMAC/Diablo levels by immunoblotting. β-actin was used as a loading control. (C, E) Quantitative analysis of the immunoblots of A549 and H358 cells (C) and HeLa cells (E) represented SMAC/Diablo level relative to the respective untreated cells, at 24 h (black bar), 48 h (dark gray bar), 72 h (light gray bar) and 96 h (white bar) (n=3); (F) HeLa, A549 and H358 cells were untreated (●), transfected with non-targeted siRNA (si-NT) (○) or SMAC/Diablo-A targeted siRNA (si-hSMAC-A) (50 nM) (▲). Cell growth was assayed at the indicated times using the SRB method (n=3); (G, H) The A549, H358, WI-38 and HaCaT cell lines were transfected with the indicated concentration (10-50 nM) of si-NT or si-hSMAC-A. After 48 h, (G) SMAC/Diablo levels in the cells were analyzed by immunoblotting and (H) cell growth was assayed; (I) A549 cells were transfected with si-NT or si-hSMAC B, C, or D (50 nM) and at the indicated times, cells were harvested and analyzed for SMAC/Diablo levels by immunoblotting. β-actin was used as a loading control. (J) Bar graph represents inhibition of growth of A549 cells treated with si-NT or si-hSMAC B, C, or D (50 nM). (K) Quantitative analysis of Ki-67 positive cells of si-NT- or si-hSMAC-A (50 nM)-treated A549 cells, as analyzed from immunofluorescence staining for Ki-67 (L) Cell cycle analysis of A549 cells treated with si-hSMAC (50 nM) by flow cytometry. Cells incubated with etoposide (10 μM, 24 h) were used as positive control. (M) ATP levels were analyzed at 24, 48 and 72 h post-transfection in HeLa (black bar), A549 (dark gray bar) and H358 cells (light gray bar) treated with si-NT or si-hSMAC-A (50 nM).
Figure 2C:
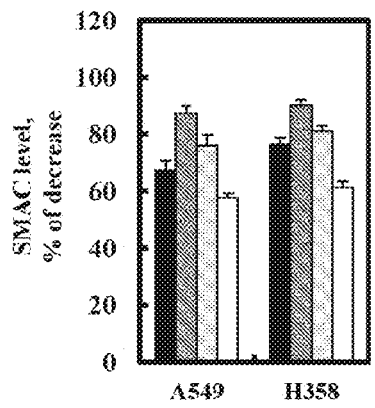
Figure 2B:
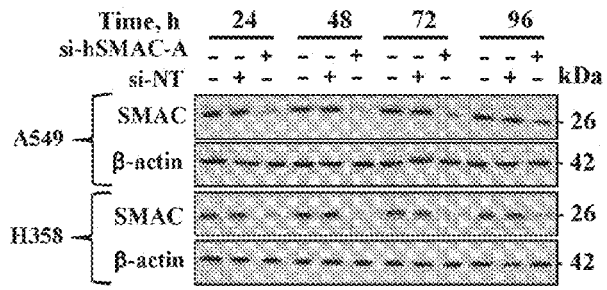
Figure 2E:
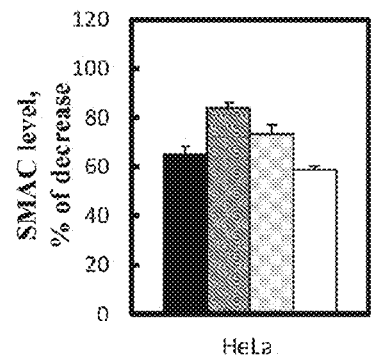
Figure 2D:
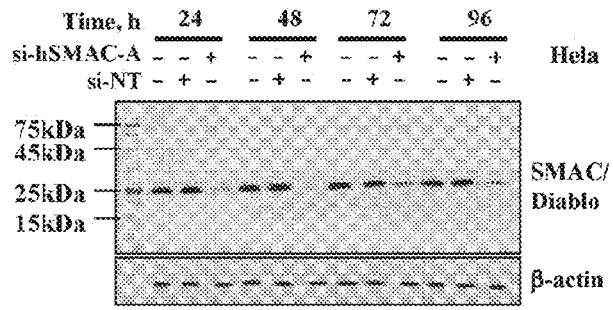
Figure 2F:
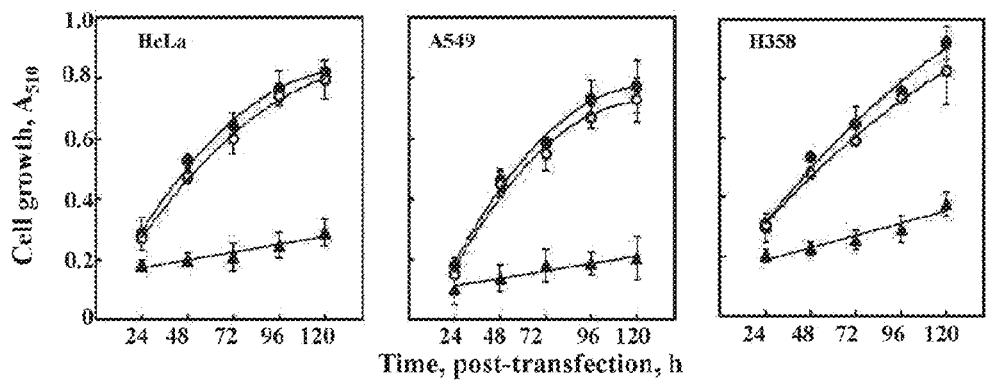
Figure 2G:
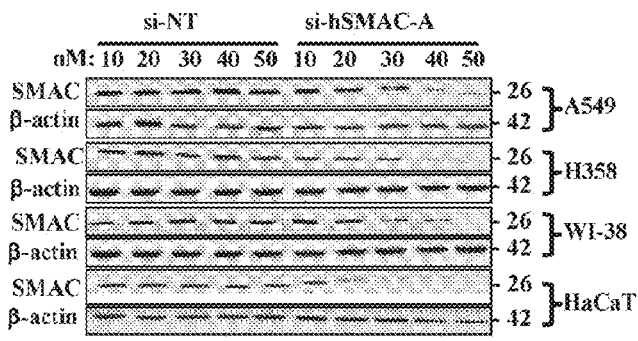
Figure 2H:
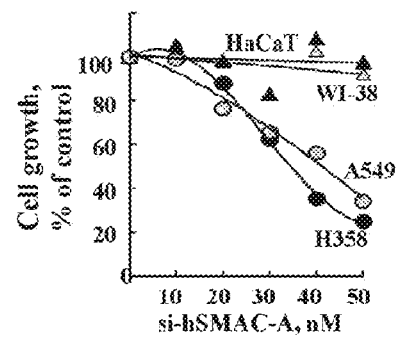
Figure 2I:
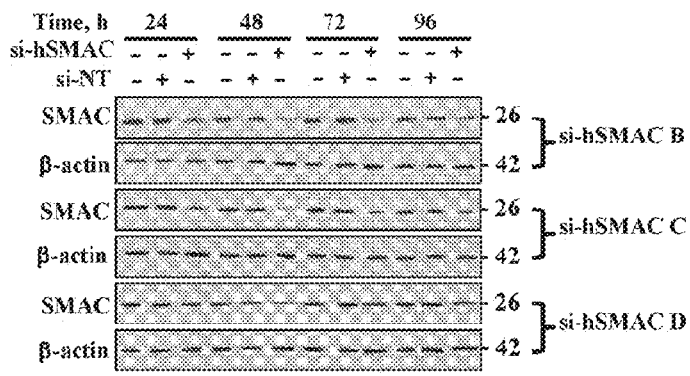
Figure 2J:
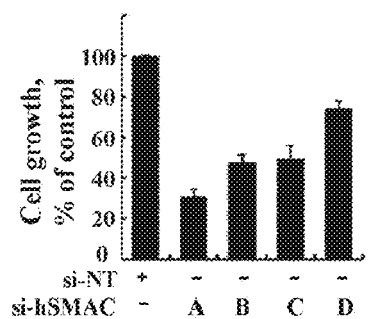
Figure 2K:
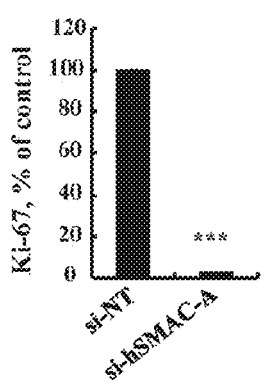

Ki-67 protein is detected during all cell cycle phases, other than resting $G_0$ phase. During S phase, Ki-67 protein levels markedly increased, with these levels being maintained in interphase and M-phase (Brunu S. et al., 1992. Cell Prolif 25, 31-40). In addition, cells treated with si-hSMAC were arrested in S phase, reflected by inhibition of BrdU incorporation and decreased DNA content in the si-hSMAC-TTs (FIG. 2K, L). The presence of SMAC/Diablo in the nucleus and its function in phospholipids synthesis is in agreement with the observation that during the S phase, the levels of phospholipids inside the nucleus were reduced (Maraldi M. M., et al. 1993. J Cell Sci 107, 853-859).

Figure 10A:
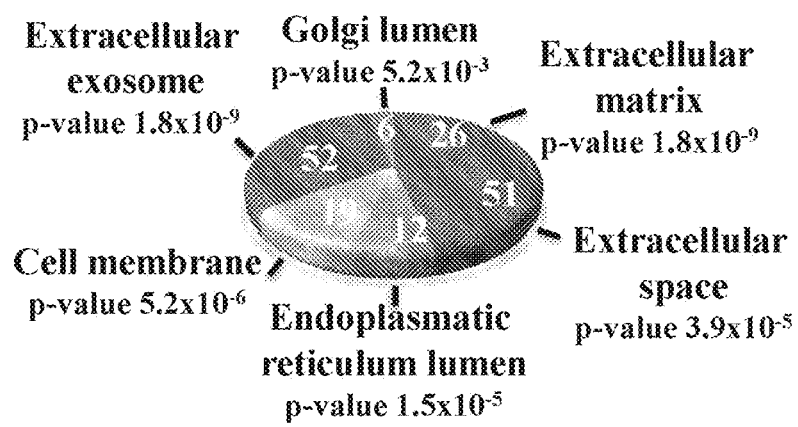
FIG. 10 depicts the differentially expressed genes and subcellular morphological alterations induced by reductions in SMAC levels in lung cancer cell derived xenografts: NGS data analysis showing selected down-regulated (A) and up-regulated (B) genes associated with the extracellular matrix, including cell-secreted collagen and proteoglycans, extracellular exosomes and proteins in the endoplasmic reticulum and Golgi lumen associated with vesicle formation. The number of genes and p-values are indicated for each category; (C) Changes (as revealed by NGS) in the expression of genes associated with lipid transport, synthesis, and degradation in si-hSMAC-A-TTs, represented as fold change, relative to their expression in si-NT-TTs; (D) Representative electron microscopic images of si-NT-TTs and si-hSMAC-A-TTs sections. Arrows points to lamellar bodies; (E) The levels of phosphatidylcholine (PC), phosphatidylethanol amine (PE) and total phospholipids (PL) in si-hSMAC-A-TTs, relative to si-NT-TTs, determined as described hereinabove; and (F) Changes in the expression of mRNA (q-PCR) associated with phosphatidylcholine synthesis in si-hSMAC-A-TTs, presented as fold change. (G) Schematic representation of diacylglycerols (a) and phosphatidylcholine synthesis (b, c) pathways, with down- and up-regulated genes identified by arrows.
Figure 10B:
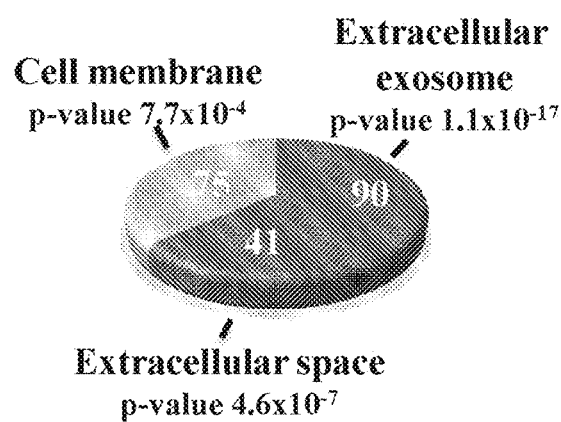

SMAC/Diablo silencing in tumors resulted in a widely altered expression of genes associated with the extracellular matrix, the cell-secreted collagen and proteoglycan matrix overlying endothelial and epithelial cells, extracellular exosomes, and proteins in the ER and Golgi lumen associated with vesicle formation (FIG. 10A, B, Table 3). These changes may indicate a role for SMAC/Diablo in vesicular trafficking, exosome release, and extracellular matrix (ECM) deposition. Exosome cargo can include proteins, lipids, miRNA, mRNA, and transcription factors with the vesicles serving as extracellular messengers, mediating cell-cell communication, and facilitating cancer progression and metastasis (Fujita, Y., et al., 2016. Cancer Sci 107, 385-390; Minciacchi, V. R., et al., (2015. Semin Cell Dev Biol 40, 41-51). Exosomes released by cancer cells can also transmit signals to stromal and inflammatory cells within the cancer microenvironment, thus impacting the cancer ECM architecture and generating the cancer microenvironment. Indeed, SMAC/Diablo-silencing also affected several factors associated with stromal activity (FIG. 8, Table 3), Tumor treated with siRNA comprising the nucleic acid sequences set forth in SEQ ID NO:20 and SEQ ID NO:21, targeted to human SMAC/Diablo (si-hSMAC-A-TTs) showed reduced expression of genes associated with inflammation and microenvironment tumorigenicity, including cytokines, chemokines and their related receptors, as well as intracellular proteins associated with inflammatory and immune responses (Table 5). Alterations in the expression of these genes may be associated with reduced tumorigenicity and invasiveness.

Figure 11A:
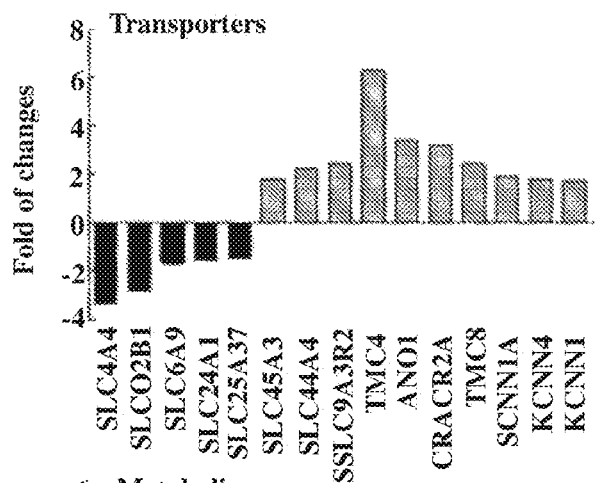
FIG. 11 depicts the genes associated with transporters, metabolism, inflammatory response, exosome and vesicles formation, differentially expressed between si-NT-TTs and si-hSMAC-A-TTs: results from NGS data showing the changes in the expression of genes associated with transporters (A) and metabolism (B) related proteins are shown as fold of changes in si-hSMAC-A-TTs relative to si-NT-TTs. (C) The changes in mRNA level (q-PCR) of the genes associated with inflammatory response, redox state regulation (RSR), and exosome are shown.

As described hereinbelow, SMAC/Diablo silencing is also associated with a modified expression of transporters of metabolites, ions, and enzymes involved in metabolism (FIG. 11A, B, Table 4). The affected enzymes include dehydrogenases and deaminases related to cholesterol, lipid, and nucleotide synthesis, amino acid metabolism, oligosaccharide biosynthesis, and protein glycosylation. Without wishing to be bound by any theory or mechanism of action, the inhibition of cell and tumor growth demonstrated herein for lung cancer cells may result from metabolic dysregulation. In this respect, most of the affected genes were reported to be associated with various cancers. In addition as discussed below, SMAC/Diablo non-apoptotic function is associated with lipid and phospholipids synthesis pathways.

Morphological analysis of A549-derived tumor sections demonstrated structural reorganization of section derived from si-hSMAC-A-treated tumors (si-hSMAC-A-TTs) into glandular, alveolar-like clusters. These structures resembled normal lung alveoli with respect to the arrangement of endothelial cells and macrophages, as visualized by anti- CD-31 (FIG. 7G) and anti-F4/80 (data not shown) antibodies staining, respectively. In contrast, the organization of endothelial cells in control sections (derived from tumors treated with non-targeted siRNA, designated herein si-NT-TTs) typically reflected ongoing tumor angiogenesis. Without wishing to be bound by any theory or mechanism of action, these findings suggest that a reduction in the expression of SMAC/Diablo triggered AT2 differentiation into AT1 cells and to morphological reorganization into lung alveoli-like structures (FIG. 7).

A549 cells are non-small cells lung carcinoma cell line, derived from primary tumor. A549 is characterized, as the pre-Alveolar Type II pneumocytes (AT2) of the human lung by expression of high numbers of multilamellar bodies (Foster K. A. et al., 1998. Exp Cell Res, 243, 359-366). While AT1 cells are flattened squamous cells accounting for ~95% of the alveolar surface and lie adjacent to capillary endothelial cells to form the pulmonary gas exchange region (FIG. 7I), AT2 cells, which cover the remaining 5% of the alveolar surface, have a compact morphology and help clear alveolar fluid via active sodium transport. Unlike terminally differentiated and non-replicating AT1 cells, AT2 cells play multiple roles and have been described as "defenders of the alveolus". AT2 cells are the main source of cells for renewal of distal lung epithelium and may either regenerate cuboidal surfactant-producing AT2 cells or trans-differentiate into AT1 cells so as to repair damage (Barkauskas, C. E., et al., 2013. J Clin Invest 123, 3025-3036) and maintain normal lung architecture and lung elasticity (Kotton, D. N., and Fine, A. 2008. Cell Tissue Res 331, 145-156; Rock, J. R., and Hogan, B. L. 2011. Annu Rev Cell Dev Biol 27, 493-512; Anversa, P., et al., 2011. Nature Med 17, 1038-1039). The increased expression of several putative AT1 cell markers, including podoplanin (Barkauskas, C. E., et al., 2013, ibid), in si-hSMAC-A-TTs (FIG. 7D) supports the notion that A549 cells undergo differentiation upon reduction of SMAC/Diablo expression.

Further support for the differentiation of cells in the residual "tumor" in si-hSMAC-A-TTs is provided by the NGS data analysis showing up-regulation of genes associated with ion transport (FIG. 11A, Table 4). Increased levels of anoctamin-1 (ANO1), a voltage-sensitive calcium-activated chloride channel that regulates transepithelial anion transport and essential for lung airway physiology (Rock, J. R., et al., 2009. J Biol Chem 284, 14875-14880), of the $Ca^{2+}$-activated potassium channel KCNN4, and of a two-pore potassium (K2P) channel, KSNK1, which are involved in airway surface liquid hydration (Zhao, K. Q., et al., 2012. Am J Physiol Lung Cell Mol Physiol 302, L4-L12), were noted. The same was also found for the epithelial $Na^+$ channel (α-ENaC/SCNN1A), a critical factor during the perinatal period of lung development, involved in clearance of lung fluid (Mustafa, S. B., et al., 2014. Exp Lung Res 40, 380-391). Other genes associated with lung maturation, including sodium bicarbonate cotransporters (SLC44A4, NBC), and the sodium- and chloride-dependent glycine transporter 1 (SLC6A9) were down-regulated in si-hSMAC-A-TTs.

Without wishing to be bound by any theory or mechanism of action, these changes in si-hSMAC-TTs may reflect functional changes with respect to airway surface liquid hydration and the clearance associated with the maturation or/and differentiation of A549 to normal-like lung cells.

Figure 8A:
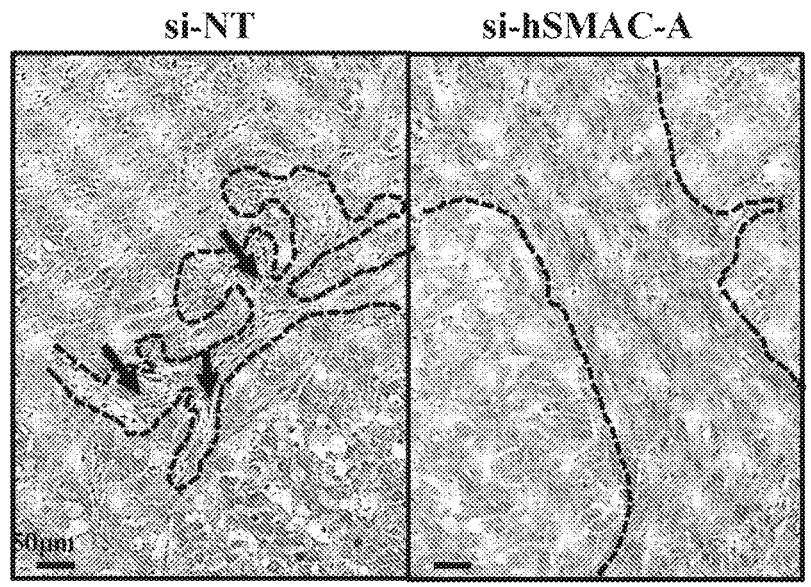
FIG. 8 depicts the staining of stromal markers in si-NT-TTs and si-hSMAC-A-TTs: (A) Representative sections from si-NT-TTs and si-hSMAC-A-TTs stained with H&E showing stromal structures; (B) vascular formation with red blood cells (arrows) in si-NT-TTs but not si-hSMAC-A-TTs; and (C) with anti-α-SMA antibodies.
Figure 8B:
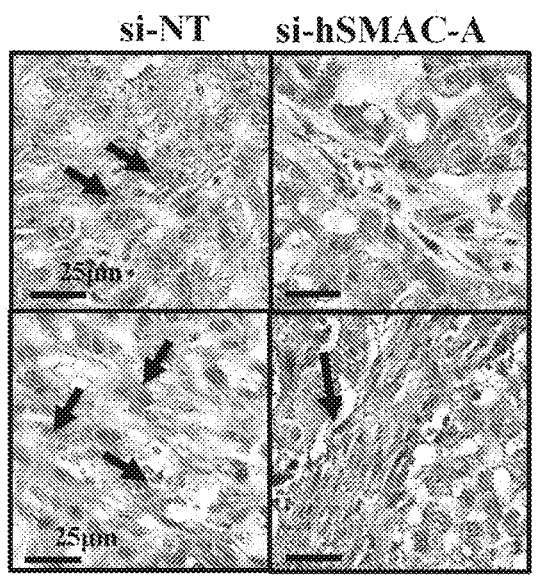
Figure 8C:
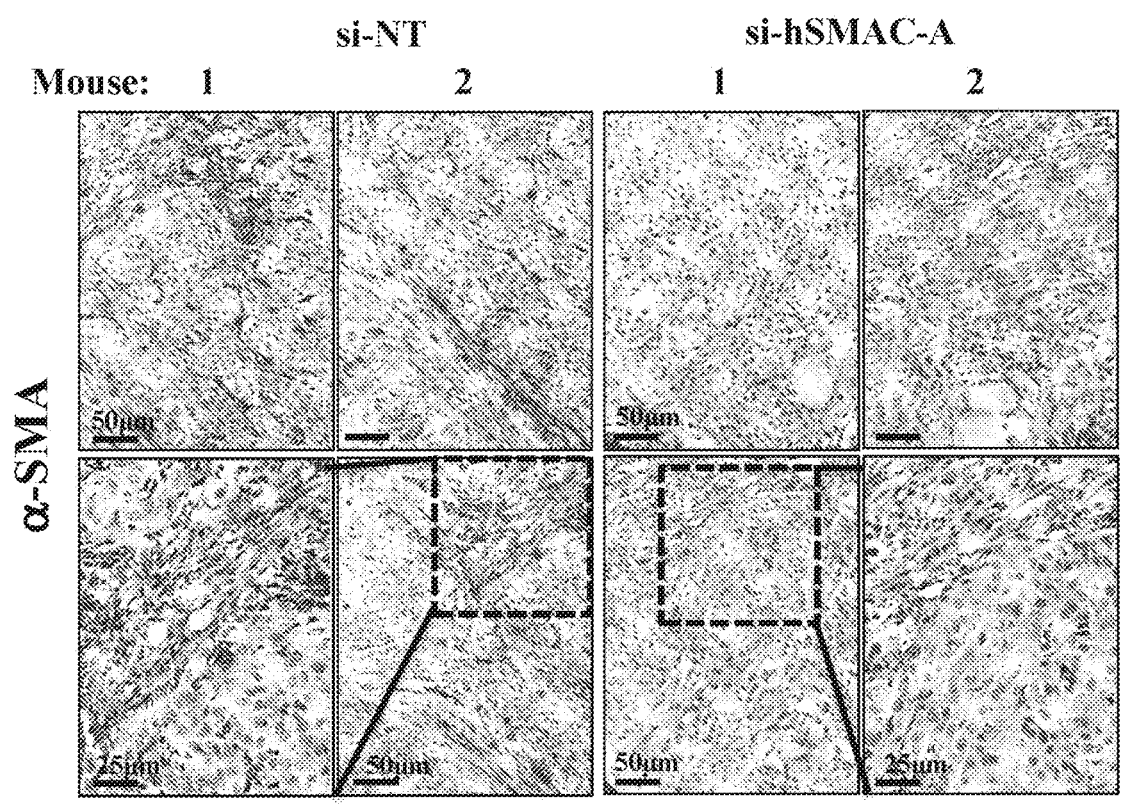

Cancer progression is associated with stromal activity, characterized by increased deposition of collagen isoforms, laminin and fibronectin, and by heparan sulphate production, as well as of extracellular matrix (ECM) degradative enzymes and metalloproteinases (MMPs). Reduction of SMAC/Diablo levels in tumors also altered stromal formation (FIG. 8). As expected for tumors, si-NT-TTs showed a thin network, dispersed throughout the tumor and enriched with vascular formations, with both supporting tumor development (FIGS. 8A and 8B). On the other hand, massive fibrotic structures, resembling scar tissue, were found in si-hSMAC-A-TTs (FIG. 8A).Moreover, the decreased expression of α-SMA and genes associated with TGF-β activity suggests reduced cancer support by the cancer-associated-fibroblasts (CAFs). NGS results demonstrate that metalloproteinase involved in cancer cells invasively, as MMP2 and MMP9 were reduced in si-hSMAC-A-TTs. There seemed to be no effect on collagen formation or vimentin staining in si-NT-TTs or si-hSMAC-A-TTs (data not shown), although α-SMA levels were markedly decreased in si-hSMAC-A-TTs, indicating differences in stromal output. While the myofibroblasts present in si-NT-TTs apparently mediate processes of stromal structures that support tumor progression. The stromal activity in si-hSMAC-A-TTs was more reminiscent of a wound-healing process, such as a scar formation.

Figure 9A:
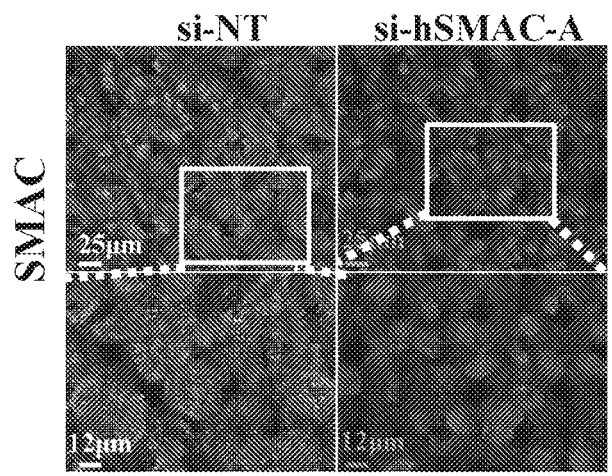
FIG. 9 depicts the nuclear and mitochondrial localization of SMAC/Diablo: (A) Representative sections from si-NT-TTs derived from A549 cells stained with anti-SMAC/Diablo antibodies and viewed by immunofluorescence. (B, C) IHC staining of SMAC/Diablo expression in cancerous lung tissue from tissue microarray slides (Biomax) indicating nuclear (B) and cytosolic (C) localization of SMAC/Diablo.
Figure 9B:
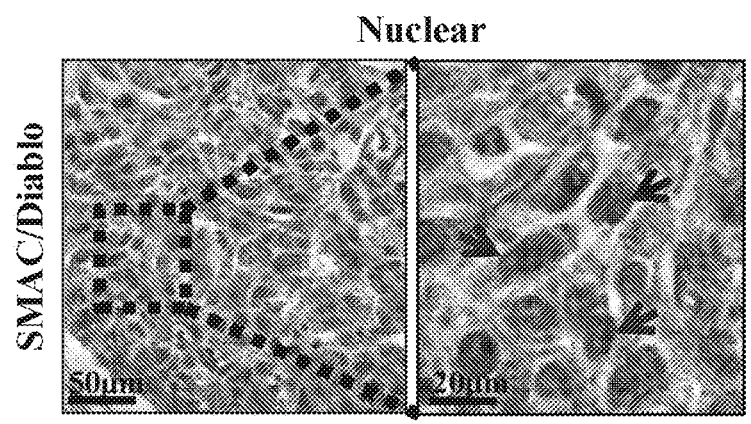
Figure 9C:
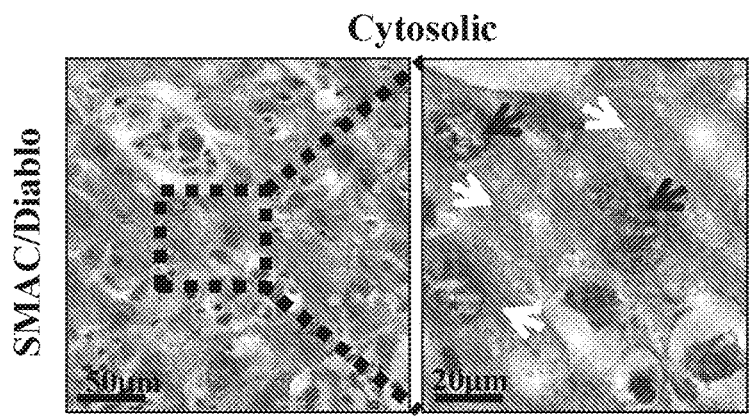

Immunofluorescent of staining si-NT-TTs showed the presence of SMAC in the nucleus (FIG. 9A). Nuclear localization of SMAC/Diablo was also detected in the nucleus of 50% of NSCLC patient samples (FIG. 9B, 9C).

Figure 12A:
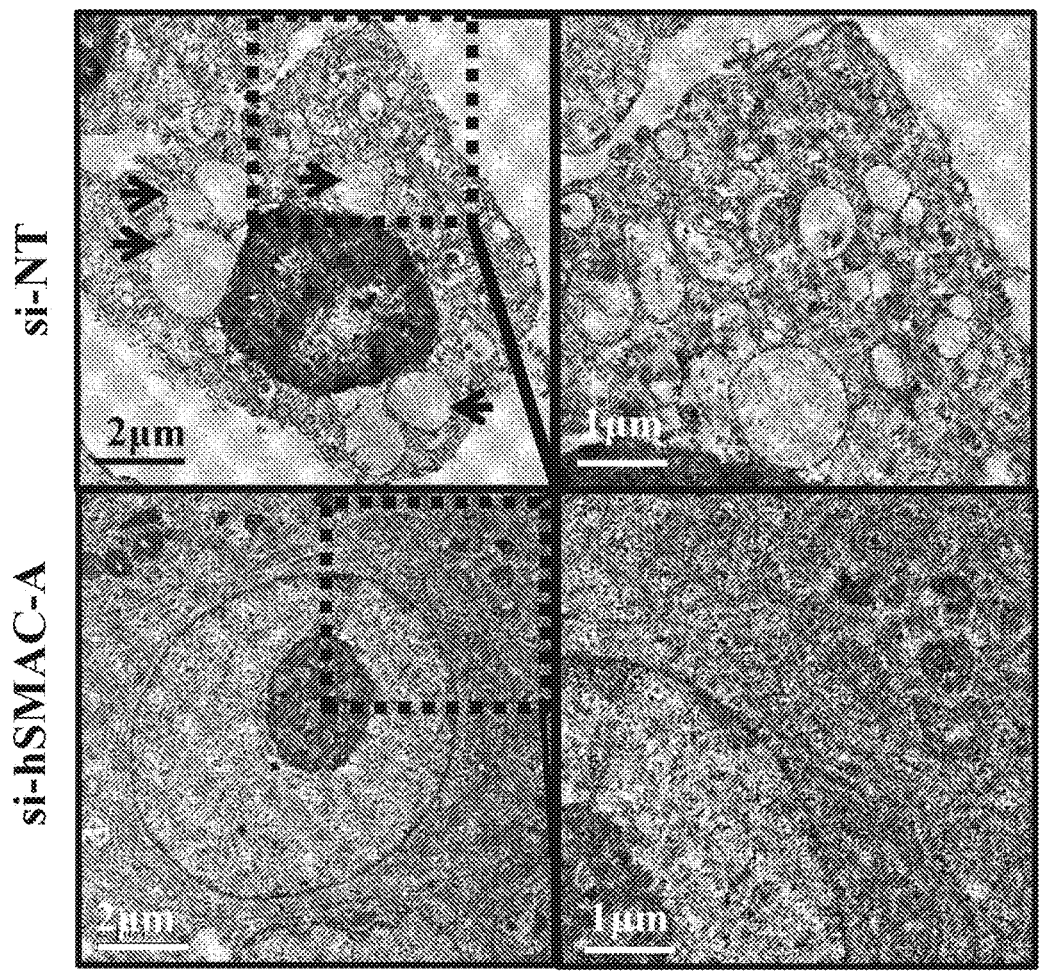
FIG. 12 depicts that EM and cell membrane network is modified in si-hSMAC-treated tumors: (A, B) Representative electron microscopic image of si-NT and si-hSMAC-A-TTs. Arrows point to lamellar bodies in the si-NT-TTs (A). Black and white arrows point to nuclear membrane and mitochondria, respectively (B).
Figure 12B:
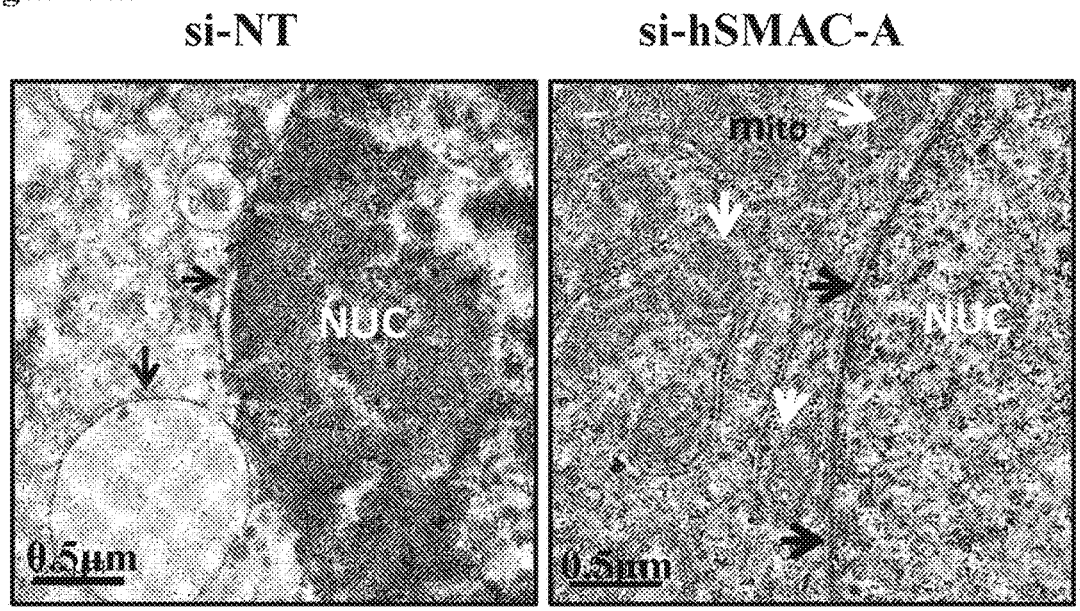
Figure 13A:
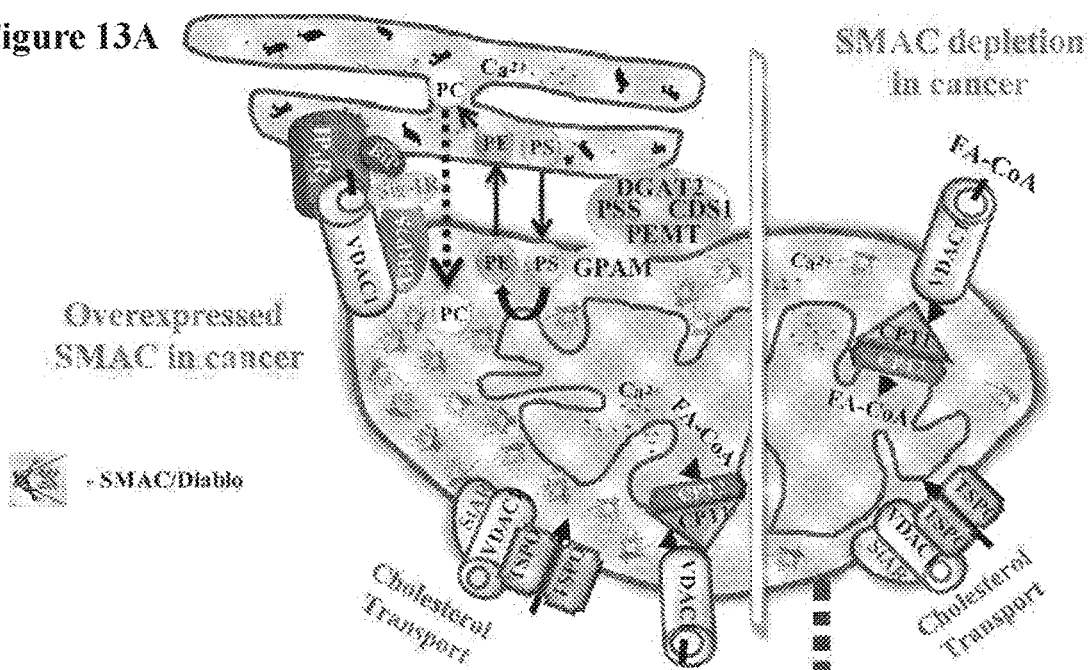
FIG. 13 is a schematic representation of the effects of SMAC/Diablo depletion on tumor morphology and properties. A schematic presentation of various membrane organelles as ER, Golgi Apparatus, and the endocytic and exocytic membrane dynamics representing intra- and extra-cellular trafficking routes in which the expression of various gens was altered upon silencing of SMAC/Diablo expression.
Figure 13B:
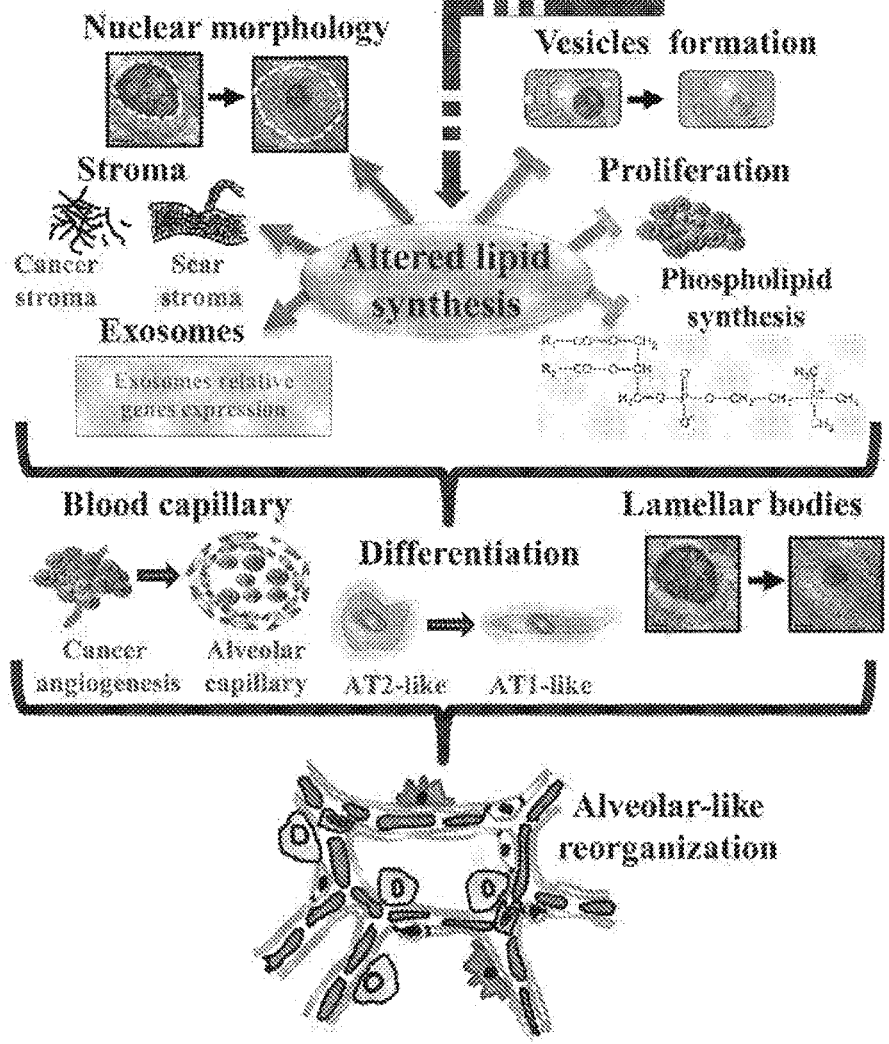

Ultrastructure analysis of si-NT-TTs and si-hSMAC-A-TTs using EM clearly demonstrated marked changes in intracellular organelles, including the nucleus (FIG. 10D, 12). These changes included decreases in intracellular vesicles of different sizes and densities, such as lysosomes and surfactant-accumulating lamellar bodies, in si-hSMAC-A-TTs (FIG. 10D, 12A). Lamellar bodies are secretory organelles found in AT2 cells that store pulmonary surfactant and are composed of 60-70% PC (Parra, E., and Perez-Gil, J. 2015. Chem Phys Lipids 185, 153-175). As discussed hereinbelow, without wishing to be bound by any specific theory or mechanism of action, the results of the present invention suggest that the observed morphological changes in si-SMAC-TTs are associated with SMAC/Diablo function in phospholipid synthesis.

As demonstrated herein, the expression levels of many genes associated with the formation of vesicle mediating intra- and extra-cellular transport and related to organelles, such as the ER and Golgi and to exosomes, were modified (FIG. 10A, B, 11C, Table 3-4). In addition, the expression levels of genes encoding several enzymes associated with cholesterol and lipid transport, synthesis, degradation and regulation were modified (FIGS. 10C, F, 11A, B). These included StAR-related lipid transfer protein 10 (STARD10), related to lipid transfer, lipase H (LIPH), phospholipase C (PLCB4), acylglycerol-3-phosphate O-acyltransferase (AGPAT2), the elongation of very long chain fatty acids protein 4 (ELOV4) and ELOV3 and ATPase phospholipid transporting 10B (ATP10B; P4-ATPase), a phospholipid flippase that can alter cell shape and which inhibits cell adhesion and spreading, and thus may be associated with the morphological changes induced by SMAC/Diablo silencing. Moreover, analysis of phospholipids and specifically PC content showed a significant decrease (40-50%) in si-hSMAC-A-TTs relative to si-NT-TTs, while phosphatidylethanolamine (PE) levels were increased 2-fold (FIG. 10E). PC is synthesized via two major distinct pathways, namely the triple methylation of PE by phosphatidylethanolamine N-methyltransferase (PEMT) and the de novo or cytidine diphosphate (CDP)-choline (Kennedy) pathway. The enzymes involved in PC biosynthesis are located at the mitochondria associated membranes (MAM) where the transport between ER and mitochondria takes place. A decrease in the expression of key enzymes in the Kennedy pathway, and increased PEMT expression have been demonstrated (FIG. 10G). SMAC/Diablo at the mitochondrial intermembrane space (IMS) may affect phospholipid synthesis via the phosphatidylserine decarboxylase (PSD), an inner mitochondrial membrane enzyme facing the IMS. PSD catalyzes the conversion of phosphatidylserine (PS) to PE with the release of $CO_2$ (Jacobs R L et al. 2010. J Biol Chem 285, 22403-22413), upon which PE is converted to PC in the ER. In this respect, a connection between mitochondrial lipid metabolism, reflected in the synthesis of mitochondrial phosphatidylethanolamine, the differentiation program of breast cancer cells and loss of tumorigenicity has been recently presented (Keckesova, Z., et al., 2017. Nature 543, 681-686). The present invention now shows (FIG. 18) that SMAC interacts with PSD and that upon SMAC deletion, PL and PC levels were decreased 2-fold, while PE levels increased 2-fold (FIG. 10E), suggesting activation of PSD in the absence of SMAC.

The presence of phospholipids in chromatin and the nuclear matrix and the roles of nuclear phospholipids in the structural organization of chromatin and nucleic acid synthesis have been demonstrated (Alessenko, A. V., and Burlakova, E. B. 2002. Bioelectrochemi 58, 13-21). As intranuclear phospholipids regulate DNA replication (Maraldi et al. 1993, ibid) changes seen in the expression of many genes upon silencing SMAC/Diablo expression (Tables 3-5) may result from the decrease in phospholipids levels in the cell (FIG. 10) and thus, in the nucleus.

Interestingly, SMAC/Diablo has been shown to interact with two nuclear proteins, the aryl hydrocarbon receptor nuclear translocator (ARNT), also known as the oxygen-independent β subunit of hypoxia-inducible factors (HIF-1β) and the Mastermind-like transcriptional co-activator MAML (Wang J et al. 2011. Mol Syst Biol 7, 536). To execute their transcriptional function, HIF factors must form a heterodimer between an oxygen-dependent α subunit (HIF-1α or HIF-2α) and an oxygen-independent subunit (HIF-1β). The HIF-2α-ARNT dimer is involved in cellular adaptation to the oxygen stress related to tumor growth and progression. ARNT is also required for nuclear localization of the transcriptional repressors NPAS1 and NPAS3 (The C H et al., 2006. J Biol Chem 281, 34617-34629). MAML2, as a transcriptional co-activator, plays an important role in Notch signaling, regulating multiple developmental pathways (McElhinny A S et al., 2008. Oncogene 27, 5138-5147). MAML2 binds to proteins such as a cyclic AMP response element-binding protein (CREB or CBP).

Thus, as nuclear SMAC/Diablo binds HIF-1β (ARNT) and MAML2, it may compete with HIF-1α, HIF-2α, NPAS1, or NPAS3 binding to ARNT. Similarly, by binding MAML2, SMAC/Diablo may interfere with interactions of MAML2 with CBP.

Without wishing to be bound by any specific theory or mechanism of action, silencing the expression of SMAC/Diablo by the RNAi molecules of the invention, or interfering with its binding capacity to HIF-1β (ARNT) and/or MAML2 within the nucleus by the peptides of the invention, together with SMAC/Diablo-mediated regulation of phospholipid synthesis and given how nuclear phospholipids control nuclear structure and function, explains the effect of SMAC/Diablo on multiple signaling pathways and on proliferation of cancerous cells.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Materials

The cell transfection agents JetPRIME and JetPEI were from PolyPlus transfection (Illkirch, France), SMAC/Diablo-siRNA were obtained from Genepharma (Suzhou, China). Propidium iodide (PI), sulforhodamine B (SRB), Triton X-100, Tween-20 were obtained from Sigma (St. Louis, Mo.). Paraformaldehyde was purchased from Emsdiasum (Hatfield, Pa.). Dulbecco's modified Eagle's medium (DMEM) was obtained from Gibco (Grand Island, N.Y.). Normal goat serum (NGS) and the supplements fetal calf serum (FCS), L-glutamine and penicillin-streptomycin were obtained from Biological Industries (Beit Haemek, Israel). Horseradish peroxidase (HRP)-conjugated anti-mouse, anti-rabbit and anti-goat antibodies were from KPL (Gaithersburg, Md.). Primary antibodies, their source, and the dilutions used are detailed in Table 1 herein below. A CellTiter-Glo luciferase-based assay and TUNEL stain was obtained from Promega (Madison, Wis.). 3,3-diaminobenzidine (DAB) was obtained from (ImmPact-DAB, Burlingame, Calif.).

TABLE 1

Antibodies used

| Antibody | Source and Cat. No. | IHC | WB |
|---|---|---|---|
| Mouse monoclonal anti-actin | Millipore, Billerica, MA, MAB1501 | — | 1:10000 |
| Mouse polyclonal anti-SMAC/Diablo | Abcam, ab8115 | 1:300 | 1:2000 |
| Rabbit monoclonal anti-pro-caspase 3 | Abcam, ab32150 | — | 1:2000 |
| Rabbit monoclonal anti-caspase 8 | Abcam, ab108333 | — | 1:1000 |
| Mouse monoclonal anti-caspase 9 | Cell Signaling, 9508S | — | 1:1500 |
| Mouse monoclonal anti-Cytochrome c | B.D Bioscience, 556432 | — | 1:2000 |
| Rabbit polyclonal anti-AIF | Abcam, ab32516 | — | 1:1000 |
| Rabbit polyclonal anti-XIAP | Abcam, ab137392 | 1:300 | 1:2000 |
| Rabbit monoclonal anti-Ki67 | Thermo Scientific, NY RM-9106-s1 | 1:100 | — |
| Rat monoclonal anti-F4/80 | Santa Cruz Biotechnology, Inc. Dallas, TX, sc52664 | 1:150 | — |
| Rabbit polyclonal anti-CD31 | Abcam, Cambridge, UK ab28364 | 1:50 | — |
| Rabbit polyclonal anti-α-SMA | Abcam, ab5694 | 1:200 | — |
| Mouse monoclonal anti-vimentin | Abcam, ab8978 | 1:200 | — |
| Mouse monoclonal anti-Podoplanin | Abcam, ab10288 | 1:400 | — |
| Rabbit polyclonal anti-Prosurfactant protein C | Abcam, ab90716 | 1:250 | — |

Cell Culture and Transfection

HeLa (human cervical carcinoma) cells, A549 (non-small lung carcinoma) cells, MCF-7 (human breast carcinoma) cells, PC3 (prostate cancer) cells, HepG2 (human hepatocellular carcinoma), MDA-MB-231 (human breast carcinoma), PANC-1 (human pancreatic carcinoma), HTB-72 (SK-MEL-28) (human melanoma), U-87MG (human glioblastoma), U-118MG (human glioblastoma) cells and non-cancerous HaCaT (spontaneously transformed aneuploid immortal keratinocyte cell line from adult human skin), HEK-293 (human embryonic kidney), TREx-293 (human Embryonic kidney), PGA (mouse primary glia and astrocyte) cells were grown in DMEM culture medium and H358 (non-small cell lung cancer), THP1 (human Leukemic monocyte), KG-1α (acute myeloid leukemia) and WI38 (fibroblast derived human lung) cells were grown in RPMI-1640 and EMEM culture medium supplemented with 10% FCS, 2 mM L-glutamine, 100 U/ml penicillin, 100 μg/ml streptomycin, 1 mM sodium pyruvate and non-essential amino acids, and maintained in a humidified atmosphere at 37° C. with 5% $CO_2$.

RNA Sequences

SMAC/Diablo Human Specific siRNA used include:

```
si-hSMAC-A:
                                     (SEQ ID NO: 20)
Sense         5'AAGCGGUGUUUCUCAGAAUUGtt3'
and (SEQ ID NO: 21)
antisense     5'AACAAUUCUGAGAAACCCGCtt3';

hSMAC-B:
                                     (SEQ ID NO: 22)
Sense,        5'GCAGAUCAGGCCUCUAUAAtt3';

(SEQ ID NO: 23)
antisense,    5'UUAUAGAGGCCUGAUCUGCtt3';

si-hSMAC-C:
                                     (SEQ ID NO: 24)
sense         5'CCCGGAAAGCAGAAACCAAtt3', (SEQ ID NO: 25)
antisense,    5'UUGGUUUCUGCUUUCCGGGtt3';

si-hSMAC-D:
                                     (SEQ ID NO: 26)
sense         5'GCUGGCAGAAGCACAGAUAtt3', (SEQ ID NO: 27)
antisense     5'UAUCUGUGCUUCUGCCAGCtt3';
``` si-hSMAC-A1: Sense 5'AAGCGGUGUUUCUCAGAAUUGtt3', wherein the nucleotides at positions 5, 10, 16 and 21 (marked in bold and underline) are derivatized by 2'-O-Me (SEQ ID NO:28) and antisense 5'AACAAUUCUGAGAAACCCGCtt3' wherein the nucleotides at positions 6, 12, and 19 (marked in bold and underline) are derivatized by 2'-O-Me (SEQ ID NO:29);

si-hSMAC-A2: Sense 5'AAGCGGUGUUUCUCAGAAUUGtt3', wherein the nucleotides at positions 6, 9, and 21 (marked in bold and underline) are derivatized by 2'-O-Me (SEQ ID NO:30) and antisense 5'AACAAUUCUGAGAAACCCGCtt3' wherein the nucleotides at positions 7 and 12 (marked in bold and underline) are derivatized by 2'-O-Me (SEQ ID NO:31);

si-hSMAC-A3: Sense 5'AAGCGGUGUUUCUCAGAAUUGtt3', wherein the nucleotides at positions 3, 7, 11, and 16 (marked in bold and underline) are derivatized by 2'-O-Me (SEQ ID NO:32) and antisense 5'AACAAUUCUGAGAAACCCGCtt3' wherein the nucleotides at positions 6, 10 and 19 (marked in bold and underline) are derivatized by 2'-O-Me (SEQ ID NO:33);

si-hSMAC-A4: Sense 5'AAGCGGUGUUUCUCAGAAUUGtt3', wherein the nucleotides at positions 3, 6, 11, and 21 (marked in bold and underline) are derivatized by 2'-O-Me (SEQ ID NO:34) and antisense 5'AACAAUUCUGAGAAACCCGCtt3' wherein the nucleotides at positions 6, and 19 (marked in bold and underline) are derivatized by 2'-O-Me (SEQ ID NO:35);

hSMAC-B1: Sense, 5'GCAGAUCAGGCCUCUAUAAtt3', wherein the nucleotides at positions 4, 9, and 15 (marked in bold and underline) are derivatized by 2'-O-Me (SEQ ID NO:36); antisense, 5'UUAUAGAGGCCUGAUCUGCtt3', wherein the nucleotides at positions 4, 9, 15, and 18 (marked in bold and underline) are derivatized by 2'-O-Me (SEQ ID NO:37);

hSMAC-B2: Sense, 5'GCAGAUCAGGCCUCUAUAAtt3', wherein the nucleotides at positions 4, 9, 13, and 17 (marked in bold and underline) are derivatized by 2'-O-Me (SEQ ID NO:38); antisense, 5'UUAUAGAGGCCUGAUCUGCtt3', wherein the nucleotides at positions 6, 12, and 18 (marked in bold and underline) are derivatized by 2'-O-Me (SEQ ID NO:39);

hSMAC-B3: Sense, 5'GCAGAUCAGGCCUCUAUAAtt3', wherein the nucleotides at positions 6, 10, and 15 (marked in bold and underline) are derivatized by 2'-O-Me (SEQ ID NO:40); antisense, 5'UUAUAGAGGCCUGAUCUGCtt3', wherein the nucleotides at positions 2, 9, and 17 (marked in bold and underline) are derivatized by 2'-O-Me (SEQ ID NO:41);

hSMAC-B4: Sense, 5'GCAGAUCAGGCCUCUAUAAtt3', wherein the nucleotides at positions 4, 13, and 17 (marked in bold and underline) are derivatized by 2'-O-Me (SEQ ID NO:42); antisense, 5'UUAUAGAGGCCUGAUCUGCtt3', wherein the nucleotides at positions 8, 13, and 18 (marked in bold and underline) are derivatized by 2'-O-Me (SEQ ID NO:43);

non-targeting siRNA (si-NT): sense: 5' GCAAACAUCCCAGAGGUAU3' (SEQ ID NO:44) antisense: 5' AUACCUCUGGGAUGUUUGC3' (SEQ ID NO:45).

The siRNAs were synthesized by Genepharma (Suzhou, China). Cells were seeded (150,000 cells/well) on 6-well culture dishes to 40-60% confluence and transfected with 10-100 nM si-NT or si-hSMAC/Diablo using the JetPRIME transfection reagent (Illkirch, France), according to the manufacturers' instructions.

Cells were transiently transfected with pcDNA3.1 plasmid (0.5-2 μg DNA) encoding SMAC/Diablo-GFP or pEGFP encoding for GFP using the JetPRIIVIE reagent according to the manufacturer's instructions.

Cell Death Analysis

Cells death was analyzed by propidium iodide (PI) staining and flow cytometer (Beckton-Dickinson, San Jose, Calif.) and BD CellQuest Pro software, or using acridine orange ethidium bromide staining (Abu-Hamad, S., et al., 2009. J Cell Sci, 122(Pt 11): p. 1906-1916).

Determination of Cellular ATP Levels

Cellular ATP levels were estimated using the luciferase-based assay (CellTiter-Glo, Promega). Cells were transfected with si-hSMAC and 48 h and 72 h post-transfection, were washed twice with PBS and seeded in 96-well plates at densities of $5 \times 10^4$ cells/ml (A549, HeLa cells and H358, non-small cell lung cancer cells). ATP levels were assayed according to the manufacturer's protocol and luminescence was recorded using an Infinite M1000 plate reader.

Cell Cycle Analysis

For cell cycle analysis, cells were harvested, washed with PBS and fixed with ice-cold 70% ethanol overnight at −20° C. The cells were then washed with PBS, incubated with RNase A (100 μg/ml) in PBS for 30 min at 37° C. Then the cells were incubated with PI (1 μg/ml) before analysis on a flow cytometer (iCyt Eclipse EC800, UK). Single cells were gated and a minimum of 10,000 cells acquired and analyzed by FACS Eclipse analyzer.

Sulforhodamine B (SRB) Cell Proliferation Assay

Twenty-four hours post-transfection with si-NT or si-hSMAC, cells (10,000/well) were counted and seeded in 96-well plates. After additional 48, 72 or 96 hours, the cells were washed with PBS, fixed with 10% trichloroacetic acid, and stained with SRB. SRB was extracted from the cells using 100 mM Tris base and absorbance at 510 nm was determined using an Infinite M1000 plate reader (Tecan, Mannedorf, Switzerland).

Xenograft Experiments

Five-week-old male athymic Swiss nude mice (weight ~19-22 g) were obtained from Envigo and allowed a week of acclimatization to their new surroundings. Lung cancer cells A549 ($3\times10^6$), or breast cancer cells MDA-MB231 ($3\times10^6$) were injected subcutaneous (s.c.) into the hind leg flanks of the mice. Approval for the experimental protocol was obtained from the Institutional Animal Care and Use Committee of the Soroka University Medical Center. Eleven days after inoculation, the developing tumors were measured in two dimensions with a digital caliper and tumor volume was calculated as follows: volume=$X^2 \times Y/2$, where X and Y are the short and long tumor dimensions, respectively. Mice with xenografts reaching a volume of 65-100 mm$^3$ were randomized to receive either non-targeting (NT) siRNA or siRNA targeted to human hSMAC (si-hSMAC); 5 animals in each group. Tumors and section thereof that received NT siRNA are designated si-NT-TTs (siRNA non-targeting treated tumors) and tumors and section thereof that received hSMAC siRNA are designated si-hSMAC-TTs (siRNA hSMAC treated tumors). Treatment substances were injected into the established s.c. tumors using the jetPEI delivery reagent (10 µg siRNA/20 µl jetPEI). The tumors were injected (at a volume equal to 10 to 20% of the tumor volume) with si-NT or the appropriate si-hSMAC every three days. Beginning on the day of inoculation, mouse weight and tumor volume were monitored twice a week using a digital caliper. At the end of the experiment, i.e. when tumor volume reached approximately 1300 mm$^3$, the mice were sacrificed using $CO_2$ gas, the tumors were excised and ex vivo weight was determined. Half of each tumor was fixed in 4% buffered formaldehyde, paraffin-embedded and processed for histological examination, while the second half was frozen in liquid nitrogen and stored in −80° C. for immunoblot analysis.

Quantitative Real-Time PCR (q-PCR)

Total RNA was isolated from cells using an RNeasy mini kit (Qiagen) according to the manufacturer's instructions. Complementary DNA was synthesized from 1 µg total RNA using a Verso cDNA synthesis kit (Thermo Scientific). q-PCR was performed using specific primers (KiCqStart Primers; Sigma Aldrich) in triplicates, using Power SYBER green master mix (Applied Biosystems, Foster City, Calif.). The levels of the target genes were normalized relative to β-actin mRNA levels. Samples were amplified by a 7300 Real Time PCR System (Applied Biosystems) 95° C. for 2 minutes and for 40 cycles using the following PCR parameters: 95° C. for 15 seconds, 60° C. for 1 minute, and 72° C. for 1 minute. The copy numbers for each sample were calculated by the CT-based calibrated standard curve method. The mean fold changes (±SEM) of the three replicates were calculated. The target genes examined and the forward and reverse sequences of the primers used are listed in Table 2 hereinbelow.

TABLE 2

Real-time PCR primers

| Gene | Primers | SEQ ID NO. |
|---|---|---|
| β-Actin | Forward 5'-ACTCTTCCAGCCTTCCTTCC-3' | 79 |
|  | Reverse 5'-TGTTGGCGTACAGGTCTTTG-3' | 80 |
| SMAC/ Diablo | Forward 5'-CTGACTTCTACTTCCAGGCTGTT-3' | 81 |
|  | Reverse 5'-GCTCCTATGATCACCTGCCA-3' | 82 |
| XIAP | Forward 5'-GCACGGATCTTTACTTTTGGG-3' | 83 |
|  | Reverse 5'-GGGTCTTCACTGGGCTTC-3' | 84 |
| cIAP1 | Forward 5'-ATCTAGTGTTCCAGTTCAGCC-3' | 85 |
|  | Reverse 5'-ACCACTTGGCATGTTCTACC-3' | 86 |
| cIAP2 | Forward 5'-CATGCCAAGTGGTTTCCAAG-3' | 87 |
|  | Reverse 5'-TCTGCATTTTCATCTCCTGGG-3' | 88 |
| AIF | Forward 5'-AAGCACGCTCTAACATCTGG-3' | 89 |
|  | Reverse 5'-TTCTCCAGCCAATCTTCCAC-3' | 90 |
| Cyto-chrome c | Forward 5'-TTTGGATCCAATGGGTGATGTTGAG-3 | 91 |
|  | Reverse 5'TTGAATTCCTCATTAGTAGCTTTTTTGAG-3 | 92 |
| caspase 8 | Forward 5'-GGAGCTGCTCTTCCGAATTA-3 | 93 |
|  | Reverse 5'-GCAGGTTCATGTCATCATCC-3' | 94 |
| caspase 9 | Forward 5'-CTAGTTTGCCCACACCCAGT-3' | 95 |
|  | Reverse 5'-TGCTCAAAGATGTCGTCCAG-3' | 96 |
| caspase 3 | Forward 5'-AGGACTCTAGACGGCATCCA-3' | 97 |
|  | Reverse 5'-TGACAGCCAGTGAGACTTGG-3' | 98 |
| Ki-67 | Forward 5'-CTTTGGGTGCGACTTGACG-3' | 99 |
|  | Reverse 5'-GTCGACCCCGCTCCTTTT-3' | 100 |
| IL-6 | Forward 5'-CTCAATATTAGAGTCTCAACCCCCA-3' | 101 |
|  | Reverse 5'-AAGGCGCTTGTGGAGAAGG-3' | 102 |

TABLE 2-continued

Real-time PCR primers

| Gene | Primers | SEQ ID NO. |
|---|---|---|
| STAT3 | Forward 5'-GCTTTTGTCAGCGATGGAGT-3' | 103 |
| | Reverse 5'-TCTGCTAATGACGTTATCCAGTT-3' | 104 |
| NOS1 | Forward 5'-CAGTGATGATAGGATAAAGGAGGGA-3' | 105 |
| | Reverse 5'-CATCATGAGCCCGTCCGC-3' | 106 |
| SOD2 | Forward 5'-TAAACGTAGTGTCCACGGCA-3' | 107 |
| | Reverse 5'-TTTCCACACGCTTATCTGCGA-3' | 108 |
| FOXRED2 | Forward 5'-TCAACCTCCCAAGTAGCTGG-3' | 109 |
| | Reverse 5'-TTAGGAGGCCAAGACAGGTG-3' | 110 |
| PTGS2 | Forward 5'-CTCCTGTGCCTGATGATTGC-3' | 111 |
| | Reverse 5'-AACTGATGCGTGAAGTGCTG-3' | 112 |
| PCSK5 | Forward 5'-TGGCACAGTCTACCGGAAAT-3' | 113 |
| | Reverse 5'-CCTGAGAGTGGAATGGTGGT-3' | 114 |
| SLC4A4 | Forward 5'-GGCTTCTTCTCTCCCACAGT-3' | 115 |
| | Reverse 5'-TTCTTGGTTTGATGCCGGTG-3' | 116 |
| GAS6 | Forward 5'-GGAGAAGACACCACCATCCA-3' | 117 |
| | Reverse 5'-TCCCAGGTTGATTCAGTCCC-3' | 118 |

Next-Generation Sequencing (NGS) and Functional Analysis

Libraries were prepared by the INCPM-RNA-seq unit (Weizmann Institute, Israel). Briefly, polyA fraction (mRNA) was purified from 500 ng of total RNA, isolated as above, followed by fragmentation and generation of double stranded cDNA. End repair, a base addition, adapter ligation and PCR amplification steps were performed according to established methods. Libraries were evaluated by Qubit and TapeStation. Sequencing libraries were constructed with barcodes to allow multiplexing of 20 samples in one lane. Between 22 and 26 million reads single-end 60-bp reads were sequenced per sample on Illumina HiSeq 2500 V4 instrument.

Bioinformatics analyses were carried out at the Bioinformatics Core Facility at the National Institute for Biotechnology in the Negev, Ben-Gurion University. Raw sequence reads were assessed for quality using FASTQC and further trimmed for removal of remaining adaptors and low quality bases using Trimmomatic. The trimmed reads from each sample were separately aligned to the human and mouse genomes (GRCh38 and GRCm38.75, respectively) using STAR v2.3.0 with default settings. An average of 23.7±0.8 million reads per sample was obtained. Of these, an average of 13, 2.6, 7.8 and 0.3 million reads were mapped to human only, mouse only, both human and mouse, and none of them, respectively. After rejection of multi-mapped reads, a total of 11.5±2.5 human-specific, uniquely mapped reads, and 2.3±1.7 mouse-specific, uniquely mapped reads were subjected for further analysis. The number of aligned reads per gene per sample were counted using HTSeq count with "intersection-nonempty" (to handle reads that overlap with more than one gene) and "no stranded" as parameters. The other parameters were set to their default. Normalization and statistical analysis for differential expression were carried out using DESeq2 v1.6.3. Fold change values were converted to linear scale, with a minus sign indicating down-regulation.

Differentially expressed genes were defined as those having a p-value <0.05, and linear fold change >1.5 and <−1.5. Functional analysis was performed using the Gene Ontology system, DAVID and Expander software tools.

Patient-Derived Samples

Chronic lymphocytic leukemia (CLL) blood samples were obtained from Soroka University Medical Center from patients not receiving any disease treatment. Blood samples were also obtained from healthy volunteers. Peripheral blood mononuclear cells (PBMCs) were isolated from venous blood of CLL patients by Ficoll-Paque PLUS (GE Healthcare) density gradient centrifugation as described previously (Admoni-Elisha, L., et al., 2016. PLoS One, 2016. 11(4): p. e0148500).

Fresh lung cancerous and non-cancerous tissue specimens were obtained from the same lung cancer patients undergoing either pneumonectomy or pulmonary lobectomy to remove tumor tissue and were immediately frozen in liquid nitrogen and maintained at −80° C. until use. Cancer and normal lung tissue surrounding the tumor were validated by hospital pathologists. Proteins were extracted from the tissue sample using a lysis buffer (50 mM Tris-HCl, pH 7.5, 150 mM NaCl, 1 mM EDTA, 1.5 mM $MgCl_2$, 10% glycerol, 1% Triton X-100, a protease inhibitor cocktail (Calbiochem), followed by sonication and centrifugation (10 min, 600 g). Protein concentration was determined and samples were stored in −80° C. until use.

The research was approved by the Soroka University Medical Center Advisory Committee on Ethics in Human Experimentation and conducted in accordance with national laws and regulations, the ethical principles set forth in the Declaration of Helsinki and with good clinical practice as described in the ICH guidelines. Written informed consent was obtained from all participants prior to entry into the study. All subjects received a copy of their signed and dated informed consent form.

Immunohistochemistry

Tissue microarrays (MC5003, LC807) containing cancer and normal tissues purchased from US Biomax (US Biomax, Inc. USA) and formalin-fixed and paraffin-embedded tumor sections were immunohistochemistry (IHC) stained. Sections were deparaffinized using xylene and a graded ethanol series. Endogenous peroxidase activity was blocked by incubating the sections in 3% $H_2O_2$ for 10 minutes. Antigen retrieval was performed in 0.01M citrate buffer (pH 6.0) in 95° C.-98° C. for 20 minutes. After washing sections with PBS containing 0.1% Triton-X100 (pH 7.4), non-specific antibody binding was reduced by incubating the sections in 10% normal goat serum for 2 hr.

After decanting excess serum, sections were incubated overnight at 4° C. with primary antibodies (sources and dilutions are detailed in Supplementary Table 1). Sections were washed with PBST. For IHC, endogenous peroxidase activity was blocked by incubating the sections in 3% $H_2O_2$ for 15 min. After washing thoroughly with PBST, the sections were incubated for 2 h with anti-mouse or anti rabbit (1:250) secondary antibodies conjugated to HRP, as appropriate. Sections were washed five times in PBST and the peroxidase reaction was subsequently visualized by incubating with 3,3-diaminobenzidine (DAB) (ImmPact-DAB, Burlingame, Calif.). After rinsing in water, the sections were counterstained with hematoxylin, and mounted with Vectashield mounting medium (Vector Laboratories, Burigame, Calif.). Finally, the sections were observed under a microscope (Leica DM2500) and images were collected at 20× magnification with the same light intensity and exposure time.

Immunoblot Staining

For immunostaining, membranes containing electrotransferred proteins following SDS-PAGE were blocked with 5% non-fat dry milk in TBS (10 mM Tris 150 mM NaCl, pH 7.8) containing 0.1% Tween-20, incubated with the primary antibodies (sources and dilutions as detailed in Table 1 or in the corresponding example). Following washing 3 times with TBST (10 mM Tris 150 mM NaCl, pH 7.8 containing 0.05% Tween-20) the membranes were incubated with HRP-conjugated anti-mouse or anti-rabbit (1:10,000) or anti-goat (1:20,000) IgG. Enhanced EZ-ECL chemiluminescence detection kit (Cat: 20-500-120), Biological Industries, Beit—Haemek, Ill.) was used for detection of HRP activity. Band intensity was quantified using FUSION-FX (Vilber Lourmat, France).

TUNEL Assay

Tumor sections were processed for the TUNEL assay using the DeadEnd Fluorometric TUNEL system (Promega, Madison, Wis.) according to the manufacturer's instructions. Sections were deparaffinized, equilibrated in PBS, permeabilized with proteinase K (20 µg/ml in PBS), post-fixed in 4% paraformaldehyde, and incubated in TdT reaction mix (Promega) for 1 h at 37° C. in the dark. Slides were then washed in 2× saline-sodium citrate (SSC) buffer and counter-stained with PI (1 µg/ml), and cover slipped with Vectashield mounting medium (Vector Laboratories, Burigame, Calif.). Fluorescent images of apoptotic cells (green) and cell nuclei (red) were captured using a confocal microscope (Olympus 1X81).

Lipid Extraction

Lipids were extracted from si-NT-TTs and si-hSMAC-A-TTs as described previously (Folch, J., M. et al., 1957. J Biol Chem, 226(1): p. 497-509.). Briefly, 10-20 mg of tissue were added to $CHCl_3$/MeOH (2:1, v/v) (7.5 mg/ml) and homogenized twice using ultrasound sonication. Water (12 µl/mg) was added to the suspension; the tube was closed with a glass cap and shaken at room temperature for 2 h at 400 rpm. The suspension was heated to 60° C. for 10 min and subsequently stored at 8° C. for more than 1 h in order to denature proteolipids. Undissolved material was separated by filtration through a Syringe Filter (0.4 µm pore). After evaporation of solvent, the residue was re-dissolved in $CHCl_3$/MeOH. The suspension was filtered and the solvent was evaporated again. The weight of the extracted lipids was determined.

Estimation of Phospholipids, Phosphatidylcholine and Phosphatidylethanolamine

Phospholipids content of the lipids extracted from si-NT-TTs and si-hSMAC-A-TTs as described above was determined based on the formation of a complex of the phospholipids with ammonium ferrothiocyanate as described previously (Stewart, J. C., 1980. Anal Biochem, 104(1): p. 10-14). The absorbance at 488 nm was determined and the amounts of phospholipids were calculated using phosphatidylcholine (PC) a standard (10-100 µg). For phosphatidylcholine (PC) determination, samples of the extracted lipids were analyzed using ammonium thiocyanatocobaltate reagent as described previously (Yoshida, Y., E. et al., 1979. J Biochem, 86(3): p. 825-828). The absorbance at 316 nm was measured and PC amount was calculated using a phosphatidylcholine standard (10-100 µg).

Phosphatidylethanolamine (PE) content of the lipids extracted from si-NT-TTs and si-hSMAC-A-TTs was measured using a fluorescence-based assay as described previously (Jae-Yeon Choi et al. 2018. J. Biol. Chem 293, 1493-1503). Briefly, samples of lipid extracted from tumors as described above were dissolved in chloroform and after then chloroform was evaporated under gas nitrogen. The dried extract was then re-suspended in 0.8 mM Triton X-100. To 20 µl of lipid samples, reaction mixture including 50 µl reaction buffer (80 mM NaCl, 2 mM KPO4, pH 7.4), 30 µL $H_2O$ and 12.5 µl borate buffer (100 mM boric acid, NaCl 75 mM, sodium tetraborate 25 mM, pH, 9) were added and placed in 96 well plate and mixed well. 12.5 µl of 100 µM distyrylbenzene-bis-aldehyde (DSB-3), kindly provided by Prof. Uwe Bunz, (Organisch-Chemisches Institute, Heidelberg, Germany) prepared in 10 mM $KH_2PO_4$, pH 7.4 were then added. After 2 h of incubation in dark with shaking at 100 rpm, fluorometric detection of PE was carried out at $\lambda ex=403$ nm, $\lambda em=508$ nm, using a plate reader. A standard curve using purified PE was carried out in parallel.

Example 1: Expression of SMAC/Diablo in Tumors

Expression levels of SMAC/Diablo in tissue microarray slides containing samples of randomly selected normal (10-20 healthy) controls and different types of malignant cancer (40 to 80) were assessed by immunohistochemistry (IHC) using SMAC/Diablo-specific antibodies (FIG. 1A). Marked increase in SMAC/Diablo expression level was observed in various cancer tissues, including lung, B-lymphoma, testis, colon, stomach, breast, prostate, and skin. No significant increase in SMAC/Diablo level was observed in brain, ovary, uterine, bladder, cervix, uterus, esophagus, head and neck, intestinal mucous membrane, kidney, liver, or oral cavity cancer tissues (data not shown).

Figure 1B:
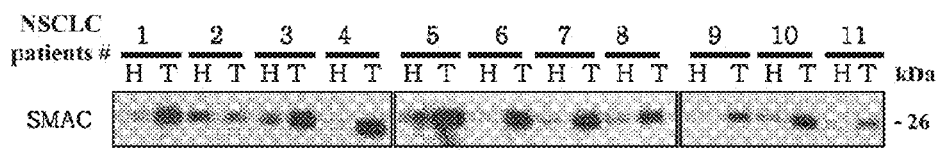
Figure 1C:
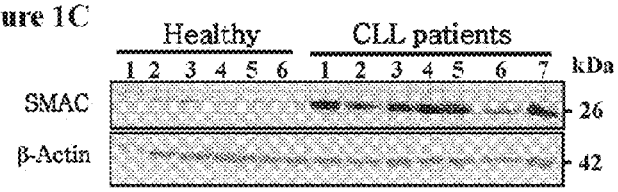
Figure 1D:
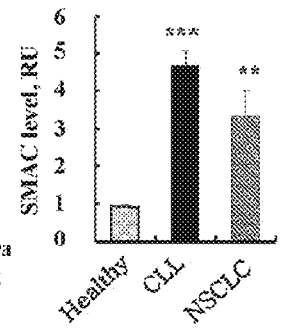

Levels of SMAC/Diablo expression were higher in samples of lung cancer (non-small cell lung cancer; NSCLC), relative to samples of adjacent healthy tissue from the same lung (FIG. 1B). Quantitative analysis showed 3.5-fold higher levels of SMAC/Diablo expression in NSCLC tissue samples, relative to corresponding healthy tissue (FIG. 1D). Immunoblotting analysis showed an approximately six-fold increase in the expression of SMAC/Diablo in peripheral blood mononuclear cells (PBMCs) from chronic lymphocytic leukemia (CLL) patients, as compared to PBMCs from healthy donors (FIG. 1C, D).

Figure 1E:
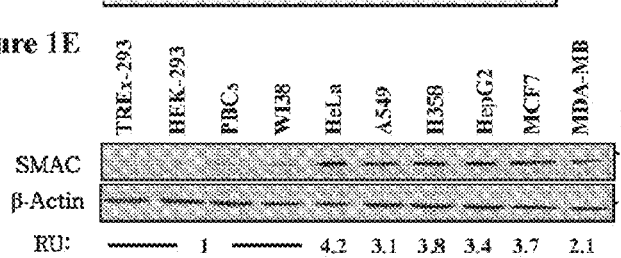
Figure 1F:
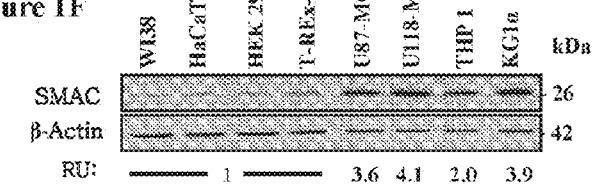

The expression level of SMAC/Diablo in cancerous cell lines, including HeLa, A549, H358, HepG2, MCF7, MDA-MB-231, U-87MG, U-118MG, THP1, and KG-1α cells, were about 2-4 fold higher compared to the non-cancerous TREx-293, HEK-293, HaCaT and WI-38 cell lines (FIG. 1E,F).

Example 2: Silencing of SMAC/Diablo Inhibits Cell Growth

The function of SMAC/Diablo in cancer was explored by silencing its expression in a number of human-derived cancer cell lines of various origins (i.e., HeLa, A549, H358, MCF-7, PC3, HepG2, MDA-MB-231, PANC-1, and HTB-72) using siRNA specific to human SMAC/Diablo (designated si-hSMAC-A, comprising a sense stand having the nucleic acid sequence set forth in SEQ ID NO: SEQ ID NO:20 and an antisense strand having the nuclkeic acid sequence set forth in SEQ ID NO:21). SMAC/Diablo protein expression levels were markedly decreased (80-90%) in all tested cell lines (FIG. 2A), with a maximum of 90% decrease seen after 48 h. Ninety-six h post-transfection, the inhibition level dropped to 65%, most probably due to degradation of the siRNA or its dilution in the growing cells (exemplified with non-small lung carcinoma cell lines A549 and H358 FIG. 2B, C and Hela Cells, FIG. 2D, E).

The effect of the SMAC/Diablo silencing on cell growth was examined using the sulforhodamine B (SRB) assay. In the three cell lines tested (HeLa, A549, and H358), a marked 70-80% decrease in cell proliferation was observed 120 h post-transfection with si-hSMAC-A, whereas the control transfected with non-targeting siRNA (si-NT) showed no significant effect on cell growth (FIG. 2F). Interestingly, in immortalized non-cancerous cell lines, including WI38 and HaCat, si-hSMAC-A decreased SMAC/Diablo expression (FIG. 2G), yet did not affect cell growth (FIG. 2H). Three other siRNAs designed to target hSMAC (B to D as described hereinabove) were also found to inhibit SMAC/Diablo expression and cell growth to various degrees (FIG. 2I, 2J).

si-hSMAC-A and si-hSMAC-B were modified by 2'-O methylation (2'-O Me) to form si-hSMAC-A1, si-hSMAC-A2 si-hSMAC-A3 si-hSMAC-A4 si-hSMAC-B1 si-hSMAC-B2 si-hSMAC-B3 and si-hSMAC-B4 described hereinabove. The effect of these modified forms on SMAC/Diablo expression and on cell proliferation was examined using 30 and 50 nM of each inhibitory RNA molecule in the lung cancer line A549. Of the examined si-hSMAC-A modified molecules, si-hSMAC-A1 and si-hSMAC-A4 were found to be most active in reducing cell proliferation (FIG. 14C), and of the examined si-hSMAC-B modified molecules, si-hSMAC-B2 and si-hSMAC-B3 were found to be most active (FIG. 14F).

Lung cancer cells (A549) treated with si-hSMAC-A, the most active siRNA, showed a significant decrease in the number of cells expressing the cell proliferation factor/marker Ki-67 as reflected by a decrease of about 85% in Ki-67 positive cells (FIG. 2K).

Figure 2L:
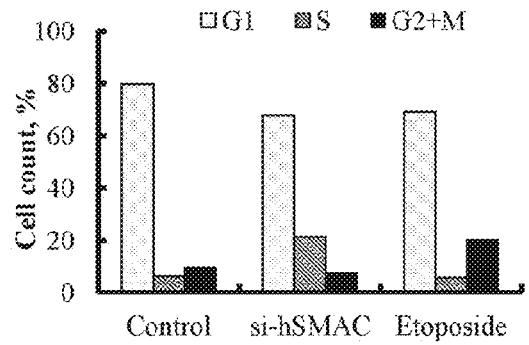

As Ki-67 levels are increased with cell cycle progression, this decrease in expression suggests that cells treated with si-hSMAC-A do not advance in the cell cycle. Cell cycle analysis revealed an about 3-fold increase in the number of cells in S-phase in si-hSMAC-treated A549 cells relative to etoposide-treated cells (a chemotherapy medication used for the treatments of a number of types of cancer, including lung cancer) (FIG. 2L), suggesting that SMAC/Diablo-depleted cells have decreased capacity to proceed in S phase.

Figure 2M:
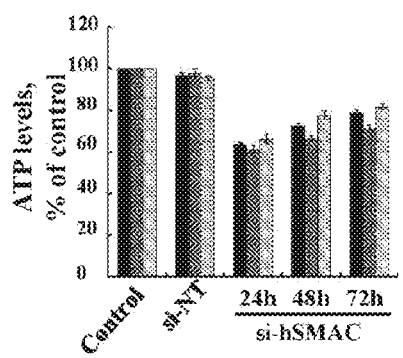

Silencing SMAC/Diablo in HeLa, A549, and H358 cells reduced cellular ATP levels by 20-35% (FIG. 2M), which may contribute to the observed inhibition of cell growth.

Figure 3A:
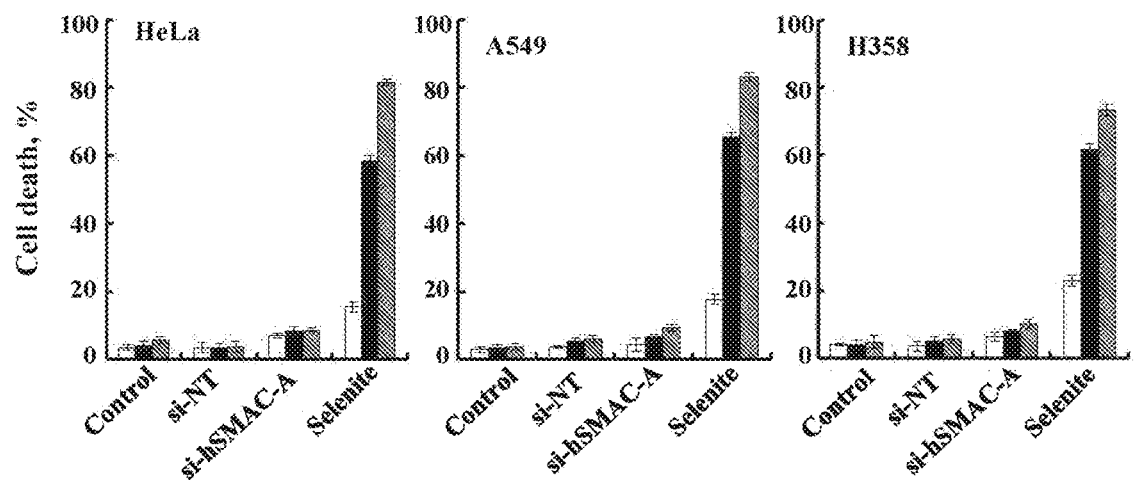
FIG. 3 depicts cell death induced by overexpression of exogenous SMAC/Diablo: (A) Bar-graph represents % of cell death induced by si-NT or si-hSMAC-A (50 nM) or selenite (5 μM) in HeLa, A549 and H358 cells. Cells were transfected with si-NT or si-hSMAC-A and analyzed for cell death after 24 h (white bar), 48 h (black bar) and 72 h (gray bar) using propidium iodide (PI) staining by flow cytometry. Selenite (5 μM) used as positive control; (B) Representative cell death analysis of A549 cells treated with si-NT or si-hSMAC-A (50 nM, 48 h) or selenite (10 μM, 24 h) using FITC-Annexin V/PI staining and flow cytometry. (C) Qantitative analysis of cell deathin cells treated for the indicated time with 50 nM si-NT (black bar) or si-hSMAC-A (gray bar) or selenite using FITC-Annexin V/PI staining by flow cytometry. (D, E) Representative immunoblot staining by anti-SMAC/Diablo antibodies of cell lysate from HeLa, A549 and H358 cells 48 h of post-transfection with pEGFP encoding plasmid (D) or SMAC/Diablo-GFPpcDNA 3.1 plasmid (0.75 μg) (E); (F) Bar-graph representing % of cell death induced by GFP or SMAC/Diablo-GFPpcDNA 3.1 plasmid (1 μg-2 μg) in HeLa, A549 and H358 cells. Cells death was analyzed after 24 and 48 hour using PI staining by flow cytometry.
Figure 3B:
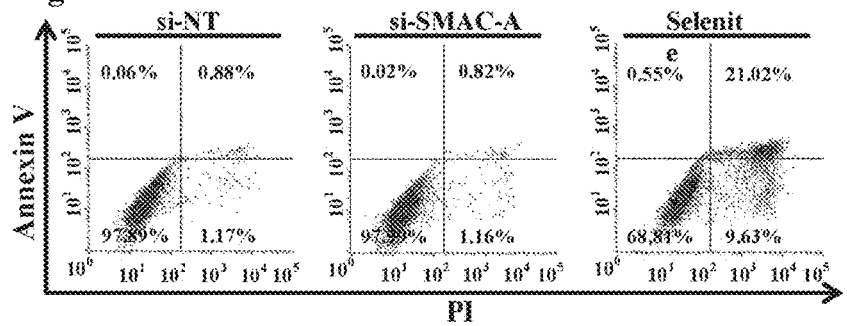
Figure 3C:
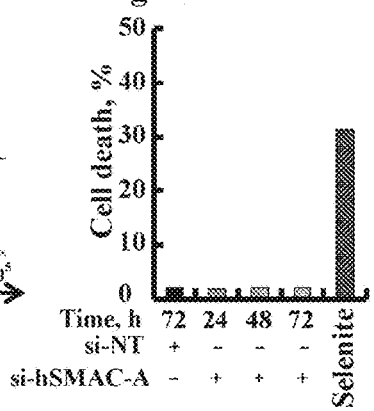
Figure 3D:
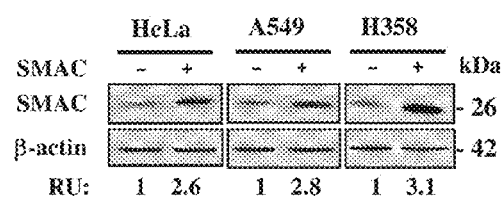
Figure 3E:
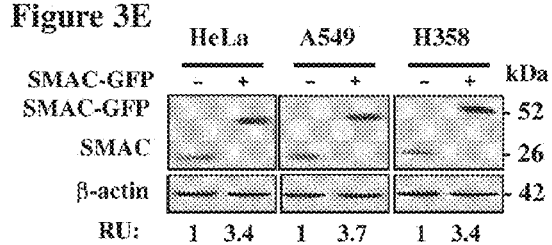
Figure 3F:
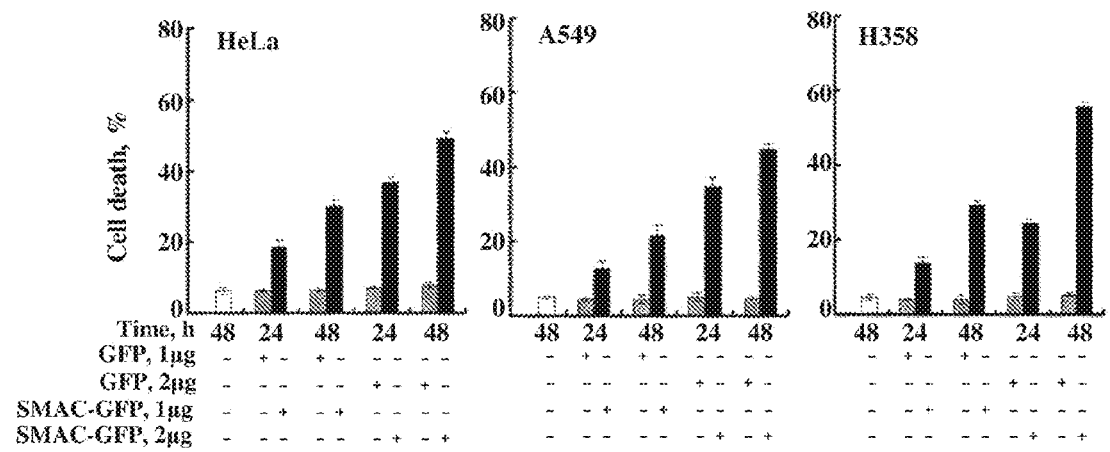

There was no significant cell death (5-10%) of HeLa, A549 or H358 cells silenced for SMAC/Diablo (FIG. 3A-C), suggesting that the decrease in cell growth was due to inhibition of cell proliferation rather than enhanced cell death. As expected, cell death was induced by selenite. Moreover, apoptosis was induced by over-expressing SMAC/Diablo or SMAC/Diablo-GFP in HeLa, A549 and H358 cells in a concentration- and time-dependent manner, again as expected (FIG. 3D-F).

Example 3: Silencing SMAC/Diablo Expression Inhibits Tumor Growth in Mice

The effect of si-hSMAC-A was tested on a sub-cutaneous (s.c) tumor xenograft of A549 cells established in nude mice (FIG. 4). Following tumor formation (75-90 mm$^3$), the mice were divided into three matched groups, and injected every 3 days with either si-NT (group 1) or si-hSMAC-A at 350 nM (group 2) or 700 nM (group 3). Tumor growth was followed for 39 days (FIG. 4A). In animals injected with si-NT-treated tumors (TTs), tumor volume increased by 13-fold, whereas 700 nM si-hSMAC-A treatment reduced growth markedly (FIG. 4A). Comparing tumor sizes at the end point revealed decrease of 50% and 85% in si-hSMAC-A-TTs at the 350 nM and 700 nM levels, respectively.

Figure 4A:
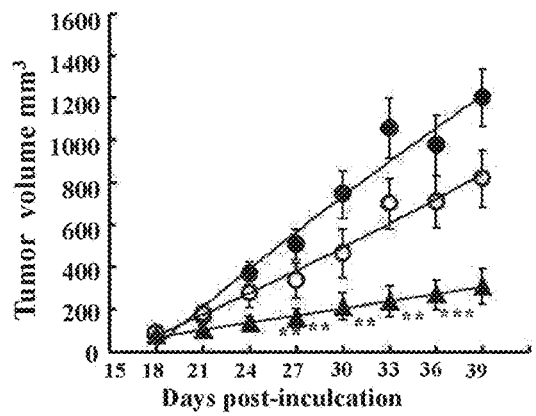
FIG. 4 depicts inhibition by si-hSMAC-A of tumor growth of lung cancer xenografts: (A) A549 cells were inoculated into nude mice ($3\times10^6$ cells/mouse). Tumor volumes were monitored, and on day 18, mice with similar average tumor volumes (75-90 mm$^3$) were divided into three groups (n=5). Xenografts were injected with si-NT (●, 50 nM) or si-hSMAC (350 nM (○) or 700 nM (▲)). The size of the xenografts was measured and average tumor volumes are presented as means±SEM, p:≤0.01; p: *≤0.001; (B) Representative tumors; (C) Weights of dissected tumors from mouse A549 cell xenografts after treatment with si-NT (si-NT treated tumors, si-NT-TTs) or si-hSMAC-A (si-hSMAC treated tumors, si-hSMAC-A-TTs); (D) Representative sections from si-NT-TTs and si-hSMAC-A-TTs stained with anti-SMAC/Diablo antibodies; (E) Expression of α- and ε-SMAC/Diablo isoforms in RNA isolated from si-NT- and si-hSMAC-A-TTs using PCR and specific primers; (F) Representative sections from si-NT-TTs and si-hSMAC-A-TTs stained with anti-Ki-67 antibodies; and (G) Quantitative analysis of Ki-67 protein (grey bars) and mRNA (q-PCR) (black bars) levels in si-NT- and si-hSMAC-A-TTs.
Figure 4B:
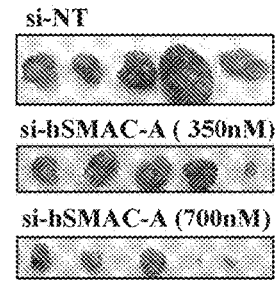
Figure 4C:
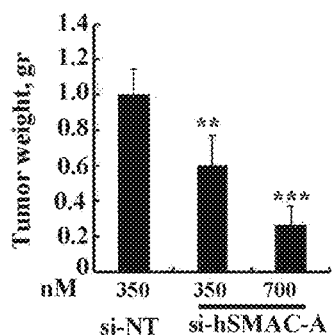
Figure 4D:
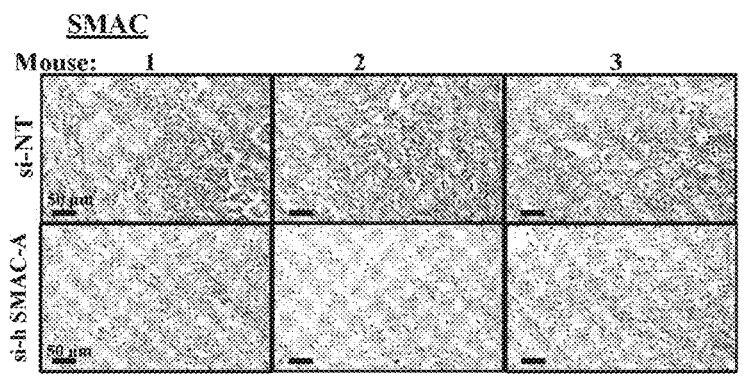
Figure 4E:
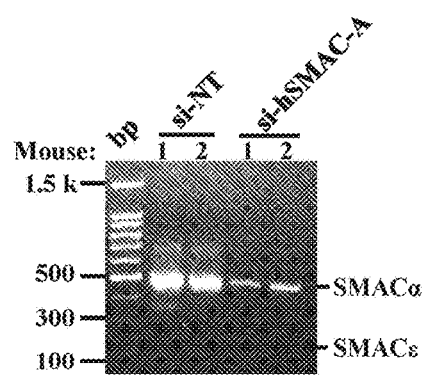
Figure 4F:
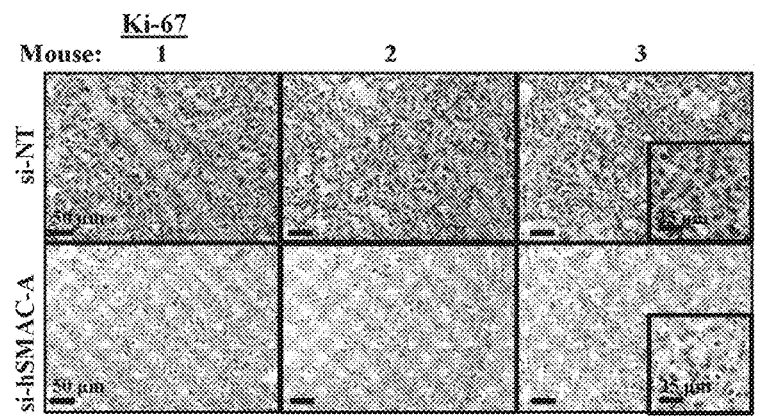
Figure 4G:
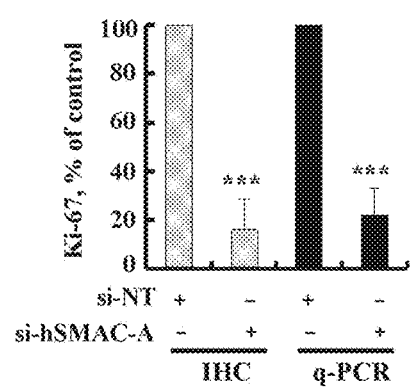
Figure 5A:
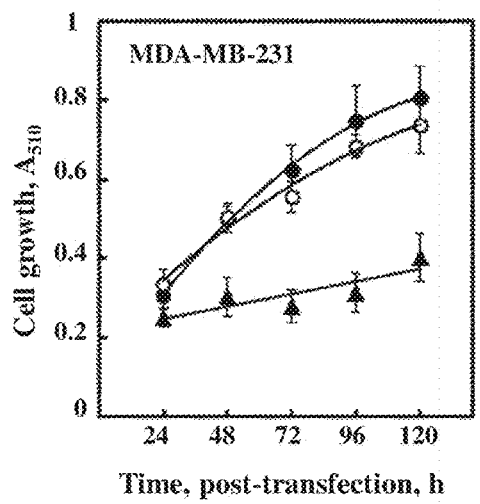
FIG. 5 depicts that si-hSMAC-A inhibited cell growth in vitro and tumor growth of breast cancer xenografts: (A) MDA-MB-231 cells were transfected with si-NT (50 nM) or si-hSMAC-A (100 nM) and analyzed for cell growth at the indicated time using the SRB method (n=3) (Control (●), si-NT (○), si-hSMAC-A (▲); (B) MDA-MB-231 cells were transfected with si-NT or si-hSMAC-A and at the indicated time cells were harvested and analyzed for SMAC/Diablo levels by immunoblotting. β-actin was used as a loading control; (C) MDA-MB-231 cells ($3\times10^6$ cells/mouse) were inoculated into nude mice. Tumor volumes were monitored (using a digital caliper) and on day 18, the mice were divided into two groups (n=8 each) with each mouse in the group containing a tumor with a volume between 60 and 100 mm$^3$ and similar average volumes measured per group. The two mice groups were subjected to the following treatments: Xenografts were injected with si-NT (●, 350 nM) or si-hSMAC-A (▲, 700 nM). (D) Represents photomicrograph of dissected tumors from mouse MDA-MB-231 cell xenografts treated with si-NT or si-hSMAC-A; (E) Bar-graph represents dissected tumors weight from MDA-MB-231 cell xenografts; calculated average tumor volumes are presented as means±SEM, ***P<0.001 (F, G) Dissected tumors were subjected to immunohistochemistry. Photomicrographs represent IHC staining of tumor sections from three mice from each group with (F) anti-SMAC/Diablo and (G) anti-Ki-67 antibodies. Bars represent 50 μm.
Figure 5B:
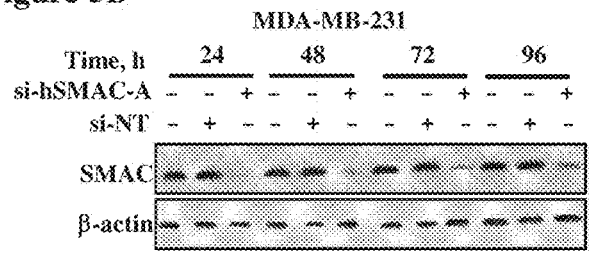
Figure 5D:
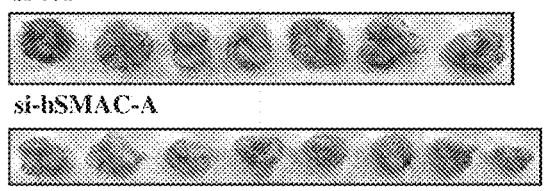
Figure 5C:
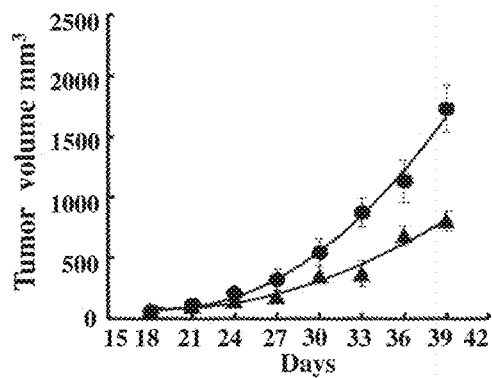
Figure 5E:
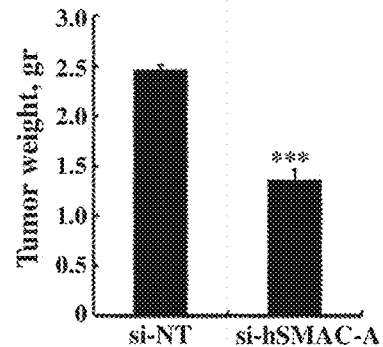
Figure 5F:
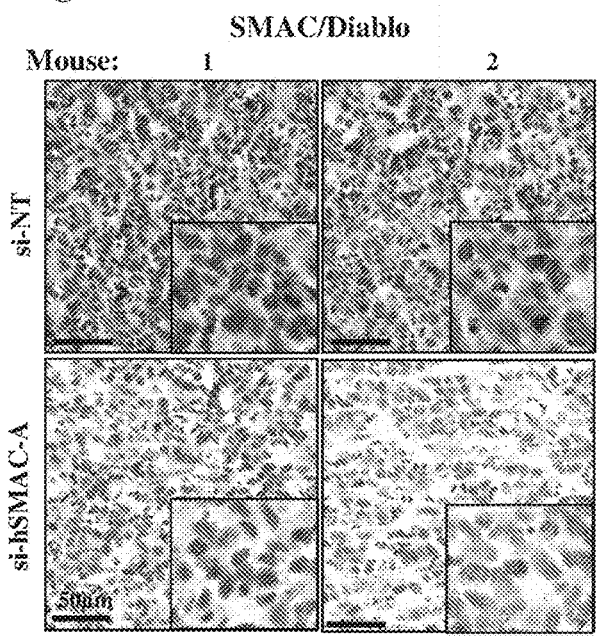
Figure 5G:
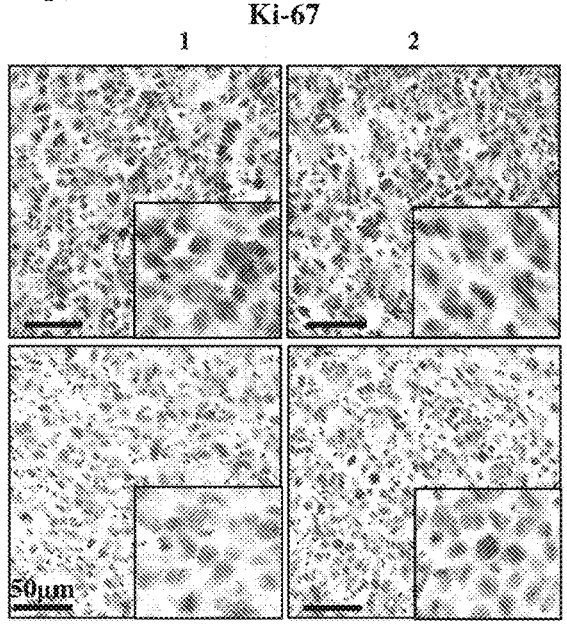

All mice were sacrificed 39 days post-cell inoculation, and the tumors were excised (FIG. 4B) and weighed (FIG. 4C). This revealed 40% and 75% decreases in tumor weight for 350 and 700 nM si-hSMAC-A-TTs, respectively, values similar to the calculated tumor volumes (FIG. 4A). Half of each tumor was next excised, fixed, and paraffin sections were analyzed by IHC. si-NT-TTs were strongly immunostained with anti-SMAC/Diablo antibodies. However, as expected, the staining was very weak in si-hSMAC-A-TTs (FIG. 4D). Similar results were obtained using qPCR (FIG. 4E). No expression of the alternative splice variant SMAC/Diablo-ε was found in the A549-derived tumors (FIG. 4E), although this isoform was previously detected in healthy human tissues and in several cancer cell lines (Martinez-Ruiz, G. U., et al., 2014. Int J Clin Exp Pathol 7, 5515-5526).

The expression levels of the cell proliferation factor Ki-67, as analyzed by IHC staining or q-PCR, were markedly decreased (~80%) in the si-hSMAC-A-TTs (FIG. 4F, G), similar to the results obtained with cancer cells in culture (FIG. 2K). Similar results were also obtained with MDA-MB-231 cells (FIG. 5).

Figure 6A:
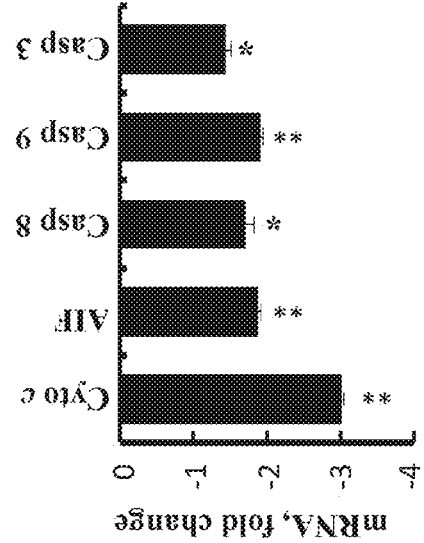
FIG. 6 depicts that silencing of SMAC/Diablo affects the expression of its associated proteins: (A, B) mRNA levels of SMAC/Diablo, XIAP, cIAP1, cIAP2, cytochrome c, AIF caspase 8, 9 and 3 as analyzed using q-PCR in siNT-TTs relative to si-hSMAC-A-TT (presented as fold change). (C) HeLa, A549 and H358 cells were transfected with si-NT or si-hSMAC-A (50 nM) and at the indicated time cells were harvested and analyzed for SMAC/Diablo, XIAP, Caspase 8, 9 and 3 by immunoblotting. β-actin was used as a loading control; (D) Quantitative analysis of the immunoblot was carried out and presented (relative units (RU)) for all cell lines at the 48 h (gray bar) and 96 h (black bar) of post-transfection (n=3); (E) Bar graph represents relative mRNA levels of SMAC/Diablo, XIAP, cIAP1 and cIAP2 using q-PCR technique in HeLa, A549 and H358 cells after 48 h (gray bar) and 96 h (black bar) of post-transfection with si-hSMAC-A (50 nM).
Figure 6B:
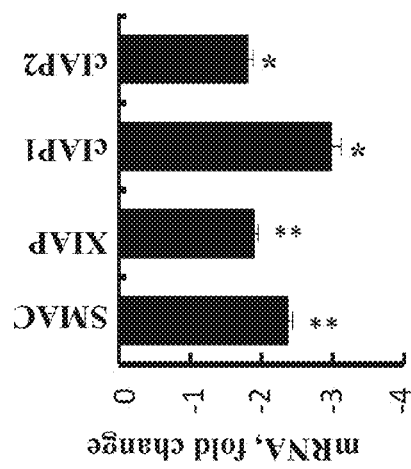

Example 4: Silencing of SMAC/Diablo Alters the Expression of Apoptosis-Associated Proteins TUNEL staining revealed a lack of significant apoptosis in either si-NT-TTs or si-hSMAC-A-TTs from A549-derived xenograft tumors (data not shown). As SMAC/Diablo released from mitochondria during apoptosis binds to and counters the activities of IAPB leading to the release of bound caspases (Verhagen, A. M., et al. 2000. Cell 102, 43-53), the expression levels of XIAP1, cIAP1, and cIAP2, as well as of pro-apoptotic proteins including caspases 3, 8, and 9, Cyto c, and AIF were analyzed. The expression levels of these genes (mRNA) were noticeably decreased, as revealed by q-PCR (FIG. 6A, B). A reduction of protein expression level was demonstrated by IHC for XIAP (data not shown).

Figure 6C:
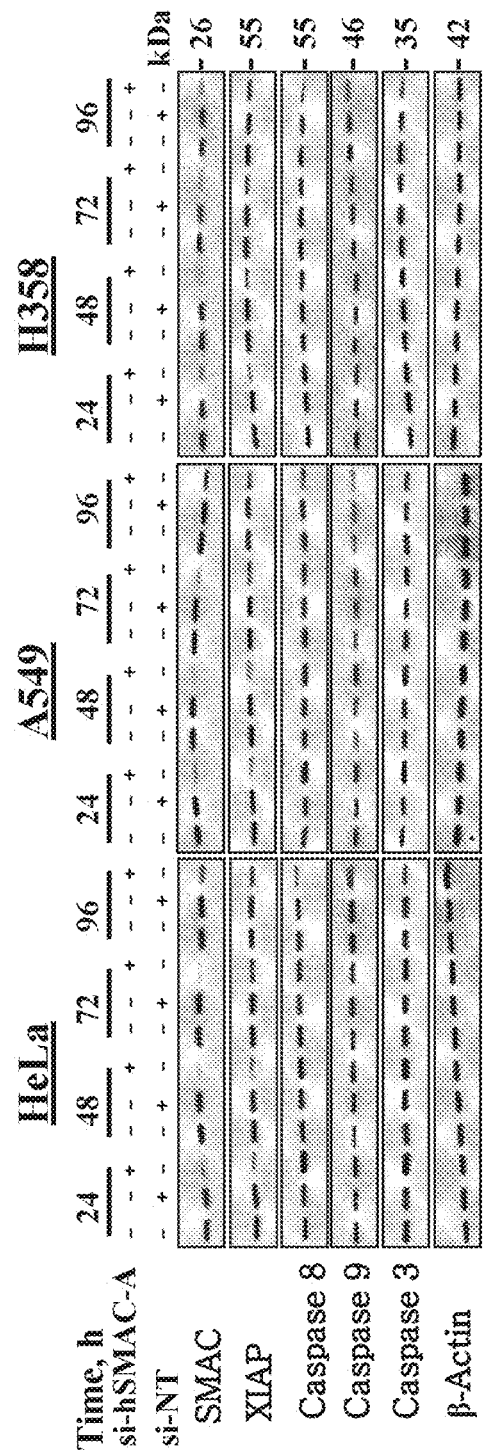
Figure 6D:
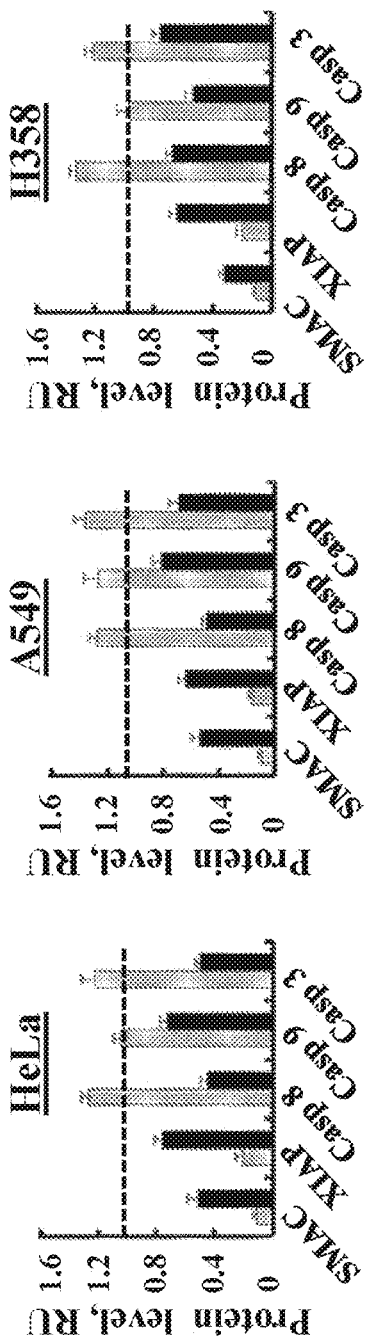
Figure 6E:
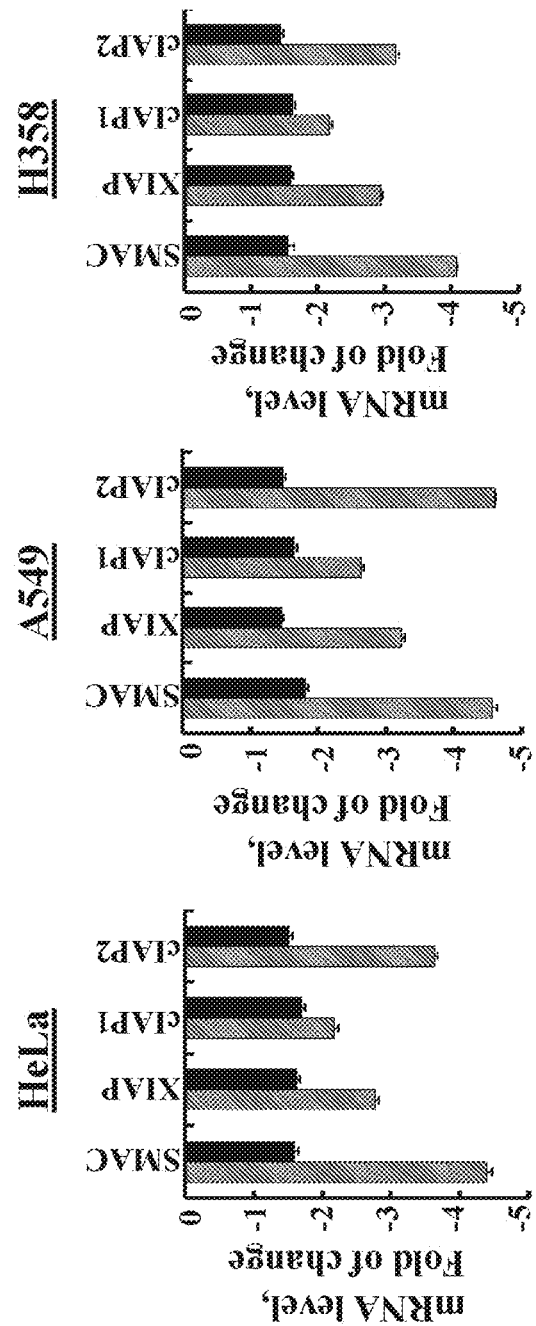

In cell culture, immunoblotting (FIG. 6C, D) and q-PCR (FIG. 6E) of HeLa, A549, and H358 cells treated with si-hSMAC-A showed decrease in the expression level not only of SMAC/Diablo but also of its binding protein, XIAP. SMAC/Diablo silencing also affected expression levels of apoptosis-related proteins, including caspases 3, 8, 9, albeit in a transient effect, with maximum inhibition being noted at 48 h, followed by a lessening of the effect 96 h after transfection.

These results suggest cross-talk between the levels of expression of SMAC/Diablo and those of a variety of apoptosis-related proteins.

Figure 7F:
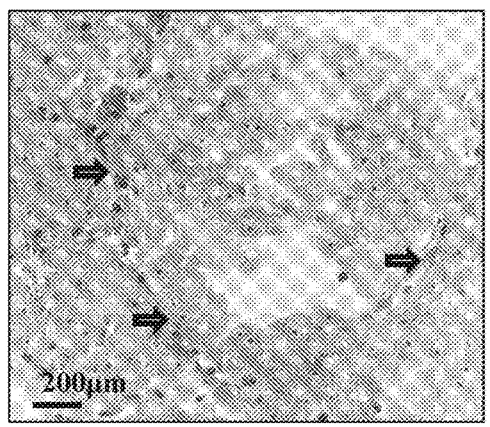
FIG. 7 depicts the morphological changes induced in tumors treated with si-hSMAC: (A) Representative sections from si-NT- and si-hSMAC-A-TTs stained with H&E; (B) Enlarged images of representative sections from si-NT- and si-hSMAC-A-TTs stained with H&E, showing glandular-like clusters surrounded by a chain of cells (arrows) in si-hSMAC-A-TTs; (C, D, E) Sections from si-NT- and si-hSMAC-A-TTs stained with anti-prosurfactant c (C) or anti-podoplanin antibodies (D, E); (F) Representative sections from si-NT- and si-hSMAC-A-TTs stained with anti-CD31 antibodies; and (G, H) Schematic presentations of alveoli (H) and a cross-section through alveoli, with major cell types indicated (I).

Example 5: Silencing SMAC/Diablo Expression Alters Residual Tumor Morphology Hematoxylin and eosin (H&E) staining of sections from si-NT-TTs and si-hSMAC-A-TTs lung cancer xenografts demonstrated a mostly similar morphology of lung cancer tissue with cyst-like structures (FIG. 7A). However, further morphological analysis revealed that in si-hSMAC-A-TTs, the cells were organized in glandular-like clusters, surrounded by a chain of cells (FIG. 7B), which were not seen in si-NT-TTs (FIG. 4B). These features can be interpreted as indicative of the cancer cells in si-hSMAC-A-TTs having undergone a differentiation process. To investigate this point, we analyzed the expression of the pulmonary-associated surfactant protein c (SP-C) (FIG. 4C), a component of the surface-active lipoprotein complex that is required for proper biophysical function of the lung, and found in alveolar epithelial type II (AT2) cells (Barkauskas, C. E. et al., 2013. J Clin Invest 123, 3025-3036). No significant differences in the staining of SP-C in si-NT-TTs and si-SMAC-A-TTs were found (FIG. 4C). The expression of the AT1 cells marker podoplanin (also known as T1α, PDPN), a membranal mucin-type sialoglycoprotein (Barkauskas et al., ibid), was also assessed (FIG. 4D, E). The higher expression levels of podoplanin in si-hSMAC-A-TTs support the suggestion that cells in the residual tumor had undergone differentiation into AT1-like cells. (FIG. 4F) Photomicrograph of si-hSMAC-A-treated tumor stained with toluidine blue. Arrows indicate glandular-like clusters surrounded by a chain of cells.

Figure 7G:
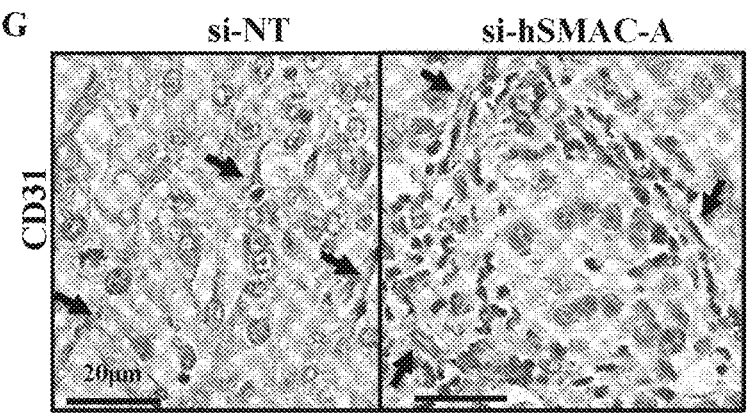
Figure 7H:
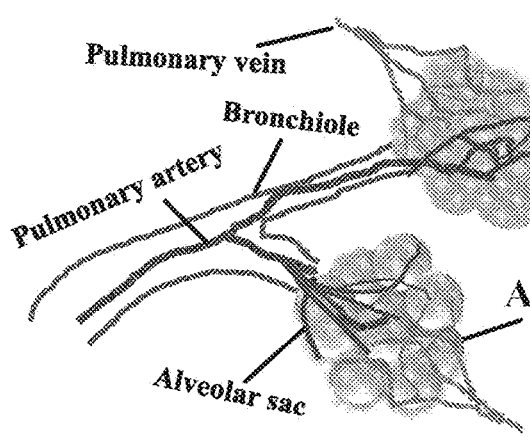
Figure 7I:
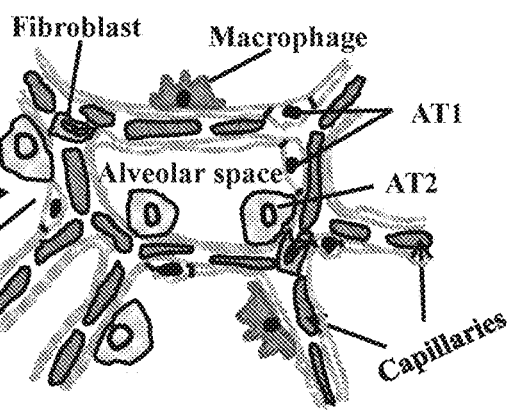

Further structural analysis revealed that the cells organized in a chain around the glandular-like structures were positively stained for the endothelial cell marker CD31 (FIG. 7G), and were organized in a manner resembling lung alveoli. In contrast, in si-NT-TTs, the CD31-positive cells were flattened and randomly dispersed over the entire area of the tumor tissue (FIG. 7G). The results of the histological analysis could reflect a scenario whereby si-NT-TTs CD31-positive cells are involved in the process of tumor angiogenesis, while in si-hSMAC-A-TTs, the cellular organization more closely resembles the normal physiological alveolar endothelial arrangement designed for $O_2$ exchange. A schematic presentation of a cross-section through alveoli is offered for comparison with the glandular/alveolar-like structures observed in the si-hSMAC-A-TTs (compare FIGS. 7H and I).

Further support for this view comes from analysis of the formation of stroma in H&E-stained si-NT-TTs and si-hSMAC-A-TTs (FIG. 8). While the stromal structures in si-NT-TTs were thin, appeared fragile, and were dispersed throughout the tissue, in si-hSMAC-TTs, massive fibrotic structures, resembling scar tissue, could be seen (FIG. 8A). In addition, the stromal structures in si-NT-TTs were enriched with vascular formations, associated with angiogenesis; these were barely noticeable in si-hSMAC-A-TTs (FIG. 8B).

Staining with Sirius red and of vimentin, staining collagen and intermediate filaments, respectively, appeared to be similar in si-NT-TTs and si-hSMAC-A-TTs (data not shown). In contrast, staining for α-SMA, a myofibroblast marker, was observed mainly in si-NT-TTs, and was significantly reduced in si-hSMAC-A-TTs (FIG. 8C), suggesting reduced myofibroblast infiltration.

Example 6: Over-Expressed SMAC/Diablo is Found in the Nucleus and Cytosol

Interestingly, it was noticed that although SMAC/Diablo is known as a mitochondrial protein, high levels were also detected in the nucleus and cytosol of NSCLC tissue microarray samples (FIG. 9). IHC analysis revealed that SMAC/Diablo was found in the nucleus in ~50% of the samples (data not shown). The sub-cellular localization of SMAC/Diablo in si-NT-TTs was further analyzed by immunofluorescence staining using anti-Cyto c antibodies as mitochondria markers and confocal microscopy (data not shown). It was found SMAC/Diablo and Cyto c were co-localized in si-NT-TTs. Here too, SMAC/Diablo was found in addition to mitochondria also in the nuclei. As expected, no SMAC/Diablo was detected in si-SMAC-A-TTs.

Nuclear localization of SMAC/Diablo was also detected in lung cancer tissue by IHC analysis (FIG. 9B). Analysis of various types of cancer (FIG. 1) detected nuclear localization of SMAC/Diablo, in addition to NSCLC, only in B diffuse lymphoma (FIG. data not shown). Cytosol-localized SMAC/Diablo was also found in patient-derived NSCLC tumors over-expressing SMAC (FIG. 9C).

Example 7: Next-Generation Sequencing (NGS) of si-NT-TTs and si-hSMAC-TTs and Functional Analysis NGS was used to investigate changes in patterns of gene expression in si-NT-TTs and si-hSMAC-A-TTs (FIG. 10, and Tables 3-5). Such analysis revealed 848 genes, half of which are of human origin (428; 50.5%) and half of which are of murine origin (420; 49.5%), that displayed significant changes (≥1.5-fold change, adjusted P value<0.05). As si-hSMAC is human-specific, any effect on mouse gene expression must be mediated by the human tumor cells.

Of the human genes the expression of which was modified following SMAC/Diablo silencing, about 186 were up-regulated and 242 were down-regulated. Functional analysis (Gene Ontology system, DAVID) of gene expression in si-NT-TTs and si-hSMAC-A-TTs revealed differential expression of genes associated with key functions and pathways related to tumorigenicity (FIG. 10, Tables 3-5). The major functional groups were changes were seen are presented below.

Genes associated with membranes, organelles and extracellular matrix—The expression of about 200 genes associated with cell membrane, exosomes, and extracellular matrix and proteins found in the lumen of the ER and Golgi were altered. While genes associated with cell membrane, extracellular exosomes and extracellular matrix were found to be both up- and down-regulated, genes associated with ER lumen and Golgi were only down-regulated (FIG. 10A, B, Table 3). Some of these results were validated by q-PCR (FIG. 11).

Genes associated with lipid transport, synthesis and regulation—Alterations in the membranal system could reflect that membrane components, such those involved in phospholipid synthesis, were impaired upon SMAC reduction. Indeed, si-SMAC-TTs showed alterations in the expression levels of genes associated with the transport, synthesis and regulation of lipids (FIG. 10C, Table 4). These included the elongation of long chain fatty acids protein 4 (ELOV4, 145-fold) and ELOV3 (7-fold); ATP10B (25-fold) that mediates the transport of phospholipids from the outer to the inner leaflet of various membranes; StARD10, involved in the transfer of phosphatidylcholine (PC) and phosphatidyetanolamline (PE) between membranes; LIPH lipase, catalyzing the production of 2-acyl lysophosphatidic acid, and phospholipase C, cleaving phospholipids, that were all up-regulated. At the same time, glycerol kinase (GK), diacylglycerol kinase delta (DGKD), that phosphorylates diacylglycerol to produce phosphatidic acid, and acyl-CoA dehydrogenase (ACAD10), that participate in the beta-oxidation of fatty acids in mitochondria, were all decreased in si-SMAC-A-TTs (FIG. 10C, Table 4). In addition, the expression of SLC44A4 that mediate choline transport was increased in si-SMAC-A-TTs (FIG. 11A).

Transporters of metabolites and ions and cell metabolism—Another interesting group of differentially expressed genes includes those related to the transport of metabolites and ions (FIG. 11A, B, Table 4). In si-hSMAC-TTs, down-regulated genes included several members of the solute carrier family (SLC), which mediate sodium/bicarbonate, sodium/potassium/calcium co-transport, the organic anion transporter, which transports the prostaglandins PGD2, PGE1, PGE2, and the mitochondrial iron transporter. Other genes down-regulated in si-hSMAC-A-TTs are associated with lung maturation, including sodium bicarbonate co-transporters (SLC4A4, NBC), and the sodium- and chloride-dependent glycine transporter 1 (SLC6A9).

Figure 14A:
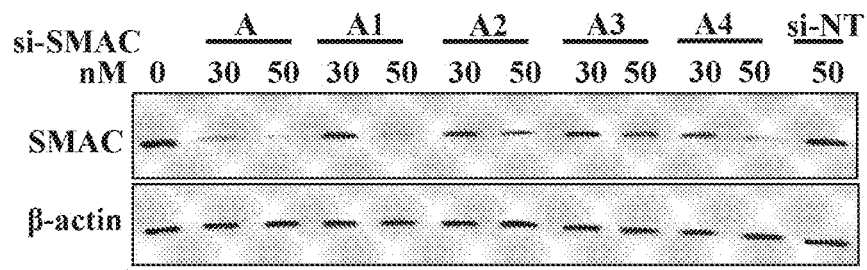
FIG. 14 demonstrates growth inhibition of the of lung cancer cell line A549 resulted from silencing of SMAC/Diablo using modified si-hSMAC-A (designated A1-A4) or modified si-hSMAC-B (designated B 1-B4) molecules. (A, D) The cells were transfected with each of the indicated si-hSMAC (30 or 50 nM) and 48 h post-transfection, levels of SMAC/Diablo in the cells were evaluated by immunoblotting. β-actin was used as a loading control. (B, E) Quantitative analysis of the immunoblots. (C, F) Growth of the cells transfected with each of the si-hSMAC at the indicated concentration was assayed using the SRB method.
Figure 14B:
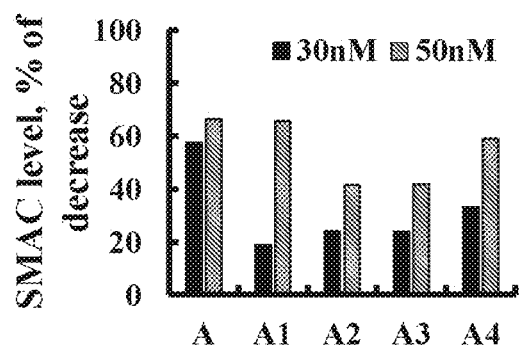
Figure 14C:
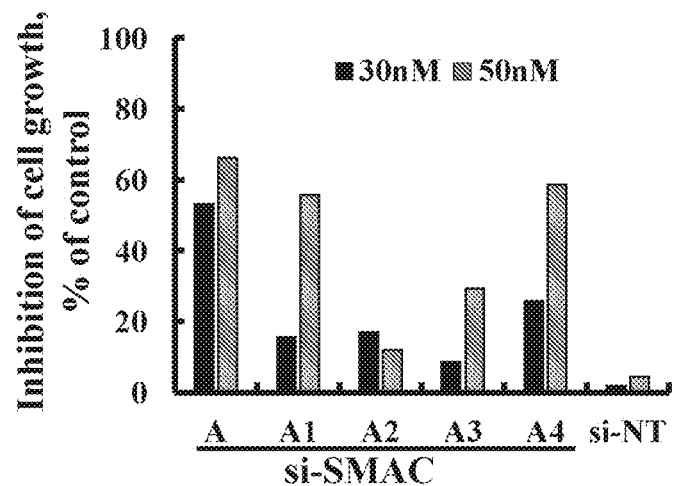
Figure 14D:
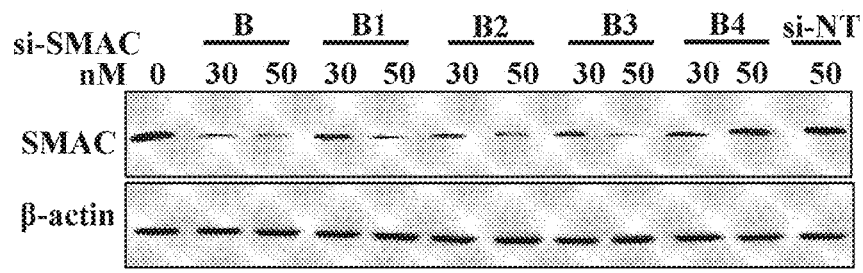
Figure 14E:
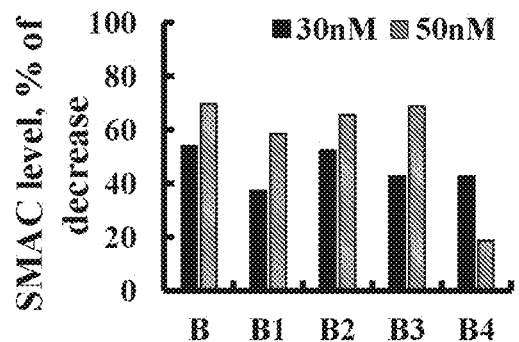
Figure 14F:
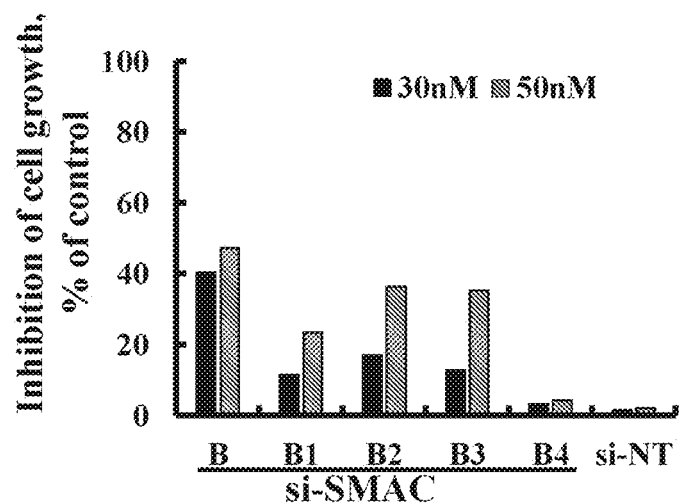

Up-regulated genes included the Ft/sucrose symporter, genes involved in the regulation of lipid metabolism, the thiamine pyrophosphate (TPP) transporter, a cation/proton antiporter, and those encoding several channels for $K^+$, $Na^+$, $Cl^-$ (FIG. 14A, Table 4). Increased levels of anoctamin-1 (ANO1), a voltage-sensitive calcium-activated chloride channel that regulates trans-epithelial anion transport that is essential for lung airway physiology (Rock, J. R., et al. 2009. J Biol Chem 284, 14875-14880) and of the $Ca^{2+}$-activated potassium channel KCNN4 and a two-pore potassium (K2P) channel, KSNK1, which are involved in airway surface liquid hydration (Zhao, K. Q et al. 2012. Am J Physiol Lung Cell Mol Physiol 302, L4-L12), were noted. The same is true for the epithelial $Na^+$ channel ($\alpha$-ENaC/SCNN1A), a critical factor during the perinatal period of lung development, involved in clearance of lung fluid ((Mustafa, S. B., et al. 2014. Exp Lung Res 40, 380-391).

Figure 11B:
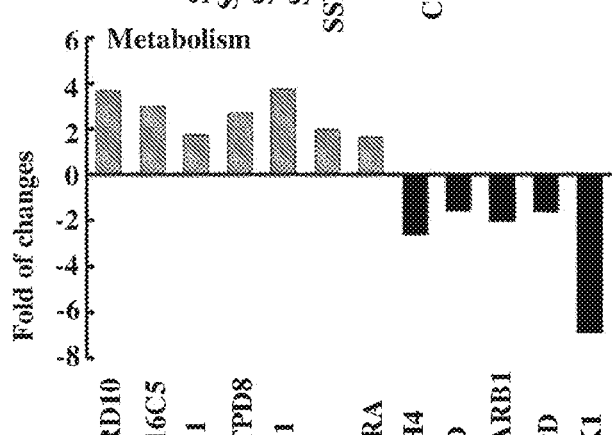

Metabolism-related genes whose expression was altered in si-hSMAC-A-TTs included dehydrogenases and deaminases responsible for mediating the conversion of oxaloacetate to phosphoenolpyruvate, alcohol dehydrogenase, hexose-6-phosphate dehydrogenase, and adenosine deaminase, all of which were down-regulated (FIG. 11B, Table 4).

Up-regulated genes encoded for enzymes involved in nucleotide synthesis (cytidine deaminase, ectonucleoside triphosphate diphosphohydrolase, calcium-activated nucleotidase 1), amino acid metabolism (peptidyl arginine deiminase, glutamic pyruvate transaminase), oligosaccharide biosynthesis, and protein glycosylation (glycosyltransferases, fucosyltransferases, beta-galactoside alpha-2,3-sialyltransferase, polypeptide N-acetylgalactosaminyltransferase) (FIG. 11B, Table 4). Most of the transporters and metabolism-related proteins with modified expression in the si-hSMAC-A-TTs have already been reported to be associated with several cancers, in addition to the lung cancer analyzed here (Table 4).

Figure 11C:
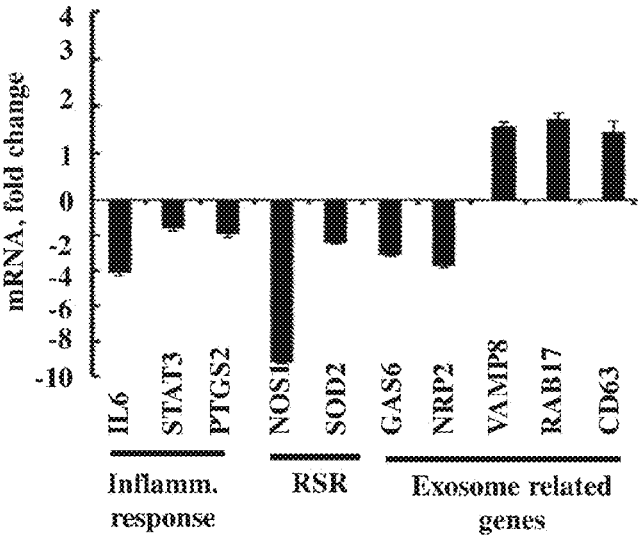

Inflammation and the tumor microenvironment—The si-hSMAC-A-TTs also showed a reduction in the expression of genes associated with inflammation and the tumor microenvironment, including cytokines, chemokines, their related receptors, and intracellular proteins associated with inflammatory and immune responses (Table 5). Selected results were confirmed by q-PCR (FIG. 11C). These results included IL-6, known to be involved in tumorgenicity and the activation of transcription factors, such as STAT3, associated with oncogenicity. In addition, the results of NGS and q-PCR analysis showed a reduction in the levels of nitric oxide synthase 1 (NOS1), an essential factor for tumorgenicity and angiogenesis, and of mitochondrial superoxide dismutase 2 (SOD2) (Table 4, FIG. 11C) as well as genes associated with the expression of transforming growth factor $\beta$ (TGF-$\beta$) and metalloproteinases (MMP2 and MMP9) in si-hSMAC-A-TTs (Table 5). Similar staining of si-NT-TTs and si-hSMAC-A-TTs with the macrophage-specific antibody F4/80 was seen (data not shown).

A conclusion following from these results is that up-regulation of the expression of SMAC/Diablo in tumor cells may be associated with an increase in the inflammatory activity that is essential for tumorigenicity, invasiveness, metastasis, and angiogenesis.

TABLE 3

List of selected genes associated with exosome and vesicle formation differentially expressed between si-NT- and si-hSMAC-A-treated A549 cells-derived tumors, based on NGS analysis

| Gene (Uniport accession) | Fold change (p value) | Proposed function | Relation to cancer |
|---|---|---|---|
| EXOSOMES | | | |
| CD9- (TSPAN29) [HGNC: 1709] | 1.5 ($1.1 \times 10^{-4}$) | Glycoprotein/integrin belongs to tetraspanin family | a prognostic biomarker in NSCLC |
| CD63- (TSPAN30) transmembrane channel-like 4 [HGNC: 22998] | 3.5 ($3.88 \times 10^{-12}$) | Glycoprotein/integrin belongs to tetraspanin family. Involved intracellular vesicular transport processes | a prognostic biomarker in NSCLC |
| TSPANS-tetraspanin 8 [HGNC: 11855] | 1.6 ($2.3 \times 10^{-5}$) | Glycoprotein/integrin belongs to tetraspanin family | A metastasis-promoting tetraspanin |
| TSPAN13- tetraspanin 13 [HGNC: 21643] | 1.8 ($5.1 \times 10^{-4}$) | GLYCOPROTEIN/INTEGRIN BELONGS TO TETRASPANIN FAMILY | Overexpressed in prostate cancer |
| VAMPS- vesicle-associated membrane protein 8 [HGNC: 12647] | 1.9 ($1.0 \times 10^{-5}$) | V-SNARE PROTEIN, INVOLVED IN DOCKING AND/OR FUSION OF SYNAPTIC VESICLES | Reduces cancer invasive activity |
| RAB17- member RAS oncogene family [HGNC: 16523] | 1.9 ($1.0 \times 10^{-4}$) | A SMALL GTPASE Associated with epithelial polarity | Reduces cancer invasive activity |
| EPCAM- epithelial cell adhesion molecule [HGNC: 11529] | 2.7 ($3.1 \times 10^{-11}$) | Epithelial cell-cell adhesion, proliferation, migration, signaling and differentiation | Poor prognosis and metastasis |

TABLE 3-continued

List of selected genes associated with exosome and vesicle formation differentially expressed between si-NT- and si-hSMAC-A-treated A549 cells-derived tumors, based on NGS analysis

| Gene (Uniport accession) | Fold change (p value) | Proposed function | Relation to cancer |
|---|---|---|---|
| CEACAM5 (CD66e)- carcinoembryonic antigen-related cell adhesion molecule 5 [HGNC: 1817] | 2.2 ($3.2 \times 10^{-5}$) | Associated with adhesion and invasion | Involved in cancer metastasis |
| CANT1- calcium activated nucleotidase 1 [HGNC: 19721] | 1.5 ($4.4 \times 10^{-4}$) | A nucleotidase with a preference for UDP | Overexpressed in prostate cancer |
| HSPG2 (Perlecan)- heparan sulfate proteoglycan 2 [HGNC: 5273] | −1.7 ($3.5 \times 10^{-6}$) | A component of the vascular extracellular matrix, involved in endothelial growth | Associated with lung cancer, melanoma brain metastasis |
| FSTL1- follistatin-like 1 [HGNC: 3972] | −1.8 ($7.6 \times 10^{-8}$) | Involved in the lung development | inhibits the invasion and metastasis |
| CD274- PD-L1 molecule [HGNC: 17635] | −1.9 ($3.3 \times 10^{-4}$) | Involved in the suppression of immune response | Associated with tumoral immune escape |
| NID2- nidogen 2 (osteonidogen) [HGNC: 13389] | −2.1 ($1.8 \times 10^{-6}$) | A basal lamina protein | Tumor suppressor |
| GAS6- growth arrest-specific 6 [HGNC: 4168] | −1.7 ($3.0 \times 10^{-3}$) | AXL receptor tyrosine kinase activation | Overexpressed in lung cancer |
| GPIBA- glycoprotein Ib (platelet), alpha polypeptide [HGNC: 4439] | −1.7 ($1.0 \times 10^{-3}$) | A receptor for von Willebrandt factor (VWF) | Associated with cachexia in metastatic melanoma |
| IGFBP7- insulin-like growth factor binding protein 7 [HGNC: 5476] | −1.8 ($2.1 \times 10^{-5}$) | It is involved in IGF high affinity interaction and cell adhesion | It is associated with NSCLC progression |
| EXTRACELLULAR SPACE | | | |
| CCL24- chemokine (C-C motif) ligand 24 [HGNC: 10623] | 1.9 ($3.0 \times 10^{-4}$) | CHEMOTACTIC FOR RESTING T LYMPHOCYTES AND EOSINOPHILS | Associated with poor prognosis in hepatocellular carcinoma (HCC) and colorectal cancer |
| CCL28- chemokine (C-C motif) ligand 28 [HGNC: 17700] | 1.9 ($8.8 \times 10^{-4}$) | Involved in inflammatory response | Support cancer metastasis |
| SPINK1- serine peptidase inhibitor, Kazal type 1 [HGNC: 11244] | 1.9 ($4.4 \times 10^{-4}$) | A serine protease inhibitor | Associated with prostate cancer |
| PROC- protein C (inactivator of coagulation factors Va and VIIIa) [HGNC: 9451] | 1.8 ($1.2 \times 10^{-3}$) | involved in hemostasis, inflammation and signal transduction | The expression is associated with an improved lung cancer prognosis |
| SPINT1- serine peptidase inhibitor, Kunitz type 1 [HGNC: 11246] | 1.7 ($6.8 \times 10^{-5}$) | A serine protease inhibitor | Associated with lung cancer malignant pleural effusion |
| LGALS3- lectin, galactoside-binding, soluble, 3 [HGNC: 6563] | 1.6 ($1.6 \times 10^{-4}$) | Associated with cell adhesion, cell activation and chemoattraction, cell growth and differentiation, cell cycle, and apoptosis | Involved in A549 cells, promoted CSC formation. Involved in involved in inflammation and fibrosis |
| CX3CL1- chemokine (C-X3-C motif) ligand 1 [HGNC: 10647] | 1.6 ($1.6 \times 10^{-4}$) | Activates integrins and elicits adhesive and migratory leukocytes functions | Associated with cancer progression |
| IGFBP1- insulin-like growth factor binding protein 1 [HGNC: 5469] | −1.6 ($8.3 \times 10^{-6}$) | Improves and inhibits IGF interaction with cells surface receptors | a tumor growth inhibitor in breast cancer cells |
| MST1- macrophage stimulating 1 (hepatocyte growth factor-like) [HGNC: 7380] | −1.6 ($1.9 \times 10^{-3}$) | Hepatocyte growth factor-like protein | Antiproliferative activity in A549 cells |
| CPM- carboxypeptidase M [HGNC: 2311] | −1.7 ($1.0 \times 10^{-4}$) | Presents in pneumocytes and involved in EGFR activation | Associated with poor prognosis in lung adenocarcinomas |
| WISP2- WNT1 inducible signaling pathway protein 2 [HGNC: 12770] | −1.7 ($9.1 \times 10^{-6}$) | The CCN family of proteins involved in cell adhesion, migration, proliferation, differentiation | Promotes a stem-like cell phenotype in breast cancer cells. Acts as a tumor suppressor in colorectal cancer |
| IGFBP3- insulin-like growth factor binding protein 3 [HGNC: 5472] | −1.8 ($4.5 \times 10^{-8}$) | blocks the access of IGF-1, 2 to IGF-1R | Functions as a tumor suppressor |

TABLE 3-continued

List of selected genes associated with exosome and vesicle formation differentially expressed
between si-NT- and si-hSMAC-A-treated A549 cells-derived tumors, based on NGS analysis

| Gene (Uniport accession) | Fold change (p value) | Proposed function | Relation to cancer |
|---|---|---|---|
| CELL MEMBRANE | | | |
| CLDN4- claudin 4 [HGNC: 2046] | 2.4 ($3.9 \times 10^{-9}$) | Involved in tight junction-specific obliteration of the intercellular space. | Associated with a good prognosis in NSCLC, SCC subgroups |
| EMP1- epithelial membrane protein 1 [HGNC: 3333] | 1.8 ($4.7 \times 10^{-5}$) | Involved in tight junction-specific obliteration of the intercellular space. | Reduced expression associated with lung cancer progression |
| BAMBI- BMP and activin membrane-bound inhibitor [HGNC: 30251] | 1.7 ($2.9 \times 10^{-4}$) | Negatively regulates TGF-beta signaling | Involved in the suppression of invasiveness |
| CDH3- cadherin 3, type 1, P-cadherin (placental) [HGNC: 1762] | 1.7 ($4.0 \times 10^{-3}$) | Cadherin protein related to stem cells properties | Associated with expression in lung cancer |
| DSC2- desmocollin 2 [HGNC: 3036] | 1.6 ($1.4 \times 10^{-5}$) | Cadherin-type protein involved in adjacent cells interaction | Reduced expression associated with poor prognosis in pancreas, colorectal and esophageal squamous cell cancers |
| TNS1- tensin 1 [HGNC: 11973] | -1.6 ($7.7 \times 10^{-6}$) | Actin-binding protein, promotes motility | Involved in EMT, tumor invasion and metastasis |
| CLMP- Coxsackie- and adenovirus receptor (CXADR)-like membrane protein [HGNC: 24039] | -1.7 ($9.1 \times 10^{-4}$) | Involved in cell-cell adhesion | Associated with poor prognosis |
| C5AR1 (CD88)- complement component 5a receptor 1 [HGNC: 1338] | -1.7 ($4.0 \times 10^{-3}$) | Complement component 5a receptor involved in inflammatory response. | Associated with poor prognosis in NSCLC |
| CNTNAP2-contactin associated protein-like 2 [HGNC: 13830] | -1.8 ($9.4 \times 10^{-5}$) | The protein of neurexin family, involved in cell adhesion. | Associated with poor prognosis in breast cancer |
| ITGA1 (CD49a)- integrin subunit alpha 1 | -1.9 ($1.1 \times 10^{-5}$) | Involved in cell-cell adhesion, inflammation and fibrosis | Involved in lung lymphangioleiomyomatosis (LAM) invasiveness |
| ACKR3- atypical chemokine receptor 3 [HGNC: 23692] | -2.2 ($1.8 \times 10^{-5}$) | a receptor for chemokines CXCL11 and CXCL12/SDF1 | Increased expression in lung SCC |
| EXTRACELLULAR MATRIX | | | |
| COL17A1 (BP180)- collagen, type XVII, alpha 1 [HGNC: 2194] | 2.1 ($3.0 \times 10^{-7}$) | involved in epidermal adhesion | Underexpression in breast cancer associated with poor prognosis |
| COL5A1- collagen, type V, alpha 1 [HGNC: 2209] | -1.5 ($5.0 \times 10^{-4}$) | Belongs to type I collagen and binds to DNA, heparan sulfate, thrombospondin, heparin, and insulin | ASSOCIATED WITH A RENAL CANCER POOR PROGNOSIS, GASTRIC, BREAST CANCERS |
| COL12A1- collagen, type XII, alpha 1 [HGNC: 2188] | -1.5 ($9.8 \times 10^{-4}$) | Interacts with type I collagen and the surrounding matrix | Associated with drug resistance in ovarian cancer cell lines, breast cancer progression, colorectal cancer metastasis |
| VCAN- versican [HGNC: 2464] | -1.5 ($1.3 \times 10^{-3}$) | Involved in cells-extracellular, matrix interaction | Associated with an advanced disease |
| SMOC1- SPARC related modular calcium binding 1 [HGNC: 20318] | -1.6 ($3.7 \times 10^{-4}$) | A matricellular protein interferes with growth factor receptor signaling | Increased in brain cancers. Involved in angiogenesis. Interacts with NID2 |
| VTN- vitronectin [HGNC: 12724] | -1.6 ($1.0 \times 10^{-2}$) | A cell adhesion and spreading factor | Not correlated with disease progression |
| COL4A2- collagen, type IV, alpha 2 [HGNC: 2203] | -1.8 ($1.1 \times 10^{-6}$) | The major structural component of glomerular basement membranes, forming a 'chicken-wire' meshwork together widi laminins, proteoglycans and entactin/nidogen | Associated with lung cancer, melanoma brain metastasis, gastric cancer |
| FBN1- fibrillin 1 [HGNC: 3603] | -1.7 ($2.0 \times 10^{-3}$) | Extracellular matrix glycoprotein serves as a structural component | Associated with an ovarian cancer progress |
| BMPER- BMP binding endothelial regulator [HGNC: 24154] | -1.7 ($4.2 \times 10^{-3}$) | Inhibitor of BMP activity | Associated with tumor growth. |

TABLE 3-continued

List of selected genes associated with exosome and vesicle formation differentially expressed between si-NT- and si-hSMAC-A-treated A549 cells-derived tumors, based on NGS analysis

| Gene (Uniport accession) | Fold change (p value) | Proposed function | Relation to cancer |
|---|---|---|---|
| BMP2-bone morphogenetic protein 2 [HGNC: 1069] | −1.8 ($5.2 \times 10^{-4}$) | Implicated in the development of bone and cartilage. Involved in the hedgehog pathway, TGF beta signaling pathway activation | Associated with tumor growth. |
| GPC6- glypican 6 [HGNC: 4454] | −1.8 ($9.6 \times 10^{-5}$) | extracellular matrix proteins, | Involved in invasion of breast cancer |
| NLGN2- neuroligin 2 [HGNC: 14290] | −1.8 ($1.4 \times 10^{-6}$) | Involved in cell-cell interactions via its interactions with neurexin family members (see CNTNAP2) | No direct association reported |
| ADAMTS9- ADAM metallopeptidase with thrombospondin type 1 motif, 9 [HGNC: 13202] | −2.2 ($2.1 \times 10^{-5}$) | Metalloproteinase and involved in the transport from the endoplasmic reticulum to the Golgi apparatus | Inhibits angiogenesis and tumor growth in ESCC and NPC |
| COL4A1- collagen, type IV, alpha 1 [HGNC: 2202] | −2.2 ($9.6 \times 10^{-7}$) | The major structural component of glomerular basement membranes (GBM), forming a 'chicken-wire' meshwork together with laminins, proteoglycans and entactin/nidogen | Associated with lung cancer, melanoma brain metastasis, gastric cancer |
| ABI3BP (TARSH)- ABI family, member 3 (NESH) binding protein [HGNC: 17265] | −2.4 ($1.1 \times 10^{-6}$) | The cellular senescence-related gene | Decreased expression is associated with lung cancer progression and metastasis |
| EDIL3 (Del1)-EGF-like repeats and discoidin I-like domains 3 [HGNC: 3173] | −2.5 ($1.6 \times 10^{-6}$) | Interacts with the αv/β3 integrin receptor and promotes adhesion of endothelial cells. | ASSOCIATED WITH LUNG CANCER CELL PROLIFERATION AND INVASION |
| CCBE1- collagen and calcium binding EGF domains 1 [HGNC: 29426] | −2.7 ($4.3 \times 10^{-7}$) | Involved in angiogenesis process | A prognostic marker for gastrointestinal stromal tumor progression |
| TGFBI-Transforming growth factor-beta-induced protein ig-h3 [HGNC: 11771] | −1.9 ($1.5 \times 10^{-5}$) | Involved in cell-collagen interactions and cells adhesion | Associated with invasion, signaling and ECM interaction in different types of cancer |
| MMP2-Metalloproteinase 2 (72 kDa type IV collagenase) [HGNC: 7166] | −2.9 ($6.9 \times 10^{-6}$) | Involved in angiogenesis, tissue repair, tumor invasion, inflammation, and adierosclerotic plaque rupture and degrading extracellular matrix proteins | Associated with cancer progression by ECM degradation in different types of tumor |
| ENDOPLASMIC AND GOLGI LUMENS | | | |
| AGR3- anterior gradient 3 [HGNC: 24167] | 4.1 ($1.33 \times 10^{-6}$) | Required for calcium-mediated regulation (ER) | Associated with ovarian cancer |
| RYR1- ryanodine receptor 1 [HGNC: 10483] [HGNC: 22998] | 2.5 ($5.6 \times 10^{-3}$) | Ca$^{2+}$ channel that mediates the release of Ca$^{2+}$ from the sarcoplasmic reticulum into the cytoplasm (ER/SR) | Associated with breast cancer |
| NCK2- NCK adaptor protein 2 [HGNC: 7665] | 2.0 ($2.04 \times 10^{-6}$) | Adapter protein which associates with tyrosine-phosphorylated growth factor receptors or their cellular substrates (ER) | Associated with ovarian cancer |
| SEC61G- Sec61 gamma subunit [HGNC: 18277] | 1.8 ($4.3 \times 10^{-4}$) | Protein translocation in the (ER). | Associated with pediatric Ependymomas |
| BACE1- beta-site APP-cleaving enzyme 1 [HGNC: 933] | −1.5 ($2.2 \times 10^{-3}$) | Amyloid precursor protein (APP) protease | May be involved in tumor angiogenesis |
| FOXRED2- FAD-dependent oxidoreductase domain containing 2 [HGNC: 26264] | −1.5 ($2.0 \times 10^{-3}$) | Functions in endoplasmic reticulum associated degradation | FOXRED2 is a transcriptomic fingerprint of KRAS |
| H6PD (GDH)- hexose-6-phosphate dehydrogenase (glucose 1-dehydrogenase) [HGNC: 4795] | −1.6 ($1.3 \times 10^{-4}$) | Oxidizes hexose-6-phosphates and glucose | Associated with breast cancer poor prognosis |
| ACAD10- acyl-CoA dehydrogenase family, member 10 [HGNC: 21597] | −1.7 ($1.6 \times 10^{-3}$) | Acyl-CoA dehydrogenase only active with R- and S-2-methyl-C15-CoA (mitochondria) | No direct association reported |

TABLE 3-continued

List of selected genes associated with exosome and vesicle formation differentially expressed between si-NT- and si-hSMAC-A-treated A549 cells-derived tumors, based on NGS analysis

| Gene (Uniport accession) | Fold change (p value) | Proposed function | Relation to cancer |
|---|---|---|---|
| TM4SF20- transmembrane 4 L six family member 20 [HGNC: 26230] | −1.7 ($1.26 \times 10^{-8}$) | Polytopic transmembrane protein that inhibits intramembrane proteolysis (RIP) of CREB3L1 (ER) | No direct association reported |
| TMEM147-AS-TMEM147 antisense RNA 1 [HGNC: 51273] | −1.7 ($8.5 \times 10^{-3}$) | Antisense to transmembrane protein (ER) | No direct association reported |
| AHCYL2- adenosylhomocysteinase-like 2 [HGNC: 22204] | −1.7 ($4.05 \times 10^{-4}$) | Regulating the sodium/bicarbonate cotransporter SLC4A4 activity and $Mg^{2+}$-sensitivity (ER) | No direct association reported |
| ITPR1-inositol 1,4,5-trisphosphate receptor, ripe 1 [HGNC: 6180] | −1.7 ($7.9 \times 10^{-4}$) | Intracellular channel mediating $Ca^{2+}$ release from the ER upon stimulation by inositol 1,4,5-trisphosphate (ER) | Associated with renal cancer |
| CHERP- calcium homeostasis endoplasmic reticulum protein [HGNC: 16930] | −1.7 ($7.05 \times 10^{-4}$) | Involved in $Ca^{2+}$ homeostasis, growth and proliferation (ER) | Associated with neuroblastoma |
| PTGS2 (COX-2)- prostaglandin-endoperoxide synthase 2 [HGNC: 9605] | −1.8 ($1.4 \times 10^{-4}$) | Converts arachidonate to prostaglandin H2 | Involved in hunor grow and metastasis |
| P4HA3- prolyl 4-hydroxylase, alpha polypeptide III [HGNC: 30135] | −1.9 ($5.5 \times 10^{-5}$) | Involved in the post-translational formation of 4-hydroxy proline in -Xaa-Pro-Gly- sequences in collagens | Associated with breast cancer progression |
| PPAP2B- phosphatidic acid phosphatase type 2B [HGNC: 9229] | −1.8 ($1.31 \times 10^{-6}$) | Catalyzes the conversion of phosphatidic acid (PA) to diacylglycerol and hydrolyzes lysophosphatidic acid (ER) | Associated with non small cells lung carcinoma |
| CYP26B1- cytochrome P450, family 26, subfamily B, polypeptide 1 [HGNC: 20581] | −1.8 ($3.85 \times 10^{-4}$) | Involved in the metabolism of retinoic acid (RA), (ER) | Associated with esophageal squamous cell carcinoma. |
| CLGN- calmegin [HGNC: 2060] | −1.9 ($8.6 \times 10^{-4}$) | A chaperone for a range of proteins (ER) | Associated with breast cancer |
| PCSK5- proprotein convertase subtilisin/kexin type 5 [HGNC: 8747] | −2.3 ($2.7 \times 10^{-6}$) | Endoprotease activity protein | Underexpressed in lung cancer |
| COX10-AS1- COX10 antisense RNA 1 [HGNC: 38873] | −2.1 ($7.12 \times 10^{-3}$) | Antisense to (ER) COX10 protein, which converts protoheme IX and farnesyl diphosphate to heme O. | No direct association reported |
| ABCC6- ATP-binding cassette, sub-family C (CFTR/MRP), member 6 [HGNC: 57] | −2.3 ($1.4 \times 10^{-3}$) | Transports glutathione conjugates as leukotriene-c4 (LTC4) and N-ethylmaleimide S-glutathione (ER). | Associated with pancreatic carcinoma |
| RIC3- RIC3 acetylcholine receptor chaperone [HGNC: 30338] | −2.7 ($1.6 \times 10^{-3}$) | Promotes functional expression of homomeric alpha-7 and alpha-8 nicotinic acetylcholine receptors at the cell surface (ER, Golgi) | No direct association reported |
| UGT1A7- UDP glucuronosyltransferase 1 family, polypeptide A7 [HGNC: 12539] | −3.5 ($4.6 \times 10^{-3}$) | UDPGT is important in the conjugation and subsequent elimination of potentially toxic xenobiotics and endogenous compounds. This isoform has specificity for phenols (ER) | Associated with lung cancer |
| CEMIP- cell migration inducing protein, hyaluronan binding [HGNC: 29213] | −3.6 ($1.06 \times 10^{-8}$) | Mediates depolymerization of hyaluronic acid (HA) via the cell membrane-associated clathrin-coated pit endocytic pathway (ER) | Associated with colorectal cancer |
| FAM20A- family with sequence similarity 20, member A [HGNC: 23015] | −4.4 ($4.8 \times 10^{-3}$) | An allosteric activator of the Golgi serine/threonine protein kinase FAM20C (ER, Golgi) | Associated with cancer stem cells |
| UGT1A9-UDP glucuronosyltransferase 1 family, polypeptide A9 [Source: HGNC Symbol; Acc: HGNC: 12541] | −17.2 ($9.8 \times 10^{-4}$) | UDPGT is important in the conjugation and subsequent elimination of potentially toxic xenobiotics and endogenous compounds. This isoform has specificity for phenols (ER) | Associated with gastrointestinal cancer |

TABLE 3-continued

List of selected genes associated with exosome and vesicle formation differentially expressed between si-NT- and si-hSMAC-A-treated A549 cells-derived tumors, based on NGS analysis

| Gene (Uniport accession) | Fold change (p value) | Proposed function | Relation to cancer |
|---|---|---|---|
| ER AND MITOCHONDRIA | | | |
| KLK6- kallikrein-related peptidase 6 [HGNC: 6367] | 25.83 ($9.83 \times 10^{-5}$) | Serine protease (ER, mitochondria) | Associated with NSCLC |
| SGK1- serum/glucocorticoid regulated kinase 1 [HGNC: 10810] | −1.7 ($7.2 \times 10^{-8}$) | Serine/threonine-protein kinase regulating a wide variety of ion channels, transporters, cellular enzymes, transcription factors (ER, mitochondria) Mitochondria | Associated with NSCLC |
| BIK- BCL2-interacting killer (apoptosis-inducing) [HGNC: 1051] | 2.1 ($2.8 \times 10^{-3}$) | Accelerates apoptosis by binding to anti- apoptosis proteins Bcl-X(L), BHRF1 or Bcl-2 suppresses this death-promoting activity (mitochondria) | Associated with lung cancer |
| ENDOG- endonuclease G [HGNC: 3346] | 1.8 ($2.09 \times 10^{-3}$) | Involved in replication of mitochondrial DNA, as AIF1 released from mitochondria in the time of apoptosis and is function, as endonuclease in Nucleus (mitochondria). | Associated with lung cancer |
| CHCHD7- coiled-coil-helix-coiled-coil-helix domain containing 7 [HGNC: 28314] | 1.6 ($1.48 \times 10^{-3}$) | Unknown (mitochondria) | No direct association reported |
| MYO19- mitochondrially encoded NADH dehydrogenase 5 [HGNC: 7461] | −1.6 ($4.33 \times 10^{-5}$) | Actin-based motor molecule with ATPase activity localized to the mitochondrion outer membrane, involved in the interaction of mitochondria with cytoskeleton (mitochondria) | Associated with glioma |
| MT-ND5- mitochondrially encoded NADH dehydrogenase 5 [HGNC: 7461] | −1.6 ($2.65 \times 10^{-4}$) | Subunit of the mitochondrial respiratory chain NADH dehydrogenase (Complex I) | It may be associated with breast cancer |
| ANXA10- annexin A10 [HGNC: 534] | −1.7 ($9.0 \times 10^{-3}$) | $Ca^{2+}$-dependent phospholipid binding (Mitochondria) | Associated with lung cancer |
| CYP24A1- cytochrome P450, family 24, subfamily A, polypeptide 1 [HGNC: 2602] | −1.9 ($1.15 \times 10^{-8}$) | Plays a role in maintaining $Ca^{2+}$ homeostasis. (Mitochondria) | It may be associated with lung cancer |
| MT-ND4L- mitochondrially encoded NADH dehydrogenase 4L [HGNC: 7460] | −1.9 ($3.36 \times 10^{-6}$) | Subunit of the mitochondrial respiratory chain NADH dehydrogenase (Complex I) (Mitochondria) | Associated with childhood acute lymphoblastic leukemia |
| C10orf2 (TWINK)- chromosome 10 open reading frame 2 [HGNC: 1160] | −1.9 ($6.5 \times 10^{-4}$) | Involved in mitochondrial DNA (mtDNA) metabolism. Could function as an adenine nucleotide-dependent DNA helicase (mitochondria) | No direct association reported |
| STARD13- StAR-related lipid transfer (START) domain containing 13 [HGNC: 19164] | −2.2 ($5.39 \times 10^{-5}$) | GTPase-activating protein for RhoA, and for Cdc42. Involved in lipid binding(mitochondria) | It is known, as a tumor suppressor in lung cancer |
| CPS1- carbamoyl-phosphate synthase 1, mitochondrial [HGNC: 2323] | −4.8 ($7.9 \times 10^{-18}$) | Involved in the urea cycle of ureotelic animals, removing excess ammonia from the cell (mitochondria) | Associated with lung cancer |

TABLE 4

Transporters and metabolism related genes differentially expressed between si-NT- and si-hSMAC-A-treated A549 cells derived lung tumors

| Gene (Uniport accession) | Fold change (p value) | Proposed function & cellular localization | Relation to cancer |
|---|---|---|---|
| TRANSPORTERS | | | |
| SLC4A4- solute carrier family 4 (sodium bicarbonate cotransporter), member 4 [HGNC: 11030] | −3.3 ($3.1 \times 10^8$) | Regulates bicarbonate influx/efflux at the basolateral membrane of cells and intracellular pH. (Cell membrane) | Plays a role in growth and migration of colon and breast cancer. |
| SLCO2B1- solute carrier organic anion transporter family, member 2B1 [HGNC: 10962] | −2.8 ($4.1 \times 10^{10}$) | Mediates the Na+-independent transport of organic anions, taurocholate, the prostaglandins PGD2, PGE1, PGE2, leukotriene C4, thromboxane B2. (Cell membrane) | Associated with prostate cancer. |
| SLC6A9- solute carrier family 6 (neurotransmitter transporter, glycine), member 9 [HGNC: 11056] | −1.7 ($5.7 \times 10^{-4}$) | Play a role in glycine transport and thus in glycine regulation of NMDA receptor-mediated neurotransmission. (Cell membrane) | Associated with Thyroid cancer |
| SLC24A1- solute carrier family 24 (sodium/ potassium/calcium exchanger), member 1 [HGNC: 10975] | −1.6 ($1 \times 10^{-3}$) | Controlling the calcium concentration of outer segments during light and darkness and plays a key role in the process of light adaptation. (Cell membrane) | No direct association reported |
| SLC25A37- solute carrier family 25 (mitochondrial iron transporter), member 37 [HGNC: 29786] | −1.5 ($1.2 \times 10^{-4}$) | Mitochondrial iron transporter mediates iron uptake in developing erythroid cells and playing a role in heme biosynthesis, (IMM) | Associated with prostate cancer |
| KCNK1- potassium channel, subfamily K, member 1 [HGNC: 6272] | 1.7 ($1.1 \times 10^{-7}$) | Contributes to passive transmembrane potassium transport and regulation of the resting membrane potential. (Cell membrane, recycling endosome and cytoplasmic vesicle) | Overexpressed in lung cancer |
| SLC45A3- solute carrier family 45, member 3 [HGNC: 8642] | 1.8 ($9.4 \times 10^{-4}$) | H+/sucrose symporter slc45a3 as an osmolyte transporter in the kidney, regulation of lipid metabolism in oligodendrocytes. (Cell membrane) | Up-regulated by androgens and play a role in prostate cancer malignancy |
| KCNN4- potassium channel calcium-activated channel, subfamily N, member 4 [HGNC: 6293] | 1.8 ($6.8 \times 10^{-5}$) | Required for maximal calcium influx and proliferation during the reactivation of naive T-cells. (Cell membrane) | Overexpressed in ovarian cancer |
| GLTP- glycolipid transfer protein [HGNC: 24867] | 1.8 ($1.4 \times 10^{-3}$) | Catalyzes the transfer of various glycosphingolipids between membranes | Overexpressed in oral squamous cell carcinoma |
| SCNN1A- sodium channel, non-voltage-gated 1 alpha subunit [HGNC: 10599] | 1.9 ($4.2 \times 10^{-5}$) | Plays an essential role in electrolyte and blood pressure homeostasis and taste perception. (Apical cell membrane) | Prognostic marker for pulmonary adenocarcinoma |
| SLC44A4- solute carrier family 44, member 4 [HGNC: 13941] | 2.2 ($2.6 \times 10^{-6}$) | Choline and Thiamine pyrophosphate (TPP) transporter (Cell membrane) | Associated with prostate and pancreatic cancers |
| TMC8- transmembrane channel-like 8 [HGNC: 20474] | 2.4 ($5.8 \times 10^{-7}$) | Play a role as ion channel. (Endoplasmic reticulum membrane) | Involved in EV-HPV oncogenicity and squamous cell carcinoma |
| SLC9A3R2- solute carrier family 9, subfamily A (NHE3, cation proton antiporter 3), member 3 regulator 2 [HGNC: 11076] | 2.5 ($6.3 \times 10^{-7}$) | Cation/proton antiporter and scaffold protein in the plasma membrane. Acts as scaffold protein in the nucleus. (Endomembrane, nucleus) | Associated widi breast cancer |
| CRACR2A- calcium release activated channel regulator 2A [HGNC: 28657] | 3.2 ($1 \times 10^{-4}$) | Acts as a cytoplasmic calcium-sensor and plays a key role in store-operated calcium entry in T-cells by regulating CRAC channel activation. (Cytoplasm) | No direct association reported |
| ANO1-anoctamin 1, calcium activated chloride channel [HGNC: 21625] | 3.4 ($3.4 \times 10^{-5}$) | A transepithelial anion transport and smooth muscle contraction. (Cell membrane, Cytoplasm) | Overexpressed in different ty pes of cancer. |
| TMC4- transmembrane channel-like 4 [HGNC: 22998] | 6.3 ($6.2 \times 10^{-12}$) | Play a role as ion channels. (Membrane) | No direct association reported |

TABLE 4-continued

Transporters and metabolism related genes differentially expressed between si-NT- and si-hSMAC-A-treated A549 cells derived lung tumors

| Gene (Uniport accession) | Fold change (p value) | Proposed function & cellular localization | Relation to cancer |
|---|---|---|---|
| ATP10B- ATPase, class V, type 10B [HGNC: 13543] | 25.5 ($7.8 \times 10^{-5}$) | Catalyzes ATP-dependent transport of aminophospholipids and ensures the maintenance of asymmetric distribution of phospholipids (cytoplasmic vesicles and ER membrane) | Overexpressed in lung adenocarcinoma and peripheral blood cells |
| METABOLISM RELATED ENZYMES | | | |
| PCK1- phosphoenolpyruvatecarboxykinase 1 [HGNC: 8724] | −6.9 ($2.3 \times 10^{-11}$) | Catalyzes the conversion of oxaloacetate to phosphoenolpyruvate. (Cytoplasm) | Low level expression associated with hepatocarcinogenesis |
| ADH4 - alcohol dehydrogenase 4 (class II) [HGNC: 252] | −2.6 ($4.2 \times 10^{-4}$) | Catalyzes the reaction: An alcohol + NAD+ → an aldehyde or ketone + NADH. (Cytoplasm) | Downregulated in ovarian and liver cancer |
| ADARB1- adenosine deaminase, RNA-specific, B1 [HGNC: 226] | −2.1 ($8.1 \times 10^{-5}$) | Hydrolytic deamination of adenosine to inosine. (Nucleus) | Associated with numerous carcinomas and sarcomas |
| ACAD 10- acyl-CoA dehydrogenase family, member 10, [HGNC: 21597] | −1.7 ($1.6 \times 10^{-3}$) | Associated with fatty acid beta oxidation. (Mitochondria) | Associated with reduced viability in melanoma and pancreatic cancer cells |
| H6PD - hexose-6-phosphate dehydrogenase [HGNC: 4795] | −1.6 ($1.2 \times 10^{-4}$) | Associated with glucose metabolic process. (Endoplasmic reticulum) | Associated with chemoresistance activity |
| CAD- carbamoyl-phosphate synthetase 2, aspartate transcarbamylase, and dihydroorotase [HGNC: 1424] | −1.6 ($1.3 \times 10^{-4}$) | Catalyzes the reaction 2 ATP + L-glutamine + HCO3— + H2O → 2 ADP + phosphate + L-glutamate + carbamoyl phosphate. (Cytoplasm and nucleus) | Associated with colorectal, prostate cancers |
| ACSL4-acyl-CoA synthetase long-chain family member 4 [HGNC: 3571] | −1.6 ($1.0 \times 10^{-2}$) | Activation of long-chain fatty acids for both synthesis of cellular lipids, and degradation via beta-oxidation | Associated with breast, colon, brain and lung cancers |
| DGKD-diacylglycerol kinase, delta 130 kDa [HGNC: 2851] | −1.5 ($2.7 \times 10^{-4}$) | Involved in 1,2-diacyl-sn-glycerol phosphorylation | Associated with prostate cancer |
| FASN-fatty acid synthase [HGNC: 3594] | −1.5 ($3.3 \times 10^{-4}$) | Catalyzes the formation of long-chain fatty acids from acetyl-CoA, malonyl-CoA and NADPH | Associated with lung cancer and others |
| ORMDL2-sphingolipid biosynthesis regulator 2 [HGNC: 16037] | 1.5 ($4.0 \times 10^{-3}$) | Negative regulator of sphingolipid synthesis | No direct association reported |
| CANT1- calcium activated nucleotidase 1 [HGNC: 19721] | 1.5 ($4.0 \times 10^{-4}$) | Nucleotidase involved in UDP, GDP, UTP, GTP dephosphorylation. (Golgi, Endoplasmatic reticulum) | Associated with melanoma |
| CMAS- cytidine monophosphate N-acetylneuraminic acid synthetase [HGNC: 18290] | 1.5 ($7.4 \times 10^{-4}$) | Involved in the pathway N-acetylneuraminate metabolism. (Nucleus) | Associated with breast cancer |
| GPT2- glutamic pyruvate transaminase (alanine aminotransferase) 2 [HGNC: 18062] | 1.5 ($1.4 \times 10^{-3}$) | Formation of pyruvate and glutamate by transamination between alanine and 2-oxoglutarate. (Mitochondria) | Associated with colon, liver cancers. |
| MGAT4B- mannosyl (alpha-1,3-)-gly coprotein beta-1,4-N-acetylglucosaminyltransferase, isozyme B [HGNC: 7048] | 1.5 ($6.7 \times 10^{-4}$) | Glycosyltransferase involved in transfer GlcNAc to the core mannose residues. (Golgi) | Associated with mouse carcinogen-induced hepatocarcinoma. |
| ST3GAL4- ST3 beta-galactoside alpha-2,3-sialyltransferase 4 [HGNC: 10864] | 1.5 ($4.5 \times 10^{-3}$) | Involved in protein glycosylation. (Golgi) | Associated with gastric carcinoma. |
| AGPAT2- 1-acylglycerol-3-phosphate O-acyltransferase 2 [HGNC: 325] | 1.6 ($8.4 \times 10^{-5}$) | Converts lysophosphatidic acid (LPA) into phosphatidic acid. (Endoplasmic reticulum membrane) | Upregulated in breast and cervical cancer. |
| GALNT5- polypeptide N-acetylgalactosaminyltransferase 5 [HGNC: 4127] | 1.6 ($1.7 \times 10^{-5}$) | Involved in protein glycosylation. (Golgi) | Associated with hepatoblastoma. |

TABLE 4-continued

Transporters and metabolism related genes differentially expressed between si-NT- and si-hSMAC-A-treated A549 cells derived lung tumors

| Gene (Uniport accession) | Fold change (p value) | Proposed function & cellular localization | Relation to cancer |
|---|---|---|---|
| GALNT12- polypeptide N-acetylgalactosaminyltransferase 12 [HGNC: 19877] | 1.6 ($3.3 \times 10^{-4}$) | Involved in protein glycosylation. (Golgi) | Associated with breast, colorectal cancers. |
| ST6GALNAC1- (alpha-N-acetyl-neuraminyl-2,3-beta-galactosyl-1,3)-N-acetylgalactosaminide alpha-2,6-sialyltransferase 1 [HGNC: 23614] | 1.6 ($6.2 \times 10^{-4}$) | Involved in protein glycosylation. (Golgi) | Associated with esophageal squamous cell carcinoma and prostate cancer. |
| PLCB4 - phospholipase C, beta 4 [HGNC: 9059] | 1.7 ($9.2 \times 10^{-4}$) | Involved in inositol phosphate metabolic process. (Cytosol, Nucleus, smooth Endoplasmic reticulum) | Biomarker for uveal melanoma. |
| BLVRA - biliverdin reductase A [HGNC: 1062] | 1.7 ($2.1 \times 10^{-3}$) | Oxidation of bilirubin using NAD(P) to biliverdin. (Cytoplasm) | Overexpressed in liver cancer. |
| GCNT3- glucosaminyl (N-acetyl) transferase 3, mucin type [HGNC: 4205] | 1.7 ($1.0 \times 10^{-2}$) | Involved in carbohydrate metabolic process. (Golgi) | Associated with pancreatic, colon cancer. |
| ADI1 - acireductone dioxygenase 1 [HGNC: 30576] | 1.8 ($1.8 \times 10^{-4}$) | Formation of formate and 2-keto-4-mediyldiiobutyrate. (Cytosol, Nucleus and Cell membrane) | Downregulated in prostate cancer. |
| FUT6- Fucosyl transferase 6 (alpha (1,3) fucosyltransferase) [HGNC: 4017] | 1.8 ($1.5 \times 10^{-3}$) | Involved in L-fucose catabolic process (Golgi) | Associated with attenuation of EGFR signaling and invasivity. |
| LIPH - lipase, member [HHGNC: 18483] | 1.9 ($3.1 \times 10^{-3}$) | Hydrolyzes specifically phosphatidic acid (PA) to produce 2-acyl lysophosphatidic acid (LPA) and fatty acid. (Membrane) | Overexpressed in lung and breast cancer. |
| GALNT6- polypeptide N-acetylgalactosaminyl transferase 6 [HGNC: 4128] | 1.9 ($1.8 \times 10^{-4}$) | Involved in O-glycan processing (Golgi) | Associated with pancreatic, breast cancers. |
| CDA - cytidine deaminase [HGNC: 1712] | 2.0 ($1.1 \times 10^{-3}$) | Cytidine deaminase. (Cytosol, extracellular region) | Overexpressed in cancer |
| FAXDC2- fatty acid hydroxy lase domain containing 2 [HGNC: 1334] | 2.1 ($5.7 \times 10^{-5}$) | Involved in fatty acid biosynthetic process. (Endoplasmatic reticulum) | Reduced expression is associated with acute myeloid leukemia and acute megakaryoblastic leukemia. |
| B3GNT6- UDP-GlcNAc: betaGal beta-1,3-N-acetylglucosaminyltransferase 6 (core 3 synthase) [HGNC: 24141] | 2.1 ($1.6 \times 10^{-4}$) | Involved in glucuronosyltransferase activity. (Golgi) | Associated with prostate cancer. |
| ENTPD8 - ectonucleoside triphosphate diphosphohydrolase 8 [HGNC: 24860] | 2.7 ($2.1 \times 10^{-3}$) | Involved in purine and pyrimidine metabolism. (Cell membrane) | May be involved in the chemical formation of DNA adducts. |
| FUT3- fucosyltransferase 3 (galactoside 3(4)-L-fucosyltransferase, Lewis blood group) [HGNC: 4014] | 2.7 ($2.9 \times 10^{-7}$) | Involved in oligosaccharide biosynthetic process. (Golgi) | Associated with metastasis and survival rate |
| CYB5R2 -cytochrome b5 reductase 2 [HGNC: 24376] | 2.8 ($3 \times 10^{-4}$) | Involved in desaturation and elongation of fatty acids, cholesterol biosynthesis, drug metabolism. (Cytosol, Nucleus, smooth ER) | Act as a tumor suppressor in nasopharyngeal carcinoma |
| DHRS9 - dehydrogenase/ reductase (SDR family) member 9 [HGNC: 16888] | 2.8 ($5.6 \times 10^{-4}$) | Involved in retinol metabolic process, (Endoplasmic reticulum) | Downregulated in colorectal cancer |
| SDR16C5- short chain dehydrogenase/reductase family 16C, member 5 [HGNC: 30311] | 3.0 ($1.1 \times 10^{-4}$) | Involved in the oxidation of retinol to retinaldehyde. (Endoplasmic reticulum) | No direct association reported |
| STARD10 - StAR-related lipid transfer (START) domain containing 10 [HGNC: 10666] | 3.7 ($1.1 \times 10^{-13}$) | Involved in phospholipid transport. (Cytosol, Nucleus) | Associated with breast cancer |
| PADI1- peptidyl arginine deiminase, type I | 3.8 ($2.1 \times 10^{-3}$) | Deamination of arginine residues. | Involve in tumor progression |

TABLE 4-continued

Transporters and metabolism related genes differentially expressed between si-NT- and si-hSMAC-A-treated A549 cells derived lung tumors

| Gene (Uniport accession) | Fold change (p value) | Proposed function & cellular localization | Relation to cancer |
|---|---|---|---|
| [HGNC: 18367] | | (Cytosol, Extracellular exosome) | |
| FAR2- fatty acyl CoA reductase 2 [HGNC: 25531] | 4.1 ($1.5 \times 10^{-5}$) | Catalyzes the reduction of fatty acyl-CoA to fatty alcohols | No direct association reported |
| DGAT2- diacylglycerol O-acyltransferase 2 [HGNC: 16940] | 4.9 ($2.5 \times 10^{-4}$) | Catalyzes the terminal step in triacylglycerol synthesis using diacylglycerol and fatty acyl CoA | Associated with Hepatocarcinoma |
| ELOVL3-fatty acid elongase 3 [HGNC: 18047] | 7.4 ($1.0 \times 10^{-3}$) | Catalyzes the long-chain fatty acids elongation toward C18 acyl-CoAs | No direct association reported |
| ELOVL4 fatty acid elongase 4 [HGNC: 18047] | 145.2 ($6.2 \times 10^{-17}$) | Catalyzes the long-chain fatty acids elongation, elongates C24:0 and C26:0 acyl-CoAs | Hypermethylated in pancreas, colorectal carcinoma |
| REDOX STATE REGULATION | | | |
| NOS1-nitric oxide synthase, neuronal [HGNC: 7872] | -5.9 ($1.6 \times 10^{-6}$) | Produces nitric oxide (NO), which is a ROS, neurotransmitter and angiogenesis regulator | Abundant in low-differentiated, breast gynaecological, central nerve system cancer and NSCLC |
| SOD2- superoxide dismutase [Mn], mitochondrial [HGNC: 11180] | -1.9 ($3.7 \times 10^{-5}$) | Inactivates ROS, as superoxide anion radicals | Increased expression in prostate, lung and colon cancer |
| GSTP1- glutathione S-transferase pi 1 [HGNC: 4638] | -1.6 ($2.4 \times 10^{-3}$) | Conjugates reduced glutathione to a wide number of exogenous and endogenous hydrophobic electrophiles (mitochondria) | Associated with lung cancer |
| TXN-Thioredoxin [Source: HGNC Symbol; Acc: HGNC: 12435] | 2.1 ($1.8 \times 10^{-4}$) | Involved in redox reactions through the reversible oxidation of dithiol to a disulfide | Prognostic biomarker in NSCLC and breast cancer |
| PXDN-peroxidasin homolog [HGNC: 14966] | 3.3 ($5.1 \times 10^{-8}$) | Participate in $H_2O_2$ metabolism and peroxidative reactions | Involved in melanoma invasion. The decreased expression is observed in myeloid leukaemia |

TABLE 5

List of selected genes associated with Inflammation differentially expressed between si-NT- and si-hSMAC-A-treated A549 cells-derived tumors, NGS analysis

| Gene (Uniport accession) | Fold change (p value) | Proposed function & cellular localization | Relation to cancer |
|---|---|---|---|
| Inflammatory ligands | | | |
| CCL24- chemokine (C-C motif) ligand 24 [HGNC: 10623] | 1.9 ($3.0 \times 10^{-4}$) | CHEMOTACTIC FOR RESTING T LYMPHOCYTES AND EOSINOPHILS | Associated with poor prognosis in HCC and colorectal cancer |
| CCL28- chemokine (C-C motif) ligand 28 [HGNC: 17700] | 1.9 ($8.8 \times 10^{-4}$) | Involved in inflammatory response | Support cancer metastasis |
| PROC- protein C (inactivator of coagulation factors Va and VIIIa) [HGNC: 9451] | 1.8 ($1.2 \times 10^{-3}$) | involved in hemostasis, inflammation and signal transduction | The expression is associated with an improved lung cancer prognosis |
| CX3CL1-chemokine (C-X3-C motif) ligand 1 [HGNC: 10647] | 1.6 ($1.6 \times 10^{-4}$) | Activates integrins and elicits adhesive and migratory leukocytes functions | Associated with cancer progression |
| TNFAIP6 (TSG6)- tumor necrosis factor, alpha-induced protein 6 [HGNC: 11898] | -1.6 ($2.2 \times 10^{-3}$) | Interacts with ECM proteins during inflammation and tumorigenesis | Associated with poor prognosis |
| C5- complement component 5 [HGNC: 1331] | -1.7 ($1.0 \times 10^{-2}$) | Involved in late complement components formation C5-C9 and inflammation progress | Associated with a favorable microenvironment for cancer progression |

TABLE 5-continued

List of selected genes associated with Inflammation differentially expressed between si-NT- and si-hSMAC-A-treated A549 cells-derived tumors, NGS analysis

| Gene (Uniport accession) | Fold change (p value) | Proposed function & cellular localization | Relation to cancer |
|---|---|---|---|
| GAS6- growth arrest-specific 6 [HGNC: 4168] | −1.7 ($3.0 \times 10^{-3}$) | AXL receptor tyrosine kinase activation | Overexpressed in lung cancer |
| TNFSF14 (LIGHT)- tumor necrosis factor superfamily, member 14 [HGNC: 11930] | −1.8 ($1.8 \times 10^{-3}$) | Involved as a costimulatory factor in anticancer lymphocytes cytotoxic activity | TNFSF14 is involved in anticancer immune-stimulatory activity |
| CD274-(PD-L1) molecule [HGNC: 17635] | −1.9 ($3.3 \times 10^{-4}$) | A costimulatory molecule, involved in the inhibition of T-cells proliferation and cytokine production | Associated with a more aggressive nsclc |
| IL6- interleukin 6 [HGNC: 6018] | −2.5 ($1.5 \times 10^{-6}$) | Involved in inflammatory response | Over-expressed in NSCLC |
| RECEPTORS AND CO-RECEPTORS | | | |
| IL1R1- interleukin 1 receptor, type I [HGNC: 5993] | −1.6 ($4.0 \times 10^{-4}$) | Receptor for IL1A, IL1B and IL1RN, mediates NF-kappa-B and MAPK activation | Associated with breast cancer cells invasivity |
| IL18BP- interleukin 18 binding protein [HGNC: 5987] | −1.6 ($1.0 \times 10^{-2}$) | Interacts with IL-18, inhibits its activity and Th1 immune response | Produced in the ovarian cancer microenvironment to regulate immune response |
| IL27RA- interleukin 27 receptor, alpha [HGNC: 17290] | −1.6 ($1.0 \times 10^{-2}$) | Receptor for IL27, acts through STAT3 and STAT1 | Resulting in the promotion of tumor growth |
| OSMR- oncostatin M receptor [HGNC: 8507] | −1.7 ($6.7 \times 10^{-6}$) | Binds IL31 together with IL31RA to activate STAT3 | Associated with poor prognosis in cervical squamous cell carcinoma |
| TLR3- toll-like receptor 3 [HGNC: 11849] | −1.7 ($5.0 \times 10^{-3}$) | A nucleotide-sensing TLR activated by double-stranded RNA, leading to NF-kappa-B activation | Associated with lung metastasis by neutrophil activation |
| MRC2 (ENDO180)- mannose receptor, C type 2 [HGNC: 16875] | −1.7 ($3.6 \times 10^{-3}$) | Involved in the remodeling of ECM cooperating with the MMPs | Associated with prostate, breast cancers and metastasis |
| C5AR1 (CD88)-complement component 5a receptor 1 [HGNC: 1338] | −1.7 ($4.0 \times 10^{-3}$) | Receptor for the chemotactic and inflammatory peptide anaphylatoxin C5a | Associated with poor prognosis |
| LBP-lipopolysaccharide binding protein [HGNC: 6517] | −2.1 ($1.2 \times 10^{-4}$) | Binds to LPS and promotes the cytokines release | It was not changed in lung adenocarcinoma |
| ACKR3- atypical chemokine receptor 3 [HGNC: 23692] | −2.2 ($1.8 \times 10^{-5}$) | a receptor for chemokines CXCL11 and CXCL12/SDF1 | Increased expression in lung SCC |
| CYTOSOLIC MOLECULES | | | |
| CREB3L3- cAMP responsive element binding protein 3-like 3 [HGNC: 18855] | 2.0 ($4.3 \times 10^{-4}$) | Transcription factor activates expression of acute phase response (APR) genes in inflammatory response | No direct association reported |
| IRF6- interferon regulatory factor 6 [HGNC: 6121] | 1.6 ($1.0 \times 10^{-3}$) | DNA-binding transcriptional activator | Involved in tumor suppression and SCCs differentiation. |
| PTGS2 (Cox-2)- prostaglandin - endoperoxide synthase 2 (prostaglandin G/H synthase and cyclooxygenase) [HGNC: 96051 | −1.8 ($1.4 \times 10^{-4}$) | Converts arachidonate to prostaglandin H2 | Involved in tumor grow and metastasis |

Example 8: Ultrastructure and Lipid Synthesis in si-NT-TTs and si-hSMAC-A-TTs As SMAC silencing resulted in morphological changes (FIG. 7), the sub-cellular ultrastructure of si-NT-TTs and si-hSMAC-A-TTs were analyzed using transmission electron microscopy (TEM) (FIGS. 10D, 12A). In si-NT-TTs, a massive amount of intracellular vesicles of different sizes and densities, such as lysosomes and large vesicles containing surfactant-accumulating lamellar bodies were seen. Such vesicles were not observed in the tumors where hSMAC/Diablo was silenced (si-hSMAC-A-TTs) (FIG. 10D, 12A).

In addition, in si-NT-TTs, the major DNA form in the nucleus is darkly staining heterochromatin, while in si-SMAC-TTs, the DNA is mainly found as euchromatin and not readily stained (FIGS. 10D, 12A, B). Interestingly, euchromatin is prevalent in cells that are active in the transcription of many genes, while heterochromatin is most abundant in cells that are less active. This may be associated with cell differentiation processes. Moreover, the sizes of nuclei in si-hSMAC-A-TTs are almost twice those in si-NT-TTs and showed lower chromatin staining (FIG. 10D, 12A, B). The large nuclei in si-NT-TTs could result from membrane fluidity and/or osmolality changes, as reflected in the modified expression of transporters (FIG. 11A, Table 4). Changes in the expression of genes associated with cell membrane, exosomes, and ER- and Golgi-related proteins (FIG. 11A, B) and in cell ultrastructure (FIG. 10D, E), are summarized in a schematic model (FIG. 12C).

Figure 10F:
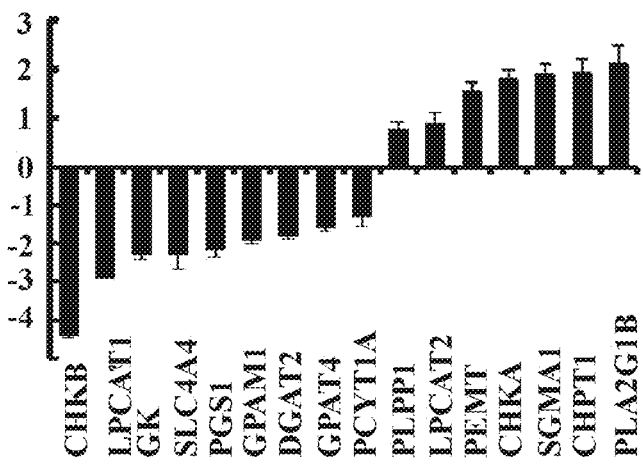
Figure 10G:
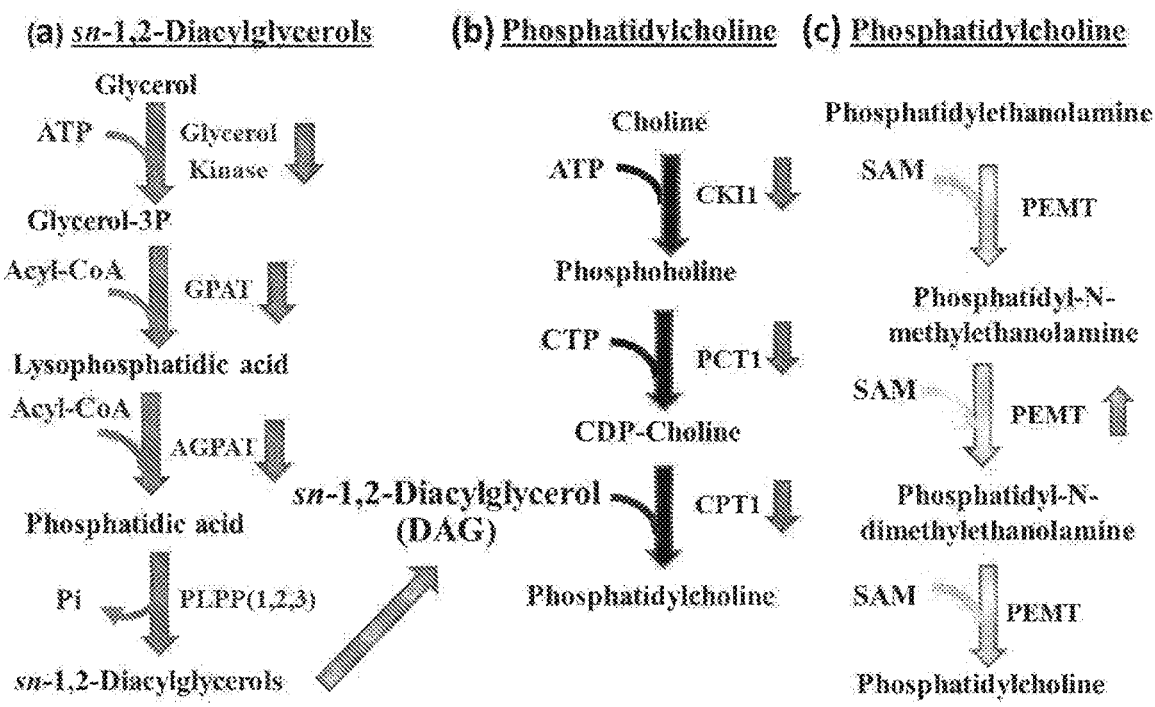

The amounts of total phospholipids and PC in si-NC-TTs and si-SMAC-A-TTs lipid extracts were analyzed (FIG. 10F). Total phospholipids and PC were decreased by 47% and 37%, respectively, in si-SMAC-A-TTs.

These results are in agreement with the findings that SMAC/Diablo silencing resulted in alterations in the expression levels of genes associated with the transport, synthesis and regulation of lipids (FIG. 10C, Table 4). Therefore, using q-PCR, the levels of genes encoding enzymes associated with diacylglycerol (DAG) synthesis, such as glycerol kinase (GK), and the mitochondrial proteins glycerol-3-phosphate acyltransferase 1 and 4 (GPAM1, GPAM4) were analyzed. All were found to be decreased in si-SMAC-TTs (FIG. 10F). In addition, levels of mRNA encoding enzymes involved in PC synthesis were also decreased (FIG. 10F), whereas those encoding other enzymes associated with PC synthesis from phosphatidylethanolamine, namely phosphatidylethanolamine N-methyltransferase (PEMT), and choline/ethanolamine kinase A (CHKA), cholinephosphotransferase 1 (CHPT1) and phospholipase A2 (PLA2G1B), were increased. These results are presented in the PC and DAG synthesis pathways depicted in FIG. 10G.

Example 9: SMAC/Diablo Interacting Peptides

Figure 15A:
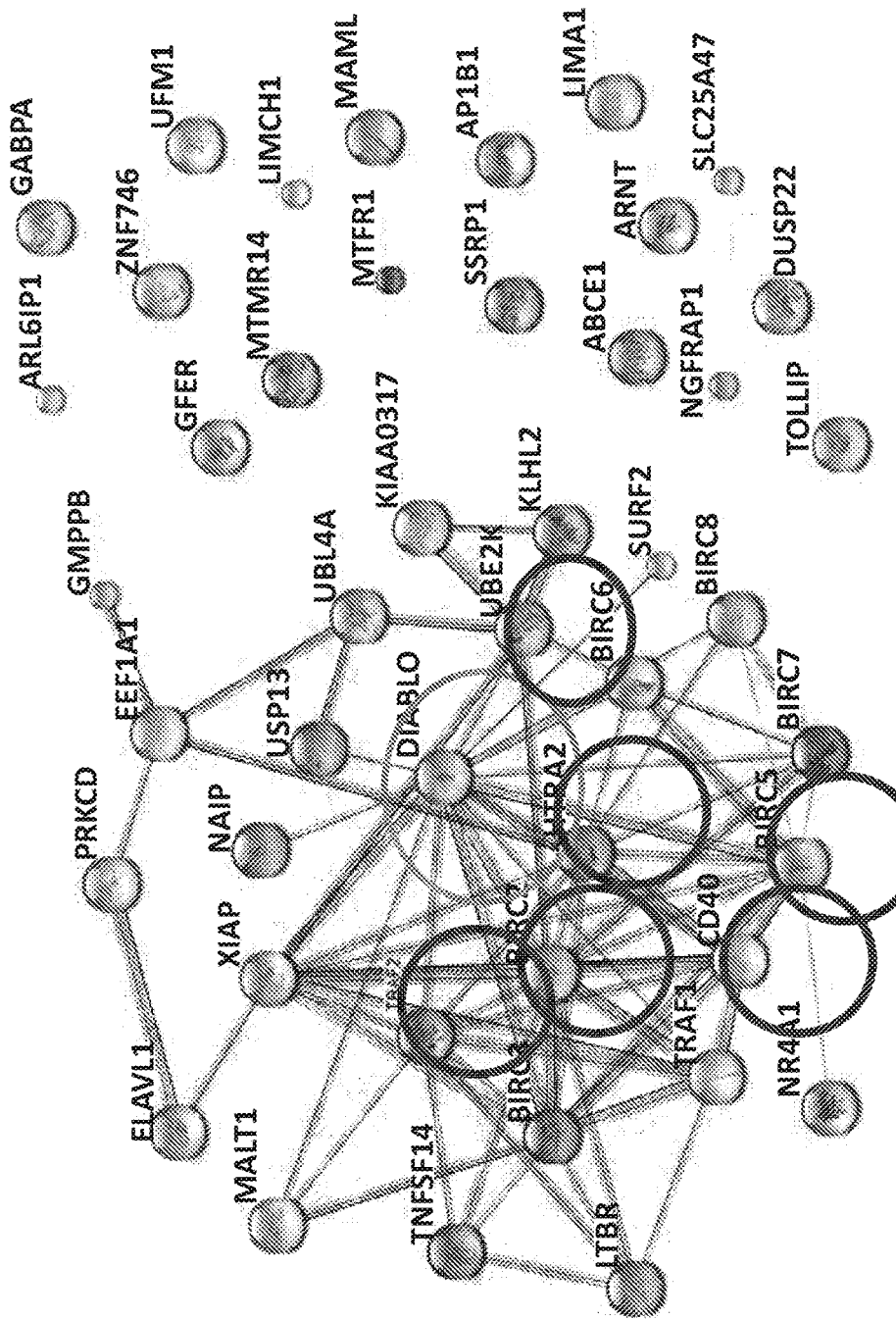
FIG. 15 shows protein interactions of SMAC/Diablo. (A) Network analysis of human proteins interacting with SMAC (B) protein interactions of SMAC/Diablo with glass-bound peptide array consisting of overlapping peptides derived from 14 SMAC/Diablo-interacting proteins. The peptide array was incubated overnight with purified SMAC/Diablo (0.8 µM) and then blotted with anti-SMAC antibodies (1:2000), followed by incubation with HRP-conjugated anti-mouse IgG and detection using a chemiluminescence kit. The black dots indicate SMAC/Diablo binding and the numbers their location on the array, allowing identification of the peptide.

A network of proteins interacting with SMAC/Diablo (FIG. 15A) was identified using Thebiogrid database for protein-protein interactions (thebiogrid.org), based on the following methods to define interactions: Two hybrid analysis;
  Affinity capture-Western blots;
  Affinity capture-MS;
  Co-crystal structure
  Biochemical activity
  Protein-peptide interaction;
  Förster resonance energy transfer Fourteen (14) proteins were selected as being associated with SMAC/Diablo, all of human (Homo sapiens) origin:
1. XIAP: X-linked inhibitor of apoptosis Protein (NP_001158.2; Uniprot-P98170)
2. HTRA2: HtrA serine peptidase 2 Protein (NP_037379.1; Uniprot-O43464)
3. BIRC2: Baculoviral IAP repeat containing 2 Protein (NP_001157.1; Uniprot-Q13490)
4. CD40: Tumor necrosis factor receptor superfamily member 5 (NP_001241.1; Uniprot-P25942)
5. TRAF2: TNF receptor associated factor 2 Protein (NP_066961.2; Uniprot-Q12933)
6. UBE2K: Ubiquitin conjugating enzyme E2 K Protein (NP_005330.1; Uniprot-P61086)
7. NR4A1: Nuclear receptor subfamily 4 group A member 1 Protein (NP_001189163.1; Uniprot-P22736)
8. MAML2: Mastermind like transcriptional coactivator 2 Protein (NP_115803.1; Uniprot-Q8IZL2)
9. ARNT: Aryl hydrocarbon receptor nuclear translocator isoform 1 Protein (NP_001659.1; Uniprot-P27540)
10. BIRC5: Baculoviral TAP repeat containing 5 Protein (NP_001159.2; Uniprot-O15392)
11. AREL1: Apoptosis resistant E3 ubiquitin protein ligase 1 Protein (NP_001034568.1; Uniprot-O15033)
12. GFER: Growth factor, augmenter of liver regeneration Protein (NP_005253.3; Uniprot-P55789)
13. MTFR1: Mitochondrial fission regulator 1 Protein (NP_055452.3; Uniprot-Q15390)
14. GMPPB: GDP-mannose pyrophosphorylase B Protein (NP_037466.2; Uniprot-Q9Y5P6).

A custom glass-bound peptide array consisting of 768 overlapping peptides (of 20-25 amino acid length) derived from the above-selected proteins was prepared by Intavis, Bioanalytical instruments, Kolen, Germany.

The peptide array was incubated overnight at 4° C. with purified SMAC (0.8 μM) and then blotted with anti-SMAC antibodies (1:2000) and incubated for additional 4 h at 4° C. followed by 2 h incubation with HRP-conjugated anti-mouse IgG and detection using the EZ-ECL chemiluminescence detection kit as described hereinabove.

Figure 15B:
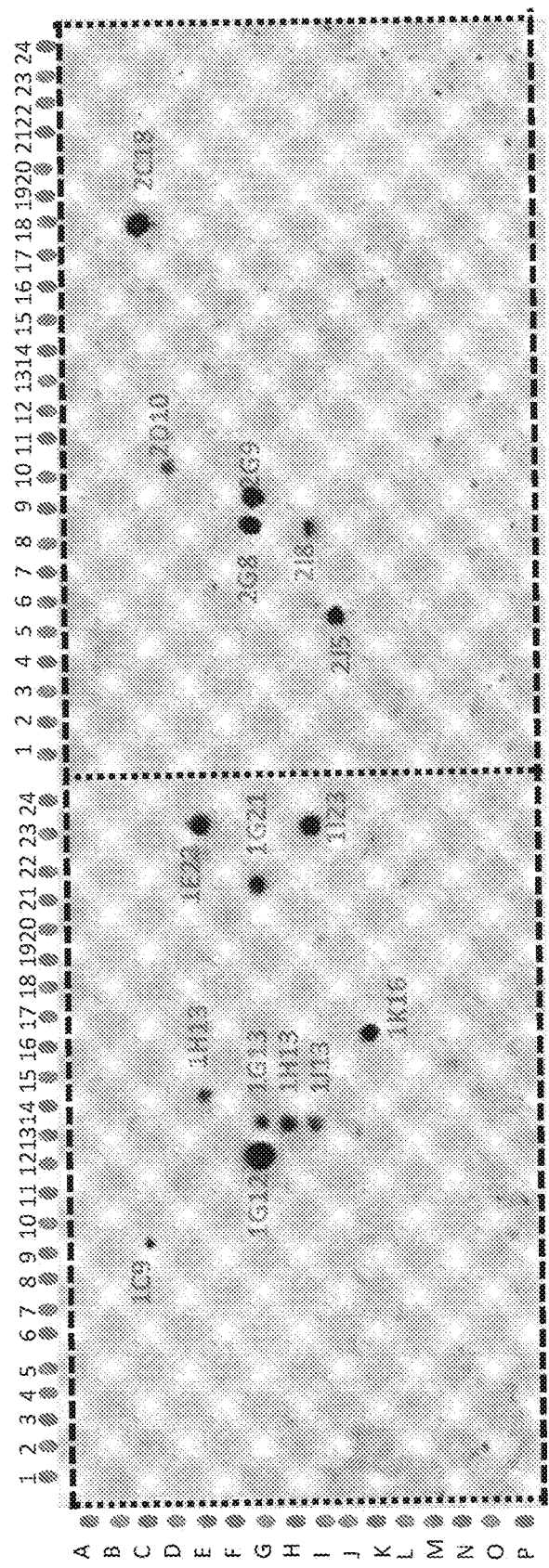

Dark spots, marked with their location on the peptide array, represent binding of SMAC to peptides derived from the SMAC-interacting proteins (FIG. 15B). The peptide origin, name and SEQ ID NOs. are presented in Table 6 below.

TABLE 6

Peptides derived from proteins associated with SMAC/Diablo that interacted with SMAC/Diablo

| SMAC/Diablo interacting protein | Peptide designation (Spot location FIG. 15) | Peptide Sequence | SEQ ID NO. |
|---|---|---|---|
| BIRC5 | 1H13 | SGCAFLSVKKQFEELTLGEFLKLD | 46 |
| UBE2K | 2C18 | VRFITKIWHPNISSVTGAICLDILK | 47 |
| BIRC2 | 1G12 | LIRKNRMALFQQLTCVLPILDNLLK | 48 |
|  | 1G13 | FQQLTCVLPILDNLLKANVINKQEH | 49 |
|  | IE23 | SASLGSTSKNTSPMRNSFAHSLSPT | 50 |
|  | 1G18 | LVKGNAAANIFKNCLKEIDSTLYKN | 51 |
|  | 1G21 | FVDKNMKYIPTEDVSGLSLEEQLRRL | 52 |
| TRAF2 | 1I23 | MAAASVTPPGSLELLQPGFSKTLLGTK | 53 |
|  | 1J20 | DGCGKKKIPREKFQDHVKTCGKCRV | 54 |
|  | 1K16 | AGRIPAIFSPAFYTSRYGYKMCLRI | 55 |
|  | 1K20 | HLSLFFVVMKGPNDALLRWPFNQKV | 56 |
| MAML2 | 2D9 | GAGLLGGGSVTPRVHSAIVERLRAR | 57 |
|  | 2G8 | QQQQQQQP*SSQPAQSLPSQPLLRS** | 58 |
|  | 2G9 | *SSQPAQSLPSQPLLRS*PLPLQQKLLL | 59 |
| ARNT | 2I14 | MAATTANPEMTSDVPSLGPAIASGN | 60 |
|  | 2J5 | VSHMKSLRGTGNTSTDGSYKPSFLT | 61 |
|  | 2J14 | DVDKLREQLSTSENALTGRILDLKT | 62 |
| NR4A1 | 1M17 | GDNASCQHYGVRTCEGCKGFFKRTV | 63 |
|  | 1N22 | ASCLKEHVAAVAGEPQPASCLSRLL | 64 |
|  | 1N23 | AVAGEPQPASCLSRLLGKLPELRTL | 65 |
| CD40 | 1I13 | LVVQQAGTNKTDVVCGPQDRLRALV | 66 |
| HTRA2 | 1C9 | ALGGIRWGRRPRLTPDLRALLTSGT | 67 |

*Letter marked in italic represent overlapping sequence within SEQ ID NO: 58 and SEQ ID NO: 59.

Example 10: SMAC/Diablo Specific Interaction with Peptides Derived from SMAC/Diablo-Interacting Proteins The effect of peptide 2C18 (SEQ ID NO:47) derived from the SMAC/Diablo interacting proteins, Ubiquitin conjugating enzyme E2 K Protein (UBEK2); and of peptide 1G12 (SEQ ID NO:48) derived from Baculoviral IAP repeat containing 2 Protein (BIRC2) on SMAC/Diablo capability to interact with these and other peptides was examined.

Figure 16A:
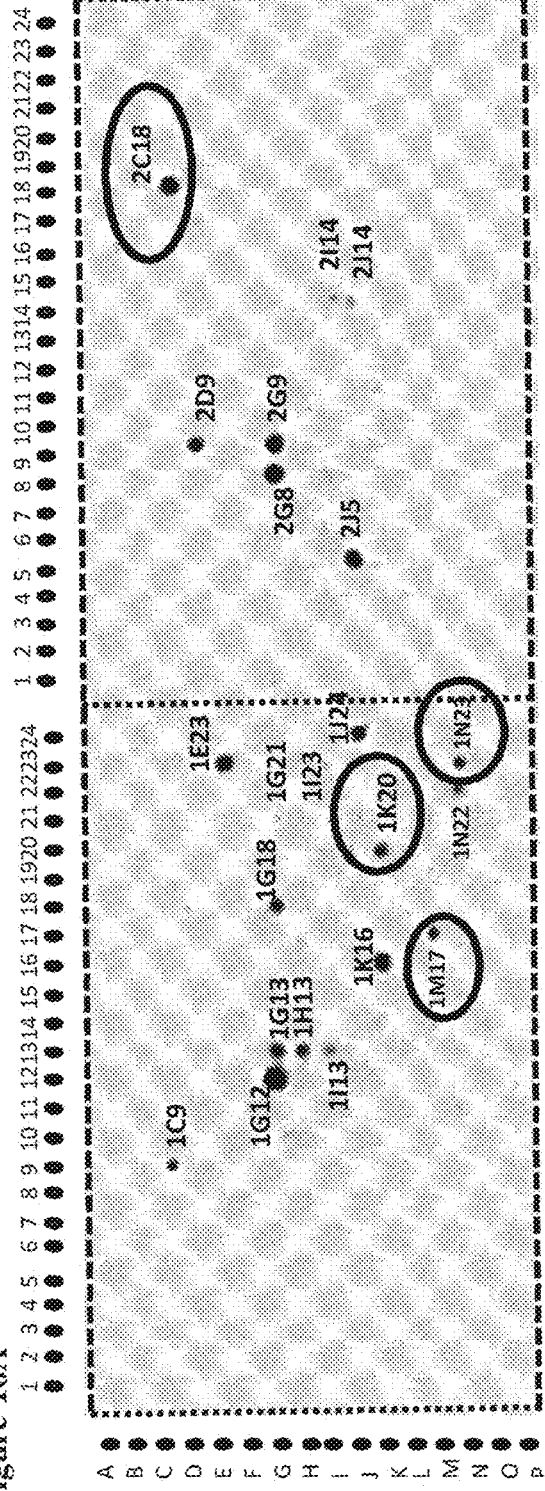
FIG. 16 demonstrates the effect of peptide 2C18 (SEQ ID NO:47) derived from the SMAC/Diablo-interacting protein Ubiquitin conjugating enzyme E2 K Protein (UBEK2) on SMAC/Diablo capability to interact with the 2C18 peptide and additional peptides of the glass-bound peptide array. (A) Peptide array incubated with free SMAC/Diablo as described for FIG. 15 hereinabove. (B) SMAC (0.8 µM) was incubated with the synthetic peptides 2C18 (2.4 µM) and blotted as in (A). The peptide spots that eliminated due to interaction with SMAC/Diablo are circled.
Figure 16B:
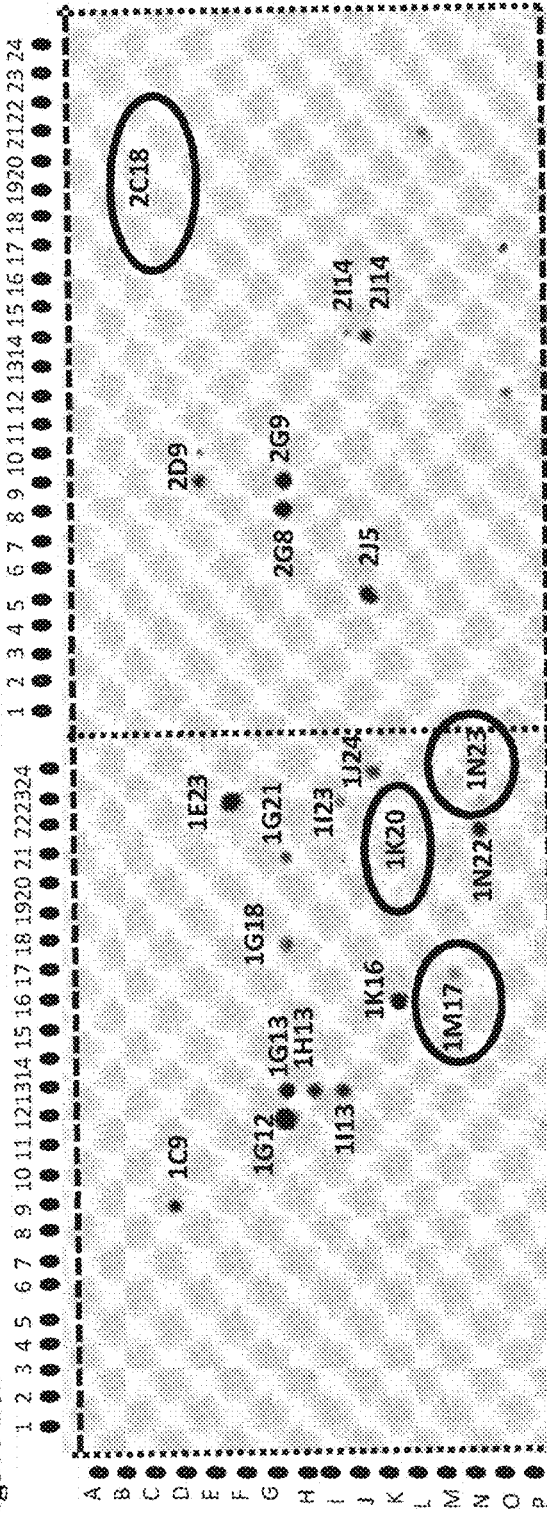
Figure 17A:
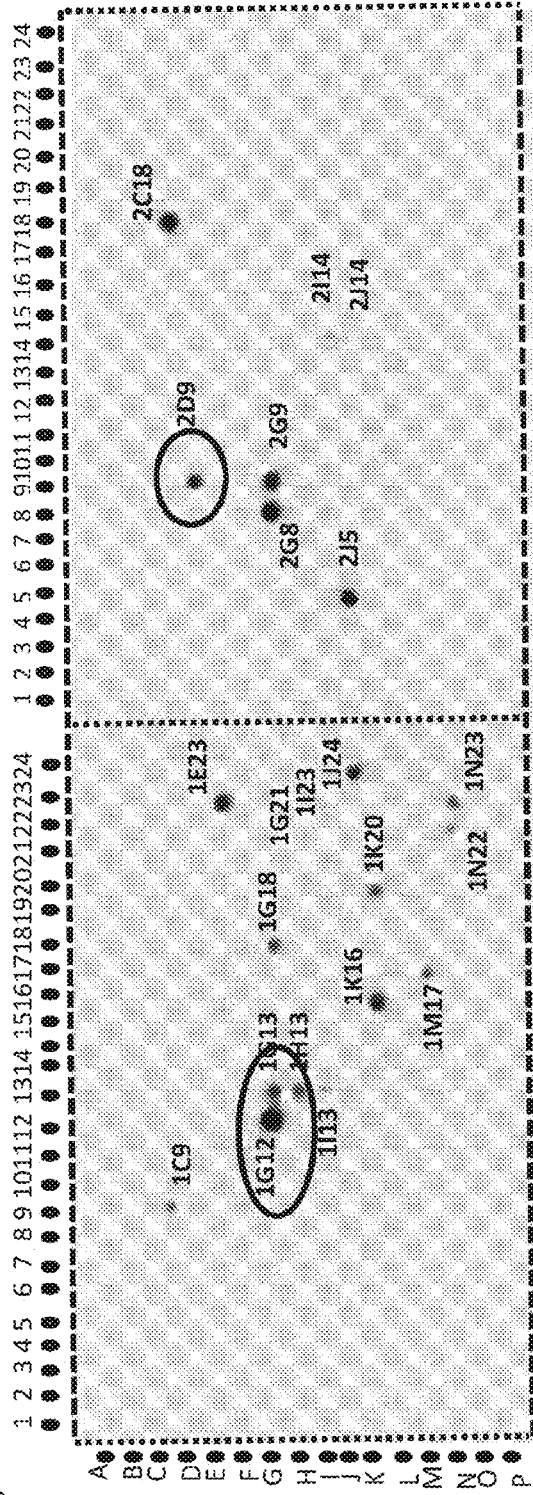
FIG. 17 demonstrates the effect of peptide 1G12 (SEQ ID NO:48) derived from the SMAC/Diablo-interacting protein Baculoviral IAP repeat containing 2 Protein (BIRC2) on SMAC/Diablo capability to interact with the 1G12 peptide and additional peptides of the glass-bound peptide array. (A) Peptide array incubated with free SMAC/Diablo as described for FIG. 15 hereinabove. (B) SMAC (0.8 µM) was incubated with the synthetic peptides derived from BIRC2 spot 1G12 (2.4 µM) blotted as in (A). The peptide spots that eliminated due to interaction with SMAC/Diablo are circled.
Figure 17B:
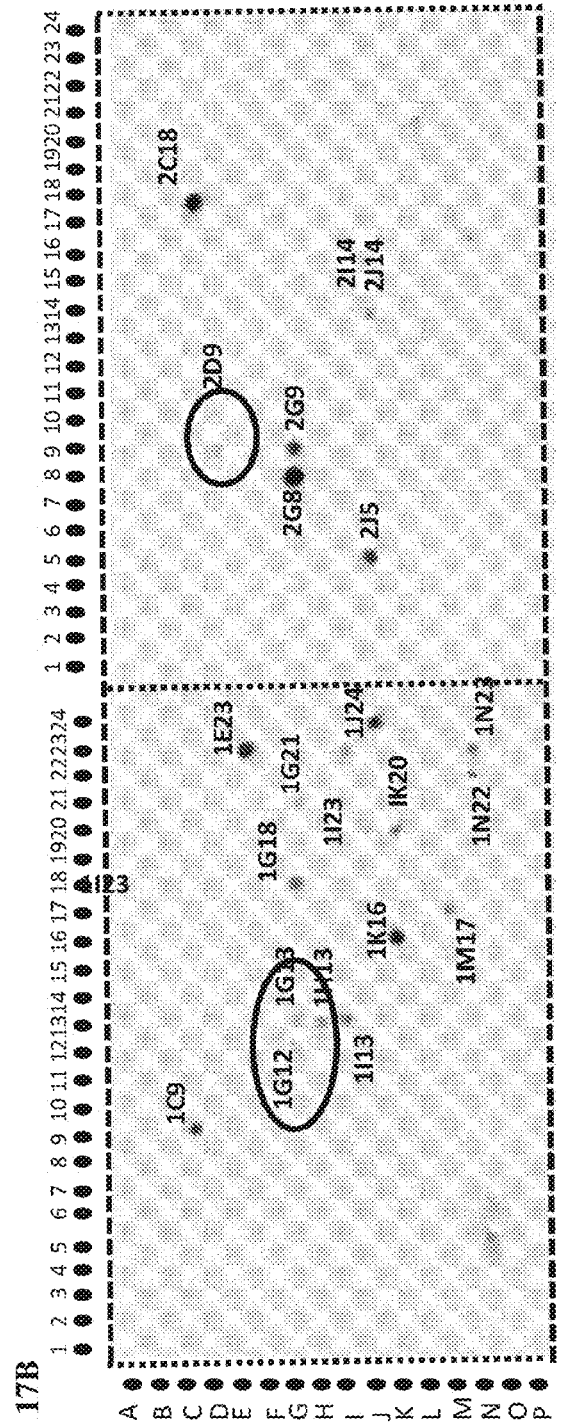

The glass-bound peptide array described hereinabove was used. SMAC/Diablo (0.8 µM) was incubated with each of the peptides—2C18 (2.4 µM) and 1G12 (2.4 µM) for 2 hr at 24° C. and then incubated with the peptide array for 4 h at 4° C. Then the slides were washed and SMAC/Diablo antibodies (1:2000) were added, followed by incubation with HRP-conjugated anti-mouse IgG after which chemiluminescent spots were detected. Corresponding glass-bound peptide array incubated overnight with 0.8 µM free SMAC/Diablo, blotted with the same concentration of SMAC/Diablo antibodies followed by incubation with HRP-conjugated anti-mouse IgG served as a control. As expected, pre-incubation of SMAC/Diablo with peptide 2C18 or peptide 1G12 significantly decreased or even prevented the interaction of SMAC/Diablo with the corresponding peptides, as the binding site is already occupied by the free peptide pre-incubated with SMAC/Diablo. This is indicated by the decreased intensity or disappearance of chemiluminescence in the peptide spot position compared to the control (FIG. 16 and FIG. 17, respectively). Moreover, pre-incubation of SMAC/Diablo with peptide 2C18 decreased SMAC/Diablo interaction with the array-bound peptides 1M17 and 1N23 derived from Nuclear receptor subfamily 4 group A member 1 Protein (NR4A1) and peptide 1K20 derived from TNF receptor associated factor 2 Protein (TRAF2) (FIG. 16B, eliminated spots are circled). Pre-incubation of SMAC/Diablo with peptide 1G12 significantly reduced SMAC/Diablo interaction with 1G12 and also the interaction with peptide 1G13, also derived from BIRC2 and having overlapping sequence with peptide 1G12, but also with peptide 1H13, derived from Baculoviral IAP repeat containing 5 Protein (BIRCS) and peptide 2D9, derived from Mastermind like transcriptional coactivator 2 Protein (MAML2) (FIG. 17B, eliminated spots are circled).

Example 11: Cell Growth Inhibition by Peptides of the Invention

Considering the presence of the overexpressed SMAC/Diablo in the mitochondria intermembrane space and in the nucleus it is important to target SMAC/Diablo interacting peptide to these compartments, facilitating the cellular uptake and nucleus and/or mitochondria localization of the peptides of the present invention is of significant importance for the therapeutic use of the peptides of the invention. Several conjugates of peptides of the invention fused to cell- and nucleus or mitochondria penetrating peptide were designed (Table 7 below).

The tetrapeptide Arg-D-Arg-Arg-Lys (Cindy A P et al. 2010. Bioorganic & Medicinal Chemistry 18:3564-3569) was used to facilitate cellular uptake and nuclear localization. The peptide is designated herein cell/nucleus penetrating peptide (nuCPP, SEQ ID NO:71).

The tetrapeptide D-Arg-Dmt-Orn-Phe, wherein Dmt=2,6-dimethyl-L-tyrosine, (Carmine Pasquale Cerrato, et al. 2015. The FASEB Journal, 29(11): 4589-4599), was used to facilitate cellular uptake and mitochondria localization. The peptide is designated herein cell/mitochondria penetrating peptide (mtCPP, SEQ ID NO:72)

A peptide comprising transferrin-receptor binding domain (Tf) having the sequence His-Ala-Ile-Tyr-Pro-Arg (SEQ ID NO:80 and a peptide comprising the *Drosophila* antennapedia (ANTP) domain having the sequence Met-Arg-Gln-Ile-Lys Ile-Trp-Phe-Gln-Asn-Arg-Arg-Met-Lys-Trp-Lys (SEQ ID NO:81) each was used to facilitate uptake of the peptide through the cell plasma membrane and into the cytosol.

TABLE 7

Examined peptide conjugates

| Conjugate description | Targeted to | SEQ ID NO. |
|---|---|---|
| 1H13-nuCPP | Nucleus | 69 |
| 1H13-mtCPP-NH$_2$ | Mitochondria | 73 |
| 1G12-nuCPP | Nucleus | 70 |
| nuCPP-1G12 | Nucleus | 71 |
| mtCPP-2C18 | Mitochondria | 74 |
| ANTP-2C18 | Cytosol | 75 |
| TF-1G12 | Cytosol | 76 |

A549 cells were seeded in 96-well plate (5000 cells/well). After 24 h cells were incubated with each of the examined peptides at a concentration of 5, 10, or 30 µM for 48 h in a serum (10%) containing medium or for 24 h in a serum-free medium. Then, cells were washed with PBS, fixed with 10% trichloroacetic acid, and analyzed for cell growth using the SRB method described herein above. Cell growth with no addition of a peptide was taken as a control (100% cell growth). Table 8 presents the cell growth in the presence of the peptide as % of control. Results are the mean±SD (n=3).

TABLE 8

Effect of cells treatment with peptides on cell growth

| Cell penetrating peptide | Targeted to | Concentration µM | Cell growth, % of control |
|---|---|---|---|
| Control | | 0 | 100 |
| 1H13-nuCPP | Nucleus | 5 | 92 ± 0.018 |
| 1H13-nuCPP | Nucleus | 10 | 57 ± 0.013 |
| 1H13-nuCPP | Nucleus | 30 | 30 ± 0.009 |
| 1H13-mtCPP-NH$_2$ | Mitochondria | 5 | 85 ± 0.022 |
| 1H13-mtCPP-NH$_2$ | Mitochondria | 10 | 60 ± 0.018 |
| 1H13-mtCPP-NH$_2$ | Mitochondria | 30 | 49 ± 0.014 |
| 1G12-nuCPP | Nucleus | 5 | 109 ± 0.013 |
| 1G12-nuCPP | Nucleus | 10 | 76 ± 0.024 |
| 1G12-nuCPP | Nucleus | 30 | 39 ± 0.013 |
| nuCPP-1G12 | Nucleus | 5 | 96 ± 0.012 |
| nuCPP-1G12 | Nucleus | 10 | 72 ± 0.01 |
| nuCPP-1G12 | Nucleus | 30 | 66 ± 0.009 |
| Tf- 1G12 | Cytosol | 5 | 99 ± 0.004 |
| Tf- 1G12 | Cytosol | 10 | 98 ± 0.005 |
| Tf- 1G12 | Cytosol | 30 | 99 ± 0.005 |
| mtCPP-2C18 | Mitochondria | 5 | 89 ± 0.005 |
| mtCPP-2C18 | Mitochondria | 10 | 74 ± 0.004 |
| mtCPP-2C18 | Mitochondria | 30 | 59 ± 0.004 |
| ANT-2C18 | Cytosol | 5 | 127 ± 0.006 |
| ANT-2C18, | Cytosol | 10 | 145 ± 0.0162 |
| ANT-2C18 | Cytosol | 30 | 97 ± 0.011 |

Table 8 clearly demonstrates that peptides derived from proteins interacting with SAMC/Diablo, shown herein to bind SMAC/Diablo, when targeted to the nucleus or the mitochondria significantly inhibit cell proliferation. These results indicate that the interaction of selected peptides with SMAC/Diablo under non-apoptotic conditions resulted in inhibition of the non-apoptotic function of SMAC/Diablo, leading to inhibited cell growth.

Example 12: Interaction of SMAC/Diablo with Phosphatidylserine Decarboxylase (PSD/PISD)

Phosphatidylserine decarboxylase or SMAC/Diablo expressing vector was expressed in *Escherichia coli* BL21 cells. Bacteria were grown at 37° C. to reach absorbance at 600 nm of 0.4, after which expression was induced with isopropyl β-D-1 thiogalactopyranoside. PSD was purified by chromatography using DEAE-cellulose column and eluted with NaCl. SMAC/Diablo was purified using nickel-nitrilotriacetic acid resin and eluted using imadazol. Representing results of the purified SMAC/Diablo and PSD are shown in FIG. 18A.

PSD activity was analyzed by following the formation of phosphatidylethanolamine (PE) analyzed as described hereinabove for lipids extracted from xenograft tumors. As is demonstrated in FIG. 18B, the purified enzyme was active. Purified SMAC was fluorescently labeled using the NanoTemper BLUE protein-labeling kit. Thermophoresis was measured using a Monolith-NT115 apparatus. As is demonstrated in FIG. 18C, SMAC/Diablo binds to PSD with a high affinity with Kd of 100 nM. The present invention shows that upon SMAC deletion, PL and PC levels were decreased 2-fold, while PE levels increased 2-fold. One of the key proteins in PL synthesis is phosphatidylserine decarboxylase (PSD), a mitochondrial enzyme which catalyzes the formation of PE from phosphatidylserine (PS). PS is produced in the ER from PC and PE by PSS1 and and PSS2, respectively (FIG. 18D). Without wishing to be bound by any specific theory or mechanism of action, the increase in PE suggests activation of mitochondrial PSD in the absence of SMAC and thus, depleting the ER from PS and PC, thus interfering with phospholipids synthesis essential for the growth of cancerous cells.

Example 13: Inhibition of Tumor Growth in Mice by the Peptides of the Invention The effect of selected peptides, particularly the peptide conjugates of SEQ ID NOs" 69-71 and 72-74 on subcutaneous (s.c) tumors is examined.

A549 ($5 \times 10^6$) or diffuse large B-cell lymphoma (DLBCL) HT (ACC-567) cells ($3 \times 10^6$) are injected sub-cutaneously into the hind leg flanks of eight week-old athymic male nude mice (Envigo). When tumor size reaches 50-100 mm$^3$, the mice are grouped and treated by intra-tumoral injection of a buffer (HBSS) or with the selected peptide/peptide conjugate to a final concentration of 30 to 60 µM. Mice are sacrificed when tumors volumes reach 10-15% of the mouse weight. Tumors are then excised; half of each tumor is fixed in 4% buffered formaldehyde, paraffin-embedded and processed for IHC, and the second half is frozen in liquid nitrogen for immunoblotting and qPCR analyses. Tumor sections are analyzed for: (a) proteins related to lipid metabolism; (b) cancer cell proliferation by staining for the proliferation factor Ki-67 using specific antibodies; (c) tissue morphology using H&E and Sirius Red staining to monitor stromal activity and anti-CD31 antibody staining for evaluating angiogenesis; and (d) apoptosis using the TUNEL assay.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating cancer associated with overexpression of second mitochondria-derived activator of caspase/direct inhibitor of apoptosis-binding protein with low pI (SMAC/Diablo) in a subject in need thereof, comprising administering to the subject an effective amount of at least one agent that inhibits the expression and/or activity of the SMAC/Diablo, wherein the agent is an inhibitory peptide targeted to a cell nucleus and/or mitochondrion or a pharmaceutical composition comprising same, the peptide is derived from hSMAC/Diablo-interacting protein and having an amino acid sequence at least 80% homologous to an amino acid sequence selected from the group consisting of SEQ ID NOs:46-67, analogs, derivatives and/or fragments thereof, and wherein the inhibitory peptide consists of 10-50 amino acids.

2. The method of claim 1, wherein the inhibiting peptide is a conjugate comprising a peptide derived from hSMAC/Diablo-interacting protein having an amino acid sequence selected from the group consisting of SEQ ID NOs:46-67, and a mitochondrion and/or nucleus targeting moiety.

3. The method of claim 2, wherein at least one of the following exist: (a) the nucleus and/or mitochondrion targeting moiety each independently is linked to the N- or C-terminus of the peptide conjugate, directly or via a linker; (b) the nucleus and/or mitochondrion targeting peptide are linked to the N- or C-terminus of the peptide conjugate in tandem, directly or via a linker.

4. The method of claim 2, wherein the peptide conjugate further comprises a cell penetration moiety enhancing the permeability of the conjugate through the cell plasma membrane.

5. The method of claim 2, wherein the nucleus or mitochondrion targeting moiety is a peptide.

6. The method of claim 5, wherein the nucleus targeting moiety comprises the amino acid sequence set forth in SEQ ID NO:68 and wherein the peptide conjugate comprises an amino acid sequence selected from the group consisting of SEQ ID NO:69, SEQ ID NO:70 and SEQ ID NO:71.

7. The method of claim 5, wherein the mitochondrion targeting moiety comprises the amino acid sequence set forth in SEQ ID NO:72, and wherein the peptide conjugate comprises an amino acid sequence selected from the group consisting of SEQ ID NO:73 and SEQ ID NO:74.

8. The method of claim 1, wherein the cancer is selected from the group consisting of lung cancer, breast cancer, colon cancer, lymphoma, sarcomas, stomach cancer, skin cancer, prostate cancer, testicular cancer, cervical cancer, pancreatic cancer, leukemia and renal cancer.

* * * * *